(12) United States Patent
Gauthier et al.

(10) Patent No.: US 11,820,824 B2
(45) Date of Patent: Nov. 21, 2023

(54) ANTIBODIES TO TIGIT

(71) Applicant: ARCUS BIOSCIENCES, INC., Hayward, CA (US)

(72) Inventors: Kelsey Sivick Gauthier, Hayward, CA (US); Nigel Pelham Clinton Walker, Hayward, CA (US); Xiaoning Zhao, Hayward, CA (US); John Lippincott, Hayward, CA (US)

(73) Assignee: ARCUS BIOSCIENCES, INC., Hayward, CA (US)

( * ) Notice: Subject to any disclaimer, the term of this patent is extended or adjusted under 35 U.S.C. 154(b) by 84 days.

(21) Appl. No.: 17/336,181

(22) Filed: Jun. 1, 2021

(65) Prior Publication Data
US 2022/0064294 A1    Mar. 3, 2022

Related U.S. Application Data

(60) Provisional application No. 63/033,609, filed on Jun. 2, 2020.

(51) Int. Cl.
C07K 16/28      (2006.01)
A61P 35/00      (2006.01)
A61K 39/00      (2006.01)

(52) U.S. Cl.
CPC .......... C07K 16/2809 (2013.01); A61P 35/00 (2018.01); A61K 2039/505 (2013.01); C07K 2317/565 (2013.01); C07K 2317/734 (2013.01); C07K 2317/92 (2013.01)

(58) Field of Classification Search
CPC .......... C07K 16/2809; C07K 2317/565; C07K 2317/734; C07K 2317/92; A61P 35/00; A61K 2039/505
See application file for complete search history.

(56) References Cited

U.S. PATENT DOCUMENTS 7,354,584 B2   4/2008   Reed et al.
7,473,423 B2   1/2009   Rodriguez et al.
7,736,647 B2   6/2010   Boumsell et al.
8,163,279 B2   4/2012   Bergstein
8,183,346 B2   5/2012   Leung et al.
8,409,573 B2   4/2013   Boumsell et al.
(Continued)

FOREIGN PATENT DOCUMENTS

CN   109 384 846 A    2/2019
FR   2 959 416 A1    11/2011
(Continued)

OTHER PUBLICATIONS

Mariuzza (Annu. Rev. Biophys. Biophys. Chem., 16: 139-159, 1987) (Year: 1987).*

(Continued)

Primary Examiner — Adam Weidner
Assistant Examiner — Ashley H. Gao
(74) Attorney, Agent, or Firm — SHEPPARD MULLIN RICHTER & HAMPTON LLP

(57) ABSTRACT

The present disclosure provides antibodies that specifically bind to TIGIT. The antibodies have the capacity for substantial activation of T cells and natural killer cells by inhibiting binding of TIGIT to CD155. The antibodies can be used for treatment of cancer and infectious disease, among other applications.

16 Claims, 22 Drawing Sheets
Specification includes a Sequence Listing.

21F8 VH

SDVQLQESGPGLVKPSQSLSLTCTVTGYSIT<u>SDYAWN</u>WIRQFPGNKLEWMG<u>YISYSGS
TSYNPSLKSR</u>ISITRDTSKNQFFLQLNSVTTEDTATYYCAR<u>FMITTFAMDY</u>WGQGTAV
TVSS

21F8 VL

DIVMTQSHKFMSTSVGDRVSITC<u>KASQHVSTAVA</u>WYQQKPGQSPKLLIY<u>SAPYRYT</u>GV
PDRFTGSGSGTDFTFTISSVQAEDLAVYYC<u>QQHYNTLWT</u>FGGGTKLEIK

30M18 VH

EVQLQQSGPELVKPGASVKISCKTSGYTF<u>TEYTMH</u>WVKQSHGKSLEWIG<u>GINPNNGGT
SYNQKFKG</u>RATLTVDKSSSTAYMELRSLTSEDSAVYYCAR<u>SGHMDYGYVY</u>WGQGTTLT
VSS

30M18 VL

DIVMTQSHKFMSTSVGDRVSITC<u>KASQYVSTAVA</u>WYQQKPGQSPKLLIY<u>SPSYRYT</u>GV
PDRFTGSGSGTDFTFTISSVQAEDLAVYYC<u>QQHYSTPWT</u>FGGGTKLEIK

(56) References Cited

U.S. PATENT DOCUMENTS

| | | | |
|---|---|---|---|
| 8,410,251 B2 | 4/2013 | Matsuura et al. | |
| 8,580,714 B2 | 11/2013 | Almagro et al. | |
| 8,715,941 B2 | 5/2014 | Abo et al. | |
| 8,858,949 B2 | 10/2014 | Yokoseki et al. | |
| 8,859,501 B2 | 10/2014 | Nodström et al. | |
| 8,962,804 B2 | 2/2015 | Williams et al. | |
| 9,127,061 B2 | 9/2015 | Zhang et al. | |
| 9,243,070 B2 | 1/2016 | Bansal | |
| 9,499,596 B2 | 11/2016 | Clark et al. | |
| 10,537,633 B2 | 1/2020 | Tso et al. | |
| 2004/0005560 A1 | 1/2004 | Isogai et al. | |
| 2004/0213791 A1 | 10/2004 | Bander et al. | |
| 2008/0032304 A1 | 2/2008 | Isogai et al. | |
| 2009/0258013 A1 | 10/2009 | Clark et al. | |
| 2011/0150903 A1 | 6/2011 | Baurin et al. | |
| 2012/0082667 A1 | 4/2012 | Yokoseki et al. | |
| 2013/0216476 A1 | 8/2013 | Boumsell | |
| 2015/0166661 A1 | 6/2015 | Chen et al. | |
| 2015/0203579 A1 | 7/2015 | Papadopoulos et al. | |
| 2015/0203580 A1 | 7/2015 | Papadopoulos et al. | |
| 2015/0210769 A1 | 7/2015 | Freeman et al. | |
| 2015/0216970 A1 | 8/2015 | Grogan et al. | |
| 2015/0218274 A1 | 8/2015 | Sabatos-Peyton et al. | |
| 2015/0259420 A1 | 9/2015 | Triebel et al. | |
| 2015/0307617 A1 | 10/2015 | Du et al. | |
| 2015/0322119 A1 | 11/2015 | Engelhardt et al. | |
| 2016/0115234 A1 | 4/2016 | Salas et al. | |
| 2016/0115467 A1 | 4/2016 | Salas | |
| 2016/0176963 A1 | 6/2016 | Maurer et al. | |
| 2016/0355589 A1 | 12/2016 | Williams et al. | |
| 2017/0281764 A1 | 10/2017 | Tso et al. | |
| 2018/0169238 A1* | 6/2018 | White | C07K 16/2809 |
| 2020/0062859 A1 | 2/2020 | Piasecki et al. | |
| 2020/0297844 A1 | 9/2020 | Tso et al. | |

FOREIGN PATENT DOCUMENTS

| | | |
|---|---|---|
| FR | 2 959 416 B1 | 11/2011 |
| JP | 2006-311857 A | 11/2006 |
| WO | WO-94/29457 A2 | 12/1994 |
| WO | WO-94/29457 A3 | 12/1994 |
| WO | WO-97/43416 A1 | 11/1997 |
| WO | WO-03/072035 A2 | 9/2003 |
| WO | WO-2004/024068 A2 | 3/2004 |
| WO | WO-2004/024068 A3 | 3/2004 |
| WO | WO-2006/124667 A2 | 11/2006 |
| WO | WO-2006/124667 A3 | 11/2006 |
| WO | WO-2007/124283 A2 | 11/2007 |
| WO | WO-2007/124283 A3 | 11/2007 |
| WO | WO-2008/092992 A1 | 8/2008 |
| WO | WO-2008/092993 A1 | 8/2008 |
| WO | WO-2009/064944 A2 | 5/2009 |
| WO | WO-2009/064944 A3 | 5/2009 |
| WO | WO-2009/073163 A1 | 6/2009 |
| WO | WO-2009/126688 A2 | 10/2009 |
| WO | WO-2009/126688 A3 | 10/2009 |
| WO | WO-2009/126688 A8 | 10/2009 |
| WO | WO 2010/119704 A1 | 10/2010 |
| WO | WO-2011/156356 A1 | 12/2011 |
| WO | WO-2012/008494 A1 | 1/2012 |
| WO | WO-2012/021834 A1 | 2/2012 |
| WO | WO-2012/058588 A2 | 5/2012 |
| WO | WO 2012/058588 A3 | 5/2012 |
| WO | WO-2012/078793 A2 | 6/2012 |
| WO | WO-2012/078793 A3 | 6/2012 |
| WO | WO-2012/078813 A2 | 6/2012 |
| WO | WO-2012/078813 A3 | 6/2012 |
| WO | WO-2012/122396 A1 | 9/2012 |
| WO | WO-2012/129227 A1 | 9/2012 |
| WO | WO-2012/135132 A1 | 10/2012 |
| WO | WO-2013/125636 A1 | 8/2013 |
| WO | WO-2013/125654 A1 | 8/2013 |
| WO | WO-2013/126810 A1 | 8/2013 |
| WO | WO-2013/147169 A1 | 10/2013 |
| WO | WO 2013/147176 A1 | 10/2013 |
| WO | WO-2013/150623 A1 | 10/2013 |
| WO | WO-2013/172961 A1 | 11/2013 |
| WO | WO-2013/184912 A2 | 12/2013 |
| WO | WO-2013/184912 A3 | 12/2013 |
| WO | WO-2013/184912 A4 | 12/2013 |
| WO | WO-2014/089169 A2 | 6/2014 |
| WO | WO-2014/089169 A3 | 6/2014 |
| WO | WO-2014/089169 A4 | 6/2014 |
| WO | WO-2014/189973 A2 | 11/2014 |
| WO | WO-2014/189973 A3 | 11/2014 |
| WO | WO-2015/045447 A1 | 4/2015 |
| WO | WO-2015/099838 A2 | 7/2015 |
| WO | WO-2015/099838 A3 | 7/2015 |
| WO | WO-2015/133882 A1 | 9/2015 |
| WO | WO-2016/011264 A1 | 1/2016 |
| WO | WO-2016/022883 A1 | 2/2016 |
| WO | WO-2016/028656 A1 | 2/2016 |
| WO | WO-2016/073282 A1 | 5/2016 |
| WO | WO-2016/081640 A1 | 5/2016 |
| WO | WO-2016/081643 A1 | 5/2016 |
| WO | WO-2016/191643 A2 | 12/2016 |
| WO | WO-2016/191643 A3 | 12/2016 |
| WO | WO-2016/191643 A4 | 12/2016 |
| WO | WO-2017/053748 A2 | 3/2017 |
| WO | WO-2017/053748 A3 | 3/2017 |
| WO | WO-2017152088 | 9/2017 |
| WO | WO-2018/033798 A1 | 2/2018 |
| WO | WO-2018/160704 A1 | 9/2018 |
| WO | WO-2018/234793 A2 | 12/2018 |
| WO | WO-2018/234793 A3 | 12/2018 |
| WO | WO-2019/023504 A1 | 1/2019 |
| WO | WO-2019/129261 A1 | 7/2019 |
| WO | WO-2019/154415 A1 | 8/2019 |
| WO | WO-2020/020281 A1 | 1/2020 |
| WO | WO-2020/098734 A1 | 5/2020 |
| WO | WO-2020/144178 A1 | 7/2020 |
| WO | WO-2020/251187 A1 | 12/2020 |
| WO | WO-2021/008523 A1 | 1/2021 |

OTHER PUBLICATIONS

McCarthy et al. (J. Immunol. Methods, 251(1-2): 137-149, 2001) (Year: 2001).*

Lin et al. (African Journal of Biotechnology, 10(79):18294-18302, 2011) (Year: 2011).*

Anderson, A.C. et al. (May 17, 2016). "Lag-3, Tim-3, and TIGIT: Co-inhibitory Receptors with Specialized Functions in Immune Regulation," *Immunity* 44(5):989-1004.

Bendig, M.M. (1995). "Humanization of Rodent Monoclonal Antibodies by CDR Grafting," Methods: A Companion to Methods in Enzymology 8:83-93.

Bruck, C. et al. (Sep. 1986). "Nucleic acid sequence of an internal image-bearing monoclonal anti-idiotype and its comparison to the sequence of the external antigen," *PNAS USA* 83(17):6578-6582.

Caldas, C. et al. (May 2003). "Humanization of the anti-CD18 antibody 6.7: an unexpected effect of a framework residue in binding to antigen," *Mol Immunol* 39(15):941-952.

Casadevall, A. et l. (Jul. 31, 2012, e-published Jul. 23, 2012). "Immunoglobulin isotype influences affinity and specificity," *PNAS USA* 109(31):12272-12273.

Dixon et al. (Apr. 15, 2018). "Functional Anti-TIGIT Antibodies Regulate Development of Autoimmunity and Antitumor Immunity," *J Immunol* 200(8):3000-3007.

Du, J. et al. (Oct. 17, 2008). "Molecular basis of recognition of human osteopontin by 23C3, a potential therapeutic antibody for treatment of rheumatoid arthritis," *J Mol Biol* 382(4):835-842.

GenBank Accession No. AAB49890.1, Jan. 30, 1997, 2 pages.

GenBank Accession No. NP_0776160.2, Nov. 15, 2015, 3 pages.

Hampe, C.S. et al. (Jul. 2005). "Quantitative evaluation of a monoclonal antibody and its fragment as potential markers for pancreatic beta cell mass," *Exp Clin Endocrinol Diabetes* 113(7):381-387.

Harris, R.J. et al. (Nov. 1, 1993). "Assessing Genetic Heterogeneity in Production Cell Lines: Detection by Peptide Mapping of a Low Level Tyr to Gln Sequence Variant in a Recombinant Antibody," *Biotechnology* 11:1293-1297.

(56) References Cited

OTHER PUBLICATIONS

International Search Report dated Jul. 7, 2017, for PCT Application No. PCT/US2017/020719, filed Mar. 3, 2017, 5 pages.
International Search Report dated Sep. 13, 2021, for PCT Application No. PCT/US2021/035268, filed Jun. 1, 2021, 6 pages.
Kofler, R. et al. (Jan. 1987). "Molecular analysis of the murine lupus-associated anti-self response: involvement of a large number of heavy and light chain variable region genes," *Eur J Immunol* 17(1):91-95.
Kunik, V. et al. (2012, e-published Feb. 23, 2012). "Structural consensus among antibodies defines the antigen binding site," *PLoS Comput Biol* 8(2):e1002388.
Leahy, D.J. et al. (Jun. 1988). "Sequences of 12 monoclonal anti-dinitrophenyl spin-label antibodies for NMR studies," *PNAS USA* 85(11):3661-3665.
Li, S. et al. (Mar. 17, 2009, e-published Mar. 3, 2009). "Efalizumab binding to the LFA-1 alphaL I domain blocks ICAM-1 binding via steric hindrance," *PNAS USA* 106(11):4349-4354.
Padlan, E.A. et al. (Feb. 1994). "Anatomy of the antibody molecule," *Mol Immunol* 31(3):169-217.
Paul, W.E. (1993). Fundamental Immunology, New York: Raven Press, 3rd edition, pp. 292-295.
Pennell, C.A. et al. (Sep. 1, 1990). "High frequency expression of S107 VH genes by peritoneal B cells of B10.H-2aH-4bP/WTS mice," *J Immunol* 145(5):1592-1597.
Preillon, J. et al. (Jan. 2021, e-published Dec. 4, 2020). "Restoration of T-cell Effector Function, Depletion of Tregs, and Direct Killing of Tumor Cells: The Multiple Mechanisms of Action of a-TIGIT Antagonist Antibodies," *Mol Cancer Ther* 20(1):121-131.
ProSci: "TIGIT Antibody [2C6]," Cat. No. SD8828, located at <https://www.prosci-inc.com/ProductLeaflet/file/getpdf/name/TIGIT_Anitbody_2C6!. pdf?fileld=105433> 3 pages.
Rudikoff, S. et al. (Mar. 1, 1982). "Single Amino Acid Substitition Altering Antigen-Binding Specificity," *PNAS USA* 79(6):1979-1983.
Stanietsky, N. et al. (Oct. 20, 2009, e-published Oct. 7, 2009). "The interaction of TIGIT with PVR and PVRL2 inhibits human NK cell cytotoxicity," *PNAS USA* 106(42):17858-17863.
Stark, S.E. et al. (Sep. 1, 1991). "Antibodies that are specific for a single amino acid interchange in a protein epitope use structurally distinct variable regions," *J Exp Med* 174(3):613-624.
Stengel, K.F. et al. (Apr. 3, 2012, e-published Mar. 15, 2012). "Structure of TIGIT immunoreceptor bound to poliovirus receptor reveals a cell-cell adhesion and signaling mechanism that requires cis-trans receptor clustering," *PNAS USA* 109(14):5399-5404.
Written Opinion dated Jul. 7, 2017, for PCT Application No. PCT/US2017/020719, filed Mar. 3, 2017, 8 pages.
Written Opinion dated Sep. 13, 2021, for PCT Application No. PCT/US2021/035268, filed Jun. 1, 2021, 7 pages.
Official Action for Panamanian Application No. 94259-01 dated Jan. 30, 2023. 2 pages.

\* cited by examiner

SDVQLQESGPGLVKPSQSLSLTCTVTGYSITSDYAWNWIRQFPGNKLEWMGYISYSGS
TSYNPSLKSRISITRDTSKNQFFLQLNSVTTEDTATYYCAREMITTFAMDYWGQGTAV
TVSS

21F8 VL

DIVMTQSHKFMSTSVGDRVSITCKASQHVSTAVAWYQQKPGQSPKLLIYSAPYRYTGV
PDRFTGSGSGTDFTFTISSVQAEDLAVYYCQQHYNTLWTFGGGTKLEIK

EVQLQQSGPELVKPGASVKISCKTSGYTFTEYTMHWVKQSHGKSLEWIGGINPNNGGT
SYNQKFKGKATLTVDKSSSTAYMELRSLTSEDSAVYYCARSGHMDYGVVYWGQGTTLT
VSS

30M18 VL

DIVMTQSHKFMSTSVGDRVSITCKASQYVSTAVAWYQQKPGQSPKLLIYSPSYRYTGV
PDRFTGSGSGTDFTFTISSVQAEDLAVYYCQQHYSTPWTFGGGTKLEIK

SDVQLQESGPDLVKPSQSLSLTCTVTGYSITSGYSWHWIRQFPGNKLDWMGYVHYSGS
TNYNPSLKSRISITRDTSKNQFFLQLNSVTTEDTATFYCARMDYGNYGGAMDYWGQGT
SVTVSS

24F8 VL

EIVMTQSHKFMSTSVGDRVSITCKASQDVRTAVAWYQQKPGQSPKLLIYSASYRYTGV
PDRFTGSGSGTDFTFTISSVQAEDLAVYYCQQYYSTQWTFGGGTKLEIK

QVQLQQSGAELVRPGTSVKMSCKAAGYTFTNHWIGWVKQRPGHGLEWIGDIYPGGGYT
NYNEKFKGKATLTADTSSSTAYMLSSLTSEDSAIYYCARSYGYDLYAMDYWGQGTSV
TVSS

5J24 VL

DIQMTQSPSSLSASLGERVSLTCRASQEISGYLSWLQQKPDGTIKRLIYAASTLGSGV
PKRFSGSRSGSDYSLTISSLESEDFADYCLQYDSYPFTFGAGTKLELK

EVQLVESGGGLVKPGGSLKLSCTASGFTFSSYAMSWVRQSPEKRLEWVAEISSGGSYT
YYTDTVTGRFTISRDNAKNTLYLEMSSLRSEDTAMYYCARKRRDYYGMDYWGQGTSVT
VSS

21B9 VL

DVQITQSPSYLAASPGETITINCRASKSISKYLAWYQEKPGKTNKLLIYSGSTLQTGI
PSRFSGSGSGTDFTLTISSLEPEDFAMYYCQQHNEYPWTFGGGTKLEIK

EVQLVESGGGLVKPGGSLKLSCAASGFTFSSYAMSWVRQSPEKRLEWVAEISSGGSYT
YYPDTVTGRFTISRDNAKNTLYLEMSSLRSEDTAMYYCARKRRDYYAMDYWGQGTSVT
VSS

22B22 VL

DVQITQSPSYLAASPGETITINCRASKSISKYLAWYQEKPGKTNKLLIYSGSTLQSGI
PSRFSGSGSGTDFTLTISSLEPEDFAMYYCQQHNEYPWTFGGGTKLEIK

QVQLQQSGAELVRPGTSVKMSCKAAGYTFTNYEIGWVKQRPGHGLDWIGDIYPGGGYT
NYNEKFKGKATLTADTSSSTAYMQLSSLTSEDSAIYYCVRFYGNYVFAYWGQGTLVTV
SA

28P24 VL

DVQITQSPSCLAASPGETITINCRASKTISKYLAWYQEKPGKTNKLLIYSGSTLQSGI
PSRFSGSGSGTDFTLTISSLEPEDFAMYYCQQHNEYPWTFGGGTKLEIK

EVQLVESGGGLVKPGGSLKLSCAASGFTFSTYAMSWVRQSPEKRLEWVAEISSGGTYT
YFPDTVTGRFTISRDNAKNTLYLEMSSLRSEDTAMYYCARKRRDYYAMDYWGQGTSVT
VSS

21B16 VL

DVQITQSPSYLAASPGETITINCRASKSISKYLAWYQEKPGKTNKLLIYSGSTLQSGI
PSRFSGSGSGTDFTLTISSLEPEDFAVYYCQQHNEYPWTFGGGTKLEIK

FIG. 1I
28O12 VH

EVQLVESGGGLVKPGGSLKLSCAASGFTFSNYAMSWVRQSPEKRLEWVAEISGGSYT
YHPDTVTGRFTISRDNAKNTLYLEMSSLRSEDTAMYYCARKRRDYYAMDYWGQGTSVT
VSS

28O12 VL

DVQITQSPSYLAASPGETITINCRASKSISKYLAWYQEKPGKTNKLLIYSGSTLQSGI
PSRFSGSGSGTDFTLTISSLEPEDFAMYYCQQHNEYPWTFGGGTKLEIK

FIG. 1J
Hu24F8.1 VH

QVQLQESGPGLVKPSETLSLTCAVYGYSITSGYSWHWIRQPPGKGLEWIGYVHYSGSTN
YNPSLKSRVTISVDTSKNQFSLKLSSVTAADTAVYYCARMDYGNYGGAMDYWGQGTLVT
VSS

Hu24F8.1 VL

EIVMTQSPATLSVSPGERATLSCKASQDVRTAVAWYQQKPGQAPRLLIYSASYRYTGIP
ARFSGSGSGTEFTLTISSLQSEDFAVYYCQQYYSTQWTFGGGTKVEIK

QVQLQESGPGLVKPSGTLSLTCAVSGYSITSGYSWHWVRQPPGKGLEWIGYVHYSGST
NYNPSLKSRVTISVDKSKNQFSLKLSSVTAADTAVYYCARMDYGNYGGAMDYWGQGTL
VTVSS

Hu24F8.2 VL

EIVMTQSPATLSVSPGERATLSCKASQDVRTAVAWYQQKPGQAPRLLIYSASYRYTGI
PARFSGSGSGTEFTLTISSLQSEDFAVYYCQQYSTQWTFGGGTKVEIK

QVQLQESGPGLVKPSGTLSLTCAVSGYSITSGYSWHWVRQPPGKGLEWIGYVHYSGSTN
YNPSLKSRVTISVDKSKNQFSLKLSSVTAADTAVYYCARMDYGNYGGAMDYWGQGTLVT
VSS

Hu24F8.3 VL

DIQMTQSPSSLSASVGDRVTITCKASQDVRTAVAWYQQKPGKAPKLLIYSASYRYT
GVPSRFSGSGSGTDFTFTISSLQPEDIATYYCQQYSTQWTFGGGTKLEIK

QVQLQESGPGLVKPSETLSLTCAVYGYSITSGYSWHWIRQPPGKGLEWIGYVHYSGSTN
YNPSLKSRVTISVDTSKNQFSLKLSSVTAADTAVYYCARMDYGNYGGAMDYWGQGTLVT
VSS

Hu24F8.4 VL

DIQMTQSPSSLSASVGDRVTITCKASQDVRTAVAWYQQKPGKAPKLLIYSASYRYT
GVPSRFSGSGSGTDFTFTISSLQPEDIATYYCQQYYSTQWTFGGGTKLEIK

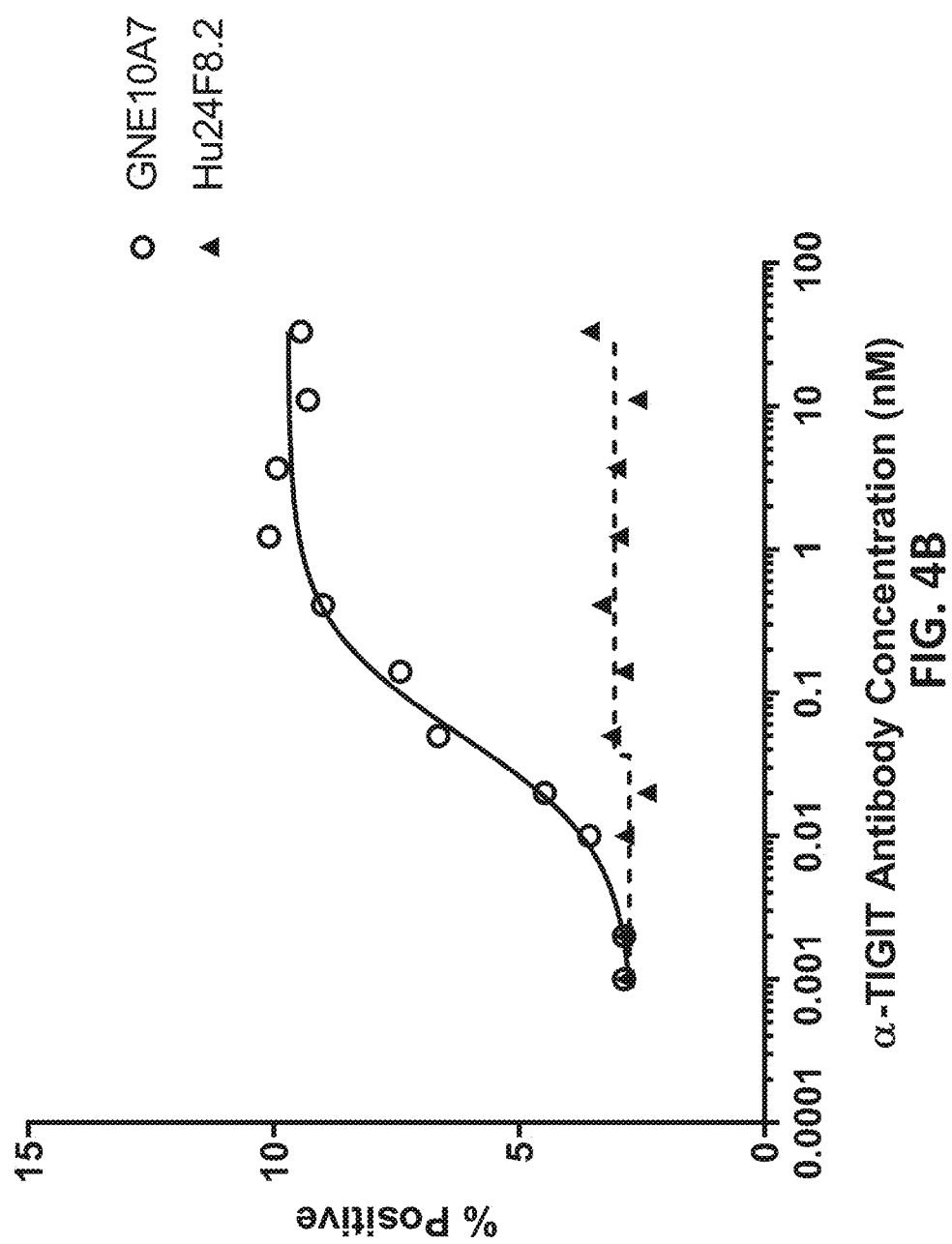

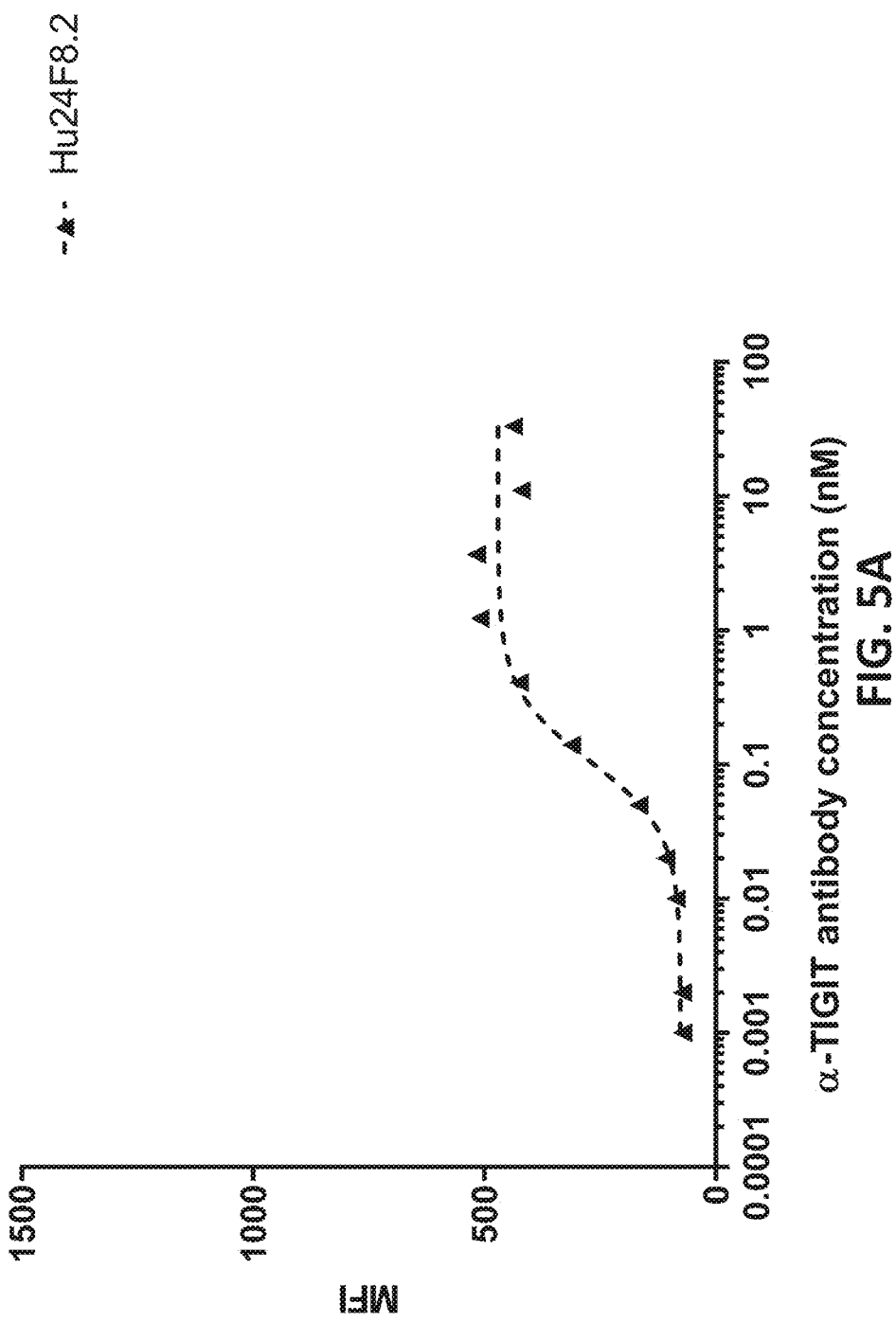

SEQUENCE LISTING

<160> NUMBER OF SEQ ID NOS: 101

<210> SEQ ID NO 1
<211> LENGTH: 120
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 21F8 heavy chain, amino acid

<400> SEQUENCE: 1

Ser Asp Val Gln Leu Gln Glu Ser Gly Pro Gly Leu Val Lys Pro Ser
1               5                   10                  15

Gln Ser Leu Ser Leu Thr Cys Thr Val Thr Gly Tyr Ser Ile Thr Ser
            20                  25                  30

Asp Tyr Ala Trp Asn Trp Ile Arg Gln Phe Pro Gly Asn Lys Leu Glu
        35                  40                  45

Trp Met Gly Tyr Ile Ser Tyr Ser Gly Ser Thr Ser Tyr Asn Pro Ser
    50                  55                  60

Leu Lys Ser Arg Ile Ser Ile Thr Arg Asp Thr Ser Lys Asn Gln Phe
65                  70                  75                  80

Phe Leu Gln Leu Asn Ser Val Thr Thr Glu Asp Thr Ala Thr Tyr Tyr
                85                  90                  95

Cys Ala Arg Phe Met Ile Thr Thr Phe Ala Met Asp Tyr Trp Gly Gln
            100                 105                 110

Gly Thr Ala Val Thr Val Ser Ser
        115                 120

<210> SEQ ID NO 2
<211> LENGTH: 107
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 21F8 light chain, amino acid

<400> SEQUENCE: 2

Asp Ile Val Met Thr Gln Ser His Lys Phe Met Ser Thr Ser Val Gly
1               5                   10                  15

Asp Arg Val Ser Ile Thr Cys Lys Ala Ser Gln His Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Pro Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Asn Thr Leu Trp
                85                  90                  95

Thr Phe Gly Gly Gly Thr Lys Leu Glu Ile Lys
            100                 105

<210> SEQ ID NO 3
<211> LENGTH: 119
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 30M18 heavy chain, amino acid

<400> SEQUENCE: 3

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
                20                  25                  30

Thr Met His Trp Val Lys Gln Ser His Gly Lys Ser Leu Glu Trp Ile
            35                  40                  45

Gly Gly Ile Asn Pro Asn Asn Gly Gly Thr Ser Tyr Asn Gln Lys Phe
50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Ser Gly His Met Asp Tyr Gly Tyr Val Tyr Trp Gly Gln Gly
            100                 105                 110

Thr Thr Leu Thr Val Ser Ser
        115

<210> SEQ ID NO 4
<211> LENGTH: 107
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 30M18 light chain, amino acid

<400> SEQUENCE: 4

Asp Ile Val Met Thr Gln Ser His Lys Phe Met Ser Thr Ser Val Gly
1               5                   10                  15

Asp Arg Val Ser Ile Thr Cys Lys Ala Ser Gln Tyr Val Ser Thr Ala
                20                  25                  30

Val Ala Trp Tyr Gln Gln Lys Pro Gly Gln Ser Pro Lys Leu Leu Ile
            35                  40                  45

Tyr Ser Pro Ser Tyr Arg Tyr Thr Gly Val Pro Asp Arg Phe Thr Gly
        50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Glu Ile Lys
            100                 105

```
<210> SEQ ID NO 5
<211> LENGTH: 122
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 24F8 heavy chain, amino acid

<400> SEQUENCE: 5

Ser Asp Val Gln Leu Gln Glu Ser Gly Pro Asp Leu Val Lys Pro Ser
1               5                   10                  15

Gln Ser Leu Ser Leu Thr Cys Thr Val Thr Gly Tyr Ser Ile Thr Ser
            20                  25                  30

Gly Tyr Ser Trp His Trp Ile Arg Gln Phe Pro Gly Asn Lys Leu Asp
        35                  40                  45

Trp Met Gly Tyr Val His Tyr Ser Gly Ser Thr Asn Tyr Asn Pro Ser
    50                  55                  60

Leu Lys Ser Arg Ile Ser Ile Thr Arg Asp Thr Ser Lys Asn Gln Phe
65                  70                  75                  80

Phe Leu Gln Leu Asn Ser Val Thr Thr Glu Asp Thr Ala Thr Phe Tyr
                85                  90                  95

Cys Ala Arg Met Asp Tyr Gly Asn Tyr Gly Gly Ala Met Asp Tyr Trp
            100                 105                 110

Gly Gln Gly Thr Ser Val Thr Val Ser Ser
        115                 120

<210> SEQ ID NO 6
<211> LENGTH: 107
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 24F8 light chain, amino acid

<400> SEQUENCE: 6

Glu Ile Val Met Thr Gln Ser His Lys Phe Met Ser Thr Ser Val Gly
1               5                   10                  15

Asp Arg Val Ser Ile Thr Cys Lys Ala Ser Gln Asp Val Arg Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln Tyr Ser Thr Gln Trp
                85                  90                  95

Thr Phe Gly Gly Gly Thr Lys Leu Glu Ile Lys
            100                 105

<210> SEQ ID NO 7
<211> LENGTH: 120
<212> TYPE: PRT
<213> ORGANISM: Artificial sequence
<220> FEATURE:
<223> OTHER INFORMATION: Synthetic construct
```

-continued

```
<220> FEATURE:
<221> NAME/KEY: MISC_FEATURE
<223> OTHER INFORMATION: Mouse mAb 5J24 heavy chain, amino acid

<400> SEQUENCE: 7

Gln Val Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Asn His
            20                  25                  30

Trp Ile Gly Trp Val Lys Gln Arg Pro Gly His Gly Leu Glu Trp Ile
        35                  40                  45

Gly Asp Ile Tyr Pro Gly Gly Tyr Thr Asn Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Tyr Leu Ser Ser Leu Thr Ser Glu Asp Ser Ala Ile Tyr Tyr Cys
                85                  90                  95

Ala Arg Ser Tyr Gly Tyr Asp Leu Tyr Ala Met Asp Tyr Trp Gly Gln
            100                 105                 110

Gly Thr Ser Val Thr Val Ser Ser
        115                 120

<210> SEQ ID NO 8
<211> LENGTH: 107
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 5J24 light chain, amino acid

<400> SEQUENCE: 8

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Gly Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Asp Ser Tyr Pro Phe
                85                  90                  95

Thr Phe Gly Ala Gly Thr Lys Leu Glu Leu Lys
            100                 105

<210> SEQ ID NO 9
<211> LENGTH: 119
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 21B9 heavy chain, amino acid
```

```
<400> SEQUENCE: 9

Glu Val Gln Leu Val Glu Ser Gly Gly Gly Leu Val Lys Pro Gly Gly
1               5                   10                  15

Ser Leu Lys Leu Ser Cys Thr Ala Ser Gly Phe Thr Phe Ser Ser Tyr
            20                  25                  30

Ala Met Ser Trp Val Arg Gln Ser Pro Glu Lys Arg Leu Glu Trp Val
        35                  40                  45

Ala Glu Ile Ser Ser Gly Gly Ser Tyr Thr Tyr Tyr Thr Asp Thr Val
    50                  55                  60

Thr Gly Arg Phe Thr Ile Ser Arg Asp Asn Ala Lys Asn Thr Leu Tyr
65                  70                  75                  80

Leu Glu Met Ser Ser Leu Arg Ser Glu Asp Thr Ala Met Tyr Tyr Cys
                85                  90                  95

Ala Arg Lys Arg Arg Asp Tyr Tyr Gly Met Asp Tyr Trp Gly Gln Gly
            100                 105                 110

Thr Ser Val Thr Val Ser Ser
            115

<210> SEQ ID NO 10
<211> LENGTH: 107
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 21B9 light chain, amino acid

<400> SEQUENCE: 10

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Thr Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Trp
                85                  90                  95

Thr Phe Gly Gly Gly Thr Lys Leu Glu Ile Lys
            100                 105

<210> SEQ ID NO 11
<211> LENGTH: 119
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 22B22 heavy chain, amino acid

<400> SEQUENCE: 11

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30
```

```
Ala Met Ser Trp Val Arg Gln Ser Pro Glu Lys Arg Leu Glu Trp Val
            35                  40                  45

Ala Glu Ile Ser Ser Gly Gly Ser Tyr Thr Tyr Tyr Pro Asp Thr Val
    50                  55                  60

Thr Gly Arg Phe Thr Ile Ser Arg Asp Asn Ala Lys Asn Thr Leu Tyr
65                  70                  75                  80

Leu Glu Met Ser Ser Leu Arg Ser Glu Asp Thr Ala Met Tyr Tyr Cys
                85                  90                  95

Ala Arg Lys Arg Arg Asp Tyr Tyr Ala Met Asp Tyr Trp Gly Gln Gly
            100                 105                 110

Thr Ser Val Thr Val Ser Ser
            115

<210> SEQ ID NO 12
<211> LENGTH: 107
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 22B22 and Mouse mAb 28O12 light
      chain, amino acid

<400> SEQUENCE: 12

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
            35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Trp
                85                  90                  95

Thr Phe Gly Gly Gly Thr Lys Leu Glu Ile Lys
            100                 105

<210> SEQ ID NO 13
<211> LENGTH: 118
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 28P24 heavy chain, amino acid

<400> SEQUENCE: 13

Gln Val Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Asn Tyr
            20                  25                  30

Phe Ile Gly Trp Val Lys Gln Arg Pro Gly His Gly Leu Asp Trp Ile
            35                  40                  45

Gly Asp Ile Tyr Pro Gly Gly Gly Tyr Thr Asn Tyr Asn Glu Lys Phe
    50                  55                  60
```

```
Lys Gly Lys Ala Thr Leu Thr Ala Asp Thr Ser Ser Thr Ala Tyr
 65                  70                  75                  80

Met Gln Leu Ser Ser Leu Thr Ser Glu Asp Ser Ala Ile Tyr Tyr Cys
                 85                  90                  95

Val Arg Phe Tyr Gly Asn Tyr Val Phe Ala Tyr Trp Gly Gln Gly Thr
            100                 105                 110

Leu Val Thr Val Ser Ala
            115

<210> SEQ ID NO 14
<211> LENGTH: 107
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 28P24 light chain, amino acid

<400> SEQUENCE: 14

Asp Val Gln Ile Thr Gln Ser Pro Ser Cys Leu Ala Ala Ser Pro Gly
  1               5                  10                  15

Glu Thr Ile Thr Ile Asn Cys Arg Ala Ser Lys Thr Ile Ser Lys Tyr
                 20                  25                  30

Leu Ala Trp Tyr Gln Glu Lys Pro Gly Lys Thr Asn Lys Leu Leu Ile
             35                  40                  45

Tyr Ser Gly Ser Thr Leu Gln Ser Gly Ile Pro Ser Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Met Tyr Tyr Cys Gln Gln His Asn Glu Tyr Pro Trp
                 85                  90                  95

Thr Phe Gly Gly Gly Thr Lys Leu Glu Ile Lys
            100                 105

<210> SEQ ID NO 15
<211> LENGTH: 119
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 21B16 heavy chain, amino acid

<400> SEQUENCE: 15

Glu Val Gln Leu Val Glu Ser Gly Gly Gly Leu Val Lys Pro Gly Gly
  1               5                  10                  15

Ser Leu Lys Leu Ser Cys Ala Ala Ser Gly Phe Thr Phe Ser Thr Tyr
                 20                  25                  30

Ala Met Ser Trp Val Arg Gln Ser Pro Glu Lys Arg Leu Glu Trp Val
             35                  40                  45

Ala Glu Ile Ser Ser Gly Gly Thr Tyr Thr Tyr Phe Pro Asp Thr Val
 50                  55                  60

Thr Gly Arg Phe Thr Ile Ser Arg Asp Asn Ala Lys Asn Thr Leu Tyr
 65                  70                  75                  80

Leu Glu Met Ser Ser Leu Arg Ser Glu Asp Thr Ala Met Tyr Tyr Cys
                 85                  90                  95
```

Ala Arg Lys Arg Arg Asp Tyr Tyr Ala Met Asp Tyr Trp Gly Gln Gly
            100                 105                 110

Thr Ser Val Thr Val Ser Ser
        115

<210> SEQ ID NO 16
<211> LENGTH: 107
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 21B16 light chain, amino acid

<400> SEQUENCE: 16

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln His Asn Glu Tyr Pro Trp
                85                  90                  95

Thr Phe Gly Gly Gly Thr Lys Leu Glu Ile Lys
            100                 105

<210> SEQ ID NO 17
<211> LENGTH: 119
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 28O12 heavy chain, amino acid

<400> SEQUENCE: 17

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Ser Pro Glu Lys Arg Leu Glu Trp Val
        35                  40                  45

Ala Glu Ile Ser Gly Gly Gly Ser Tyr Thr Tyr His Pro Asp Thr Val
    50                  55                  60

Thr Gly Arg Phe Thr Ile Ser Arg Asp Asn Ala Lys Asn Thr Leu Tyr
65                  70                  75                  80

Leu Glu Met Ser Ser Leu Arg Ser Glu Asp Thr Ala Met Tyr Tyr Cys
                85                  90                  95

Ala Arg Lys Arg Arg Asp Tyr Tyr Ala Met Asp Tyr Trp Gly Gln Gly
            100                 105                 110

Thr Ser Val Thr Val Ser Ser
        115

```
<210> SEQ ID NO 18
<211> LENGTH: 360
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 21F8 heavy chain, nucleotide

<400> SEQUENCE: 18

Thr Cys Thr Gly Ala Thr Gly Thr Gly Cys Ala Gly Cys Thr Thr Cys
1               5                   10                  15

Ala Gly Gly Ala Gly Thr Cys Gly Gly Gly Ala Cys Cys Thr Gly Gly
            20                  25                  30

Cys Cys Thr Gly Gly Thr Gly Ala Ala Ala Cys Cys Thr Thr Cys Thr
        35                  40                  45

Cys Ala Gly Thr Cys Thr Cys Thr Gly Thr Cys Cys Cys Thr Cys Ala
    50                  55                  60

Cys Cys Thr Gly Cys Ala Cys Thr Gly Thr Cys Ala Cys Thr Gly Gly
65                  70                  75                  80

Cys Thr Ala Cys Thr Cys Ala Ala Thr Cys Ala Cys Cys Ala Gly Thr
                85                  90                  95

Gly Ala Thr Thr Ala Thr Gly Cys Cys Thr Gly Gly Ala Ala Cys Thr
            100                 105                 110

Gly Gly Ala Thr Cys Cys Gly Gly Cys Ala Gly Thr Thr Thr Cys Cys
        115                 120                 125

Ala Gly Gly Ala Ala Ala Cys Ala Ala Ala Cys Thr Gly Gly Ala Gly
    130                 135                 140

Thr Gly Gly Ala Thr Gly Gly Gly Cys Thr Ala Cys Ala Thr Ala Ala
145                 150                 155                 160

Gly Cys Thr Ala Cys Ala Gly Thr Gly Gly Thr Ala Gly Cys Ala Cys
                165                 170                 175

Thr Ala Gly Cys Thr Ala Cys Ala Ala Cys Cys Cys Ala Thr Cys Thr
            180                 185                 190

Cys Thr Cys Ala Ala Ala Ala Gly Thr Cys Gly Ala Ala Thr Cys Thr
        195                 200                 205

Cys Thr Ala Thr Cys Ala Cys Thr Cys Gly Ala Gly Ala Cys Ala Cys
    210                 215                 220

Ala Thr Cys Cys Ala Ala Gly Ala Ala Cys Cys Ala Gly Thr Thr Cys
225                 230                 235                 240

Thr Thr Cys Cys Thr Gly Cys Ala Gly Thr Thr Gly Ala Ala Thr Thr
                245                 250                 255

Cys Thr Gly Thr Gly Ala Cys Thr Ala Cys Thr Gly Ala Gly Gly Ala
            260                 265                 270

Cys Ala Cys Ala Gly Cys Cys Ala Cys Ala Thr Ala Thr Thr Ala Cys
        275                 280                 285

Thr Gly Thr Gly Cys Ala Ala Gly Ala Thr Thr Thr Ala Thr Gly Ala
    290                 295                 300

Thr Thr Ala Cys Gly Ala Cys Gly Thr Thr Thr Gly Cys Thr Ala Thr
305                 310                 315                 320

Gly Gly Ala Cys Thr Ala Cys Thr Gly Gly Gly Gly Thr Cys Ala Ala
                325                 330                 335
```

Gly Gly Ala Ala Cys Cys Gly Cys Ala Gly Thr Cys Ala Cys Cys Gly
            340                 345                 350

Thr Cys Thr Cys Cys Thr Cys Ala
            355                 360

<210> SEQ ID NO 19
<211> LENGTH: 321
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 21F8 light chain, nucleotide

<400> SEQUENCE: 19

Gly Ala Cys Ala Thr Thr Gly Thr Gly Ala Thr Gly Ala Cys Cys Cys
1               5                   10                  15

Ala Gly Thr Cys Thr Cys Ala Cys Ala Ala Thr Thr Cys Ala Thr Thr
                20                  25                  30

Gly Thr Cys Ala Ala Cys Ala Thr Cys Ala Gly Thr Ala Gly Gly Ala
            35                  40                  45

Gly Ala Cys Ala Gly Gly Gly Thr Cys Ala Gly Cys Ala Thr Cys Ala
        50                  55                  60

Cys Cys Thr Gly Cys Ala Ala Gly Gly Cys Cys Ala Gly Thr Cys Ala
65                  70                  75                  80

Gly Cys Ala Thr Gly Thr Gly Ala Gly Thr Ala Cys Thr Gly Cys Thr
                85                  90                  95

Gly Thr Ala Gly Cys Cys Thr Gly Gly Thr Ala Thr Cys Ala Ala Cys
            100                 105                 110

Ala Gly Ala Ala Ala Cys Cys Ala Gly Gly Ala Cys Ala Ala Thr Cys
        115                 120                 125

Thr Cys Cys Thr Ala Ala Ala Cys Thr Ala Cys Thr Gly Ala Thr Thr
130                 135                 140

Thr Ala Cys Thr Cys Gly Gly Cys Ala Cys Cys Thr Ala Cys Cys
145                 150                 155                 160

Gly Gly Thr Ala Cys Ala Cys Thr Gly Gly Ala Gly Thr Cys Cys Cys
                165                 170                 175

Thr Gly Ala Thr Cys Gly Cys Thr Thr Cys Ala Cys Thr Gly Gly Cys
            180                 185                 190

Ala Gly Thr Gly Gly Ala Thr Cys Thr Gly Gly Gly Ala Cys Gly Gly
        195                 200                 205

Ala Thr Thr Thr Cys Ala Cys Thr Thr Cys Ala Cys Cys Ala Thr
    210                 215                 220

Cys Ala Gly Cys Ala Gly Thr Gly Thr Gly Cys Ala Gly Gly Cys Thr
225                 230                 235                 240

Gly Ala Ala Gly Ala Cys Cys Thr Gly Gly Cys Ala Gly Thr Thr Thr
                245                 250                 255

Ala Thr Thr Ala Cys Thr Gly Cys Ala Gly Cys Ala Ala Cys Ala
            260                 265                 270

Thr Thr Ala Thr Ala Ala Thr Ala Cys Thr Cys Thr Gly Thr Gly Gly
        275                 280                 285

Ala Cys Gly Thr Thr Cys Gly Gly Thr Gly Gly Ala Gly Gly Cys Ala
    290                 295                 300

```
Cys Cys Ala Ala Gly Cys Thr Gly Gly Ala Ala Thr Cys Ala Ala
305                 310                 315                 320

Ala
```

<210> SEQ ID NO 20
<211> LENGTH: 357
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 30M18 heavy chain, nucleotide

<400> SEQUENCE: 20

```
Gly Ala Gly Gly Thr Cys Cys Ala Gly Cys Thr Gly Cys Ala Ala
1               5                   10                  15

Ala Gly Thr Cys Thr Gly Gly Ala Cys Cys Thr Gly Ala Gly Cys Thr
            20                  25                  30

Gly Gly Thr Gly Ala Ala Gly Cys Cys Thr Gly Gly Gly Gly Cys Thr
            35                  40                  45

Thr Cys Ala Gly Thr Gly Ala Ala Gly Ala Thr Cys Cys
        50                  55                  60

Gly Cys Ala Ala Gly Ala Cys Thr Thr Cys Thr Gly Gly Ala Thr Ala
65                  70                  75                  80

Cys Ala Cys Ala Thr Thr Cys Ala Cys Thr Gly Ala Ala Thr Ala Cys
                85                  90                  95

Ala Cys Cys Ala Thr Gly Cys Ala Cys Thr Gly Gly Gly Thr Gly Ala
                100                 105                 110

Ala Gly Cys Ala Gly Ala Gly Cys Cys Ala Thr Gly Gly Ala Ala Ala
            115                 120                 125

Gly Ala Gly Cys Cys Thr Thr Gly Ala Gly Thr Gly Gly Ala Thr Thr
            130                 135                 140

Gly Gly Ala Gly Gly Thr Ala Thr Thr Ala Ala Thr Cys Cys Thr Ala
145                 150                 155                 160

Ala Cys Ala Ala Thr Gly Gly Thr Gly Gly Thr Ala Cys Thr Ala Gly
                165                 170                 175

Thr Thr Ala Thr Ala Ala Cys Cys Ala Gly Ala Ala Gly Thr Thr Thr
                180                 185                 190

Ala Ala Gly Gly Gly Cys Ala Ala Gly Gly Cys Cys Ala Cys Ala Thr
            195                 200                 205

Thr Gly Ala Cys Thr Gly Thr Ala Gly Ala Cys Ala Ala Gly Thr Cys
            210                 215                 220

Cys Thr Cys Cys Ala Gly Cys Ala Cys Ala Gly Cys Cys Thr Ala Cys
225                 230                 235                 240

Ala Thr Gly Gly Ala Gly Cys Thr Cys Gly Cys Ala Gly Cys Cys
                245                 250                 255

Thr Gly Ala Cys Ala Thr Cys Thr Gly Ala Gly Gly Ala Thr Thr Cys
            260                 265                 270

Thr Gly Cys Ala Gly Thr Cys Thr Ala Thr Thr Ala Cys Thr Gly Thr
            275                 280                 285

Gly Cys Ala Ala Gly Ala Thr Cys Gly Gly Gly Gly Cys Ala Thr Ala
        290                 295                 300

Thr Gly Gly Ala Cys Thr Ala Cys Gly Gly Cys Thr Ala Cys Gly Thr
305                 310                 315                 320
```

```
Cys Thr Ala Cys Thr Gly Gly Gly Gly Cys Ala Ala Gly Gly Cys
                    325                 330                 335

Ala Cys Cys Ala Cys Thr Cys Thr Cys Ala Cys Ala Gly Thr Cys Thr
                340                 345                 350

Cys Cys Thr Cys Ala
        355

<210> SEQ ID NO 21
<211> LENGTH: 321
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 30M18 light chain, nucleotide

<400> SEQUENCE: 21

Gly Ala Cys Ala Thr Thr Gly Thr Gly Ala Thr Gly Ala Cys Cys Cys
1               5                   10                  15

Ala Gly Thr Cys Thr Cys Ala Cys Ala Ala Thr Thr Cys Ala Thr
            20                  25                  30

Gly Thr Cys Cys Ala Cys Ala Thr Cys Ala Gly Thr Ala Gly Gly Ala
        35                  40                  45

Gly Ala Cys Ala Gly Gly Gly Thr Cys Ala Gly Cys Ala Thr Cys Ala
    50                  55                  60

Cys Cys Thr Gly Cys Ala Ala Gly Gly Cys Cys Ala Gly Thr Cys Ala
65                  70                  75                  80

Ala Thr Ala Thr Gly Thr Gly Ala Gly Thr Ala Cys Thr Gly Cys Thr
                85                  90                  95

Gly Thr Ala Gly Cys Cys Thr Gly Gly Thr Ala Thr Cys Ala Ala Cys
                100                 105                 110

Ala Gly Ala Ala Ala Cys Cys Ala Gly Gly Ala Cys Ala Ala Thr Cys
            115                 120                 125

Thr Cys Cys Thr Ala Ala Ala Cys Thr Ala Cys Thr Gly Ala Thr Thr
        130                 135                 140

Thr Ala Cys Thr Cys Gly Cys Cys Ala Cys Cys Thr Ala Cys Cys
145                 150                 155                 160

Gly Gly Thr Ala Cys Ala Cys Thr Gly Gly Ala Gly Thr Cys Cys Cys
                165                 170                 175

Thr Gly Ala Thr Cys Gly Cys Thr Thr Cys Ala Cys Thr Gly Gly Cys
                180                 185                 190

Ala Gly Thr Gly Gly Ala Thr Cys Thr Gly Gly Ala Cys Gly Gly
            195                 200                 205

Ala Thr Thr Thr Cys Ala Cys Thr Cys Thr Cys Ala Cys Cys Ala Thr
        210                 215                 220

Cys Ala Gly Cys Ala Gly Thr Gly Thr Gly Cys Ala Gly Gly Cys Thr
225                 230                 235                 240

Gly Ala Ala Gly Ala Cys Cys Thr Gly Gly Cys Ala Gly Thr Thr Thr
                245                 250                 255

Ala Thr Thr Ala Cys Thr Gly Cys Ala Gly Cys Ala Ala Cys Ala
            260                 265                 270

Thr Thr Ala Thr Ala Gly Thr Ala Cys Thr Cys Cys Gly Thr Gly Gly
        275                 280                 285

Ala Cys Gly Thr Thr Cys Gly Gly Thr Gly Gly Ala Gly Gly Cys Ala
    290                 295                 300
```

```
Cys Cys Ala Ala Gly Cys Thr Gly Gly Ala Ala Thr Cys Ala Ala
305                 310                 315                 320

Ala

<210> SEQ ID NO 22
<211> LENGTH: 366
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 24F8 heavy chain, nucleotide

<400> SEQUENCE: 22

Thr Cys Thr Gly Ala Thr Gly Thr Gly Cys Ala Gly Cys Thr Cys
1               5                   10                  15

Ala Gly Gly Ala Gly Thr Cys Ala Gly Gly Ala Cys Cys Thr Gly Ala
                20                  25                  30

Cys Cys Thr Gly Gly Thr Gly Ala Ala Ala Cys Cys Thr Thr Cys Thr
                35                  40                  45

Cys Ala Gly Thr Cys Ala Cys Thr Thr Thr Cys Ala Cys Thr Cys Ala
                50                  55                  60

Cys Cys Thr Gly Cys Ala Cys Thr Gly Thr Cys Ala Cys Thr Gly Gly
65                  70                  75                  80

Cys Thr Ala Cys Thr Cys Cys Ala Thr Cys Ala Cys Cys Ala Gly Thr
                85                  90                  95

Gly Gly Thr Thr Ala Thr Ala Gly Cys Thr Gly Gly Cys Ala Cys Thr
                100                 105                 110

Gly Gly Ala Thr Cys Cys Gly Gly Cys Ala Gly Thr Thr Thr Cys Cys
                115                 120                 125

Ala Gly Gly Ala Ala Cys Ala Ala Ala Cys Thr Gly Gly Ala Gly Thr
                130                 135                 140

Thr Gly Gly Ala Thr Gly Gly Gly Cys Thr Ala Cys Gly Thr Thr Cys
145                 150                 155                 160

Ala Cys Thr Ala Cys Ala Gly Thr Gly Gly Thr Ala Gly Cys Ala Cys
                165                 170                 175

Thr Ala Ala Cys Thr Ala Cys Ala Ala Cys Cys Cys Ala Thr Cys Thr
                180                 185                 190

Cys Thr Cys Ala Ala Ala Gly Thr Cys Gly Ala Ala Thr Cys Thr Cys
                195                 200                 205

Cys Thr Ala Thr Cys Ala Cys Thr Cys Gly Ala Gly Ala Cys Ala Cys
                210                 215                 220

Ala Thr Cys Cys Ala Ala Gly Ala Ala Cys Cys Ala Gly Thr Thr Cys
225                 230                 235                 240

Thr Thr Cys Cys Thr Gly Cys Ala Gly Thr Thr Gly Ala Ala Thr Thr
                245                 250                 255

Cys Thr Gly Thr Gly Ala Cys Thr Ala Cys Thr Gly Ala Gly Gly Ala
                260                 265                 270

Cys Ala Cys Ala Gly Cys Cys Ala Cys Ala Thr Thr Thr Thr Ala Cys
                275                 280                 285

Thr Gly Thr Gly Cys Ala Ala Gly Ala Ala Thr Gly Gly Ala Cys Thr
                290                 295                 300

Ala Thr Gly Gly Thr Ala Ala Cys Thr Ala Cys Gly Gly Gly Gly Gly
305                 310                 315                 320
```

Gly Gly Cys Thr Ala Thr Gly Gly Ala Cys Thr Ala Cys Thr Gly Gly
                    325                 330                 335

Gly Gly Thr Cys Ala Ala Gly Gly Ala Ala Cys Cys Thr Cys Ala Gly
            340                 345                 350

Thr Cys Ala Cys Cys Gly Thr Cys Thr Cys Cys Thr Cys Ala
        355                 360                 365

<210> SEQ ID NO 23
<211> LENGTH: 321
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 24F8 light chain, nucleotide

<400> SEQUENCE: 23

Gly Ala Gly Ala Thr Thr Gly Thr Gly Ala Thr Gly Ala Cys Cys Cys
1               5                   10                  15

Ala Gly Thr Cys Thr Cys Ala Cys Ala Ala Thr Thr Cys Ala Thr Thr
            20                  25                  30

Gly Thr Cys Cys Ala Cys Ala Thr Cys Ala Gly Thr Ala Gly Gly Gly
        35                  40                  45

Gly Ala Cys Ala Gly Gly Thr Cys Ala Gly Cys Ala Thr Cys Ala
    50                  55                  60

Cys Cys Thr Gly Cys Ala Ala Gly Gly Cys Cys Ala Gly Thr Cys Ala
65                  70                  75                  80

Gly Gly Ala Thr Gly Thr Gly Ala Gly Ala Cys Thr Gly Cys Thr
                85                  90                  95

Gly Thr Ala Gly Cys Cys Thr Gly Gly Thr Ala Thr Cys Ala Ala Cys
            100                 105                 110

Ala Gly Ala Ala Ala Cys Cys Ala Gly Gly Ala Cys Ala Ala Thr Cys
        115                 120                 125

Thr Cys Cys Thr Ala Ala Ala Cys Thr Ala Cys Thr Gly Ala Thr Thr
    130                 135                 140

Thr Ala Thr Thr Cys Gly Gly Cys Ala Thr Cys Cys Thr Ala Cys Cys
145                 150                 155                 160

Gly Gly Thr Ala Cys Ala Cys Thr Gly Gly Ala Gly Thr Cys Cys Cys
                165                 170                 175

Thr Gly Ala Thr Cys Gly Cys Thr Thr Cys Ala Cys Thr Gly Gly Cys
            180                 185                 190

Ala Gly Thr Gly Gly Ala Thr Cys Thr Gly Gly Gly Ala Cys Gly Gly
        195                 200                 205

Ala Thr Thr Thr Cys Ala Cys Thr Cys Thr Cys Ala Cys Cys Ala Thr
    210                 215                 220

Cys Ala Gly Cys Ala Gly Thr Gly Thr Gly Cys Ala Gly Gly Cys Thr
225                 230                 235                 240

Gly Ala Ala Gly Ala Cys Cys Thr Gly Gly Cys Ala Gly Thr Thr Thr
                245                 250                 255

Ala Thr Thr Ala Cys Thr Gly Cys Ala Gly Cys Ala Ala Thr Ala
            260                 265                 270

Thr Thr Ala Thr Ala Gly Thr Ala Cys Thr Cys Ala Gly Thr Gly Gly
        275                 280                 285

Ala Cys Gly Thr Thr Cys Gly Gly Thr Gly Gly Ala Gly Gly Cys Ala
    290                 295                 300

```
Cys Cys Ala Ala Gly Cys Thr Gly Gly Ala Ala Thr Cys Ala Ala
305                 310                 315                 320

Ala

<210> SEQ ID NO 24
<211> LENGTH: 360
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 5J24 heavy chain, nucleotide

<400> SEQUENCE: 24

Cys Ala Gly Gly Thr Cys Cys Ala Gly Cys Thr Gly Cys Ala Gly Cys
1               5                   10                  15

Ala Gly Thr Cys Thr Gly Gly Ala Gly Cys Thr Gly Ala Gly Cys Thr
                20                  25                  30

Gly Gly Thr Ala Ala Gly Gly Cys Cys Thr Gly Gly Gly Ala Cys Thr
                35                  40                  45

Thr Cys Ala Gly Thr Gly Ala Ala Gly Ala Thr Gly Thr Cys Cys Thr
            50                  55                  60

Gly Cys Ala Ala Gly Gly Cys Thr Thr Cys Thr Gly Gly Ala Thr Ala
65                  70                  75                  80

Cys Ala Cys Cys Thr Thr Cys Ala Cys Thr Ala Ala Cys Thr Ala Cys
                85                  90                  95

Thr Gly Gly Ala Thr Ala Gly Gly Thr Thr Gly Gly Gly Thr Ala Ala
                100                 105                 110

Ala Gly Cys Ala Gly Ala Gly Gly Cys Cys Thr Gly Gly Ala Cys Ala
                115                 120                 125

Thr Gly Gly Cys Cys Thr Thr Gly Ala Gly Thr Gly Gly Ala Thr Thr
                130                 135                 140

Gly Gly Ala Gly Ala Thr Ala Thr Thr Ala Cys Cys Cys Thr Gly Gly
145                 150                 155                 160

Gly Ala Gly Gly Thr Gly Gly Thr Thr Ala Thr Ala Cys Thr Ala Ala
                165                 170                 175

Cys Thr Ala Cys Ala Ala Thr Gly Ala Gly Ala Ala Gly Thr Thr Cys
                180                 185                 190

Ala Ala Gly Gly Gly Cys Ala Ala Gly Gly Cys Cys Ala Cys Ala Cys
                195                 200                 205

Thr Gly Ala Cys Thr Gly Cys Ala Gly Ala Cys Ala Cys Ala Thr Cys
                210                 215                 220

Cys Thr Cys Cys Ala Gly Cys Ala Cys Ala Gly Cys Cys Thr Ala Cys
225                 230                 235                 240

Ala Thr Gly Thr Ala Cys Cys Thr Cys Ala Gly Cys Ala Gly Cys Cys
                245                 250                 255

Thr Gly Ala Cys Ala Thr Cys Thr Gly Ala Gly Gly Ala Cys Thr Cys
                260                 265                 270

Thr Gly Cys Cys Ala Thr Cys Thr Ala Thr Thr Ala Cys Thr Gly Thr
                275                 280                 285

Gly Cys Ala Ala Gly Ala Thr Cys Cys Thr Ala Thr Gly Gly Thr Thr
                290                 295                 300

Ala Cys Gly Ala Cys Cys Thr Thr Ala Thr Gly Cys Thr Ala Thr Gly
305                 310                 315                 320
```

```
Gly Gly Ala Cys Thr Ala Cys Thr Gly Gly Gly Thr Cys Ala Ala
                325                 330                 335

Gly Gly Ala Ala Cys Cys Thr Cys Ala Gly Thr Cys Ala Cys Cys Gly
                340                 345                 350

Thr Cys Thr Cys Cys Thr Cys Ala
        355                 360

<210> SEQ ID NO 25
<211> LENGTH: 321
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 5J24 light chain, nucleotide

<400> SEQUENCE: 25

Gly Ala Cys Ala Thr Cys Cys Ala Gly Ala Thr Gly Ala Cys Cys Cys
1               5                   10                  15

Ala Gly Thr Cys Thr Cys Cys Ala Thr Cys Cys Thr Cys Cys Thr Thr
                20                  25                  30

Ala Thr Cys Thr Gly Cys Cys Thr Cys Thr Cys Thr Gly Gly Gly Ala
            35                  40                  45

Gly Ala Ala Ala Gly Ala Gly Thr Cys Ala Gly Thr Cys Thr Cys Ala
        50                  55                  60

Cys Thr Thr Gly Thr Cys Gly Gly Cys Ala Ala Gly Thr Cys Ala
65                  70                  75                  80

Gly Gly Ala Ala Ala Thr Thr Ala Gly Thr Gly Gly Thr Thr Ala Cys
                85                  90                  95

Thr Thr Ala Ala Gly Cys Thr Gly Gly Cys Thr Thr Cys Ala Gly Cys
                100                 105                 110

Ala Gly Ala Ala Ala Cys Cys Ala Gly Ala Thr Gly Gly Ala Ala Cys
            115                 120                 125

Thr Ala Thr Thr Ala Ala Ala Cys Gly Cys Cys Thr Gly Ala Thr Cys
        130                 135                 140

Thr Ala Cys Gly Cys Cys Gly Cys Ala Thr Cys Cys Ala Cys Thr Thr
145                 150                 155                 160

Thr Ala Gly Gly Thr Thr Cys Thr Gly Gly Thr Gly Thr Cys Cys Cys
                165                 170                 175

Ala Ala Ala Ala Ala Gly Gly Thr Thr Cys Ala Gly Thr Gly Gly Cys
                180                 185                 190

Ala Gly Thr Ala Gly Gly Thr Cys Thr Gly Gly Gly Thr Cys Ala Gly
            195                 200                 205

Ala Thr Thr Ala Thr Thr Cys Thr Cys Thr Cys Ala Cys Cys Ala Thr
        210                 215                 220

Cys Ala Gly Cys Ala Gly Cys Cys Thr Gly Ala Gly Thr Cys Thr
225                 230                 235                 240

Gly Ala Ala Gly Ala Thr Thr Thr Gly Cys Ala Gly Ala Cys Thr
                245                 250                 255

Ala Thr Thr Ala Cys Thr Gly Cys Thr Ala Cys Ala Ala Thr Ala
                260                 265                 270

Thr Gly Ala Thr Ala Gly Thr Thr Ala Thr Cys Cys Gly Thr Thr Cys
            275                 280                 285

Ala Cys Gly Thr Thr Cys Gly Gly Thr Gly Cys Thr Gly Gly Gly Ala
        290                 295                 300
```

Cys Cys Ala Ala Gly Cys Thr Gly Gly Ala Gly Cys Thr Gly Ala Ala
305                 310                 315                 320

Ala

<210> SEQ ID NO 26
<211> LENGTH: 357
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 21B9 heavy chain, nucleotide

<400> SEQUENCE: 26

Gly Ala Ala Gly Thr Gly Cys Ala Gly Cys Thr Gly Gly Thr Gly Gly
1               5                   10                  15

Ala Gly Thr Cys Thr Gly Gly Gly Gly Ala Gly Gly Cys Thr Thr Thr
                20                  25                  30

Ala Gly Thr Gly Ala Ala Gly Cys Cys Thr Gly Gly Ala Gly Gly Gly
                35                  40                  45

Thr Cys Cys Cys Thr Gly Ala Ala Ala Cys Thr Cys Thr Cys Cys Thr
        50                  55                  60

Gly Thr Ala Cys Ala Gly Cys Cys Thr Cys Thr Gly Gly Ala Thr Thr
65                  70                  75                  80

Cys Ala Cys Thr Thr Thr Cys Ala Gly Thr Ala Gly Cys Thr Ala Thr
                    85                  90                  95

Gly Cys Cys Ala Thr Gly Thr Cys Thr Thr Gly Gly Gly Thr Thr Cys
                100                 105                 110

Gly Cys Cys Ala Gly Ala Cys Thr Cys Cys Ala Gly Ala Gly Ala Ala
                115                 120                 125

Gly Ala Gly Gly Cys Thr Gly Gly Ala Gly Thr Gly Gly Gly Thr Cys
                130                 135                 140

Gly Cys Ala Gly Ala Ala Ala Thr Thr Ala Gly Thr Ala Gly Thr Gly
145                 150                 155                 160

Gly Thr Gly Gly Thr Ala Gly Thr Thr Ala Cys Ala Cys Cys Thr Ala
                165                 170                 175

Cys Thr Ala Thr Ala Cys Ala Gly Ala Cys Ala Cys Thr Gly Thr Gly
                180                 185                 190

Ala Cys Gly Gly Gly Cys Cys Gly Ala Thr Thr Cys Ala Cys Cys Ala
                195                 200                 205

Thr Cys Thr Cys Cys Ala Gly Ala Gly Ala Cys Ala Ala Thr Gly Cys
                210                 215                 220

Cys Ala Ala Gly Ala Ala Cys Ala Cys Cys Cys Thr Gly Thr Ala Cys
225                 230                 235                 240

Cys Thr Gly Gly Ala Ala Ala Thr Gly Ala Gly Cys Ala Gly Thr Cys
                245                 250                 255

Thr Gly Ala Gly Gly Thr Cys Thr Gly Ala Gly Gly Ala Cys Ala Cys
                260                 265                 270

Gly Gly Cys Cys Ala Thr Gly Thr Ala Thr Thr Ala Cys Thr Gly Thr
                275                 280                 285

Gly Cys Ala Ala Gly Gly Ala Ala Cys Gly Ala Cys Gly Gly Gly
                290                 295                 300

Ala Thr Thr Ala Cys Thr Ala Thr Gly Gly Thr Ala Thr Gly Gly Ala
305                 310                 315                 320

```
Cys Thr Ala Cys Thr Gly Gly Gly Thr Cys Ala Gly Gly Ala
                325                 330                 335

Ala Cys Cys Thr Cys Ala Gly Thr Cys Ala Cys Gly Thr Cys Thr
                340                 345                 350

Cys Cys Thr Cys Ala
        355

<210> SEQ ID NO 27
<211> LENGTH: 321
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 21B9 light chain, nucleotide

<400> SEQUENCE: 27

Gly Ala Thr Gly Thr Cys Cys Ala Gly Ala Thr Ala Cys Cys Cys
1               5                   10                  15

Ala Gly Thr Cys Thr Cys Cys Ala Thr Cys Thr Ala Thr Cys Thr
                20                  25                  30

Thr Gly Cys Thr Gly Cys Ala Thr Cys Thr Cys Thr Gly Gly Ala
                35                  40                  45

Gly Ala Ala Ala Cys Cys Ala Thr Thr Ala Cys Thr Ala Thr Ala
                50                  55                  60

Ala Thr Thr Gly Cys Ala Gly Gly Gly Cys Ala Ala Gly Thr Ala
65                  70                  75                  80

Gly Ala Gly Cys Ala Thr Thr Ala Gly Cys Ala Ala Thr Ala Thr
                85                  90                  95

Thr Thr Ala Gly Cys Cys Thr Gly Gly Thr Ala Thr Cys Ala Ala
                100                 105                 110

Ala Gly Ala Ala Ala Cys Cys Thr Gly Gly Ala Ala Ala Ala Cys
                115                 120                 125

Thr Ala Ala Thr Ala Ala Gly Cys Thr Thr Cys Thr Thr Ala Thr Cys
                130                 135                 140

Thr Ala Thr Thr Cys Thr Gly Gly Ala Thr Cys Cys Ala Cys Thr Thr
145                 150                 155                 160

Thr Gly Cys Ala Ala Cys Thr Gly Gly Ala Ala Thr Cys Cys
                165                 170                 175

Ala Thr Cys Ala Ala Gly Gly Thr Thr Cys Ala Gly Thr Gly Gly Cys
                180                 185                 190

Ala Gly Thr Gly Gly Ala Thr Cys Thr Gly Gly Thr Ala Cys Ala Gly
                195                 200                 205

Ala Thr Thr Thr Cys Ala Cys Thr Cys Thr Cys Ala Cys Cys Ala Thr
                210                 215                 220

Cys Ala Gly Thr Ala Gly Cys Cys Thr Gly Gly Ala Gly Cys Cys Thr
225                 230                 235                 240

Gly Ala Ala Gly Ala Thr Thr Thr Thr Gly Cys Ala Ala Thr Gly Thr
                245                 250                 255

Ala Thr Thr Ala Cys Thr Gly Thr Cys Ala Ala Cys Ala Gly Cys Ala
                260                 265                 270

Thr Ala Ala Thr Gly Ala Ala Thr Ala Cys Cys Cys Gly Thr Gly Gly
                275                 280                 285

Ala Cys Gly Thr Thr Cys Gly Gly Thr Gly Gly Ala Gly Gly Cys Ala
                290                 295                 300
```

Cys Cys Ala Ala Gly Cys Thr Gly Gly Ala Ala Thr Cys Ala Ala
305                 310                 315                 320

Ala

<210> SEQ ID NO 28
<211> LENGTH: 357
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 22B22 heavy chain, nucleotide

<400> SEQUENCE: 28

Gly Ala Ala Gly Thr Gly Cys Ala Gly Cys Thr Gly Gly Thr Gly
1               5                   10                  15

Ala Gly Thr Cys Thr Gly Gly Gly Gly Ala Gly Gly Cys Thr Thr
                20                  25                  30

Ala Gly Thr Gly Ala Ala Gly Cys Cys Thr Gly Gly Ala Gly Gly
                35                  40                  45

Thr Cys Cys Cys Thr Gly Ala Ala Ala Cys Thr Cys Thr Cys Thr
50                  55                  60

Gly Thr Gly Cys Ala Gly Cys Cys Thr Cys Thr Gly Gly Ala Thr Thr
65                  70                  75              80

Cys Ala Cys Thr Thr Thr Cys Ala Gly Thr Ala Gly Cys Thr Ala Thr
                85                  90                  95

Gly Cys Cys Ala Thr Gly Thr Cys Thr Thr Gly Gly Gly Thr Thr Cys
                100                 105                 110

Gly Cys Cys Ala Gly Thr Cys Thr Cys Cys Ala Gly Ala Gly Ala Ala
                115                 120                 125

Gly Ala Gly Gly Cys Thr Gly Gly Ala Gly Thr Gly Gly Gly Thr Cys
                130                 135                 140

Gly Cys Ala Gly Ala Ala Ala Thr Thr Ala Gly Thr Ala Gly Thr Gly
145                 150                 155                 160

Gly Thr Gly Gly Thr Ala Gly Thr Thr Ala Cys Ala Cys Cys Thr Ala
                165                 170                 175

Cys Thr Ala Thr Cys Cys Ala Gly Ala Cys Ala Cys Thr Gly Thr Gly
                180                 185                 190

Ala Cys Gly Gly Gly Cys Cys Gly Ala Thr Thr Cys Ala Cys Cys Ala
                195                 200                 205

Thr Cys Thr Cys Cys Ala Gly Ala Gly Ala Cys Ala Ala Thr Gly Cys
                210                 215                 220

Cys Ala Ala Gly Ala Ala Cys Ala Cys Cys Cys Thr Gly Thr Ala Cys
225                 230                 235                 240

Cys Thr Gly Gly Ala Ala Ala Thr Gly Ala Gly Cys Ala Gly Thr Cys
                245                 250                 255

Thr Gly Ala Gly Gly Thr Cys Thr Gly Ala Gly Gly Ala Cys Ala Cys
                260                 265                 270

Gly Gly Cys Cys Ala Thr Gly Thr Ala Thr Thr Ala Cys Thr Gly Thr
                275                 280                 285

Gly Cys Ala Ala Gly Gly Ala Ala Cys Gly Ala Cys Gly Gly Gly
                290                 295                 300

Ala Thr Thr Ala Cys Thr Ala Thr Gly Cys Thr Ala Thr Gly Gly Ala
305                 310                 315                 320

```
Cys Thr Ala Cys Thr Gly Gly Gly Thr Cys Ala Gly Gly Ala
                325                 330                 335

Ala Cys Cys Thr Cys Ala Gly Thr Cys Ala Cys Gly Thr Cys Thr
                340                 345                 350

Cys Cys Thr Cys Ala
        355

<210> SEQ ID NO 29
<211> LENGTH: 321
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 22B22 light chain, nucleotide

<400> SEQUENCE: 29

Gly Ala Thr Gly Thr Cys Cys Ala Gly Ala Thr Ala Cys Cys Cys
1               5                   10                  15

Ala Gly Thr Cys Thr Cys Cys Ala Thr Cys Thr Ala Thr Cys Thr
                20                  25                  30

Thr Gly Cys Thr Gly Cys Ala Thr Cys Thr Cys Thr Gly Gly Ala
                35                  40                  45

Gly Ala Ala Ala Cys Cys Ala Thr Thr Ala Cys Thr Ala Thr Ala
                50                  55                  60

Ala Thr Thr Gly Cys Ala Gly Gly Gly Cys Ala Ala Gly Thr Ala
65                  70                  75                  80

Gly Ala Gly Cys Ala Thr Thr Ala Gly Cys Ala Ala Thr Ala Thr
                85                  90                  95

Thr Thr Ala Gly Cys Cys Thr Gly Gly Thr Ala Thr Cys Ala Ala
                100                 105                 110

Ala Gly Ala Ala Ala Cys Cys Thr Gly Gly Ala Ala Ala Ala Cys
                115                 120                 125

Thr Ala Ala Thr Ala Ala Gly Cys Thr Thr Cys Thr Thr Ala Thr
                130                 135                 140

Thr Ala Cys Thr Cys Thr Gly Gly Ala Thr Cys Cys Ala Cys Thr
145                 150                 155                 160

Thr Gly Cys Ala Ala Thr Cys Thr Gly Gly Ala Ala Thr Cys Cys
                165                 170                 175

Ala Thr Cys Ala Ala Gly Gly Thr Thr Cys Ala Gly Thr Gly Cys
                180                 185                 190

Ala Gly Thr Gly Gly Ala Thr Cys Thr Gly Gly Thr Ala Cys Ala
                195                 200                 205

Ala Thr Thr Thr Cys Ala Cys Thr Cys Thr Cys Ala Cys Cys Ala
                210                 215                 220

Cys Ala Gly Thr Ala Gly Cys Cys Thr Gly Gly Ala Gly Cys Thr
225                 230                 235                 240

Gly Ala Ala Gly Ala Thr Thr Thr Thr Gly Cys Ala Ala Thr Thr
                245                 250                 255

Thr Ala Thr Thr Ala Cys Thr Gly Thr Cys Ala Ala Cys Ala Thr
                260                 265                 270

Thr Thr Thr Thr Gly Gly Ala Gly Thr Ala Cys Cys Cys Ala Cys
                275                 280                 285

Gly Thr Thr Cys Gly Gly Ala Gly Gly Gly Gly Gly Gly Ala Cys
                290                 295                 300
```

Cys Cys Ala Ala Gly Cys Thr Gly Gly Ala Ala Thr Cys Ala Ala
305                 310                 315                 320

Ala

<210> SEQ ID NO 30
<211> LENGTH: 354
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 28P24 heavy chain, nucleotide

<400> SEQUENCE: 30

Cys Ala Gly Gly Thr Cys Cys Ala Gly Cys Thr Gly Cys Ala Gly Cys
1               5                   10                  15

Ala Gly Thr Cys Thr Gly Gly Ala Gly Cys Thr Gly Ala Ala Cys Thr
                20                  25                  30

Gly Gly Thr Ala Ala Gly Gly Cys Cys Thr Gly Gly Gly Ala Cys Thr
                35                  40                  45

Thr Cys Ala Gly Thr Gly Ala Ala Gly Ala Thr Gly Thr Cys Cys Thr
        50                  55                  60

Gly Cys Ala Ala Gly Gly Cys Thr Gly Cys Thr Gly Gly Ala Thr Ala
65                  70                  75                  80

Cys Ala Cys Cys Thr Thr Cys Ala Cys Thr Ala Ala Cys Thr Ala Cys
                85                  90                  95

Thr Thr Thr Ala Thr Ala Gly Gly Thr Thr Gly Gly Gly Thr Ala Ala
                100                 105                 110

Ala Gly Cys Ala Gly Ala Gly Gly Cys Cys Thr Gly Gly Ala Cys Ala
            115                 120                 125

Thr Gly Gly Cys Cys Thr Thr Gly Ala Cys Thr Gly Gly Ala Thr Thr
        130                 135                 140

Gly Gly Ala Gly Ala Thr Ala Thr Thr Ala Cys Cys Cys Thr Gly
145                 150                 155                 160

Gly Ala Gly Gly Thr Gly Gly Thr Thr Ala Thr Ala Cys Thr Ala Ala
                165                 170                 175

Cys Thr Ala Cys Ala Ala Thr Gly Ala Gly Ala Ala Gly Thr Thr Cys
            180                 185                 190

Ala Ala Gly Gly Gly Cys Ala Ala Gly Gly Cys Cys Ala Cys Ala Cys
            195                 200                 205

Thr Gly Ala Cys Thr Gly Cys Ala Gly Ala Cys Ala Cys Ala Thr Cys
        210                 215                 220

Cys Thr Cys Cys Ala Gly Cys Ala Cys Ala Gly Cys Cys Thr Ala Cys
225                 230                 235                 240

Ala Thr Gly Cys Ala Gly Cys Thr Cys Ala Gly Cys Ala Gly Cys Cys
                245                 250                 255

Thr Gly Ala Cys Ala Thr Cys Thr Gly Ala Gly Gly Ala Cys Thr Cys
            260                 265                 270

Thr Gly Cys Cys Ala Thr Cys Thr Ala Thr Thr Ala Cys Thr Gly Thr
        275                 280                 285

Gly Thr Ala Ala Gly Ala Thr Thr Cys Thr Gly Gly Thr Ala
    290                 295                 300

Ala Cys Thr Ala Cys Gly Thr Gly Thr Thr Thr Gly Cys Thr Thr Ala
305                 310                 315                 320

-continued

```
Cys Thr Gly Gly Gly Cys Cys Ala Ala Gly Gly Ala Cys Thr
                325                 330                 335

Cys Thr Gly Gly Thr Cys Ala Cys Thr Gly Thr Cys Thr Gly
                340                 345                 350

Cys Ala

<210> SEQ ID NO 31
<211> LENGTH: 321
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 28P24 light chain, nucleotide

<400> SEQUENCE: 31

Gly Ala Thr Gly Thr Cys Cys Ala Gly Ala Thr Ala Cys Cys Cys
1               5                   10                  15

Ala Gly Thr Cys Thr Cys Cys Ala Thr Cys Thr Gly Thr Cys Thr
                20                  25                  30

Thr Gly Cys Thr Gly Cys Ala Thr Cys Thr Cys Cys Thr Gly Gly Ala
            35                  40                  45

Gly Ala Ala Cys Cys Ala Thr Thr Ala Cys Thr Ala Thr Thr Ala
        50                  55                  60

Ala Thr Thr Gly Cys Ala Gly Gly Gly Cys Ala Ala Gly Thr Ala Ala
65                  70                  75                  80

Ala Ala Cys Cys Ala Thr Thr Ala Gly Cys Ala Ala Ala Thr Ala Thr
                85                  90                  95

Thr Thr Ala Gly Cys Cys Thr Gly Gly Thr Ala Thr Cys Ala Ala Gly
                100                 105                 110

Ala Gly Ala Ala Ala Cys Cys Thr Gly Gly Gly Ala Ala Ala Cys
            115                 120                 125

Thr Ala Ala Thr Ala Ala Gly Cys Thr Thr Cys Thr Ala Thr Cys
            130                 135                 140

Thr Ala Cys Thr Cys Thr Gly Gly Ala Thr Cys Cys Ala Cys Thr Thr
145                 150                 155                 160

Thr Gly Cys Ala Ala Thr Cys Thr Gly Gly Ala Ala Thr Cys Cys
                165                 170                 175

Ala Thr Cys Ala Ala Gly Gly Thr Cys Ala Gly Thr Gly Gly Cys
                180                 185                 190

Ala Gly Thr Gly Gly Ala Thr Cys Thr Gly Gly Thr Ala Cys Ala Gly
            195                 200                 205

Ala Thr Thr Thr Cys Ala Cys Thr Cys Thr Cys Ala Cys Cys Ala Thr
        210                 215                 220

Cys Ala Gly Thr Ala Gly Cys Cys Thr Gly Gly Ala Gly Cys Cys Thr
225                 230                 235                 240

Gly Ala Ala Gly Ala Thr Thr Thr Thr Gly Cys Ala Ala Thr Gly Thr
                245                 250                 255

Ala Thr Thr Ala Cys Thr Gly Thr Cys Ala Ala Cys Ala Gly Cys Ala
                260                 265                 270

Thr Ala Ala Thr Gly Ala Ala Thr Ala Cys Cys Gly Thr Gly Gly
            275                 280                 285

Ala Cys Gly Thr Thr Cys Gly Gly Thr Gly Gly Ala Gly Gly Cys Ala
            290                 295                 300
```

Cys Cys Ala Ala Gly Cys Thr Gly Gly Ala Ala Thr Cys Ala Ala
305                 310                 315                 320

Ala

<210> SEQ ID NO 32
<211> LENGTH: 357
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 21B16 heavy chain, nucleotide

<400> SEQUENCE: 32

Gly Ala Ala Gly Thr Gly Cys Ala Gly Cys Thr Gly Thr Gly Gly
1               5                   10                  15

Ala Gly Thr Cys Thr Gly Gly Gly Gly Ala Gly Gly Cys Thr Thr
                20                  25                  30

Ala Gly Thr Gly Ala Ala Gly Cys Cys Thr Gly Gly Ala Gly Gly
                35                  40                  45

Thr Cys Cys Thr Gly Ala Ala Ala Cys Thr Cys Thr Cys Cys Thr
                50                  55                  60

Gly Thr Gly Cys Ala Gly Cys Cys Thr Cys Thr Gly Gly Ala Thr Thr
65                  70                  75                  80

Cys Ala Cys Thr Thr Thr Cys Ala Gly Thr Ala Cys Cys Thr Ala
                    85                  90                  95

Gly Cys Cys Ala Thr Gly Thr Cys Thr Thr Gly Gly Gly Thr Thr Cys
                100                 105                 110

Gly Cys Cys Ala Gly Thr Cys Thr Cys Cys Ala Gly Ala Gly Ala Ala
                    115                 120                 125

Gly Ala Gly Gly Cys Thr Gly Gly Ala Gly Thr Gly Gly Gly Thr Cys
130                 135                 140

Gly Cys Ala Gly Ala Ala Ala Thr Thr Ala Gly Thr Ala Gly Thr Gly
145                 150                 155                 160

Gly Thr Gly Gly Thr Ala Cys Thr Thr Ala Cys Ala Cys Cys Thr Ala
                    165                 170                 175

Cys Thr Thr Thr Cys Cys Ala Gly Ala Cys Ala Cys Thr Gly Thr Gly
                    180                 185                 190

Ala Cys Gly Gly Gly Cys Cys Gly Ala Thr Thr Cys Ala Cys Cys Ala
                    195                 200                 205

Thr Cys Thr Cys Cys Ala Gly Ala Gly Ala Cys Ala Ala Thr Gly Cys
                    210                 215                 220

Cys Ala Ala Gly Ala Ala Cys Ala Cys Cys Cys Thr Gly Thr Ala Cys
225                 230                 235                 240

Cys Thr Gly Gly Ala Ala Ala Thr Gly Ala Gly Cys Ala Gly Thr Cys
                    245                 250                 255

Thr Gly Ala Gly Gly Thr Cys Thr Gly Ala Gly Gly Ala Cys Ala Cys
                    260                 265                 270

Gly Gly Cys Cys Ala Thr Gly Thr Ala Thr Thr Ala Cys Thr Gly Thr
                    275                 280                 285

Gly Cys Ala Ala Gly Gly Ala Ala Cys Gly Ala Cys Gly Ala Gly
                    290                 295                 300

Ala Thr Thr Ala Cys Thr Ala Thr Gly Cys Thr Ala Thr Gly Gly Ala
305                 310                 315                 320

-continued

```
Cys Thr Ala Cys Thr Gly Gly Gly Gly Thr Cys Ala Gly Gly Ala
                325                 330                 335

Ala Cys Cys Thr Cys Ala Gly Thr Cys Ala Cys Gly Thr Cys Thr
                340                 345                 350

Cys Cys Thr Cys Ala
        355

<210> SEQ ID NO 33
<211> LENGTH: 321
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 21B16 light chain, nucleotide

<400> SEQUENCE: 33

Gly Ala Thr Gly Thr Cys Cys Gly Ala Thr Ala Ala Cys Cys Cys
1               5                   10                  15

Ala Gly Thr Cys Thr Cys Cys Ala Thr Cys Thr Ala Thr Cys Thr
                20                  25                  30

Thr Gly Cys Thr Gly Cys Ala Thr Cys Thr Cys Thr Gly Gly Ala
                35                  40                  45

Gly Ala Ala Ala Cys Cys Ala Thr Thr Ala Cys Thr Ala Thr Ala
                50                  55                  60

Ala Thr Thr Gly Cys Ala Gly Gly Gly Cys Ala Ala Gly Thr Ala
65                  70                  75                  80

Gly Ala Gly Cys Ala Thr Thr Ala Gly Cys Ala Ala Thr Ala Thr
                85                  90                  95

Thr Thr Ala Gly Cys Cys Thr Gly Gly Thr Ala Thr Cys Ala Gly
                100                 105                 110

Ala Gly Ala Ala Ala Cys Cys Thr Gly Gly Ala Ala Ala Ala Cys
            115                 120                 125

Thr Ala Ala Thr Ala Ala Gly Cys Thr Thr Cys Thr Thr Ala Thr
            130                 135                 140

Thr Ala Cys Thr Cys Thr Gly Gly Ala Thr Cys Cys Ala Cys Thr
145                 150                 155                 160

Thr Gly Cys Ala Ala Thr Cys Thr Gly Gly Ala Ala Thr Cys Cys
                165                 170                 175

Ala Thr Cys Ala Ala Gly Gly Thr Thr Cys Ala Gly Thr Gly Cys
            180                 185                 190

Ala Gly Thr Gly Gly Ala Thr Cys Thr Gly Gly Thr Ala Cys Ala Gly
            195                 200                 205

Ala Thr Thr Thr Cys Ala Cys Thr Cys Thr Cys Ala Cys Cys Ala Thr
            210                 215                 220

Cys Ala Gly Thr Ala Gly Cys Cys Thr Gly Gly Ala Gly Cys Cys Thr
225                 230                 235                 240

Gly Ala Ala Gly Ala Thr Thr Thr Thr Gly Cys Ala Gly Thr Gly Thr
                245                 250                 255

Ala Thr Thr Ala Cys Thr Gly Cys Ala Ala Cys Ala Gly Cys Ala
                260                 265                 270

Thr Ala Ala Thr Gly Ala Ala Thr Ala Cys Cys Cys Gly Thr Gly Gly
            275                 280                 285

Ala Cys Gly Thr Thr Cys Gly Gly Thr Gly Gly Ala Gly Gly Cys Ala
            290                 295                 300
```

Cys Cys Ala Ala Gly Cys Thr Gly Gly Ala Ala Thr Cys Ala Ala
305                 310                 315                 320

Ala

<210> SEQ ID NO 34
<211> LENGTH: 357
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 28O12 heavy chain, nucleotide

<400> SEQUENCE: 34

Gly Ala Ala Gly Thr Gly Cys Ala Gly Cys Thr Gly Gly Thr Gly
1               5                   10                  15

Ala Gly Thr Cys Thr Gly Gly Gly Gly Ala Gly Gly Cys Thr Thr
                20                  25                  30

Ala Gly Thr Gly Ala Ala Gly Cys Cys Thr Gly Gly Ala Gly Gly
                35                  40                  45

Thr Cys Cys Cys Thr Gly Ala Ala Ala Cys Thr Cys Thr Cys Thr
50                  55                  60

Gly Thr Gly Cys Ala Gly Cys Cys Thr Cys Thr Gly Gly Ala Thr Thr
65                  70                  75                  80

Cys Ala Cys Thr Thr Thr Cys Ala Gly Thr Ala Ala Cys Thr Ala Thr
                85                  90                  95

Gly Cys Cys Ala Thr Gly Thr Cys Thr Thr Gly Gly Gly Thr Thr Cys
                100                 105                 110

Gly Thr Cys Ala Gly Thr Cys Thr Cys Cys Ala Gly Ala Gly Ala Ala
                115                 120                 125

Gly Ala Gly Gly Cys Thr Gly Gly Ala Gly Thr Gly Gly Gly Thr Cys
                130                 135                 140

Gly Cys Ala Gly Ala Ala Ala Thr Thr Ala Gly Thr Gly Gly Thr Gly
145                 150                 155                 160

Gly Thr Gly Gly Thr Ala Gly Thr Thr Ala Cys Ala Cys Gly Thr Ala
                165                 170                 175

Cys Cys Ala Thr Cys Cys Ala Gly Ala Cys Ala Cys Thr Gly Thr Gly
                180                 185                 190

Ala Cys Gly Gly Gly Cys Cys Gly Ala Thr Thr Cys Ala Cys Cys Ala
                195                 200                 205

Thr Cys Thr Cys Cys Ala Gly Ala Gly Ala Cys Ala Ala Thr Gly Cys
                210                 215                 220

Cys Ala Ala Gly Ala Ala Cys Ala Cys Cys Cys Thr Gly Thr Ala Cys
225                 230                 235                 240

Cys Thr Gly Gly Ala Ala Ala Thr Gly Ala Gly Cys Ala Gly Thr Cys
                245                 250                 255

Thr Gly Ala Gly Gly Thr Cys Thr Gly Ala Gly Gly Ala Cys Ala Cys
                260                 265                 270

Gly Gly Cys Cys Ala Thr Gly Thr Ala Thr Thr Ala Cys Thr Gly Thr
                275                 280                 285

Gly Cys Ala Ala Gly Gly Ala Ala Cys Gly Ala Cys Gly Gly Gly
                290                 295                 300

Ala Thr Thr Ala Cys Thr Ala Thr Gly Cys Thr Ala Thr Gly Gly Ala
305                 310                 315                 320

```
Cys Thr Ala Cys Thr Gly Gly Gly Thr Cys Ala Gly Gly Ala
                325                 330                 335

Ala Cys Cys Thr Cys Ala Gly Thr Cys Ala Cys Gly Thr Cys Thr
                340                 345                 350

Cys Cys Thr Cys Ala
        355

<210> SEQ ID NO 35
<211> LENGTH: 322
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mouse mAb 28O12 light chain, nucleotide

<400> SEQUENCE: 35

Gly Ala Thr Gly Thr Cys Cys Ala Gly Ala Thr Ala Cys Cys Cys
1               5                   10                  15

Ala Gly Thr Cys Thr Cys Cys Ala Thr Cys Thr Ala Thr Cys Thr
                20                  25                  30

Thr Gly Cys Thr Gly Cys Ala Thr Cys Thr Cys Thr Gly Gly Ala
                35                  40                  45

Gly Ala Ala Ala Cys Cys Ala Thr Thr Ala Cys Thr Ala Thr Ala
                50                  55                  60

Ala Thr Thr Gly Cys Ala Gly Gly Gly Cys Ala Ala Gly Thr Ala
65                  70                  75                  80

Gly Ala Gly Cys Ala Thr Thr Ala Gly Cys Ala Ala Thr Ala Thr
                85                  90                  95

Thr Thr Ala Gly Cys Cys Thr Gly Gly Thr Ala Thr Cys Ala Gly
                100                 105                 110

Ala Gly Ala Ala Ala Cys Cys Thr Gly Gly Ala Ala Ala Ala Cys
                115                 120                 125

Thr Ala Ala Thr Ala Ala Gly Cys Thr Thr Cys Thr Thr Ala Thr
                130                 135                 140

Thr Ala Cys Thr Cys Thr Gly Gly Ala Thr Cys Cys Ala Cys Thr
145                 150                 155                 160

Thr Gly Cys Ala Ala Thr Cys Thr Gly Gly Ala Ala Thr Cys Cys
                165                 170                 175

Ala Thr Cys Ala Ala Gly Gly Thr Cys Ala Gly Gly Thr Gly Cys
                180                 185                 190

Ala Gly Thr Gly Gly Ala Thr Cys Thr Gly Gly Thr Ala Cys Ala
                195                 200                 205

Ala Thr Thr Thr Cys Ala Cys Thr Cys Thr Cys Ala Cys Cys Ala
                210                 215                 220

Cys Ala Gly Thr Ala Gly Cys Cys Thr Gly Ala Gly Cys Cys Thr
225                 230                 235                 240

Gly Ala Ala Gly Ala Thr Thr Thr Gly Cys Ala Ala Thr Gly Thr
                245                 250                 255

Ala Thr Thr Ala Cys Thr Gly Cys Ala Gly Cys Ala Gly Cys Ala
                260                 265                 270

Thr Ala Ala Thr Gly Ala Ala Thr Ala Cys Cys Cys Gly Thr Gly
                275                 280                 285

Ala Cys Gly Thr Thr Cys Gly Gly Thr Gly Gly Ala Gly Gly Cys Ala
                290                 295                 300
```

```
Cys Cys Ala Ala Gly Cys Thr Gly Gly Ala Ala Ala Thr Cys Ala Ala
305                 310                 315                 320

Ala Cys

<210> SEQ ID NO 36
<211> LENGTH: 6
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 21F8 HC-CDR1

<400> SEQUENCE: 36

Ser Asp Tyr Ala Trp Asn
1               5

<210> SEQ ID NO 37
<211> LENGTH: 16
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 21F8 HC-CDR2

<400> SEQUENCE: 37

Tyr Ile Ser Tyr Ser Gly Ser Thr Ser Tyr Asn Pro Ser Leu Lys Ser
1               5                   10                  15

<210> SEQ ID NO 38
<211> LENGTH: 10
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 21F8 HC-CDR3

<400> SEQUENCE: 38

Phe Met Ile Thr Thr Phe Ala Met Asp Tyr
1               5                   10

<210> SEQ ID NO 39
<211> LENGTH: 11
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 21F8 LC-CDR1

<400> SEQUENCE: 39

Lys Ala Ser Gln His Val Ser Thr Ala Val Ala
1               5                   10

<210> SEQ ID NO 40
<211> LENGTH: 7
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 21F8 LC-CDR2
```

```
<400> SEQUENCE: 40

Ser Ala Pro Tyr Arg Tyr Thr
1               5

<210> SEQ ID NO 41
<211> LENGTH: 9
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 21F8 LC-CDR3

<400> SEQUENCE: 41

Gln Gln His Tyr Asn Thr Leu Trp Thr
1               5

<210> SEQ ID NO 42
<211> LENGTH: 5
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 30M18 HC-CDR1

<400> SEQUENCE: 42

Glu Tyr Thr Met His
1               5

<210> SEQ ID NO 43
<211> LENGTH: 17
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 30M18 HC-CDR2

<400> SEQUENCE: 43

Gly Ile Asn Pro Asn Asn Gly Gly Thr Ser Tyr Asn Gln Lys Phe Lys
1               5                   10                  15

Gly

<210> SEQ ID NO 44
<211> LENGTH: 10
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 30M18 HC-CDR3

<400> SEQUENCE: 44

Ser Gly His Met Asp Tyr Gly Tyr Val Tyr
1               5                   10

<210> SEQ ID NO 45
<211> LENGTH: 11
<212> TYPE: PRT
<213> ORGANISM: Artificial sequence
<220> FEATURE:
<223> OTHER INFORMATION: Synthetic construct
```

```
<220> FEATURE:
<221> NAME/KEY: MISC_FEATURE
<223> OTHER INFORMATION: mAb 30M18 LC-CDR1

<400> SEQUENCE: 45

Lys Ala Ser Gln Tyr Val Ser Thr Ala Val Ala
1               5                   10

<210> SEQ ID NO 46
<211> LENGTH: 7
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 30M18 LC-CDR2

<400> SEQUENCE: 46

Ser Pro Ser Tyr Arg Tyr Thr
1               5

<210> SEQ ID NO 47
<211> LENGTH: 9
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 30M18 LC-CDR3

<400> SEQUENCE: 47

Gln Gln His Tyr Ser Thr Pro Trp Thr
1               5

<210> SEQ ID NO 48
<211> LENGTH: 6
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 24F8 HC-CDR1

<400> SEQUENCE: 48

Ser Gly Tyr Ser Trp His
1               5

<210> SEQ ID NO 49
<211> LENGTH: 16
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 24F8 HC-CDR2

<400> SEQUENCE: 49

Tyr Val His Tyr Ser Gly Ser Thr Asn Tyr Asn Pro Ser Leu Lys Ser
1               5                   10                  15

<210> SEQ ID NO 50
<211> LENGTH: 12
<212> TYPE: PRT
<213> ORGANISM: Artificial sequence
```

```
<220> FEATURE:
<223> OTHER INFORMATION: Synthetic construct
<220> FEATURE:
<221> NAME/KEY: MISC_FEATURE
<223> OTHER INFORMATION: mAb 24F8 HC-CDR3

<400> SEQUENCE: 50

Met Asp Tyr Gly Asn Tyr Gly Gly Ala Met Asp Tyr
1               5                   10

<210> SEQ ID NO 51
<211> LENGTH: 11
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 24F8 LC-CDR1

<400> SEQUENCE: 51

Lys Ala Ser Gln Asp Val Arg Thr Ala Val Ala
1               5                   10

<210> SEQ ID NO 52
<211> LENGTH: 7
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 24F8 LC-CDR2

<400> SEQUENCE: 52

Ser Ala Ser Tyr Arg Tyr Thr
1               5

<210> SEQ ID NO 53
<211> LENGTH: 9
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 24F8 LC-CDR3

<400> SEQUENCE: 53

Gln Gln Tyr Tyr Ser Thr Gln Trp Thr
1               5

<210> SEQ ID NO 54
<211> LENGTH: 5
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 5J24 HC-CDR1

<400> SEQUENCE: 54

Asn His Trp Ile Gly
1               5
```

```
<210> SEQ ID NO 55
<211> LENGTH: 17
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 5J24 and mAb 28P24 HC-CDR2

<400> SEQUENCE: 55

Asp Ile Tyr Pro Gly Gly Gly Tyr Thr Asn Tyr Asn Glu Lys Phe Lys
1               5                   10                  15

Gly

<210> SEQ ID NO 56
<211> LENGTH: 11
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 5J24 HC-CDR3

<400> SEQUENCE: 56

Ser Tyr Gly Tyr Asp Leu Tyr Ala Met Asp Tyr
1               5                   10

<210> SEQ ID NO 57
<211> LENGTH: 11
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 5J24 LC-CDR1

<400> SEQUENCE: 57

Arg Ala Ser Gln Glu Ile Ser Gly Tyr Leu Ser
1               5                   10

<210> SEQ ID NO 58
<211> LENGTH: 7
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 5J24 LC-CDR2

<400> SEQUENCE: 58

Ala Ala Ser Thr Leu Gly Ser
1               5

<210> SEQ ID NO 59
<211> LENGTH: 9
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 5J24 LC-CDR3
```

-continued

```
<400> SEQUENCE: 59

Leu Gln Tyr Asp Ser Tyr Pro Phe Thr
1               5

<210> SEQ ID NO 60
<211> LENGTH: 5
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 21B9 and mAb 22B22 HC-CDR1

<400> SEQUENCE: 60

Ser Tyr Ala Met Ser
1               5

<210> SEQ ID NO 61
<211> LENGTH: 17
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 21B9 HC-CDR2

<400> SEQUENCE: 61

Glu Ile Ser Ser Gly Gly Ser Tyr Thr Tyr Tyr Thr Asp Thr Val Thr
1               5                   10                  15

Gly

<210> SEQ ID NO 62
<211> LENGTH: 10
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 21B9 HC-CDR3

<400> SEQUENCE: 62

Lys Arg Arg Asp Tyr Tyr Gly Met Asp Tyr
1               5                   10

<210> SEQ ID NO 63
<211> LENGTH: 11
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 21B9, mAb 22B22, mAb 21B16, mAb 21B16, and
      mAb 28O12 LC-CDR1

<400> SEQUENCE: 63

Arg Ala Ser Lys Ser Ile Ser Lys Tyr Leu Ala
1               5                   10

<210> SEQ ID NO 64
<211> LENGTH: 7
<212> TYPE: PRT
<213> ORGANISM: Artificial sequence
<220> FEATURE:
<223> OTHER INFORMATION: Synthetic construct
```

```
<220> FEATURE:
<221> NAME/KEY: MISC_FEATURE
<223> OTHER INFORMATION: mAb 21B9 LC-CDR2

<400> SEQUENCE: 64

Ser Gly Ser Thr Leu Gln Thr
1               5

<210> SEQ ID NO 65
<211> LENGTH: 9
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 21B9, mAb 22B22, mAb 28P24, mAb 21B16, and
      mAb 28O12 LC-CDR3

<400> SEQUENCE: 65

Gln Gln His Asn Glu Tyr Pro Trp Thr
1               5

<210> SEQ ID NO 66
<211> LENGTH: 17
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 22B22 HC-CDR2

<400> SEQUENCE: 66

Glu Ile Ser Ser Gly Gly Ser Tyr Thr Tyr Tyr Pro Asp Thr Val Thr
1               5                   10                  15

Gly

<210> SEQ ID NO 67
<211> LENGTH: 10
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 22B22, mAb 21B16, and mAb 28O12 HC-CDR3

<400> SEQUENCE: 67

Lys Arg Arg Asp Tyr Tyr Ala Met Asp Tyr
1               5                   10

<210> SEQ ID NO 68
<211> LENGTH: 7
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 22B22, mAb 28P24, mAb 21B16, and mAb 28O12
      LC-CDR2

<400> SEQUENCE: 68

Ser Gly Ser Thr Leu Gln Ser
1               5
```

```
<210> SEQ ID NO 69
<211> LENGTH: 5
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 28P24 HC-CDR1

<400> SEQUENCE: 69

Asn Tyr Phe Ile Gly
1               5

<210> SEQ ID NO 70
<211> LENGTH: 9
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 28P24 HC-CDR3

<400> SEQUENCE: 70

Phe Tyr Gly Asn Tyr Val Phe Ala Tyr
1               5

<210> SEQ ID NO 71
<211> LENGTH: 11
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 28P24 LC-CDR1

<400> SEQUENCE: 71

Arg Ala Ser Lys Thr Ile Ser Lys Tyr Leu Ala
1               5                   10

<210> SEQ ID NO 72
<211> LENGTH: 5
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 21B16 HC-CDR1

<400> SEQUENCE: 72

Thr Tyr Ala Met Ser
1               5

<210> SEQ ID NO 73
<211> LENGTH: 17
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 21B16 HC-CDR2
```

<400> SEQUENCE: 73

Glu Ile Ser Ser Gly Gly Thr Tyr Thr Tyr Phe Pro Asp Thr Val Thr
1               5                   10                  15

Gly

<210> SEQ ID NO 74
<211> LENGTH: 5
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 28O12 HC-CDR1

<400> SEQUENCE: 74

Asn Tyr Ala Met Ser
1               5

<210> SEQ ID NO 75
<211> LENGTH: 17
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mAb 28O12 HC-CDR2

<400> SEQUENCE: 75

Glu Ile Ser Gly Gly Gly Ser Tyr Thr Tyr His Pro Asp Thr Val Thr
1               5                   10                  15

Gly

<210> SEQ ID NO 76
<211> LENGTH: 121
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Hu24F8.1 AND HU24F8.4 heavy chain variable
      region, amino acid

<400> SEQUENCE: 76

Gln Val Gln Leu Gln Glu Ser Gly Pro Gly Leu Val Lys Pro Ser Glu
1               5                   10                  15

Thr Leu Ser Leu Thr Cys Ala Val Tyr Gly Tyr Ser Ile Thr Ser Gly
            20                  25                  30

Tyr Ser Trp His Trp Ile Arg Gln Pro Pro Gly Lys Gly Leu Glu Trp
        35                  40                  45

Ile Gly Tyr Val His Tyr Ser Gly Ser Thr Asn Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Met Asp Tyr Gly Asn Tyr Gly Gly Ala Met Asp Tyr Trp Gly
            100                 105                 110

Gln Gly Thr Leu Val Thr Val Ser Ser
        115                 120

```
<210> SEQ ID NO 77
<211> LENGTH: 107
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Hu24F8.1 AND HU24F8.4 heavy chain variable
      region, amino acid

<400> SEQUENCE: 77

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asp Val Arg Thr Ala
            20                  25                  30

Val Ala Trp Tyr Gln Gln Lys Pro Gly Gln Ala Pro Arg Leu Leu Ile
        35                  40                  45

Tyr Ser Ala Ser Tyr Arg Tyr Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Tyr Ser Thr Gln Trp
                85                  90                  95

Thr Phe Gly Gly Gly Thr Lys Val Glu Ile Lys
            100                 105

<210> SEQ ID NO 78
<211> LENGTH: 121
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Hu24F8.1 AND HU24F8.4 heavy chain variable
      region, amino acid

<400> SEQUENCE: 78

Gln Val Gln Leu Gln Glu Ser Gly Pro Gly Leu Val Lys Pro Ser Gly
1               5                   10                  15

Thr Leu Ser Leu Thr Cys Ala Val Ser Gly Tyr Ser Ile Thr Ser Gly
            20                  25                  30

Tyr Ser Trp His Trp Val Arg Gln Pro Pro Gly Lys Gly Leu Glu Trp
        35                  40                  45

Ile Gly Tyr Val His Tyr Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Met Asp Tyr Gly Asn Tyr Gly Gly Ala Met Asp Tyr Trp Gly
            100                 105                 110

Gln Gly Thr Leu Val Thr Val Ser Ser
        115                 120

<210> SEQ ID NO 79
<211> LENGTH: 107
<212> TYPE: PRT
<213> ORGANISM: Artificial sequence
<220> FEATURE:
<223> OTHER INFORMATION: Synthetic construct
```

```
<220> FEATURE:
<221> NAME/KEY: MISC_FEATURE
<223> OTHER INFORMATION: Hu24F8.1 AND HU24F8.4 heavy chain variable
      region, amino acid

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Arg Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Tyr Ser Thr Gln Trp
                85                  90                  95

Thr Phe Gly Gly Gly Thr Lys Leu Glu Ile Lys
            100                 105

<210> SEQ ID NO 80
<211> LENGTH: 244
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: hTIGIT full length, amino acid

<400> SEQUENCE: 80

Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile Pro Leu Leu Gly
    130                 135                 140

Ala Met Ala Ala Thr Leu Val Val Ile Cys Thr Ala Val Ile Val Val
145                 150                 155                 160

Val Ala Leu Thr Arg Lys Lys Lys Ala Leu Arg Ile His Ser Val Glu
                165                 170                 175

Gly Asp Leu Arg Arg Lys Ser Ala Gly Gln Glu Glu Trp Ser Pro Ser
            180                 185                 190

Ala Pro Ser Pro Pro Gly Ser Cys Val Gln Ala Glu Ala Ala Pro Ala
        195                 200                 205
```

```
Gly Leu Cys Gly Glu Gln Arg Gly Glu Asp Cys Ala Glu Leu His Asp
            210                 215                 220

Tyr Phe Asn Val Leu Ser Tyr Arg Ser Leu Gly Asn Cys Ser Phe Phe
225                 230                 235                 240

Thr Glu Thr Gly

<210> SEQ ID NO 81
<211> LENGTH: 223
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: mature human TIGIT, amino acid

<400> SEQUENCE: 81

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
            100                 105                 110

His Gly Ala Arg Phe Gln Ile Pro Leu Leu Gly Ala Met Ala Ala Thr
        115                 120                 125

Leu Val Val Ile Cys Thr Ala Val Ile Val Val Val Ala Leu Thr Arg
    130                 135                 140

Lys Lys Lys Ala Leu Arg Ile His Ser Val Glu Gly Asp Leu Arg Arg
145                 150                 155                 160

Lys Ser Ala Gly Gln Glu Glu Trp Ser Pro Ser Ala Pro Ser Pro Pro
                165                 170                 175

Gly Ser Cys Val Gln Ala Glu Ala Ala Pro Ala Gly Leu Cys Gly Glu
            180                 185                 190

Gln Arg Gly Glu Asp Cys Ala Glu Leu His Asp Tyr Phe Asn Val Leu
        195                 200                 205

Ser Tyr Arg Ser Leu Gly Asn Cys Ser Phe Phe Thr Glu Thr Gly
    210                 215                 220

<210> SEQ ID NO 82
<211> LENGTH: 120
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: hTIGIT extracellular domain, amino acid
```

<400> SEQUENCE: 82

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
            100                 105                 110

His Gly Ala Arg Phe Gln Ile Pro
        115                 120

<210> SEQ ID NO 83
<211> LENGTH: 128
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: hTIGIT-His, amino acid

<400> SEQUENCE: 83

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Gly Gly Gly
            100                 105                 110

Gly Ala Gly Gly Gly Gly His His His His His His His His
        115                 120                 125

<210> SEQ ID NO 84
<211> LENGTH: 312
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: cTIGIT full length, amino acid

<400> SEQUENCE: 84

Met Ala Phe Leu Val Ala Pro Pro Met Gln Phe Val Tyr Leu Leu Lys
1               5                   10                  15

Thr Leu Cys Val Phe Asn Met Val Phe Ala Lys Pro Gly Phe Ser Glu
            20                  25                  30

Thr Val Phe Ser His Arg Leu Ser Phe Thr Val Leu Ser Ala Val Gly
        35                  40                  45

Tyr Phe Arg Trp Gln Lys Arg Pro His Leu Leu Pro Val Ser Pro Leu
    50                  55                  60

Gly Arg Ser Met Arg Trp Cys Leu Phe Leu Ile Trp Ala Gln Gly Leu
65                  70                  75                  80

Arg Gln Ala Pro Leu Ala Ser Gly Met Met Thr Gly Thr Ile Glu Thr
                85                  90                  95

Thr Gly Asn Ile Ser Ala Lys Lys Gly Gly Ser Val Ile Leu Gln Cys
            100                 105                 110

His Leu Ser Ser Thr Met Ala Gln Val Thr Gln Val Asn Trp Glu Gln
        115                 120                 125

His Asp His Ser Leu Leu Ala Ile Arg Asn Ala Glu Leu Gly Trp His
    130                 135                 140

Ile Tyr Pro Ala Phe Lys Asp Arg Val Ala Pro Gly Pro Gly Leu Gly
145                 150                 155                 160

Leu Thr Leu Gln Ser Leu Thr Met Asn Asp Thr Gly Glu Tyr Phe Cys
                165                 170                 175

Thr Tyr His Thr Tyr Pro Asp Gly Thr Tyr Arg Gly Arg Ile Phe Leu
            180                 185                 190

Glu Val Leu Glu Ser Ser Val Ala Glu His Ser Ala Arg Phe Gln Ile
        195                 200                 205

Pro Leu Leu Gly Ala Met Ala Met Met Leu Val Val Ile Cys Ile Ala
    210                 215                 220

Val Ile Val Val Val Val Leu Ala Arg Lys Lys Lys Ser Leu Arg Ile
225                 230                 235                 240

His Ser Val Glu Ser Gly Leu Gln Arg Lys Ser Thr Gly Gln Glu Glu
                245                 250                 255

Gln Ile Pro Ser Ala Pro Ser Pro Gly Ser Cys Val Gln Ala Glu
            260                 265                 270

Ala Ala Pro Ala Gly Leu Cys Gly Glu Gln Gln Gly Asp Asp Cys Ala
        275                 280                 285

Glu Leu His Asp Tyr Phe Asn Val Leu Ser Tyr Arg Ser Leu Gly Ser
    290                 295                 300

Cys Ser Phe Phe Thr Glu Thr Gly
305                 310

<210> SEQ ID NO 85
<211> LENGTH: 129
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: cTIGIT-His extracellular domain, amino acid

<400> SEQUENCE: 85

```
Met Met Thr Gly Thr Ile Glu Thr Thr Gly Asn Ile Ser Ala Lys Lys
1               5                   10                  15

Gly Gly Ser Val Ile Leu Gln Cys His Leu Ser Ser Thr Met Ala Gln
            20                  25                  30

Val Thr Gln Val Asn Trp Glu Gln Gln Asp His Ser Leu Leu Ala Ile
        35                  40                  45

Arg Asn Ala Glu Leu Gly Trp His Ile Tyr Pro Ala Phe Lys Asp Arg
    50                  55                  60

Val Ala Pro Gly Pro Gly Leu Gly Leu Thr Leu Gln Ser Leu Thr Met
65                  70                  75                  80

Asn Asp Thr Gly Glu Tyr Phe Cys Thr Tyr His Thr Tyr Pro Asp Gly
                85                  90                  95

Thr Tyr Arg Gly Arg Ile Phe Leu Glu Val Leu Glu Ser Ser Gly Gly
            100                 105                 110

Gly Gly Ala Gly Gly Gly Gly His His His His His His His His
        115                 120                 125

His
```

<210> SEQ ID NO 86
<211> LENGTH: 323
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Mature extracellular region of human CD155, amino acid

<400> SEQUENCE: 86

```
Trp Pro Pro Pro Gly Thr Gly Asp Val Val Gln Ala Pro Thr Gln
1               5                   10                  15

Val Pro Gly Phe Leu Gly Asp Ser Val Thr Leu Pro Cys Tyr Leu Gln
            20                  25                  30

Val Pro Asn Met Glu Val Thr His Val Ser Gln Leu Thr Trp Ala Arg
        35                  40                  45

His Gly Glu Ser Gly Ser Met Ala Val Phe His Gln Thr Gln Gly Pro
    50                  55                  60

Ser Tyr Ser Glu Ser Lys Arg Leu Glu Phe Val Ala Ala Arg Leu Gly
65                  70                  75                  80

Ala Glu Leu Arg Asn Ala Ser Leu Arg Met Phe Gly Leu Arg Val Glu
                85                  90                  95

Asp Glu Gly Asn Tyr Thr Cys Leu Phe Val Thr Phe Pro Gln Gly Ser
            100                 105                 110

Arg Ser Val Asp Ile Trp Leu Arg Val Leu Ala Lys Pro Gln Asn Thr
        115                 120                 125

Ala Glu Val Gln Lys Val Gln Leu Thr Gly Glu Pro Val Pro Met Ala
    130                 135                 140

Arg Cys Val Ser Thr Gly Gly Arg Pro Pro Ala Gln Ile Thr Trp His
145                 150                 155                 160

Ser Asp Leu Gly Gly Met Pro Asn Thr Ser Gln Val Pro Gly Phe Leu
                165                 170                 175

Ser Gly Thr Val Thr Val Thr Ser Leu Trp Ile Leu Val Pro Ser Ser
            180                 185                 190
```

```
Gln Val Asp Gly Lys Asn Val Thr Cys Lys Val Glu His Glu Ser Phe
            195                 200                 205
Glu Lys Pro Gln Leu Leu Thr Val Asn Leu Thr Val Tyr Tyr Pro Pro
    210                 215                 220
Glu Val Ser Ile Ser Gly Tyr Asp Asn Asn Trp Tyr Leu Gly Gln Asn
225                 230                 235                 240
Glu Ala Thr Leu Thr Cys Asp Ala Arg Ser Asn Pro Glu Pro Thr Gly
            245                 250                 255
Tyr Asn Trp Ser Thr Thr Met Gly Pro Leu Pro Pro Phe Ala Val Ala
            260                 265                 270
Gln Gly Ala Gln Leu Leu Ile Arg Pro Val Asp Lys Pro Ile Asn Thr
            275                 280                 285
Thr Leu Ile Cys Asn Val Thr Asn Ala Leu Gly Ala Arg Gln Ala Glu
    290                 295                 300
Leu Thr Val Gln Val Lys Glu Gly Pro Pro Ser Glu His Ser Gly Met
305                 310                 315                 320
Ser Arg Asn

<210> SEQ ID NO 87
<211> LENGTH: 339
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: hTIGIT-mFc, amino acid

<400> SEQUENCE: 87

Met Met Thr Gly Thr Ile Glu Thr Gly Asn Ile Ser Ala Glu Lys
1               5                   10                  15
Gly Gly Ser Ile Ile Leu Gln Cys His Leu Ser Ser Thr Thr Ala Gln
            20                  25                  30
Val Thr Gln Val Asn Trp Glu Gln Gln Asp Gln Leu Leu Ala Ile Cys
        35                  40                  45
Asn Ala Asp Leu Gly Trp His Ile Ser Pro Ser Phe Lys Asp Arg Val
    50                  55                  60
Ala Pro Gly Pro Gly Leu Gly Leu Thr Leu Gln Ser Leu Thr Val Asn
65                  70                  75                  80
Asp Thr Gly Glu Tyr Phe Cys Ile Tyr His Thr Tyr Pro Asp Gly Thr
            85                  90                  95
Tyr Thr Gly Arg Ile Phe Leu Glu Val Leu Glu Ser Ser Gly Gly Gly
            100                 105                 110
Gly Ala Gly Gly Gly Cys Lys Pro Cys Ile Cys Thr Val Pro Glu
            115                 120                 125
Val Ser Ser Val Phe Ile Phe Pro Pro Lys Pro Lys Asp Val Leu Thr
            130                 135                 140
Ile Thr Leu Thr Pro Lys Val Thr Cys Val Val Val Asp Ile Ser Lys
145                 150                 155                 160
Asp Asp Pro Glu Val Gln Phe Ser Trp Phe Val Asp Asp Val Glu Val
            165                 170                 175
His Thr Ala Gln Thr Gln Pro Arg Glu Glu Gln Phe Asn Ser Thr Phe
            180                 185                 190
Arg Ser Val Ser Glu Leu Pro Ile Met His Gln Asp Trp Leu Asn Gly
            195                 200                 205
```

```
Lys Glu Phe Lys Cys Arg Val Asn Ser Ala Ala Phe Pro Ala Pro Ile
    210                 215                 220

Glu Lys Thr Ile Ser Lys Thr Lys Gly Arg Pro Lys Ala Pro Gln Val
225                 230                 235                 240

Tyr Thr Ile Pro Pro Lys Glu Gln Met Ala Lys Asp Lys Val Ser
                245                 250                 255

Leu Thr Cys Met Ile Thr Asp Phe Phe Pro Glu Asp Ile Thr Val Glu
            260                 265                 270

Trp Gln Trp Asn Gly Gln Pro Ala Glu Asn Tyr Lys Asn Thr Gln Pro
                275                 280                 285

Ile Met Asp Thr Asp Gly Ser Tyr Phe Val Tyr Ser Lys Leu Asn Val
        290                 295                 300

Gln Lys Ser Asn Trp Glu Ala Gly Asn Thr Phe Thr Cys Ser Val Leu
305                 310                 315                 320

His Glu Gly Leu His Asn His His Thr Glu Lys Ser Leu Ser His Ser
                325                 330                 335

Pro Gly Lys

<210> SEQ ID NO 88
<211> LENGTH: 249
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: MTIGIT full length, amino acid

<400> SEQUENCE: 88

Met His Gly Trp Leu Leu Leu Val Trp Val Gln Gly Leu Ile Gln Ala
1               5                   10                  15

Ala Phe Leu Ala Thr Ala Ile Gly Ala Thr Ala Gly Thr Ile Asp Thr
            20                  25                  30

Lys Arg Asn Ile Ser Ala Glu Glu Gly Gly Ser Val Ile Leu Gln Cys
        35                  40                  45

His Phe Ser Ser Asp Thr Ala Glu Val Thr Gln Val Asp Trp Lys Gln
    50                  55                  60

Gln Asp Gln Leu Leu Ala Ile Tyr Ser Val Asp Leu Gly Trp His Val
65                  70                  75                  80

Ala Ser Val Phe Ser Asp Arg Val Val Pro Gly Pro Ser Leu Gly Leu
                85                  90                  95

Thr Phe Gln Ser Leu Thr Met Asn Asp Thr Gly Glu Tyr Phe Cys Thr
            100                 105                 110

Tyr His Thr Tyr Pro Gly Gly Ile Tyr Lys Gly Arg Ile Phe Leu Lys
        115                 120                 125

Val Gln Glu Ser Ser Asp Asp Arg Asn Gly Leu Ala Gln Phe Gln Thr
    130                 135                 140

Ala Pro Leu Gly Gly Thr Met Ala Ala Val Leu Gly Leu Ile Cys Leu
145                 150                 155                 160

Met Val Thr Gly Val Thr Val Leu Ala Arg Lys Asp Lys Ser Ile Arg
                165                 170                 175

Met His Ser Ile Glu Ser Gly Leu Gly Arg Thr Glu Ala Glu Pro Gln
            180                 185                 190

Glu Trp Asn Leu Arg Ser Leu Ser Ser Pro Gly Ser Pro Val Gln Thr
        195                 200                 205
```

Gln Thr Ala Pro Ala Gly Pro Cys Gly Glu Gln Ala Glu Asp Asp Tyr
            210                 215                 220

Ala Asp Pro Gln Glu Tyr Phe Asn Val Leu Ser Tyr Arg Ser Leu Glu
225                 230                 235                 240

Ser Phe Ile Ala Val Ser Lys Thr Gly
                245

<210> SEQ ID NO 89
<211> LENGTH: 242
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: RTIGIT full length, amino acid

<400> SEQUENCE: 89

Met His Gly Trp Met Leu Leu Val Trp Val Gln Gly Leu Thr Glu Thr
1               5                   10                  15

Ala Phe Leu Ala Ala Gly Ala Thr Ala Gly Thr Met Glu Thr Lys Gly
            20                  25                  30

Asn Ile Ser Ala Glu Glu Gly Gly Ser Val Val Leu Gln Cys His Phe
        35                  40                  45

Ser Ser Asp Thr Ala Glu Val Thr Gln Val Asn Trp Glu Gln Arg Asp
50                  55                  60

Gln Leu Leu Ala Val Tyr Ser Val Asp Leu Gly Trp Tyr Val Pro Ser
65                  70                  75                  80

Val Phe Ser Asp Arg Val Val Pro Gly Pro Ser Leu Gly Leu Thr Phe
                85                  90                  95

Gln Ser Leu Thr Thr Asn Asp Thr Gly Glu Tyr Phe Cys Thr Tyr His
            100                 105                 110

Thr Tyr Pro Asp Gly Ile Tyr Lys Gly Arg Ile Phe Leu Lys Val Gln
        115                 120                 125

Glu Ser Ser Val Ala His Phe Gln Ile Ala Leu Pro Gly Gly Thr Met
130                 135                 140

Ala Ala Val Leu Gly Leu Ile Cys Leu Met Ala Thr Gly Val Thr Val
145                 150                 155                 160

Leu Ala Arg Lys Lys Ser Ile Arg Met His Ser Val Glu Ser Gly Leu
                165                 170                 175

Gly Arg Thr Glu Ala Glu Pro Gln Glu Trp Asn Leu Arg Ile Leu Leu
            180                 185                 190

Ser Pro Ser Gly Pro Val Gln Thr Gln Ala Ala Pro Ala Asp Leu Cys
        195                 200                 205

Gly Glu Gln Thr Glu Asp Asp Tyr Thr Asp Pro Gln Asp Tyr Phe Asn
    210                 215                 220

Val Leu Ser Tyr Arg Ser Leu Glu Ser Phe Ile Ala Leu Ser Lys Thr
225                 230                 235                 240

Gly Gln

<210> SEQ ID NO 90
<211> LENGTH: 124
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: HTIGIT-HIS, amino acid (crystallography)

-continued

<400> SEQUENCE: 90

Met Met Thr Gly Thr Ile Glu Thr Thr Gly Gln Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
    50                  55                  60

Ala Pro Gly Pro Gly Leu Gly Leu Thr Leu Gln Ser Leu Thr Val Gln
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Gly Gly Gly
            100                 105                 110

Gly Ala Gly Gly Gly Gly His His His His His His
        115                 120

<210> SEQ ID NO 91
<211> LENGTH: 116
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: CD155 extracellular domain, amino acid
      (crystallography)

<400> SEQUENCE: 91

Asp Val Val Gln Ala Pro Thr Gln Val Pro Gly Phe Leu Gly Asp
1               5                   10                  15

Ser Val Thr Leu Pro Cys Tyr Leu Gln Val Pro Asn Met Glu Val Thr
            20                  25                  30

His Val Ser Gln Leu Thr Trp Ala Arg His Gly Glu Ser Gly Ser Met
        35                  40                  45

Ala Val Phe His Gln Thr Gln Gly Pro Ser Tyr Ser Glu Ser Lys Arg
    50                  55                  60

Leu Glu Phe Val Ala Ala Arg Leu Gly Ala Glu Leu Arg Asn Ala Ser
65                  70                  75                  80

Leu Arg Met Phe Gly Leu Arg Val Glu Asp Glu Gly Asn Tyr Thr Cys
                85                  90                  95

Leu Phe Val Thr Phe Pro Gln Gly Ser Arg Ser Val Asp Ile Trp Leu
            100                 105                 110

Arg Val Leu Ala
        115

<210> SEQ ID NO 92
<211> LENGTH: 451
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: This sequence is Hu24F8.2 (24F8.2 heavy chain
      full length amino acid IgG1; wild-type IMGT allele IGHG1*01)

```
<400> SEQUENCE: 92

Gln Val Gln Leu Gln Glu Ser Gly Pro Gly Leu Val Lys Pro Ser Gly
  1               5                  10                  15

Thr Leu Ser Leu Thr Cys Ala Val Ser Gly Tyr Ser Ile Thr Ser Gly
             20                  25                  30

Tyr Ser Trp His Trp Val Arg Gln Pro Pro Gly Lys Gly Leu Glu Trp
         35                  40                  45

Ile Gly Tyr Val His Tyr Ser Gly Ser Thr Asn Tyr Asn Pro Ser Leu
 50                  55                  60

Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
             85                  90                  95

Ala Arg Met Asp Tyr Gly Asn Tyr Gly Gly Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415
```

```
Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 93
<211> LENGTH: 214
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: This sequence is Hu24F8.2 (24F8.2 Light Chain
      Full length Amino acid sequence (kappa IMGT allele IGKC*01))

<400> SEQUENCE: 93

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asp Val Arg Thr Ala
            20                  25                  30

Val Ala Trp Tyr Gln Gln Lys Pro Gly Gln Ala Pro Arg Leu Leu Ile
        35                  40                  45

Tyr Ser Ala Ser Tyr Arg Tyr Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Tyr Ser Thr Gln Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 94
<211> LENGTH: 330
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: heavy chain constant region IGG1; wild-type
      IMGT allele IGHG1*01,EU numbering  118-447
```

```
<400> SEQUENCE: 94

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 95
<211> LENGTH: 107
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Light chain constant region, kappa IMGT allele
      IGKC*01
```

<400> SEQUENCE: 95

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 96
<211> LENGTH: 451
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: This sequence is Hu24F8.2 (24F8.2 heavy chain full length amino acid IgG1.AA; IMGT allele IGHG1*01 (L234A, L235A) eu numbering)

<400> SEQUENCE: 96

```
Gln Val Gln Leu Gln Glu Ser Gly Pro Gly Leu Val Lys Pro Ser Gly
1               5                   10                  15

Thr Leu Ser Leu Thr Cys Ala Val Ser Gly Tyr Ser Ile Thr Ser Gly
            20                  25                  30

Tyr Ser Trp His Trp Val Arg Gln Pro Pro Gly Lys Gly Leu Glu Trp
        35                  40                  45

Ile Gly Tyr Val His Tyr Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Met Asp Tyr Gly Asn Tyr Gly Gly Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 97
<211> LENGTH: 330
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: heavy chain constant region IgG1.AA; IMGT
      allele IGHG1*01 (L234A,L235A) eu numbering

<400> SEQUENCE: 97

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

```
Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 98
<211> LENGTH: 451
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: This sequence is Hu24F8.2 (24F8.2 heavy chain
      full length amino acid IgG1.DLE; IMGT allele IGHG1*01 (S239D,
      A330L, I332E) eu numbering)

<400> SEQUENCE: 98

Gln Val Gln Leu Gln Glu Ser Gly Pro Gly Leu Val Lys Pro Ser Gly
1               5                   10                  15

Thr Leu Ser Leu Thr Cys Ala Val Ser Gly Tyr Ser Ile Thr Ser Gly
            20                  25                  30

Tyr Ser Trp His Trp Val Arg Gln Pro Pro Gly Lys Gly Leu Glu Trp
        35                  40                  45

Ile Gly Tyr Val His Tyr Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Met Asp Tyr Gly Asn Tyr Gly Gly Ala Met Asp Tyr Trp Gly
            100                 105                 110
```

Gln Gly Thr Leu Val Thr Val Ser Ser Ala Ser Thr Lys Gly Pro Ser
115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Asp Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Leu Pro Glu
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 99
<211> LENGTH: 330
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: heavy chain constant region IgG1.DLE; IMGT
    allele IGHG1*01(S239D, A330L, I332E) eu numbering

<400> SEQUENCE: 99

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Asp Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Leu Pro Glu Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

<210> SEQ ID NO 100
<211> LENGTH: 448
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: This sequence is Hu24F8.2 (24F8.2 heavy chain
full length amino acid IgG4.P; IMGT allele IGHG4*01 (S228P) EU
Numbering)

```
<400> SEQUENCE: 100

Gln Val Gln Leu Gln Glu Ser Gly Pro Gly Leu Val Lys Pro Ser Gly
1               5                   10                  15

Thr Leu Ser Leu Thr Cys Ala Val Ser Gly Tyr Ser Ile Thr Ser Gly
            20                  25                  30

Tyr Ser Trp His Trp Val Arg Gln Pro Pro Gly Lys Gly Leu Glu Trp
        35                  40                  45

Ile Gly Tyr Val His Tyr Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Met Asp Tyr Gly Asn Tyr Gly Gly Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415
```

```
Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 101
<211> LENGTH: 327
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: heavy chain constant region IgG4.P; IMGT allele
      IGHG4*01 (S228P)eu numbering

<400> SEQUENCE: 101

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300
```

-continued

```
Cys Ser Val Met His Glu Ala Leu His Asn His Tyr Thr Gln Lys Ser
305                 310                 315                 320

Leu Ser Leu Ser Leu Gly Lys
                325
```

US 11,820,824 B2

ANTIBODIES TO TIGIT

CROSS-REFERENCE TO RELATED APPLICATION

This application claims priority to U.S. Provisional Patent Application No. 63/033,609, filed Jun. 2, 2020, the disclosure of which is incorporated by reference herein in its entirety, including any drawings.

FIELD

Provided herein, inter alia, are antibodies that specifically bind to TIGIT, as well as uses of the same for the treatment of cancer and infectious disease, among other applications.

INCORPORATION OF THE SEQUENCE LISTING

This application contains a Sequence Listing, which is hereby incorporated herein by reference in its entirety. The accompanying Sequence Listing text file, named 050658_531001WO_Sequence_Listing_ST25 was created on May 31, 2021 and is 143 KB.

BACKGROUND

In tumors, there exist highly suppressive microenvironments where the function of T cells and NK cells is regulated by cell surface checkpoint receptors, allowing cancer cells to evade the immune system. Functional blockade of the inhibitory checkpoint receptors such as cytotoxic T-lymphocyte-associated protein 4 (CTLA-4) and programmed cell death 1 (PD-1) has yielded encouraging outcomes for patients, generating substantial interest in seeking additional co-inhibitory molecules that may act as potential interfering targets.

TIGIT (T cell immunoreceptor with Ig and ITIM domains), a member of the immunoglobulin superfamily with an immunoreceptor tyrosine-based inhibitory motif (ITIM) in the cytoplasmic tail, is a co-inhibitory receptor expressed by regulatory T cells (Tregs), activated T cells, and natural killer (NK) cells. Several groups have reported that TIGIT expression was elevated on CD8$^+$ tumor infiltrating lymphocytes (TILs) and Tregs in a variety of tumors. It has also been reported that effector CD8$^+$ T cells during HIV infection in blood and SIV infection in lymphoid tissue exhibit higher levels of TIGIT. Moreover, TIGIT blockade has exhibited activating activity in human T cell cultures and therapeutic benefits in animal models of different tumors. Therefore, TIGIT plays an important role in anti-tumor immunity and may serve as a promising therapeutic target for management of cancer and other various diseases and conditions. As such, there exists a need for molecules that can interfere with TIGIT binding for beneficial therapeutic purposes.

SUMMARY

The present disclosure relates to, inter alia, an anti-TIGIT antibody.

Provided herein is an anti-TIGIT antibody or an antigen-binding fragment thereof, including (a) a heavy chain variable region including a heavy chain (HC) complementarity determining region (CDR) 1 having at least 80% sequence identity to SEQ ID NO: 36, an HC-CDR2 having at least 80% sequence identity to SEQ ID NO: 37, and an HC-CDR3 having at least 80% sequence identity to SEQ ID NO: 38; and a light chain variable region including a light chain (LC) CDR1 having at least 80% sequence identity to SEQ ID NO: 39, an LC-CDR2 having at least 80% sequence identity to SEQ ID NO: 40, and an LC-CDR3 having at least 80% sequence identity to SEQ ID NO: 41; (b) a heavy chain variable region including an HC-CDR1 having at least 80% sequence identity to SEQ ID NO: 42, an HC-CDR2 having at least 80% sequence identity to SEQ ID NO: 43, and an HC-CDR3 having at least 80% sequence identity to SEQ ID NO: 44; and a light chain variable region including an LC-CDR1 having at least 80% sequence identity to SEQ ID NO: 45, an LC-CDR2 having at least 80% sequence identity to SEQ ID NO: 46, and an LC-CDR3 having at least 80% sequence identity to SEQ ID NO: 47; (c) a heavy chain variable region including an HC-CDR1 having at least 80% sequence identity to SEQ ID NO: 48, an HC-CDR2 having at least 80% sequence identity to SEQ ID NO: 49, and an HC-CDR3 having at least 80% sequence identity to SEQ ID NO: 50; and a light chain variable region including an LC-CDR1 having at least 80% sequence identity to SEQ ID NO: 51, an LC-CDR2 having at least 80% sequence identity to SEQ ID NO: 52, and an LC-CDR3 having at least 80% sequence identity to SEQ ID NO: 53; (d) a heavy chain variable region including an HC-CDR1 having at least 80% sequence identity to SEQ ID NO: 54, an HC-CDR2 having at least 80% sequence identity to SEQ ID NO: 55, and an HC-CDR3 having at least 80% sequence identity to SEQ ID NO: 56; and a light chain variable region including an LC-CDR1 having at least 80% sequence identity to SEQ ID NO: 57, an LC-CDR2 having at least 80% sequence identity to SEQ ID NO: 58, and an LC-CDR3 having at least 80% sequence identity to SEQ ID NO: 59; (e) a heavy chain variable region including an HC-CDR1 having at least 80% sequence identity to SEQ ID NO: 60, an HC-CDR2 having at least 80% sequence identity to SEQ ID NO: 61, and an HC-CDR3 having at least 80% sequence identity to SEQ ID NO: 62; and a light chain variable region including an LC-CDR1 having at least 80% sequence identity to SEQ ID NO: 63, an LC-CDR2 having at least 80% sequence identity to SEQ ID NO: 64, and an LC-CDR3 having at least 80% sequence identity to SEQ ID NO: 65; (f) a heavy chain variable region including an HC-CDR1 having at least 80% sequence identity to SEQ ID NO: 60, an HC-CDR2 having at least 80% sequence identity to SEQ ID NO: 66, and an HC-CDR3 having at least 80% sequence identity to SEQ ID NO: 67; and a light chain variable region including an LC-CDR1 having at least 80% sequence identity to SEQ ID NO: 63, an LC-CDR2 having at least 80% sequence identity to SEQ ID NO: 68, and an LC-CDR3 having at least 80% sequence identity to SEQ ID NO: 65; (g) a heavy chain variable region including an HC-CDR1 having at least 80% sequence identity to SEQ ID NO: 69, an HC-CDR2 having at least 80% sequence identity to SEQ ID NO: 55, and an HC-CDR3 having at least 80% sequence identity to SEQ ID NO: 70; and a light chain variable region including an LC-CDR1 having at least 80% sequence identity to SEQ ID NO: 71, an LC-CDR2 having at least 80% sequence identity to SEQ ID NO: 68, and an LC-CDR3 having at least 80% sequence identity to SEQ ID NO: 65; (h) a heavy chain variable region including an HC-CDR1 having at least 80% sequence identity to SEQ ID NO: 72, an HC-CDR2 having at least 80% sequence identity to SEQ ID NO: 73, and an HC-CDR3 having at least 80% sequence identity to SEQ ID NO: 67; and a light chain variable region including an LC-CDR1 having at least 80% sequence identity to SEQ ID NO: 63, an LC-CDR2 having at least 80% sequence identity to SEQ ID NO: 68, and an LC-CDR3 having at least 80% sequence identity to SEQ ID NO: 65; or (i) a heavy chain variable region including an HC-CDR1 having at least 80% sequence identity to SEQ ID NO: 74, an HC-CDR2 having at least 80% sequence identity to SEQ ID NO: 75, and an HC-CDR3 having at least 80% sequence identity to SEQ ID NO: 67; and a light chain variable region including an LC-CDR1 having at least 80% sequence identity to SEQ ID NO: 63, an LC-CDR2 having at least 80% sequence identity to SEQ ID NO: 68, and an LC-CDR3 having at least 80% sequence identity to SEQ ID NO: 65.

In some embodiments, the anti-TIGIT antibody or an antigen-binding fragment thereof includes (a) a heavy chain variable region having at least 80% sequence identity to SEQ ID NO: 1, and a light chain variable region having at least 80% sequence identity to SEQ ID NO: 2; (b) a heavy chain variable region having at least 80% sequence identity to SEQ ID NO: 3, and a light chain variable region having at least 80% sequence identity to SEQ ID NO: 4; (c) a heavy chain variable region having at least 80% sequence identity to SEQ ID NO: 5, and a light chain variable region having at least 80% sequence identity to SEQ ID NO: 6; (d) a heavy chain variable region having at least 80% sequence identity to SEQ ID NO: 7, and a light chain variable region having at least 80% sequence identity to SEQ ID NO: 8; (e) a heavy chain variable region having at least 80% sequence identity to SEQ ID NO: 9, and a light chain variable region having at least 80% sequence identity to SEQ ID NO: 10; (f) a heavy chain variable region having at least 80% sequence identity to SEQ ID NO: 11, and a light chain variable region having at least 80% sequence identity to SEQ ID NO: 12; (g) a heavy chain variable region having at least 80% sequence identity to SEQ ID NO: 13, and a light chain variable region having at least 80% sequence identity to SEQ ID NO: 14; (h) a heavy chain variable region having at least 80% sequence identity to SEQ ID NO: 15, and a light chain variable region having at least 80% sequence identity to SEQ ID NO: 16; (i) a heavy chain variable region having at least 80% sequence identity to SEQ ID NO: 17, and a light chain variable region having at least 80% sequence identity to SEQ ID NO: 12; (j) a heavy chain variable region having at least 80% sequence identity to SEQ ID NO: 76, and a light chain variable region having at least 80% sequence identity to SEQ ID NO: 77; (k) a heavy chain variable region having at least 80% sequence identity to SEQ ID NO: 78, and a light chain variable region having at least 80% sequence identity to SEQ ID NO: 77; (l) a heavy chain variable region having at least 80% sequence identity to SEQ ID NO: 76, and a light chain variable region having at least 80% sequence identity to SEQ ID NO: 79; or (m) a heavy chain variable region having at least 80% sequence identity to SEQ ID NO: 78, and a light chain variable region having at least 80% sequence identity to SEQ ID NO: 79.

Provided herein are anti-TIGIT antibodies, or antigen-binding fragments thereof, that bind to an epitope that includes at least one of the following amino acid residues of TIGIT: T55, Q56, N58, E60, D72, S80, and K82 of SEQ ID NO: 80. In some embodiments, the anti-TIGIT antibody binds to an epitope that includes at least the following residues of TIGIT: D72 of SEQ ID NO: 80 and at least one of T55, Q56, N58, E60, S80, and K82 of SEQ ID NO: 80. In some embodiments, the anti-TIGIT antibody binds to an epitope that includes at least the following residues of TIGIT: E60 and D72 of SEQ ID NO: 80 and optionally at least one of T55, Q56, N58, S80, and K82 of SEQ ID NO: 80. In some embodiments, the anti-TIGIT antibody binds to an epitope that includes at least the following residues of TIGIT: D72 and K82 of SEQ ID NO: 80 and optionally at least one of T55, Q56, N58, E60, and S80 of SEQ ID NO: 80. In some embodiments, the anti-TIGIT antibody binds to an epitope that includes at least the following residues of TIGIT: E60, D72 and K82 of SEQ ID NO: 80 and optionally at least one of T55, Q56, N58, and S80 of SEQ ID NO: 80. In some embodiments, the antibodies have the structural features of CDRs and variable sequences as described herein.

The anti-TIGIT antibodies of the present disclosure can be an isolated antibody. In some embodiments, the anti-TIGIT antibody or antigen-binding fragment thereof is a monoclonal antibody. In some embodiments, the anti-TIGIT antibody or antigen-binding fragment thereof is a chimeric, humanized, or veneered antibody. In some embodiments, the chimeric antibody includes a human IgG1/kappa Fab constant domain. In some embodiments, the anti-TIGIT antibody or antigen-binding fragment thereof is a human antibody. In some embodiments, the anti-TIGIT antibody or antigen binding fragment thereof inhibits binding of TIGIT to CD155.

Provided herein is a pharmaceutical composition including an anti-TIGIT antibody as described in the present disclosure and pharmaceutically acceptable carrier.

Provided herein is a method of treating or effecting prophylaxis of cancer including administering to a subject having or at risk of cancer an effective regime or a therapeutically effective amount of any anti-TIGIT antibody described in the present disclosure. In some embodiments, the cancer is a hematological cancer. In some embodiments, the cancer is acute myeloid leukemia or adult T-cell leukemia. In some embodiments, the cancer is a solid tumor, non-small cell lung carcinoma, melanoma, cervical cancer, multiple myeloma, lymphoma, non-hodgkin lymphoma, diffuse large B-cell lymphoma, gastric cancer, gastroesophageal junction adenocarcinoma, or esophageal cancer. In some embodiments, the subject is also administered tumor infiltrating T cells. In some embodiments, the subject is also administered a vaccine inducing an immune response against the cancer. In some embodiments, the vaccine includes an antigen or a fragment thereof expressed on the surface of cancer cells. In some embodiments, the subject is also administered natural killer cells whose cytotoxicity against the cancer is enhanced by the antibody. In some embodiments, the subject is further administered a second antibody that specifically binds to an antigen expressed on the surface of cells of cancer, whereby an effector mediated cytotoxicity of the second antibody against the cancer is enhanced by an anti-TIGIT antibody of the present disclosure. In some embodiments, the subject is further administered a second antibody that specifically binds to an antigen expressed on the surface of an immune cell. In some embodiments, the immune cell is a T cell or a natural killer cell. In some embodiments, the antigen is CTLA-4, PD-1 or PD-L1. In some embodiments, the subject is further administered one or more therapies selected from the group consisting of chemotherapy, radiation, cell-based therapy, and surgery. In some embodiments, the subject is further administered an inhibitor of one or more immune-checkpoint receptors or ligands. In some embodiments, the one or more immune-checkpoint receptors or ligands are selected from the group consisting of CTLA-4, PD-1, PD-L1, TIM-3, LAG-3, PVRIG, BTLA, VISTA, CD96, $A_{2a}R$, $A_{2b}R$, $A_{2a}/A_{2b}R$, arginase, CD39, CD73, IDO and TDO. In some embodiments, the one or more immune-checkpoint receptors or ligands are selected from the group consisting of CTLA-4, PD-1, PD-L1, $A_{2a}R$, $A_{2b}R$, $A_{2a}/A_{2b}R$, arginase, CD39, and CD73. In some embodiments, the inhibitor is selected from the group consisting of ipilimumab, tremelimumab, nivolumab, pembrolizumab, lambrolizumab, cemiplimab, tislelizumab, zimberelimab, durvalumab, and atezolizumab.

Provided herein is a method of aiding in the treatment of cancer including administering to a subject having cancer a therapeutically effective amount of any of the anti-TIGIT antibodies described herein. In some embodiments, the cancer is a hematological cancer. In some embodiments, the cancer is acute myeloid leukemia or adult T-cell leukemia. In some embodiments, the cancer is a solid tumor, non-small cell lung carcinoma, melanoma, cervical cancer, multiple myeloma, lymphoma, hon-hodgkin lymphoma, diffuse large B-cell lymphoma, gastric cancer, gastroesophageal junction adenocarcinoma, or esophageal cancer. In some embodiments, the subject is also administered tumor infiltrating T cells which are activated by the antibody. In some embodiments, the subject is also administered a vaccine inducing an immune response against the cancer, which is enhanced by the antibody. In some embodiments, the vaccine includes an antigen expressed on the surface of cancer cells or a fragment thereof. In some embodiments, the subject is also administered natural killer cells whose cytotoxicity against the cancer is enhanced by an anti-TIGIT antibody of the present disclosure. In some embodiments, the subject is also administered a second antibody that specifically binds to an antigen expressed on the surface of cells of cancer, whereby an effector mediated cytotoxicity of the second antibody against the cancer is enhanced by an anti-TIGIT antibody of the present disclosure. In some embodiments, the subject is further administered a second antibody that specifically binds to an antigen expressed on the surface of an immune cell. In some embodiments, the immune cell is a T cell or a natural killer cell. In some embodiments, the antigen is CTLA-4, PD-1 or PD-L1. In some embodiments, the subject is further administered one or more therapies selected from the group consisting of chemotherapy, radiation, cell-based therapy, and surgery. In some embodiments, the subject is further administered an inhibitor of one or more immune-checkpoint receptors or ligands. In some embodiments, the one or more immune-checkpoint receptors or ligands are selected from the group consisting of CTLA-4, PD-1, PD-L1, TIM-3, LAG-3, PVRIG, BTLA, VISTA, CD96, $A_{2a}R$, $A_{2b}R$, $A_{2a}/A_{2b}R$, arginase, CD39, CD73, IDO and TDO. In some embodiments, the one or more immune-checkpoint receptors or ligands are selected from the group consisting of CTLA-4, PD-1, PD-L1, $A_{2a}R$, $A_{2b}R$, $A_{2a}/A_{2b}R$, arginase, CD39, and CD73. In some embodiments, the inhibitor is selected from the group consisting of ipilimumab, tremelimumab, nivolumab, pembrolizumab, lambrolizumab, cemiplimab, tislelizumab, zimberelimab, durvalumab, and atezolizumab.

Each of the aspects and embodiments described herein are capable of being used together, unless excluded either explicitly or clearly from the context of the embodiment or aspect.

BRIEF DESCRIPTION OF THE DRAWINGS

FIG. 1A shows the amino acid sequence of the mature VH of 21F8 (SEQ ID NO: 1) and the mature VL of 21F8 (SEQ ID NO: 2). The CDR1, CDR2 and CDR3 amino acid sequences of VH are underlined and identified as HC-CDR1 (SEQ ID NO: 36), HC-CDR2 (SEQ ID NO: 37), and HC-CDR3 (SEQ ID NO: 38), respectively. The CDR1, CDR2 and CDR3 amino acid sequences of VL are underlined and identified as LC-CDR1 (SEQ ID NO: 39), LC-CDR2 (SEQ ID NO: 40), and LC-CDR3 (SEQ ID NO: 41), respectively.

FIG. 1B shows the amino acid sequence of the mature VH of 30M18 (SEQ ID NO: 3) and the mature VL of 30M18 (SEQ ID NO: 4). The CDR1, CDR2 and CDR3 amino acid sequences of VH are underlined and identified as HC-CDR1 (SEQ ID NO: 42), HC-CDR2 (SEQ ID NO: 43), and HC-CDR3 (SEQ ID NO: 44), respectively. The CDR1, CDR2 and CDR3 amino acid sequences of VL are underlined and identified as LC-CDR1 (SEQ ID NO: 45), LC-CDR2 (SEQ ID NO: 46), and LC-CDR3 (SEQ ID NO: 47), respectively.

FIG. 1C shows the amino acid sequence of the mature VH of 24F8 (SEQ ID NO: 5) and the mature VL of 24F8 (SEQ ID NO: 6). The CDR1, CDR2 and CDR3 amino acid sequences of VH are underlined and identified as HC-CDR1 (SEQ ID NO: 48), HC-CDR2 (SEQ ID NO: 49), and HC-CDR3 (SEQ ID NO: 50), respectively. The CDR1, CDR2 and CDR3 amino acid sequences of VL are underlined and identified as LC-CDR1 (SEQ ID NO: 51), LC-CDR2 (SEQ ID NO: 52), and LC-CDR3 (SEQ ID NO: 53), respectively.

FIG. 1D shows the amino acid sequence of the mature VH of 5J24 (SEQ ID NO: 7) and the mature VL of 5J24 (SEQ ID NO: 8). The CDR1, CDR2 and CDR3 amino acid sequences of VH are underlined and identified as HC-CDR1 (SEQ ID NO: 54), HC-CDR2 (SEQ ID NO: 55), and HC-CDR3 (SEQ ID NO: 56), respectively. The CDR1, CDR2 and CDR3 amino acid sequences of VL are underlined and identified as LC-CDR1 (SEQ ID NO: 57), LC-CDR2 (SEQ ID NO: 58), and LC-CDR3 (SEQ ID NO: 59), respectively.

FIG. 1E shows the amino acid sequence of the mature VH of 21B9 (SEQ ID NO: 9) and the mature VL of 21B9 (SEQ ID NO: 10). The CDR1, CDR2 and CDR3 amino acid sequences of VH are underlined and identified as HC-CDR1 (SEQ ID NO: 60), HC-CDR2 (SEQ ID NO: 61), and HC-CDR3 (SEQ ID NO: 62), respectively. The CDR1, CDR2 and CDR3 amino acid sequences of VL are underlined and identified as LC-CDR1 (SEQ ID NO: 63), LC-CDR2 (SEQ ID NO: 64), and LC-CDR3 (SEQ ID NO: 65), respectively.

FIG. 1F shows the amino acid sequence of the mature VH of 22B22 (SEQ ID NO: 11) and the mature VL of 22B22 (SEQ ID NO: 12). The CDR1, CDR2 and CDR3 amino acid sequences of VH are underlined and identified as HC-CDR1 (SEQ ID NO: 60), HC-CDR2 (SEQ ID NO: 66), and HC-CDR3 (SEQ ID NO: 67), respectively. The CDR1, CDR2 and CDR3 amino acid sequences of VL are underlined and identified as LC-CDR1 (SEQ ID NO: 63), LC-CDR2 (SEQ ID NO: 68), and LC-CDR3 (SEQ ID NO: 65), respectively.

FIG. 1G shows the amino acid sequence of the mature VH of 28P24 (SEQ ID NO: 13) and the mature VL of 28P24 (SEQ ID NO: 14). The CDR1, CDR2 and CDR3 amino acid sequences of VH are underlined and identified as HC-CDR1 (SEQ ID NO: 69), HC-CDR2 (SEQ ID NO: 55), and HC-CDR3 (SEQ ID NO: 70), respectively. The CDR1, CDR2 and CDR3 amino acid sequences of VL are underlined and identified as LC-CDR1 (SEQ ID NO: 71), LC-CDR2 (SEQ ID NO: 68), and LC-CDR3 (SEQ ID NO: 65), respectively.

FIG. 1H shows the amino acid sequence of the mature VH of 21B16 (SEQ ID NO: 15) and the mature VL of 21B16 (SEQ ID NO: 16). The CDR1, CDR2 and CDR3 amino acid sequences of VH are underlined and identified as HC-CDR1

(SEQ ID NO: 72), HC-CDR2 (SEQ ID NO: 73), and HC-CDR3 (SEQ ID NO: 67), respectively. The CDR1, CDR2 and CDR3 amino acid sequences of VL are underlined and identified as LC-CDR1 (SEQ ID NO: 63), LC-CDR2 (SEQ ID NO: 68), and LC-CDR3 (SEQ ID NO: 65), respectively.

FIG. 1I shows the amino acid sequence of the mature VH of 28O12 (SEQ ID NO: 17) and the mature VL of 28O12 (SEQ ID NO: 12). The CDR1, CDR2 and CDR3 amino acid sequences of VH are underlined and identified as HC-CDR1 (SEQ ID NO: 74), HC-CDR2 (SEQ ID NO: 75), and HC-CDR3 (SEQ ID NO: 67), respectively. The CDR1, CDR2 and CDR3 amino acid sequences of VL are underlined and identified as LC-CDR1 (SEQ ID NO: 63), LC-CDR2 (SEQ ID NO: 68), and LC-CDR3 (SEQ ID NO: 65), respectively.

FIG. 1J shows the amino acid sequence of the mature VH of Hu24F8.1 (SEQ ID NO: 76) and the mature VL of Hu24F8.1 (SEQ ID NO: 77). The CDR1, CDR2 and CDR3 amino acid sequences of VH are underlined and identified as HC-CDR1 (SEQ ID NO: 48), HC-CDR2 (SEQ ID NO: 49), and HC-CDR3 (SEQ ID NO: 50), respectively. The CDR1, CDR2 and CDR3 amino acid sequences of VL are underlined and identified as LC-CDR1 (SEQ ID NO: 51), LC-CDR2 (SEQ ID NO: 52), and LC-CDR3 (SEQ ID NO: 53), respectively.

FIG. 1K shows the amino acid sequence of the mature VH of Hu24F8.2 (SEQ ID NO: 78) and the mature VL of Hu24F8.2 (SEQ ID NO: 77). The CDR1, CDR2 and CDR3 amino acid sequences of VH are underlined and identified as HC-CDR1 (SEQ ID NO: 48), HC-CDR2 (SEQ ID NO: 49), and HC-CDR3 (SEQ ID NO: 50), respectively. The CDR1, CDR2 and CDR3 amino acid sequences of VL are underlined and identified as LC-CDR1 (SEQ ID NO: 51), LC-CDR2 (SEQ ID NO: 52), and LC-CDR3 (SEQ ID NO: 53), respectively.

FIG. 1L shows the amino acid sequence of the mature VH of Hu24F8.3 (SEQ ID NO: 78) and the mature VL of Hu24F8.3 (SEQ ID NO: 79). The CDR1, CDR2 and CDR3 amino acid sequences of VH are underlined and identified as HC-CDR1 (SEQ ID NO: 48), HC-CDR2 (SEQ ID NO: 49), and HC-CDR3 (SEQ ID NO: 50), respectively. The CDR1, CDR2 and CDR3 amino acid sequences of VL are underlined and identified as LC-CDR1 (SEQ ID NO: 51), LC-CDR2 (SEQ ID NO: 52), and LC-CDR3 (SEQ ID NO: 53), respectively.

Figure 2:
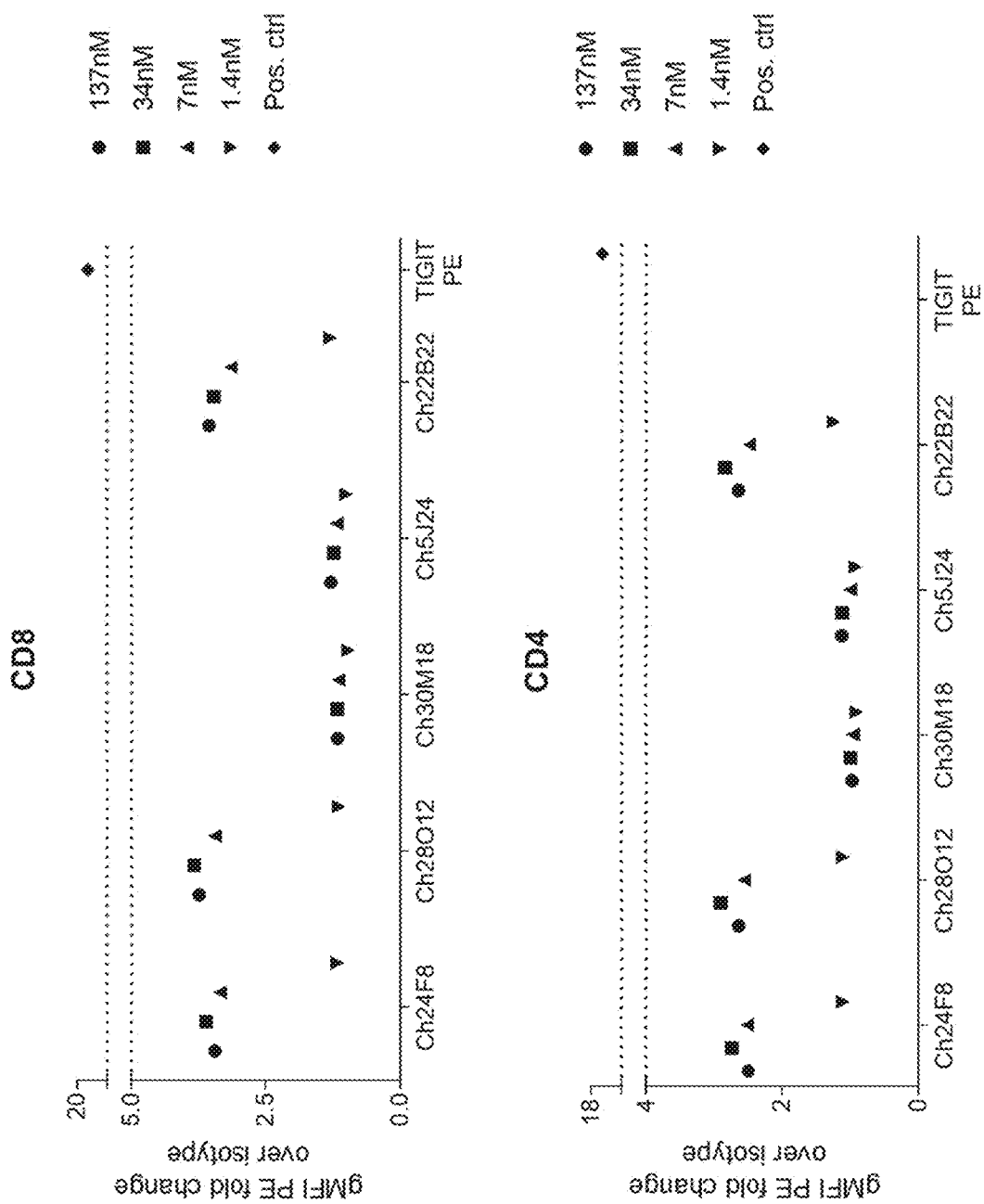

FIG. 1M shows the amino acid sequence of the mature VH of Hu24F8.4 (SEQ ID NO: 76) and the mature VL of Hu24F8.4 (SEQ ID NO: 79). The CDR1, CDR2 and CDR3 amino acid sequences of VH are underlined and identified as HC-CDR1 (SEQ ID NO: 48), HC-CDR2 (SEQ ID NO: 49), and HC-CDR3 (SEQ ID NO: 50), respectively. The CDR1, CDR2 and CDR3 amino acid sequences of VL are underlined and identified as LC-CDR1 (SEQ ID NO: 51), LC-CDR2 (SEQ ID NO: 52), and LC-CDR3 (SEQ ID NO: 53), respectively FIG. 2 shows that Ch24F8, Ch28O12 and Ch22B22 were capable of binding to cyno TIGIT expressed on cyno CD4$^+$ and CD8$^+$ cells. The geometric mean of the fluorescent intensity (gMFI) was obtained, and data were presented as fold of gMFI over isotype control.

Figure 3A:
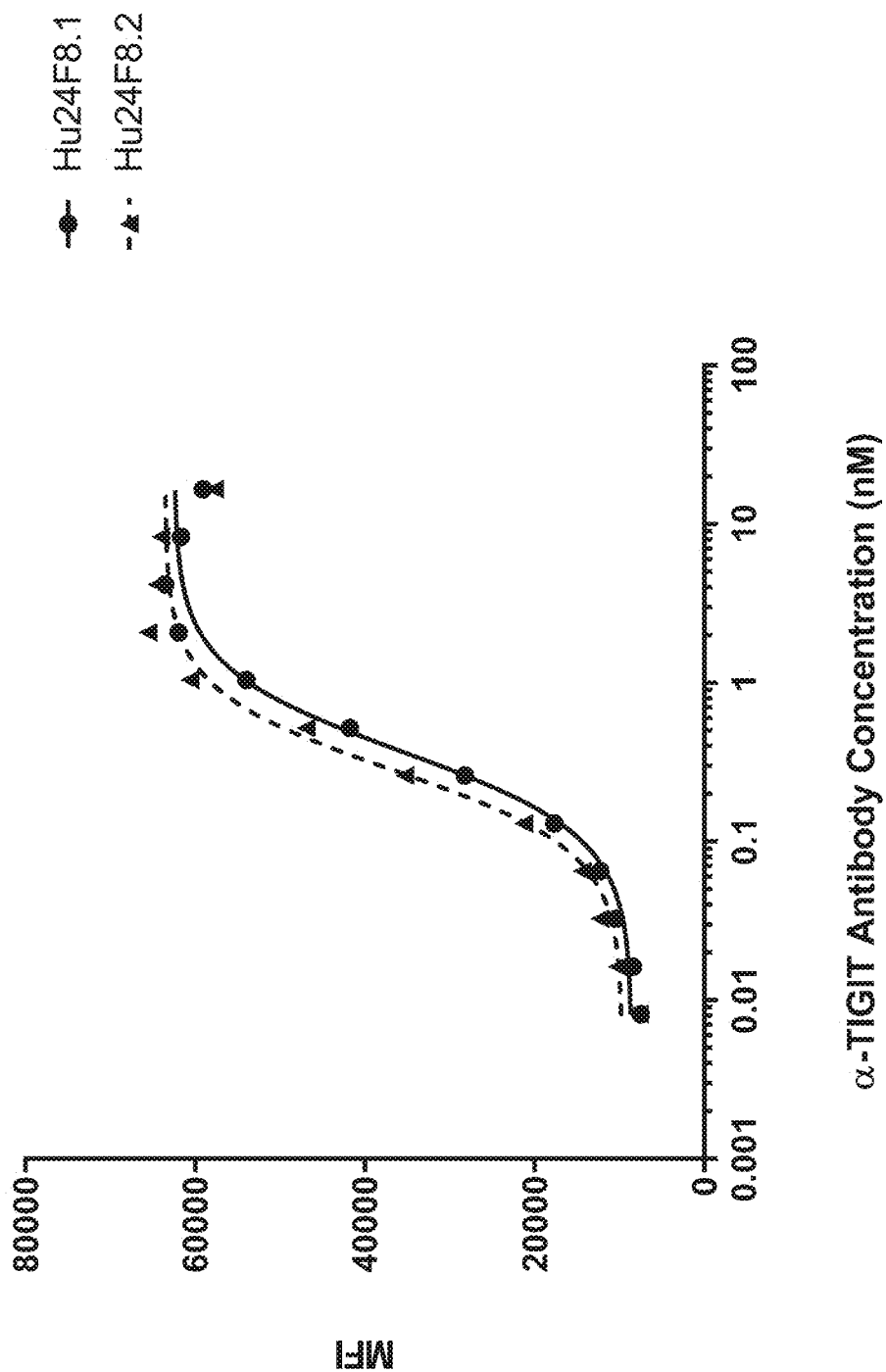

FIG. 3A is a graph showing binding of humanized anti-TIGIT antibodies to CHO-K1 cells overexpressing human TIGIT.

Figure 3B:
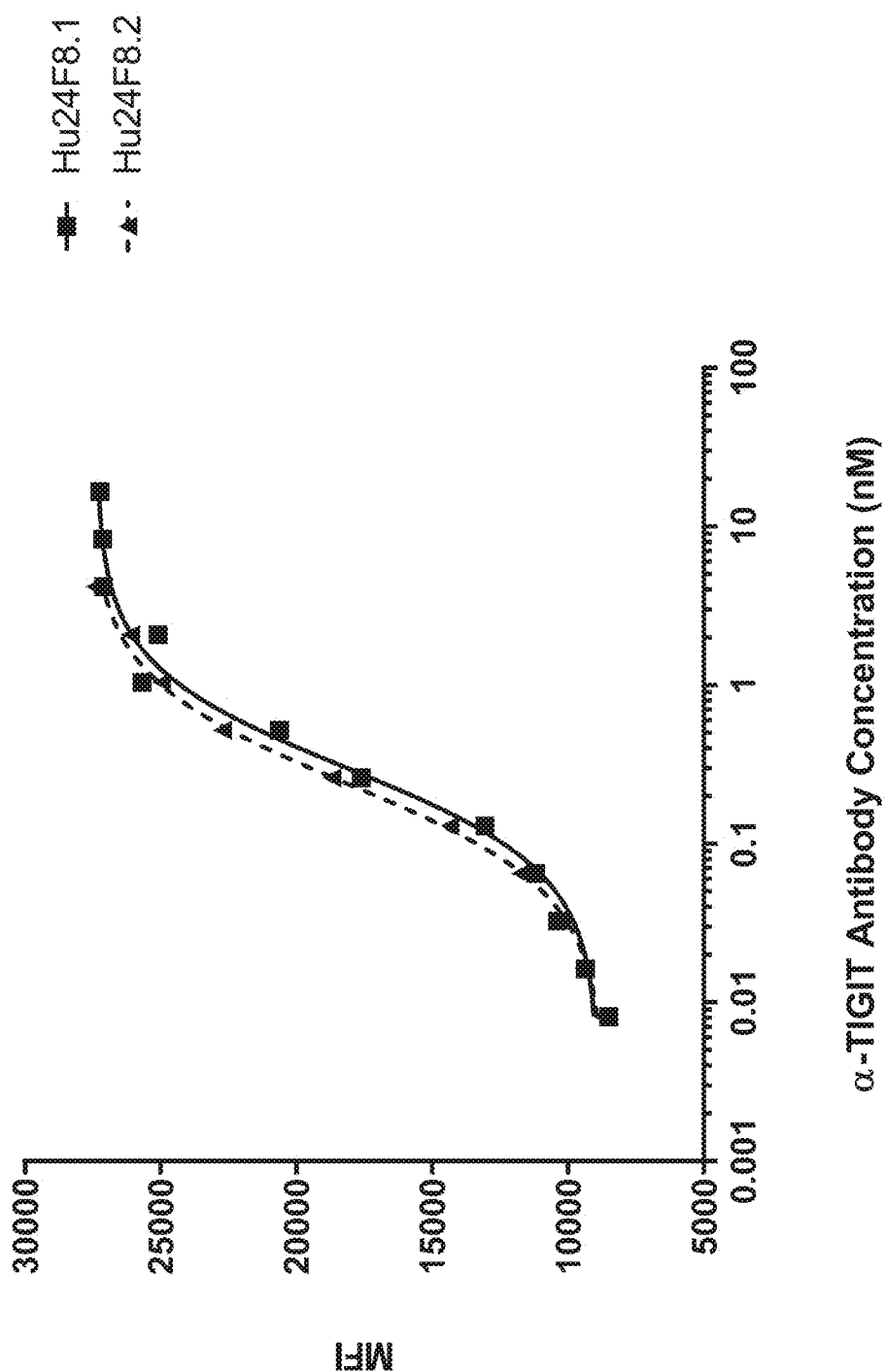

FIG. 3B is a graph showing binding of humanized anti-TIGIT antibodies to CHO-K1 cells overexpressing cynomolgus monkey TIGIT.

Figure 4A:
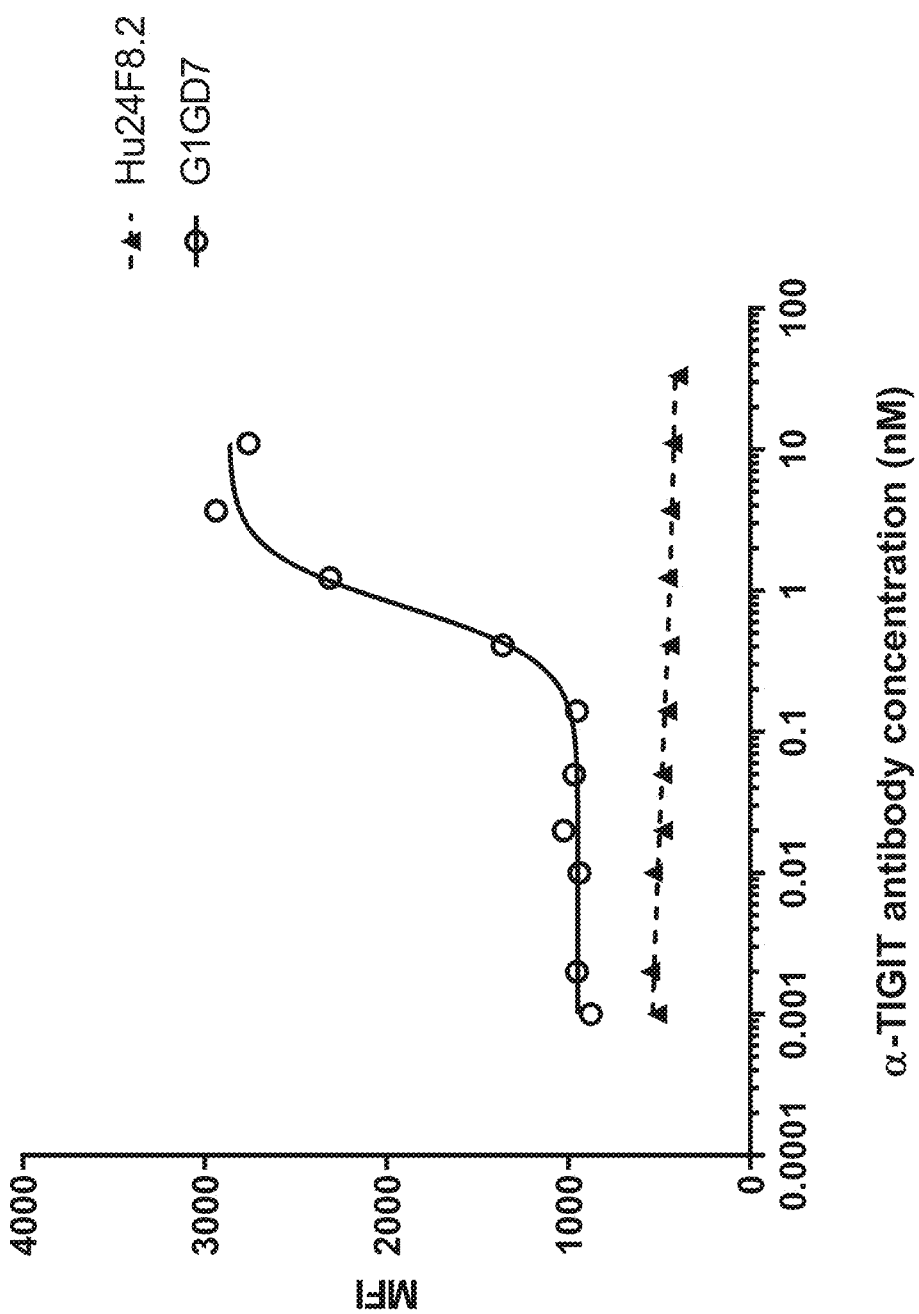

FIG. 4A is a graph showing binding of humanized anti-TIGIT to CHO-K1 cells overexpressing mouse TIGIT.

FIG. 4B is a graph showing binding of humanized anti-TIGIT to CHO-K1 cells overexpressing rat TIGIT.

FIG. 5A is a graph showing binding of humanized anti-TIGIT antibodies to human not activated CD8$^+$ T cells.

Figure 5B:
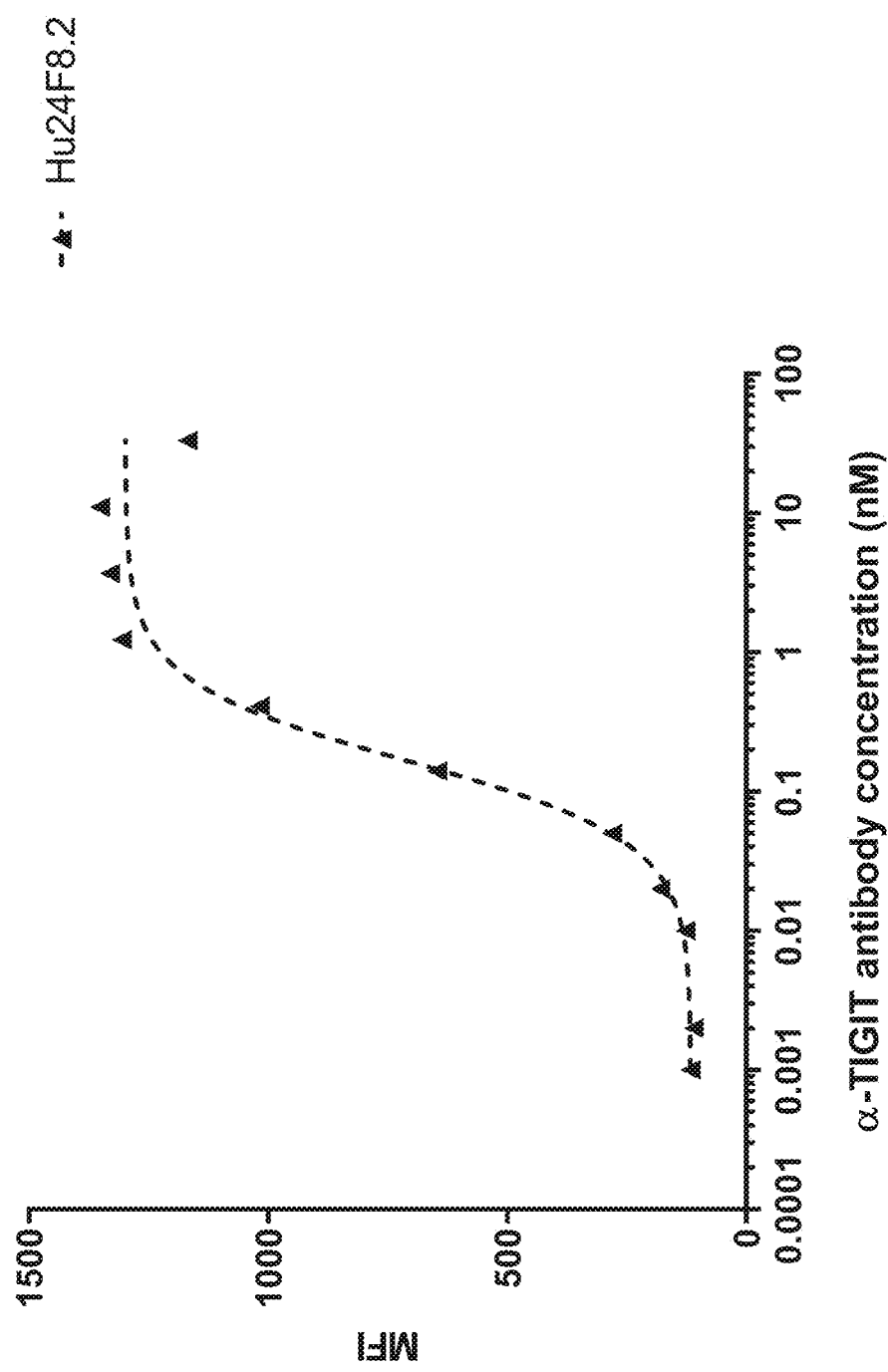

FIG. 5B is a graph showing binding of humanized anti-TIGIT antibodies to human activated CD8$^+$ T cells.

Figure 6:
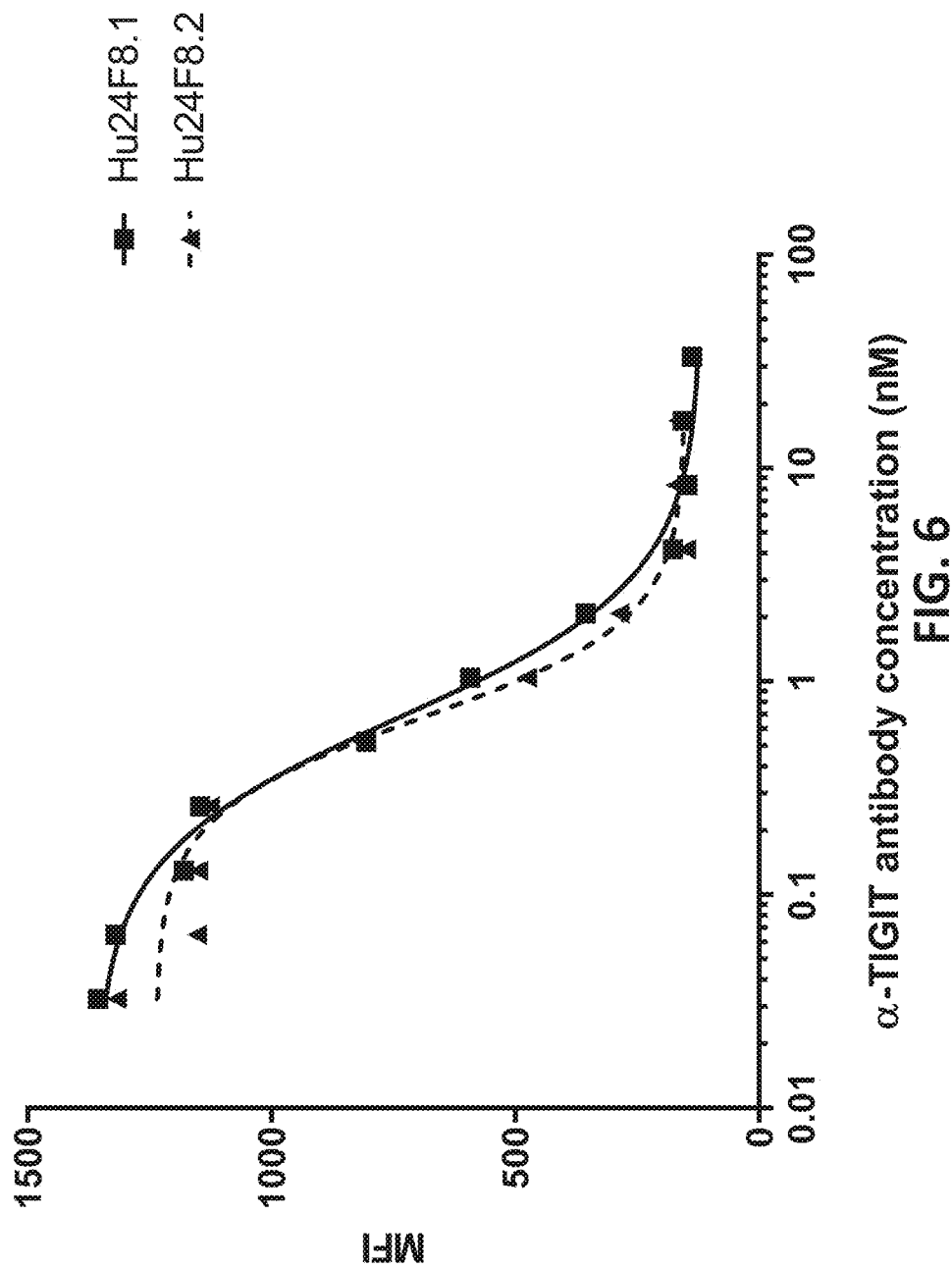

FIG. 6 is a graph showing inhibition of human CD155 binding to CHO-K1 cells overexpressing human TIGIT by humanized anti-TIGIT antibodies.

Figure 7:
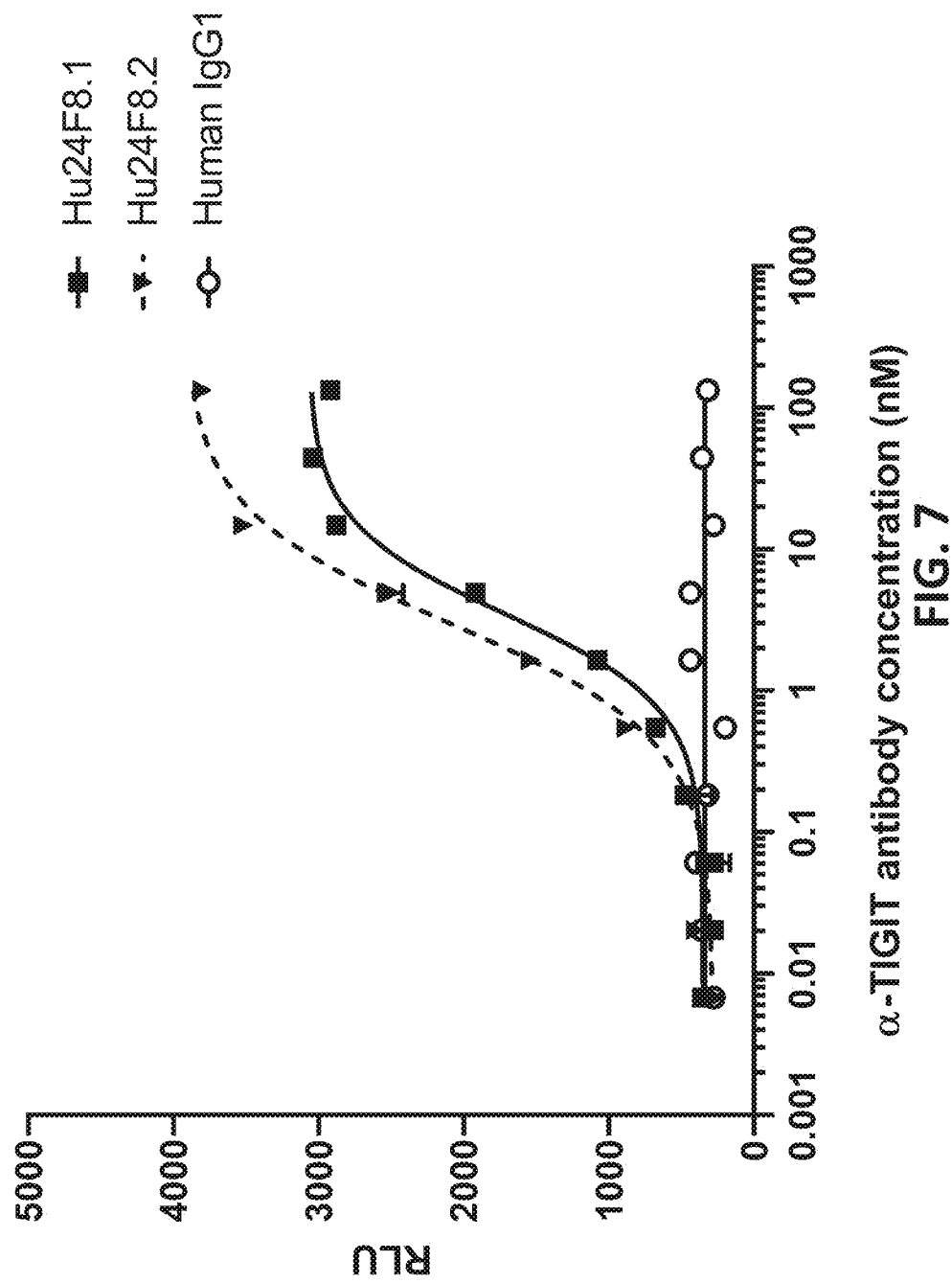

FIG. 7 is a graph showing inhibition of human CD155 binding to human TIGIT by humanized anti-TIGIT antibodies in a Jurkat Dual Reporter Cell Line Blockade Assay.

Figure 8:
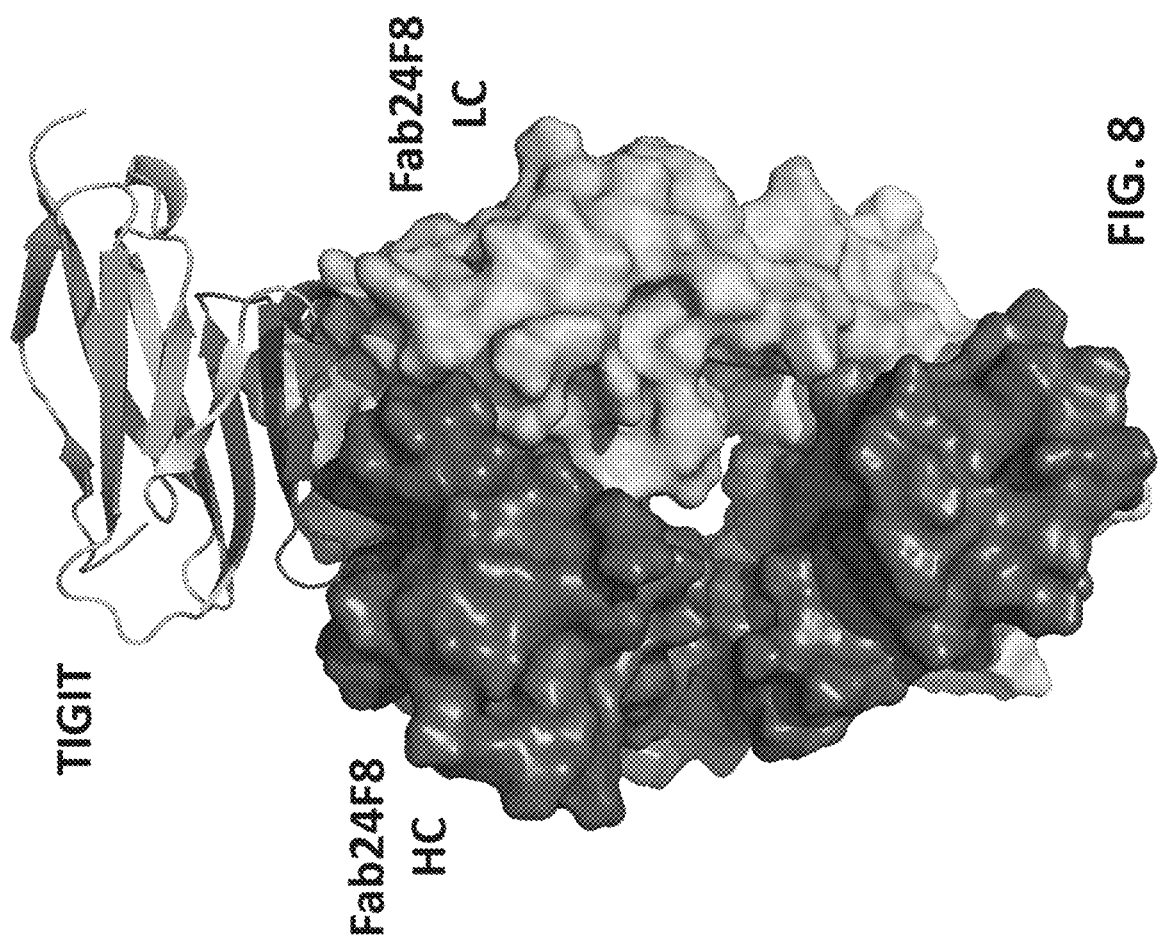

FIG. 8 shows binding of Fab24F8 to TIGIT.

Figure 9:
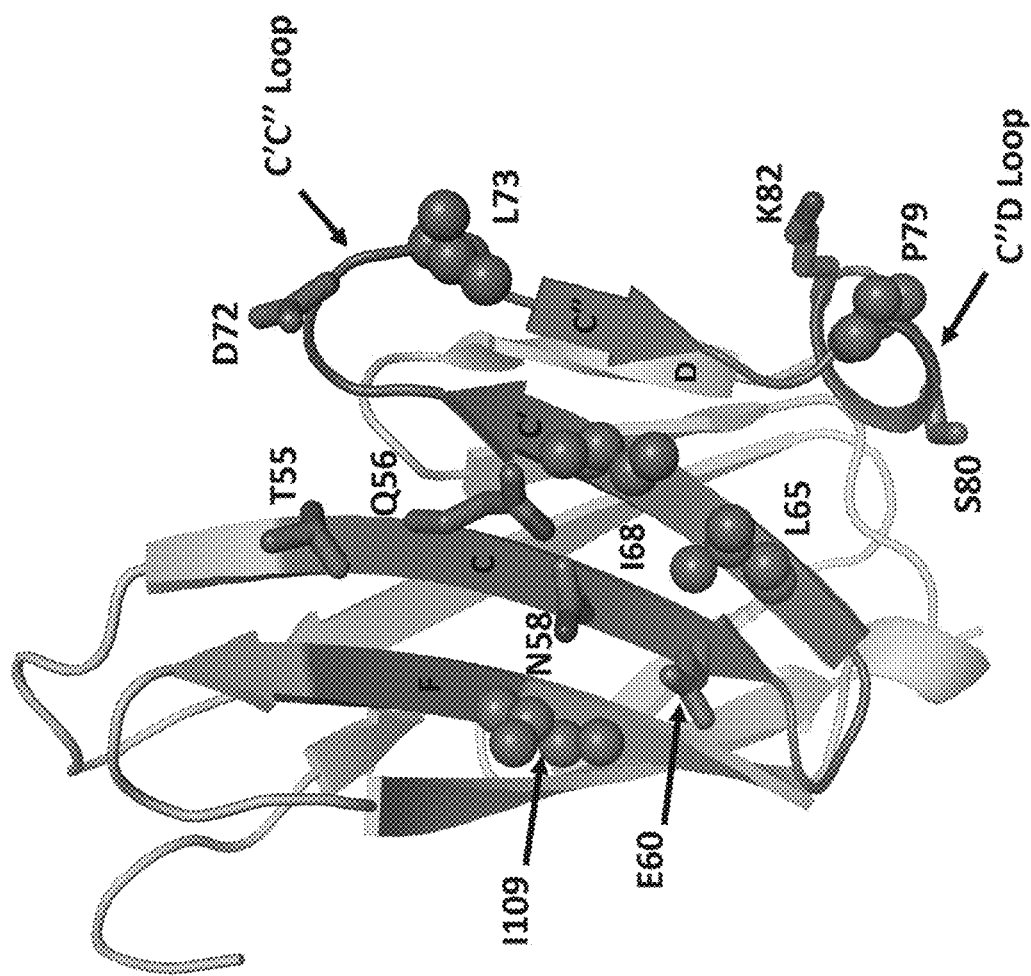

FIG. 9 shows TIGIT residues having hydrogen bonding, salt bridge and van der Waals interactions with Fab24F8.

Figure 10B:
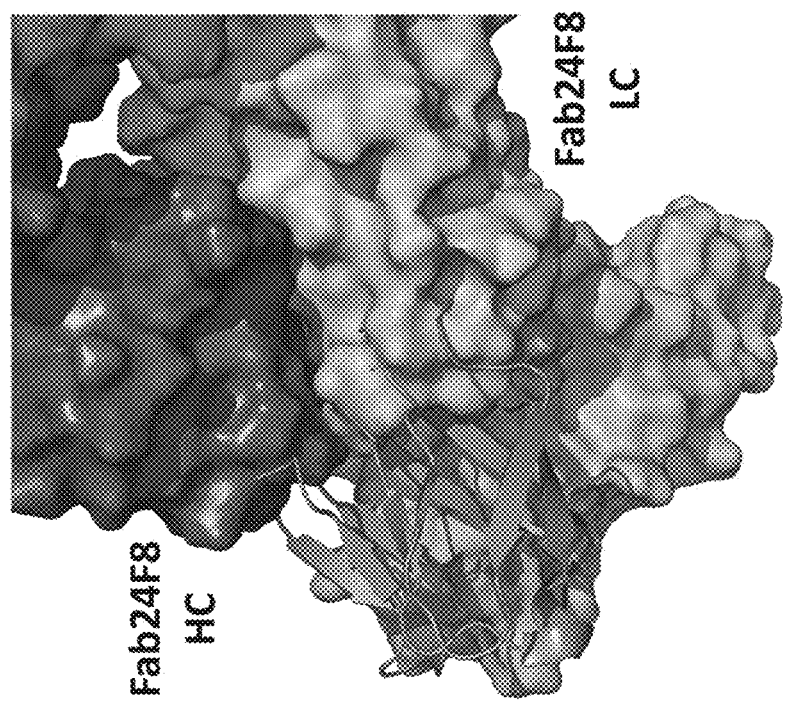
Figure 10A:
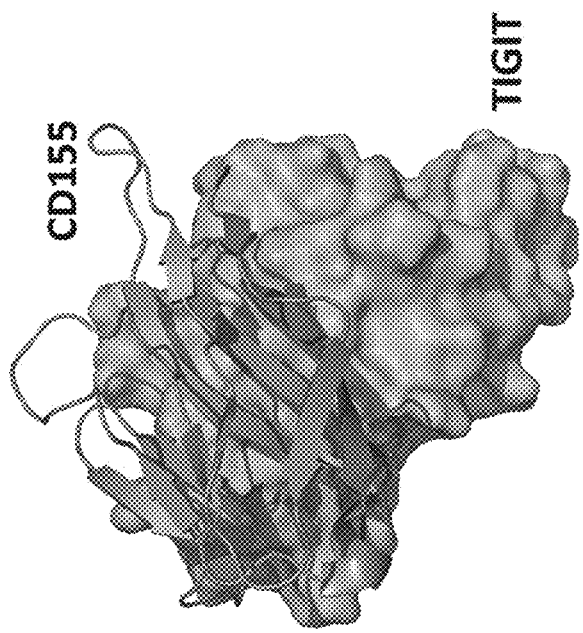

FIG. 10A and FIG. 10B show that the binding of CD155 to TIGIT is blocked by Fab24F8. FIG. 10A shows a schematic of the complex structure of human CD155 (in ribbon representation) bound to human TIGIT (represented as a molecular surface). FIG. 10B shows the superimposition of CD155, in the same orientation as FIG. 10A, onto a schematic of the crystal structure complex of Fab24F8 bound to TIGIT (each represented by a molecular surface).

Figure 11:
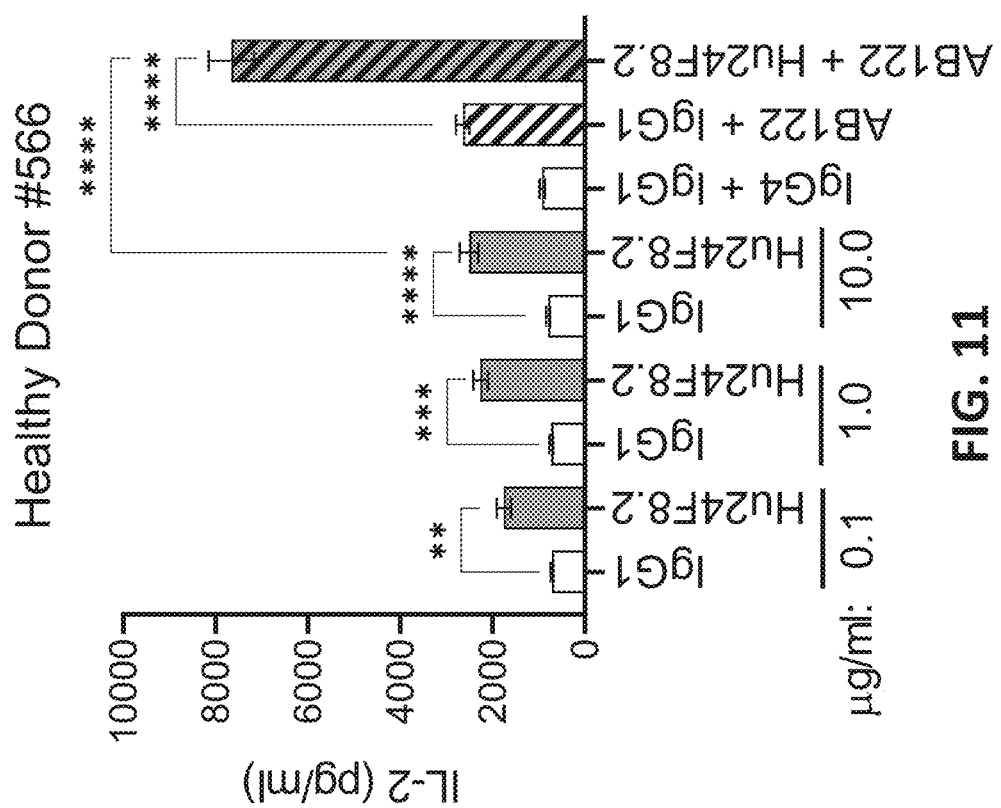

FIG. 11 shows a single subject, IL-2 response to SEA in the presence of Hu24F8.2-IgG1, AB122, AB122 and Hu24F8.2-IgG1, or isotype control. Bars and error depict mean±standard error mean. $p<0.01$, *$p<0.001$, ****$p<0.0001$, One way ANOVA with Sidak's multiple comparisons test (Hu24F8.2-IgG1 vs. IgG1 for each concentration and AB122+Hu24F8.2-IgG1 vs. AB122 alone or Hu24F8.2-IgG1 alone).

Figure 12A:
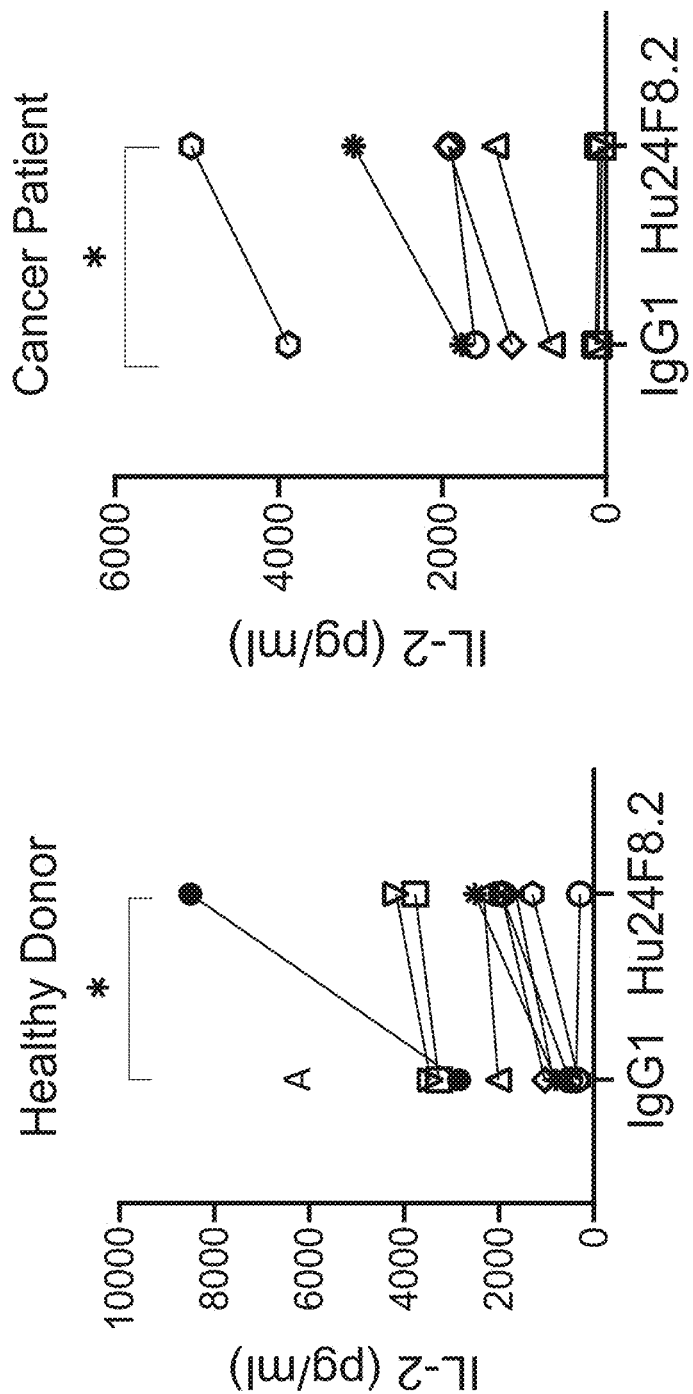

FIG. 12A shows IL-2 response of healthy or cancer subject PBMCs to SEA in the presence of Hu24F8.2-IgG1 or isotype control. Each symbol represents an individual subject. *$p<0.05$, Paired t-test.

Figure 12B:
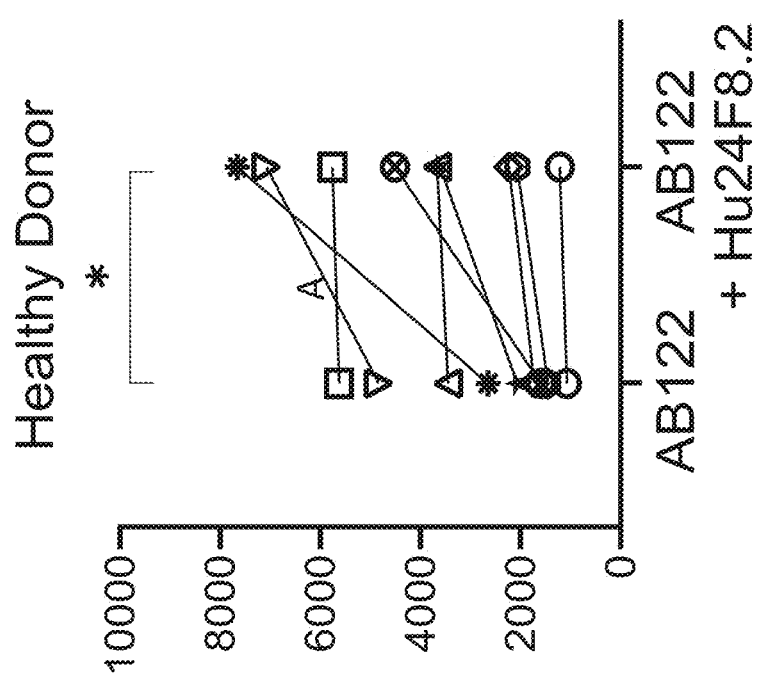

FIG. 12B shows IL-2 response of healthy subject PBMCs to SEA in the presence of AB122 compared to AB122 and Hu24F8.2-IgG1. Each symbol represents an individual subject. *$p<0.05$, Paired t-test.

DETAILED DESCRIPTION

The present disclosure provides, inter alia, antibodies that specifically bind to the extracellular domain of TIGIT. Antibodies of the present disclosure, also referred to herein as "anti-TIGIT antibodies", inhibit binding of TIGIT to CD155 and can thereby activate T cells and/or NK cells. The antibodies can be also used for treatment of cancer and infectious disease, among other applications. Additional structural and functional features of an anti-TIGIT antibody of the present disclosure are described in further detail below.

I. Definitions

Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The singular form "a", "an", and "the" include plural references unless the context clearly dictates otherwise. For example, the term "a cell" includes one or more cells, including mixtures thereof "A and/or B" is used herein to include all of the following alternatives: "A", "B", "A or B", and "A and B".

The term "antibody" includes intact antibodies and binding fragments thereof that specifically bind to a single antigen or that specifically bind to multiple antigens (e.g., multispecific antibodies such as a bispecific antibody, a trispecific antibody, etc.). Thus, any reference to an antibody should be understood to refer to the antibody in intact form or a binding fragment unless the context requires otherwise. Additional functionality (e.g., antigen binding) contemplated in the context of the present disclosure includes anti-PD-1, anti-PD-LI, anti-TIM-3, anti-LAG-3, anti-PVRIG, anti-VISTA, anti-CTLA-4, anti-4-1BB, anti-BTLA, anti-CD39, anti-CD73, anti-OX40L, and anti-OX40 fragments.

The term "binding fragment" which can be used interchangeably with "antigen-binding fragment," refers herein to an antibody fragment formed from a portion of an antibody comprising one or more CDRs, or any other antibody fragment that specifically binds to an antigen but does not comprise an intact native antibody structure. Examples of antigen-binding fragment include, without limitation, a diabody, a Fab, a Fab', a F(ab')$_2$, a F(ab)$_c$, an Fv fragment, a disulfide stabilized Fv fragment (dsFv), a, (dsFv)$_2$, a bispecific dsFv (dsFv-dsFv'), a disulfide stabilized diabody (ds diabody), a triabody, a tetrabody, a single-chain antibody molecule (scFv), an scFv dimer, a multispecific antibody, a camelized single domain antibody, a nanobody, a minibody, a domain antibody, a bivalent domain antibody, a IgNAR, a V-NAR, and a hcIgG. Typically, binding fragments compete with the intact antibody from which they were derived for specific binding. Binding fragments can be produced by recombinant DNA techniques, or by enzymatic or chemical separation of intact immunoglobulins.

"Fab" with regard to an antibody refers to that portion of the antibody consisting of a single light chain (both variable and constant regions) bound to the variable region and first constant region of a single heavy chain by a disulfide bond.

"Fab'" refers to a Fab fragment that includes a portion of the hinge region.

"F(ab')$_2$" refers to a dimer of Fab'.

"Fc" with regard to an antibody refers to that portion of the antibody consisting of the second and third constant regions of a first heavy chain bound to the second and third constant regions of a second heavy chain via disulfide bonding. The Fc portion of the antibody is responsible for various effector functions such as ADCC, and CDC, but does not function in antigen binding.

"Fv" with regard to an antibody refers to the smallest fragment of the antibody to bear the complete antigen binding site. An Fv fragment consists of the variable region of a single light chain bound to the variable region of a single heavy chain.

"Single-chain Fv antibody" or "scFv" refers to an engineered antibody consisting of a light chain variable region and a heavy chain variable region connected to one another directly or via a peptide linker sequence (Huston J. S. et al., *Proc Natl Acad Sci USA*, 85:5879(1988)).

"Single-chain Fv-Fc antibody" or "scFv-Fc" refers to an engineered antibody consisting of a scFv connected to the Fc region of an antibody.

"Camelized single domain antibody," "heavy chain antibody," or "HCAb" refers to an antibody that contains two $V_H$ domains and no light chains (Riechmann L. and Muyldermans S., *J Immunol Methods*. December 10; 231(1-2): 25-38 (1999); Muyldermans S., J Biotechnol. June; 74(4): 277-302 (2001); WO94/04678; WO94/25591; U.S. Pat. No. 6,005,079). Heavy chain antibodies were originally derived from Camelidae (camels, dromedaries, and llamas). Although devoid of light chains, camelized antibodies have an authentic antigen-binding repertoire (Hamers-Casterman C. et al., *Nature*. June 3; 363(6428):446-8 (1993); Nguyen V. K. et al. "Heavy-chain antibodies in Camelidae; a case of evolutionary innovation," *Immunogenetics*. April; 54(1):39-47 (2002); Nguyen V. K. et al. *Immunology*. May; 109(1): 93-101 (2003)). The variable domain of a heavy chain antibody (VHH domain) represents the smallest known antigen-binding unit generated by adaptive immune responses (Koch-Nolte F. et al., *FASEB J*. November; 21(13):3490-8. Epub 2007 Jun. 15 (2007)).

A "nanobody" refers to an antibody fragment that consists of a VHH domain from a heavy chain antibody and two constant domains, CH2 and CH3.

"Diabodies" include small antibody fragments with two antigen-binding sites, wherein the fragments comprise a $V_H$ domain connected to a $V_L$ domain in the same polypeptide chain ($V_H$-$V_L$ or $V_L$-$V_H$) (see, e.g., Holliger P. et al., *Proc Natl Acad Sci USA*. July 15; 90(14):6444-8 (1993); EP404097; WO93/11161). By using a linker that is too short to allow pairing between the two domains on the same chain, the domains are forced to pair with the complementary domains of another chain, thereby creating two antigen-binding sites. The antigen-binding sites can target the same or different antigens (or epitopes).

A "domain antibody" refers to an antibody fragment containing only the variable region of a heavy chain or the variable region of a light chain. In certain instances, two or more $V_H$ domains are covalently joined with a peptide linker to create a bivalent or multivalent domain antibody. The two $V_H$ domains of a bivalent domain antibody can target the same or different antigens.

In certain embodiments, a "(dsFv)$_2$" comprises three peptide chains: two $V_H$ moieties linked by a peptide linker and bound by disulfide bridges to two $V_L$ moieties.

In certain embodiments, a "bispecific ds diabody" comprises $V_{H1}$-$V_{L2}$ (linked by a peptide linker) bound to $V_{L1}$-$V_{H2}$ (also linked by a peptide linker) via a disulfide bridge between $V_{H1}$ and $V_{L1}$.

In certain embodiments, a "bispecific dsFv" or dsFv-dsFv'" comprises three peptide chains: a $V_{H1}$-$V_{H2}$ moiety wherein the heavy chains are linked by a peptide linker (e.g., a long flexible linker) and bound to $V_{L1}$ and $V_{L2}$ moieties, respectively, via disulfide bridges, wherein each disulfide paired heavy and light chain has a different antigen specificity.

In certain embodiments, an "scFv dimer" is a bivalent diabody or bivalent ScFv (BsFv) comprising $V_H$-$V_L$ (linked by a peptide linker) dimerized with another $V_H$-$V_L$ moiety such that $V_H$'s of one moiety coordinate with the $V_L$'s of the other moiety and form two binding sites which can target the same antigens (or epitopes) or different antigens (or epitopes). In other embodiments, an "scFv dimer" is a bispecific diabody comprising $V_{H1}$-$V_{L2}$ (linked by a peptide linker) associated with Vu-$V_{H2}$ (also linked by a peptide linker) such that $V_{H1}$ and $V_{L1}$ coordinate and $V_{H2}$ and $V_{L2}$ coordinate and each coordinated pair has a different antigen specificity. An "isolated" antibody is one which has been separated from a component of its natural environment. In some embodiments, an isolated antibody is purified to greater than 95% or 99% purity as determined by methods known in the art.

"Monoclonal antibody," as used herein, refers to an antibody that is derived from a single copy or clone, including e.g., any eukaryotic, prokaryotic, or phage clone. "Monoclonal antibody" is not limited to antibodies produced by any particular method. For instance, monoclonal antibodies can be produced using hybridoma techniques, as well as recombinant technologies, phage display technologies, synthetic technologies or combinations of such technologies and other technologies readily known in the art.

The term "humanized antibody," as used herein, refers to antibodies that contain sequences from both human and non-human (e.g., mouse or rat) antibodies.

The term "human antibody," as used herein, means the antibody has or consists of amino acid sequence(s), in particular antigen-binding residues, corresponding to that of an antibody produced by a human or a human immune cell, or derived from a non-human source such as a transgenic non-human animal that utilizes human antibody repertoires or other human antibody encoding sequences. In certain embodiments, a fully human antibody does not comprise amino acid residues (in particular antigen-binding residues) derived from a non-human antibody.

The basic antibody structural unit, for instance as exemplified by a native, intact antibody, is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region, means a light chain variable region without the light chain signal peptide. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. (See generally, *Fundamental Immunology* (Paul, W., ed., 2nd ed. Raven Press, N.Y., 1989), Ch. 7) (incorporated by reference in its entirety for all purposes).

The mature variable regions of each light/heavy chain pair form the antibody binding site. Thus, an intact, native antibody has two, identical binding sites; a bispecific antibody has two, non-identical binding sites; a trispecific antibody has three, non-identical binding sites; etc. The mature variable regions of heavy and light chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains include the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md., 1987 and 1991), or Chothia & Lesk, *J. Mol. Biol.* 196:901-917 (1987); Chothia et al., *Nature* 342:878-883 (1989). Kabat also provides a widely used numbering convention (Kabat numbering) in which corresponding residues between different heavy chains or between different light chains are assigned the same number.

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, X-ray crystallography and 2-dimensional nuclear magnetic resonance. See, e.g., Epitope Mapping Protocols, in *Methods in Molecular Biology*, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined by X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some but not all amino acid mutations that reduce or eliminate binding of one antibody reduce or eliminate binding of the other.

Competition between antibodies is determined by an assay in which an antibody under test conditions inhibits the specific binding of a reference antibody to a common antigen (see, e.g., Junghans et al., *Cancer Res.* 50:1495, 1990). A test antibody competes with a reference antibody if an excess of the test antibody (e.g., at least 2×, 3×, 4×, 5×, 6×, 7×, 8×, 9×, 10×, 15×, 20×, 25×, 30×, 35×, 40×, 45×, 50×, 60×, 70×, 80×, 90×, 100×, or more, inclusive of numbers falling in between these values) inhibits binding of the reference antibody by at least about 50%, such as by at least about 75%, 90%, or 99%. In other embodiments, a test antibody competes with a reference antibody if an excess of the test antibody inhibits binding of the reference antibody by any of at least about 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% as measured in a competitive binding assay. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. A reference antibody can be a commercially available monoclonal antibody with functions similar to a therapeutic antibody candidate, a polyclonal antibody functionally interacting with the target protein of interest, or an antibody reconstructed from sequences available in the public domain. For example, without limitation, a reference antibody binding to TIGIT comprises a heavy chain having an amino acid sequence comprising SEQ ID NO: 92 and a light chain having an amino acid sequence comprising SEQ ID NO: 93.

As used herein, the terms "specific binding" and "specifically binds to" refers to a measurable and reproducible interaction, such as binding between an antigen (e.g., TIGIT) and an antibody. For example, an antibody that specifically binds to an antigen is an antibody that binds this target with greater affinity, avidity, more readily, and/or with greater duration than it binds to other antigens. Affinity and a molecule's equilibrium dissociation constant (KD) for an antigen are inversely related. A high affinity for an antigen is measured by a low KD value. As used herein, an antibody that specifically binds to an antigen has a KD for the antigen of $10^{-6}$ M or lower, alternatively $10^{-7}$ M or lower, alternatively $10^{-8}$ M or lower, alternatively $10^{-9}$ M or lower, alternatively $10^{-10}$ M or lower, alternatively $10^{-11}$ M or lower; or a KD in the range of $10^{-6}$ M to $10^{-13}$ M, or $10^{-9}$ M to $10^{-13}$ M, or $10^{-9}$ M to $10^{-12}$ M, or $10^{-10}$ M to $10^{-13}$ M, or $10^{-10}$ M to $10^{-12}$ M, or $10^{-11}$ M to $10^{-13}$ M, or $10^{-10}$ M to $10^{-11}$ M, or $10^{-11}$ M to $10^{-12}$ M, measured by surface plasmon resonance. In one embodiment, the term "specific binding" refers to binding where a molecule binds to a particular polypeptide or epitope on a particular polypeptide without substantially binding to any other polypeptide or polypeptide epitope.

As used herein, an "individual" or a "subject" includes animals, such as human (e.g., human individuals) and non-human animals. In some embodiments, an "individual" or "subject" is a patient under the care of a physician. Thus, the subject can be a human patient or an individual who has, is at risk of having, or is suspected of having a disease of interest (e.g., cancer) and/or one or more symptoms of the disease. The subject can also be an individual who is diagnosed with a risk of the condition of interest at the time of diagnosis or later. The term "non-human animals" includes all vertebrates, e.g., mammals, e.g., rodents, e.g., mice, non-human primates, and other mammals, such as e.g., sheep, dogs, cows, chickens, and non-mammals, such as amphibians, reptiles, etc.

As used herein, an amino acid residue of an amino acid sequence of interest that "corresponds to" or is "corresponding to" or in "correspondence with" an amino acid residue of a reference amino acid sequence indicates that the amino acid residue of the sequence of interest is at a location homologous or equivalent to an enumerated residue in the reference amino acid sequence. One skilled in the art can determine whether a particular amino acid residue position in a polypeptide, such as a TIGIT polypeptide, corresponds to that of a homologous reference sequence. For example, the sequence of a TIGIT polypeptide can be aligned with that of a reference sequence using known techniques (e.g., basic local alignment search tool (BLAST), ClustalW2, Structure based sequences alignment program (STRAP), or the like). In addition, crystal structure coordinates of a reference sequence can be used as an aid in determining a homologous polypeptide residue's three-dimensional structure (Stengel et al., *Proc. Natl. Acad. Sci. USA.* 109:5399-5404, 2012). In another aspect, equivalent residues can be identified by determining homology at the level of tertiary structure. Using such methods, the amino acid residues of a TIGIT polypeptide variant can be numbered according to the corresponding amino acid residue position numbering of the reference sequence. For example, the amino acid sequence of SEQ ID NO: 80 can be used for determining amino acid residue position numbering of each amino acid residue of a human TIGIT variant of interest or epitope. In some embodiments, one amino acid sequence corresponds to another amino acid sequence if it shares at least about 80%, 81%, 82%, 83%, 84%, 85%, 86%, 87%, 88%, 89%, 90%, 91%, 92%, 93%, 94%, 95%, 96%, 97%, 98%, 99%, or 100% sequence identity.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" or "including," or any grammatical variant thereof, one or more recited elements can include other elements not specifically recited. For example, a composition that includes antibody can contain the antibody alone or in combination with other ingredients.

Certain ranges are presented herein with numerical values being preceded by the term "about." The term "about" is used herein has its original meaning of approximately and is to provide literal support for the exact number that it precedes, as well as a number that is near to or approximately the number that the term precedes. In determining whether a number is near to or approximately a specifically recited number, the near or approximating unrecited number can be a number which, in the context in which it is presented, provides the substantial equivalent of the specifically recited number. For example, if the degree of approximation is not otherwise clear from the context, "about" means either within plus or minus 10% of the provided value, or rounded to the nearest significant figure, in all cases inclusive of the provided value. Where ranges are provided, they are inclusive of the boundary values.

The term "substantially" and any grammatical variant thereof, as used herein, is a broad term and is used in its ordinary sense, including, without limitation, being almost wholly or to a large extent, but not entirely. For example, the term can refer to a numerical value that may not be 100% the full numerical value, wherein the numerical value can be less than 0.1%, less than 0.5%, less than about 1%, less than about 2%, less than about 3%, less than about 4%, less than about 5%, less than about 6%, less than about 7%, less than about 8%, less than about 9%, less than about 10%, less than about 11%, less than about 12%, less than about 13%, less than about 14%, less than about 15%, less than about 16%, less than about 17%, less than about 18%, less than about 19%, or less than about 20% of the full numerical value. For example, a subject antibody or antigen-binding fragment thereof can be substantially from a corresponding reference antibody or antigen-binding fragment thereof when the subject antibody or antigen-binding fragment thereof has at least about 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.9% sequence identity to the corresponding reference antibody or antigen-binding fragment thereof. In another example, a CDR in a subject antibody can be substantially from a corresponding CDR in a reference antibody when the CDR in the subject antibody has at least about 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.9% sequence identity to the corresponding CDR in the reference antibody. In yet another example, without limitation, a CDR in a subject antibody can be substantially from a corresponding CDR in a reference antibody when no more than two amino acids are substituted, deleted, or added in the CDR in the subject antibody in reference to the corresponding CDR in the reference antibody.

It is appreciated that certain features of the disclosure, which are, for clarity, described in the context of separate embodiments, can also be provided in combination in a single embodiment. Conversely, various features of the disclosure, which are, for brevity, described in the context of a single embodiment, can also be provided separately or in any suitable sub-combination. All combinations of the embodiments pertaining to the disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub combination was individually and explicitly disclosed herein.

II. Target Molecules

Unless otherwise indicated TIGIT means human TIGIT (hTIGIT). Cyno TIGIT or cTIGIT refers to a cynomolgus monkey TIGIT.

An exemplary hTIGIT sequence is assigned Swiss-Prot accession number Q495A1. The complete hTIGIT sequence has 244 amino acids (SEQ ID NO: 80) of which amino acids 1-21 are a signal peptide and 22-244 constitute the mature protein (SEQ ID NO: 81). Approximately residues 22-141 constitute an extracellular domain of hTIGIT (SEQ ID NO: 82). Approximately residues 142-162 constitute a transmembrane domain of hTIGIT, and approximately residues 163-244 constitute a cytoplasmic domain of hTIGIT. In some embodiments, the extracellular domain hTIGIT is HIS tagged (SEQ ID NO: 83). An exemplary cyno TIGIT sequence is assigned Swiss-Prot A0A2K5UW92. The complete cyno TIGIT sequence has 312 amino acids (SEQ ID NO: 84). In some embodiments, the extracellular domain of cyno TIGIT is HIS tagged (SEQ ID NO: 85).

Unless otherwise indicated CD155 refers to the human form of this protein. An exemplary human sequence for human CD155 is designated Swiss-Prot P15151, which is a protein of 417 amino acids of which approximately residues 1-20 are a signal peptide, 21-343 constitute an extracellular domain (SEQ ID NO: 86), 344-367 constitute a transmembrane domain, and 368-417 constitute a cytoplasmic domain.

Unless otherwise apparent from the context, reference to one of the above proteins means at least the extracellular domain of the protein and usually the complete protein other than a cleavable signal peptide.

III. Antibodies of the Disclosure

A. Binding Specificity and Functional Properties

The present disclosure provides antibodies that specifically bind to TIGIT, more particularly to epitopes within the extracellular domain of TIGIT protein. In certain embodiments, the anti-TIGIT antibodies of the present disclosure have a KD for TIGIT of $10^{-8}$ M or lower (e.g., $10^{-8}$, $10^{-9}$, $10^{-10}$, etc.), measured by surface plasmon resonance (SPR). In various embodiments, the anti-TIGIT antibodies of the present disclosure have a KD for TIGIT in the range of about $1\times10^{-9}$ M to about $1\times10^{-13}$ M, or about $1\times10^{-9}$ M to about $1\times10^{-12}$ M, or about $1\times10^{-10}$ M to about $1\times10^{-13}$ M, or about $1\times10^{-10}$ M to about $1\times10^{-12}$ M, or about $1\times10^{-11}$ M to about $1\times10^{-13}$ M, or about $1\times10^{-10}$ M to about $1\times10^{-11}$ M, or about $1\times10^{-11}$ M to about $1\times10^{-12}$ M. Antibodies designated 21F8, 30M18, 24F8, 5J24, 21B9, 22B22, 28P24, 21B16, and 28O12 are nine such exemplary mouse antibodies. Antibodies designated Ch22B22, Ch21B16, Ch28O12, Ch5J24, Ch21B9, Ch24F8, and Ch30M18 are seven such exemplary chimera antibodies. Antibodies designated Hu24F8.1. Hu24F8.2, Hu24F8.3 and Hu24F8.4 are exemplary humanized antibodies. The sequences of the heavy and light chain mature variable regions and the CDRs of the mouse and humanized antibodies are shown in Table 1 and Table 2, respectively.

TABLE 1

The Sequences of the Heavy and Light Chain Mature Variable Regions

| Antibody | Heavy chain variable region | Light chain variable region |
|---|---|---|
| 21F8 | SEQ ID NO: 1 | SEQ ID NO: 2 |
| 30M18 | SEQ ID NO: 3 | SEQ ID NO: 4 |
| 24F8 | SEQ ID NO: 5 | SEQ ID NO: 6 |
| 5J24 | SEQ ID NO: 7 | SEQ ID NO: 8 |
| 21B9 | SEQ ID NO: 9 | SEQ ID NO: 10 |
| 22B22 | SEQ ID NO: 11 | SEQ ID NO: 12 |
| 28P24 | SEQ ID NO: 13 | SEQ ID NO: 14 |
| 21B16 | SEQ ID NO: 15 | SEQ ID NO: 16 |
| 28O12 | SEQ ID NO: 17 | SEQ ID NO: 12 |
| Hu24F8.1 | SEQ ID NO: 76 | SEQ ID NO: 77 |
| Hu24F8.2 | SEQ ID NO: 78 | SEQ ID NO: 77 |
| Hu24F8.3 | SEQ ID NO: 78 | SEQ ID NO: 79 |
| Hu24F8.4 | SEQ ID NO: 76 | SEQ ID NO: 79 |

TABLE 2

The Sequences of the Heavy and Light Chain CDRs (Kabat definition)

| Antibody | HC-CDR1 (SEQ ID NO) | HC-CDR2 (SEQ ID NO) | HC-CDR3 (SEQ ID NO) | LC-CDR1 (SEQ ID NO) | LC-CDR2 (SEQ ID NO) | LC-CDR3 (SEQ ID NO) |
|---|---|---|---|---|---|---|
| 21F8 | 36 | 37 | 38 | 39 | 40 | 41 |
| 30M18 | 42 | 43 | 44 | 45 | 46 | 47 |
| 24F8 | 48 | 49 | 50 | 51 | 52 | 53 |
| 5J24 | 54 | 55 | 56 | 57 | 58 | 59 |
| 21B9 | 60 | 61 | 62 | 63 | 64 | 65 |
| 22B22 | 60 | 66 | 67 | 63 | 68 | 65 |
| 28P24 | 69 | 55 | 70 | 71 | 68 | 65 |
| 21B16 | 72 | 73 | 67 | 63 | 68 | 65 |
| 28O12 | 74 | 75 | 67 | 63 | 68 | 65 |

Some antibodies of the present disclosure bind to the same or overlapping epitope as an antibody designated 21F8, 30M18, 24F8, 5J24, 21B9, 22B22, 28P24, 21B16, or 28O12, or an antibody designated Hu24F8.1, Hu24F8.2, Hu24F8.3, or Hu24F8.4. Other antibodies having such a binding specificity can be produced by immunizing mice with TIGIT or a portion thereof including the desired epitope, and screening resulting antibodies for binding to the extracellular domain of TIGIT, optionally in competition with 21F8, 30M18, 24F8, 5J24, 21B9, 22B22, 28P24, 21B16, 28O12, Hu24F8.1, Hu24F8.2, Hu24F8.3, or Hu24F8.4. Antibodies can also be screened against mutagenized forms of the TIGIT antigen to identify an antibody showing the same or similar binding profile to collection of mutational changes as 21F8, 30M18, 24F8, 5J24, 21B9, 22B22, 28P24, 21B16, 28O12, Hu24F8.1, Hu24F8.2, Hu24F8.3, or Hu24F8.4. The mutations can be systematic replacement substitution with alanine (or serine if an alanine is present already) one residue at a time, or more broadly spaced intervals, throughout the extracellular domain of TIGIT antibody or through a section thereof in which an epitope is known to reside. In some embodiments, some antibodies of the present disclosure bind to at least one of the following epitope residues of TIGIT: T55, Q56, N58, E60, D72, S80, and K82 of SEQ ID NO: 80. In some embodiments, some antibodies of the present disclosure bind to two, three, four, five, or six of the following epitope residues of TIGIT: T55, Q56, N58, E60, D72, S80, and K82 of SEQ ID NO: 80. In some embodiments, some antibodies of the present disclosure bind to the following epitope residues of TIGIT: T55, Q56, N58, E60, D72, S80, and K82. In some embodiments, the anti-TIGIT antibody binds to an epitope that includes at least the following residues of TIGIT: D72 of SEQ ID NO: 80 and at least one of T55, Q56, N58, E60, S80, and K82 of SEQ ID NO: 80. In some embodiments, the anti-TIGIT antibody binds to an epitope that includes at least the following residues of TIGIT: E60 and D72 of SEQ ID NO: 80 and optionally at least one of T55, Q56, N58, S80, and K82 of SEQ ID NO: 80. In some embodiments, the anti-TIGIT antibody binds to an epitope that includes at least the following residues of TIGIT: D72 and K82 of SEQ ID NO: 80 and optionally at least one of T55, Q56, N58, E60, and S80 of SEQ ID NO: 80. In some embodiments, the anti-TIGIT antibody binds to an epitope that includes at least the following residues of TIGIT: E60, D72 and K82 of SEQ ID NO: 80 and optionally at least one of T55, Q56, N58, and S80 of SEQ ID NO: 80.

Antibodies having the binding specificity of a selected murine antibody (e.g., 21F8, 30M18, 24F8, 5J24, 21B9, 22B22, 28P24, 21B16, or 28O12) or of a selected humanized antibody (e.g., Hu24F8.1, Hu24F8.2, Hu24F8.3, or Hu24F8.4) can also be produced using a variant of the phage display method. See Winter, WO 92/20791. This method is particularly suitable for producing human antibodies. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions can, for example, be obtained from a library of rearranged human heavy chain variable regions. A phage showing strong specific binding for TIGIT (e.g., at least $10^8$ or at least $10^9$ $M^{-1}$) is selected. The heavy chain variable region from this phage then serves as a starting material for constructing a further phage library. In this library, each phage displays the same heavy chain variable region (i.e., the region identified from the first display library) and a different light chain variable region. The light chain variable regions can be obtained, for example, from a library of rearranged human variable light chain regions. Again, phage showing strong specific binding for TIGIT are selected. The resulting antibodies usually have the same or similar epitope specificity as the murine starting material.

Some antibodies have a mature heavy chain variable region including HC-CDR1, HC-CDR2, and HC-CDR3 and a mature light chain region including LC-CDR1, LC-CDR2, and LC-CDR3 entirely or substantially from mAb 21F8. Some antibodies have a mature heavy chain variable region including HC-CDR1, HC-CDR2, and HC-CDR3 and a mature light chain region including LC-CDR1, LC-CDR2, and LC-CDR3 entirely or substantially from mAb 30M18. Some antibodies have a mature heavy chain variable region including HC-CDR1, HC-CDR2, and HC-CDR3 and a mature light chain region including LC-CDR1, LC-CDR2, and LC-CDR3 entirely or substantially from mAb 24F8. Some antibodies have a mature heavy chain variable region including HC-CDR1, HC-CDR2, and HC-CDR3 and a mature light chain region including LC-CDR1, LC-CDR2, and LC-CDR3 entirely or substantially from mAb 5J24. Some antibodies have a mature heavy chain variable region including HC-CDR1, HC-CDR2, and HC-CDR3 and a mature light chain region including LC-CDR1, LC-CDR2, and LC-CDR3 entirely or substantially from mAb 21B9. Some antibodies have a mature heavy chain variable region including HC-CDR1, HC-CDR2, and HC-CDR3 and a mature light chain region including LC-CDR1, LC-CDR2, and LC-CDR3 entirely or substantially from mAb 22B22. Some antibodies have a mature heavy chain variable region including HC-CDR1, HC-CDR2, and HC-CDR3 and a mature light chain region including LC-CDR1, LC-CDR2, and LC-CDR3 entirely or substantially from mAb 28P24. Some antibodies have a mature heavy chain variable region including HC-CDR1, HC-CDR2, and HC-CDR3 and a mature light chain region including LC-CDR1, LC-CDR2, and LC-CDR3 entirely or substantially from mAb 21B16. Some antibodies have a mature heavy chain variable region including HC-CDR1, HC-CDR2, and HC-CDR3 and a mature light chain region including LC-CDR1, LC-CDR2, and LC-CDR3 entirely or substantially from mAb 28O12. CDRs can be defined by any conventional definition including Kabat, Chothia, Kabat and Chothia composite, AbM or Contact definition as shown in the Table 3 below:

TABLE 3

| Loop | Kabat | AbM | Chothia | Contact |
|---|---|---|---|---|
| L1 | L-24-L34 | L24-34 | L24-L34 | L30-L36 |
| L2 | L50-L56 | L50-l56 | L50-L56 | L46-L55 |
| L3 | L89-L97 | L89-97 | L89-L97 | L89-L96 |
| H1 | H31-H35B (Kabat Numbering) | H26-H35b | H26-H32 . . . 34 | H30-H35B |
| H1 | H31-H35 (Chothia Numbering) | H26-H35 | H26-H32 | H30-H35 |
| H2 | H50-H65 | H50-H58 | H52-H56 | H47-H58 |
| H3 | H95-H102 | H95-H102 | H95-H102 | H93-H10 |

Other antibodies can be obtained by mutagenesis of cDNA encoding the heavy and light chains of an exemplary antibody, such as 21F8, 30M18, 24F8, 5J24, 21B9, 22B22, 28P24, 21B16, or 28O12. Antibodies that are at least any of about 80%, 81%, 82%, 83%, 84%, 85%, 86%, 87%, 88%, 89%, 90%, 91%, 92%, 93%, 94%, 95%, 96%, 97%, 98%, 99% or 100% identical to 21F8, 30M18, 24F8, 5J24, 21B9, 22B22, 28P24, 21B16, or 28O12 in amino acid sequence of the mature heavy and/or light chain variable regions and maintain its functional properties, and/or which differ from the respective antibody by a small number of functionally inconsequential amino acid substitutions (e.g., conservative substitutions), deletions, or insertions are also included in the present disclosure. Amino acids in the variable region frameworks likely important for binding can be identified as described in the sections on humanization below. Antibodies having at least one, and in some embodiments all six, CDR(s) as defined by Kabat that are any of about 80%, 81%, 82%, 83%, 84%, 85%, 86%, 87%, 88%, 89%, 90%, 91%, 92%, 93%, 94%, 95%, 96%, 97%, 98%, 99% or 100% identical to corresponding CDRs of 21F8, 30M18, 24F8, 5J24, 21B9, 22B22, 28P24, 21B16, or 28O12 are also included.

In some embodiments, the antibodies have one or more of the following characteristics (i) inhibiting binding of human TIGIT to human CD155, (ii) inhibiting binding of TIGIT to other ligands, such as CD112, and CD113, (iii) increasing antigen-specific T cell responses, (iv) activating natural killer cells, (v) stimulating intrinsic T cell activations, and (vi) stimulating production of one or more immunostimulatory cytokines and/or reducing production of one or more immunosuppressive cytokines by T cells and other cells of the immune system.

In some embodiments, antibodies described herein completely or partially inhibit binding of TIGIT to CD155. Anti-TIGIT antibodies of the present disclosure can inhibit such interaction with a half maximal inhibitory concentration for inhibition (IC50) of about 0.1 nM to about 10 nM, or about 0.1 nM to about 8 nM, or about 0.1 nM to about 5 nM, or about 0.1 nM to about 4 nM, or about 0.1 nM to about 3 nM, or about 0.1 nM to about 2 nM, or about 0.1 nM to about 1 nM measured as in Example 1. In certain embodiments, some anti-TIGIT antibodies of the present disclosure can inhibit binding of TIGIT to CD155 with an IC50 of about 0.1 nM to about 2 nM, or about 0.2 nM to about 2 nM, measured as in Example 1. In certain embodiments, some anti-TIGIT antibodies of the present disclosure can inhibit binding of TIGIT to CD155 with an IC50 of about 0.2 nM to about 2 nM, about 0.2 nM to about 0.8 nM, about 0.4 nM to about 0.8 nM, or about 0.6 nM to about 0.8 nM, measured as in Example 1. Some antibodies can inhibit such interaction with a half maximal inhibitory concentration for inhibition ($IC_{50}$) of any of about 25-300 ng/ml, 25-75 ng/ml, 25-50 ng/ml, 40-75 ng/ml, 50-75 ng/ml, 50-90 ng/ml, 50-100 ng/ml, 75-100 ng/ml, 50-150 ng/ml, 75-175 ng/ml, 100-200 ng/ml, 125-225 ng/ml, 100-250 ng/ml, 150-300 ng/ml, 175-250 ng/ml, 200-300 ng/ml, 25-275 ng/ml, 250-300 ng/ml, 49+/−10% ng/ml, 65+/−10% ng/ml or 76+/−10% ng/ml, measured as in Example 1. In other embodiments, the antibodies can completely or partially inhibit binding of TIGIT to CD155 with an IC50 of any of at least about 25 ng/ml, 50 ng/ml, 75 ng/ml, 100 ng/ml, 125 ng/ml, 150 ng/ml, 175 ng/ml, 200 ng/ml, 225 ng/ml, 250 ng/ml, 275 ng/ml, or 300 ng/ml, or more, inclusive of concentrations falling in between these values. In addition, some antibodies can increase antigen-specific T cell responses by 1.5-3 fold, such as any of about 1.5, 1.6, 1.7, 1.8, 1.9, 2, 2.1, 2.2, 2.3, 2.4, 2.5, 2.6, 2.7, 2.8, 2.9, or 3 fold or more. Alternatively or in addition, some antibodies can increase production of 1, 2, 3 or all of IL-2, IL-6, TNFα and IFNγ by NK cells and/or T cells by 1.5 to 3 fold, such as any of about 1.5, 1.6, 1.7, 1.8, 1.9, 2, 2.1, 2.2, 2.3, 2.4, 2.5, 2.6, 2.7, 2.8, 2.9, or 3 fold or more. Alternatively or in addition, some antibodies can increase intrinsic T cell activation by 1.5-3 fold, such as any of about 1.5, 1.6, 1.7, 1.8, 1.9, 2, 2.1, 2.2, 2.3, 2.4, 2.5, 2.6, 2.7, 2.8, 2.9, or 3 fold or more. Alternatively, or in addition, some antibodies can inhibit a cancer or an infectious disease as shown in an animal model or clinical trial. Animal models of cancer in which human cancer cells are injected into an immunodeficient laboratory animal, such as a mouse or rat, are widely available.

In an exemplary embodiment, an antibody specifically binds to TIGIT and comprises a mature heavy chain variable region including HC-CDR1, HC-CDR2, and HC-CDR3 and a mature light chain region including LC-CDR1, LC-CDR2, and LC-CDR3 entirely or substantially from antibody 24F8. In various embodiments, the antibody can (i) have an equilibrium binding constant (KD) of about $0.01 \times 10^{-11}$ M to about $100 \times 10^{-11}$ M, about $0.1 \times 10^{-11}$ M to about $100 \times 10^{-11}$ M, about $0.1 \times 10^{-11}$ M to about $10 \times 10^{-11}$ M, about $1 \times 10^{-11}$ M to about $100 \times 10^{-11}$ M, measured by surface plasmon resonance, and/or (ii) block binding of soluble human CD155 ligand to cell surface human TIGIT with a half maximal inhibitor concentration (IC50) of about 0.2 nM to about 2 nM, about 0.2 nM to about 0.8 nM, about 0.4 nM to about 0.8 nM, or about 0.6 nM to about 0.8 nM, measured as in Example 1. Alternatively and or in addition to the individual binding and blocking properties above or their combination, in some embodiments the antibody binds to an epitope that includes at least the following residues of TIGIT: (i) D72 of SEQ ID NO: 80 and at least one of T55, Q56, N58, E60, S80, and K82 of SEQ ID NO: 80, (ii) E60 and D72 of SEQ ID NO: 80 and optionally at least one of T55, Q56, N58, S80, and K82 of SEQ ID NO: 80, (iii) D72 and K82 of SEQ ID NO: 80 and optionally at least one of T55, Q56, N58, E60, and S80 of SEQ ID NO: 80, (iv) E60, D72 and K82 of SEQ ID NO: 80 and optionally at least one of T55, Q56, N58, and S80 of SEQ ID NO: 80, or (v) T55, Q56, N58, E60, D72, S80, and K82 of SEQ ID NO: 80.

Humanizing or chimerizing antibodies increases in vivo half-life relative to starting mouse antibodies. The resulting half-life can be 10-50 days, for example, in humans. Half-live can be measured by pharmacokinetic studies, such as described by Kim et al, *Eur J of Immunol* 24:542 (1994).

B. Non-Human Antibodies

The production of other non-human antibodies, e.g., murine, guinea pig, primate, rabbit, chicken or rat, against TIGIT can be accomplished by, for example, immunizing the animal with TIGIT or a fragment thereof, or cells bearing TIGIT. See Harlow & Lane, *Antibodies, A Laboratory Manual* (CSHP NY, 1988) (incorporated by reference for all purposes). Such an immunogen can be obtained from a natural source, by peptide synthesis or by recombinant expression. Optionally, the immunogen can be administered fused or otherwise complexed with a carrier protein. Optionally, the immunogen can be administered with an adjuvant. Several types of adjuvant can be used as described below. Complete Freund's adjuvant followed by incomplete adjuvant can be used for immunization of laboratory animals. Rabbits or guinea pigs are typically used for making polyclonal antibodies. Mice are typically used for making monoclonal antibodies. Antibodies are screened for specific binding to TIGIT. Optionally, antibodies are further screened for binding to a specific region of TIGIT. Such screening can be accomplished by determining binding of an antibody to a collection of deletion mutants of TIGIT and determining which deletion mutants bind to the antibody. Binding can be assessed, for example, by Western blot, FACS or ELISA.

C. Humanized Antibodies

Reduction or elimination of a HAMA (human anti-mouse (also applicable to human anti-rat or human anti-rabbit or human anti-hamster, etc.) antibody) response is a significant aspect of clinical development of suitable therapeutic agents. See, e.g., Khaxzaeli et al., *J. Natl. Cancer Inst.* (1988), 80:937; Jaffers et al., *Transplantation* (1986), 41:572; Shawler et al., *J. Immunol.* (1985), 135:1530; Sears et al., *J. Biol. Response Mod.* (1984), 3:138; Miller et al., *Blood* (1983), 62:988; Hakimi et al., *J. Immunol.* (1991), 147:1352; Reichmann et al., *Nature* (1988), 332:323; Junghans et al., *Cancer Res.* (1990), 50:1495. As described herein, the present disclosure provides antibodies that are humanized such that a HAMA response is reduced or eliminated. Variants of these antibodies can further be obtained using routine methods known in the art, some of which are further described below.

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539, Carter, U.S. Pat. No. 6,407,213, Adair, U.S. Pat. Nos. 5,859,205, 6,881,557, Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having some or all CDRs entirely or substantially from a donor antibody and variable region framework sequences and constant regions, if present, entirely or substantially from human antibody sequences. Similarly, a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly, a humanized light chain has at least one, two and usually all three CDRs entirely or substantially from a donor antibody light chain, and a light chain variable region framework sequence and light chain constant region, if present, substantially from human light chain variable region framework and constant region sequences. Here as elsewhere in the application, a CDR in a subject antibody is substantially from a corresponding CDR in a reference antibody when at least about 80%, 81%, 82%, 83%, 84%, 85%, 86%, 87%, 88%, 89%, 90%, 91%, 92%, 93%, 94%, 95%, 96%, 97%, 98%, 99% or 100% of corresponding residues (as defined by Kabat) are identical between the respective CDRs; however, a CDR H2 as defined by Kabat in a subject antibody is substantially from a corresponding CDR in a reference antibody when at least about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% of corresponding residues (as defined by Kabat) are identical between the respective CDRs. The variable region framework sequences of an antibody chain or the constant region of an antibody chain are substantially from a human variable region framework sequence or human constant region respectively when at least about 80%, 81%, 82%, 83%, 84%, 85%, 86%, 87%, 88%, 89%, 90%, 91%, 92%, 93%, 94%, 95%, 96%, 97%, 98%, 99% or 100% of corresponding residues defined by Kabat are identical.

Although humanized antibodies often incorporate all six CDRs (such as defined by Kabat) from a non-human (e.g. mouse) antibody, they can also be made with less than all CDRs (e.g., at least 3, 4, or 5) CDRs from a non-human antibody (e.g., Pascalis et al., *J. Immunol.* 169:3076, 2002; Vajdos et al., *Journal of Molecular Biology*, 320: 415-428, 2002; Iwahashi et al., *Mol. Immunol.* 36:1079-1091, 1999; Tamura et al, *Journal of Immunology*, 164:1432-1441, 2000).

In some antibodies only part of the CDRs, namely the subset of CDR residues required for binding, termed the SDRs, are needed to retain binding in a humanized antibody. CDR residues not contacting antigen and not in the SDRs can be identified based on previous studies (for example, residues H60-H65 in CDR H2 are often not required), from regions of Kabat CDRs lying outside Chothia hypervariable loops (Chothia, *J Mol. Biol.* 196:901, 1987), by molecular modeling and/or empirically, or as described in Gonzales et al., *Mol. Immunol.* 41: 863, 2004. In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity can be avoided. Positions for substitution within CDRs and amino acids to substitute can also be selected empirically.

While the acceptor can be identical in sequence to the human framework sequence selected, whether that is from a human immunoglobulin or a human consensus framework, the present disclosure contemplates that the acceptor sequence can include pre-existing amino acid substitutions relative to the human immunoglobulin sequence or human consensus framework sequence. These pre-existing substitutions can be minimal; generally four, three, two or one amino acid differences only relative to the human immunoglobulin sequence or consensus framework sequence.

The human acceptor antibody sequences can optionally be selected from among the many known human antibody sequences to provide a high degree of sequence identity (e.g., 65-85% identity) between a human acceptor sequence variable region frameworks and corresponding variable region frameworks of a donor antibody chain.

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a non-human variable region framework residue and a selected human variable region framework residue, the human framework amino acid can be substituted by the equivalent framework amino acid from the non-human antibody when it is reasonably expected that the amino acid:

(1) noncovalently binds antigen directly,
(2) is adjacent to a CDR region,
(3) otherwise interacts with a CDR region (e.g. is within about 6 Å of a CDR region).

Other candidates for substitution are acceptor human framework amino acids that are unusual for a human immunoglobulin at that position. These amino acids can be substituted with amino acids from the equivalent position of the non-human donor antibody or from the equivalent positions of more typical human immunoglobulins. Other candidates for substitution are acceptor human framework amino acids that are unusual for a human immunoglobulin at that position.

In some embodiments, a humanized anti-TIGIT antibody has a mature heavy chain variable region including a CDR1 comprising an amino acid sequence of SEQ ID NO: 48 with zero to two amino acid substitutions or deletions, a CDR2 comprising an amino acid sequence of SEQ ID NO: 49 with zero to two amino acid substitutions or deletions, a CDR3 comprising an amino acid sequence of SEQ ID NO: 50 with zero to two amino acid substitutions or deletions, and framework regions having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity to the framework regions of GenBank accession number AAV40102.1 or to the framework regions of GenBank accession number ADX65334.1; and has a mature light chain variable region including a CDR1 comprising an amino acid sequence of SEQ ID NO: 51 with zero to two amino acid substitutions or deletions, a CDR2 comprising an amino acid sequence of SEQ ID NO: 52 with zero to two amino acid substitutions or deletions, a CDR3 comprising an amino acid sequence of SEQ ID NO: 53 with zero to two amino acid substitutions or deletions, and framework regions having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity to the framework regions of GenBank accession number ACY78416.1 or to the framework regions of GenBank accession number ADU32611.1. Framework regions for AAV40102.1, ADX65334.1, ACY78416.1, and ADU32611.1 are determined according to Kabat definitions, see Example 2 or see SEQ ID NOs: 76-79, which contains the framework regions of AAV40102.1, ADX65334.1, ACY78416.1, and ADU32611.1 and donor CDRs. In some embodiments, the mature heavy chain variable region is linked to at least a portion of a heavy chain constant region and the mature light chain variable region is linked to at least a portion of a light chain constant region. In some embodiments, for expression of a full-length antibody, the mature heavy chain variable region is linked to a heavy chain constant region and the mature light chain variable region is linked to a light chain constant region. Suitable constant regions are described in further detail in Section III(F). In certain embodiments of the above, the heavy chain constant region has functional FcγR binding capability. In still further embodiments, the heavy chain constant region comprises or consists of SEQ ID NO: 94 and the light chain constant region comprises of consists of SEQ ID NO: 95. In certain embodiments of the above, the heavy chain constant region has reduced functional FcγR binding capability. In further embodiments, the heavy chain constant region comprises or consists of SEQ ID NO: 97 and the light chain constant region comprises of consists of SEQ ID NO: 95. In still further embodiments, the heavy chain constant region comprises or consists of SEQ ID NO: 101 and the light chain constant region comprises of consists of SEQ ID NO: 95. In certain embodiments of the above, the heavy chain constant region has enhanced functional FcγR binding capability. In further embodiments, the heavy chain constant region comprises or consists of SEQ ID NO: 99 and the light chain constant region comprises of consists of SEQ ID NO: 95.

In some embodiments, a humanized anti-TIGIT antibody has a mature heavy chain variable region having at least about 80%, 81%, 82%, 83%, 84%, 85%, 86%, 87%, 88%, 89%, 90%, 91%, 92%, 93%, 94%, 95%, 96%, 97%, 98%, 99%, or less than 100% identity to SEQ ID NO: 76 and a mature light chain variable region having at least about 80%, 81%, 82%, 83%, 84%, 85%, 86%, 87%, 88%, 89%, 90%, 91%, 92%, 93%, 94%, 95%, 96%, 97%, 98%, 99%, or less than 100% identity to SEQ ID NO: 77. In some embodiments, any variation occurs at variable region framework residues other than those identified as likely important to binding. In some embodiments, any variation is a conservative amino acid substitution. In some embodiments, the antibody includes a mature heavy chain variable region with the sequence of SEQ ID NO: 76 and a mature light chain variable region with the sequence of SEQ ID NO: 77. Hu24F8.1 antibodies of the present disclosure comprise a mature heavy chain variable region with the sequence of SEQ ID NO: 76 and a mature light chain variable region with the sequence of SEQ ID NO: 77. In some embodiments of the above, the mature heavy chain variable region is linked to at least a portion of a heavy chain constant region and the mature light chain variable region is linked to at least a portion of a light chain constant region. In some embodiments, for expression of a full-length antibody, the mature heavy chain variable region is linked to a heavy chain constant region and the mature light chain variable region is linked to a light chain constant region. Suitable constant regions are described in further detail in Section III(F). In certain embodiments of the above, the heavy chain constant region can induce Fcγ receptor (FcγR)-mediated signaling, measured in commercially available antibody-dependent cell-mediated toxicity report bioassay kits according to manufacturer's instructions. In still further embodiments, the heavy chain constant region comprises or consists of SEQ ID NO: 94 and the light chain constant region comprises of consists of SEQ ID NO: 95. In other embodiments, the heavy chain constant region does not induce Fcγ receptor (FcγR)-mediated signaling, measured in commercially available antibody-dependent cell-mediated toxicity report bioassay kits according to manufacturer's instructions.

In some embodiments, a humanized anti-TIGIT antibody has a mature heavy chain variable region having at least about 80%, 81%, 82%, 83%, 84%, 85%, 86%, 87%, 88%, 89%, 90%, 91%, 92%, 93%, 94%, 95%, 96%, 97%, 98%, 99%, or less than 100% identity to SEQ ID NO: 78 and a mature light chain variable region having at least about 80%, 81%, 82%, 83%, 84%, 85%, 86%, 87%, 88%, 89%, 90%, 91%, 92%, 93%, 94%, 95%, 96%, 97%, 98%, 99%, or less than 100% identity to SEQ ID NO: 77. In some embodiments, any variation occurs at variable region framework residues other than those identified as likely important to binding. In some embodiments, any variation is a conservative amino acid substitution. In some embodiments, the antibody includes a mature heavy chain variable region with the sequence of SEQ ID NO: 78 and a mature light chain variable region with the sequence of SEQ ID NO: 77. Hu24F8.2 antibodies of the present disclosure comprise a mature heavy chain variable region with the sequence of SEQ ID NO: 78 and a mature light chain variable region with the sequence of SEQ ID NO: 77. In some embodiments of the above, the mature heavy chain variable region is linked to at least a portion of a heavy chain constant region and the mature light chain variable region is linked to at least a portion of a light chain constant region. In some embodiments, for expression of a full-length antibody, the mature heavy chain variable region is linked to a heavy chain constant region and the mature light chain variable region is linked to a light chain constant region. Suitable constant regions are described in further detail in Section III(F). In certain embodiments of the above, the heavy chain constant region can induce Fcγ receptor (FcγR)-mediated signaling, measured in commercially available antibody-dependent cell-mediated toxicity report bioassay kits according to manufacturer's instructions. In still further embodiments, the heavy chain constant region comprises or consists of SEQ ID NO: 94 and the light chain constant region comprises of consists of SEQ ID NO: 95. In other embodiments, the heavy chain constant region does not induce Fcγ receptor (FcγR)-mediated signaling, measured in commercially available antibody-dependent cell-mediated toxicity report bioassay kits according to manufacturer's instructions. In some embodiments, the heavy chain constant region comprises or consists of SEQ ID NO: 97 and the light chain constant region comprises of consists of SEQ ID NO: 95. In other embodiments, the heavy chain constant region comprises or consists of SEQ ID NO: 101 and the light chain constant region comprises of consists of SEQ ID NO: 95. In other embodiments, the heavy chain constant region induces enhanced Fcγ receptor (FcγR)-mediated signaling, measured in commercially available antibody-dependent cell-mediated toxicity report bioassay kits according to manufacturer's instructions. In some embodiments, the heavy chain constant region comprises or consists of SEQ ID NO: 99 and the light chain constant region comprises of consists of SEQ ID NO: 95.

In some embodiments, a humanized anti-TIGIT antibody has a mature heavy chain variable region having at least about 80%, 81%, 82%, 83%, 84%, 85%, 86%, 87%, 88%, 89%, 90%, 91%, 92%, 93%, 94%, 95%, 96%, 97%, 98%, 99%, or less than 100% identity to SEQ ID NO: 76 and a mature light chain variable region having at least about 80%, 81%, 82%, 83%, 84%, 85%, 86%, 87%, 88%, 89%, 90%, 91%, 92%, 93%, 94%, 95%, 96%, 97%, 98%, 99%, or less than 100% identity to SEQ ID NO: 79. In some embodiments, any variation occurs at variable region framework residues other than those identified as likely important to binding. In some embodiments, any variation is a conservative amino acid substitution. In some embodiments, the antibody includes a mature heavy chain variable region with the sequence of SEQ ID NO: 76 and a mature light chain variable region with the sequence of SEQ ID NO: 79. Hu24F8.3 antibodies of the present disclosure comprise a mature heavy chain variable region with the sequence of SEQ ID NO: 78 and a mature light chain variable region with the sequence of SEQ ID NO: 79. In some embodiments of the above, the mature heavy chain variable region is linked to at least a portion of a heavy chain constant region and the mature light chain variable region is linked to at least a portion of a light chain constant region. In some embodiments, for expression of a full-length antibody, the mature heavy chain variable region is linked to a heavy chain constant region and the mature light chain variable region is linked to a light chain constant region. Suitable constant regions are described in further detail in Section III(F). In certain embodiments of the above, the heavy chain constant region can induce Fcγ receptor (FcγR)-mediated signaling, measured in commercially available antibody-dependent cell-mediated toxicity report bioassay kits according to manufacturer's instructions. In still further embodiments, the heavy chain constant region comprises or consists of SEQ ID NO: 94 and the light chain constant region comprises of consists of SEQ ID NO: 95. In other embodiments, the heavy chain constant region does not induce Fcγ receptor (FcγR)-mediated signaling, measured in commercially available antibody-dependent cell-mediated toxicity report bioassay kits according to manufacturer's instructions. In some embodiments, the heavy chain constant region comprises or consists of SEQ ID NO: 97 and the light chain constant region comprises of consists of SEQ ID NO: 95. In other embodiments, the heavy chain constant region comprises or consists of SEQ ID NO: 101 and the light chain constant region comprises of consists of SEQ ID NO: 95. In other embodiments, the heavy chain constant region induces enhanced Fcγ receptor (FcγR)-mediated signaling, measured in commercially available antibody-dependent cell-mediated toxicity report bioassay kits according to manufacturer's instructions. In some embodiments, the heavy chain In some embodiments, a humanized anti-TIGIT antibody has a mature heavy chain variable region having at least about 80%, 81%, 82%, 83%, 84%, 85%, 86%, 87%, 88%, 89%, 90%, 91%, 92%, 93%, 94%, 95%, 96%, 97%, 98%, 99%, or less than 100% identity to SEQ ID NO: 78 and a mature light chain variable region having at least about 80%, 81%, 82%, 83%, 84%, 85%, 86%, 87%, 88%, 89%, 90%, 91%, 92%, 93%, 94%, 95%, 96%, 97%, 98%, 99%, or less than 100% identity to SEQ ID NO: 79. In some embodiments, any variation occurs at variable region framework residues other than those identified as likely important to binding. In some embodiments, any variation is a conservative amino acid substitution. In some embodiments, the antibody includes a mature heavy chain variable region with the sequence of SEQ ID NO: 78 and a mature light chain variable region with the sequence of SEQ ID NO: 79. Hu24F8.4 antibodies of the present disclosure comprise a mature heavy chain variable region with the sequence of SEQ ID NO: 76 and a mature light chain variable region with the sequence of SEQ ID NO: 79. In some embodiments of the above, the mature heavy chain variable region is linked to at least a portion of a heavy chain constant region and the mature light chain variable region is linked to at least a portion of a light chain constant region. In some embodiments, for expression of a full-length antibody, the mature heavy chain variable region is linked to a heavy chain constant region and the mature light chain variable region is linked to a light chain constant region. Suitable constant regions are described in further detail in Section III(F). In certain embodiments of the above, the heavy chain constant region can induce Fcγ receptor (FcγR)-mediated signaling, measured in commercially available antibody-dependent cell-mediated toxicity report bioassay kits according to manufacturer's instructions. In still further embodiments, the heavy chain constant region comprises or consists of SEQ ID NO: 94 and the light chain constant region comprises of consists of SEQ ID NO: 95. In other embodiments, the heavy chain constant region does not induce Fcγ receptor (FcγR)-mediated signaling, measured in commercially available antibody-dependent cell-mediated toxicity report bioassay kits according to manufacturer's instructions. In some embodiments, the heavy chain constant region comprises or consists of SEQ ID NO: 97 and the light chain constant region comprises of consists of SEQ ID NO: 95. In other embodiments, the heavy chain constant region comprises or consists of SEQ ID NO: 101 and the light chain constant region comprises of consists of SEQ ID NO: 95. In other embodiments, the heavy chain constant region induces enhanced Fcγ receptor (FcγR)-mediated signaling, measured in commercially available antibody-dependent cell-mediated toxicity report bioassay kits according to manufacturer's instructions. In some embodiments, the heavy chain constant region comprises or consists of SEQ ID NO: 99 and the light chain constant region comprises of consists of SEQ ID NO: 95.

In further embodiments for each of the above, the humanized anti-TIGIT antibodies can (i) have an equilibrium binding constant (KD) of about $0.01 \times 10^{-11}$ M to about $100 \times 10^{-11}$ M, about $0.1 \times 10^{-11}$ M to about $100 \times 10^{-11}$ M, about $0.1 \times 10^{-11}$ M to about $10 \times 10^{-11}$ M, about $1 \times 10^{-11}$ M to about $100 \times 10^{-11}$ M, or even about $1 \times 10^{-11}$ M to about $10 \times 10^{-11}$ M, measured by surface plasmon resonance, and/or (ii) block binding of soluble human CD155 ligand to cell surface human TIGIT with a half maximal inhibitor concentration (IC50) of about 0.2 nM to about 2 nM, about 0.2 nM to about 0.8 nM, about 0.4 nM to about 0.8 nM, or about 0.6 nM to about 0.8 nM, measured as in Example 1. Alternatively and or in addition to the individual binding and blocking properties above or their combination, in some embodiments the humanized anti-TIGIT antibody binds to an epitope that includes at least the following residues of TIGIT: (i) D72 of SEQ ID NO: 80 and at least one of T55, Q56, N58, E60, S80, and K82 of SEQ ID NO: 80, (ii) E60 and D72 of SEQ ID NO: 80 and optionally at least one of T55, Q56, N58, S80, and K82 of SEQ ID NO: 80, (iii) D72 and K82 of SEQ ID NO: 80 and optionally at least one of T55, Q56, N58, E60, and S80 of SEQ ID NO: 80, (iv) E60, D72 and K82 of SEQ ID NO: 80 and optionally at least one of T55, Q56, N58, and S80 of SEQ ID NO: 80, or (v) T55, Q56, N58, E60, D72, S80, and K82 of SEQ ID NO: 80.

D. Chimeric and Veneered Antibodies

The present disclosure further provides chimeric and veneered forms of non-human antibodies, particularly the 21F8, 30M18, 24F8, 5J24, 21B9, 22B22, 28P24, 21B16, and 28O12 antibodies of the examples.

A chimeric antibody is an antibody in which the mature variable regions of light and heavy chains of a non-human antibody (e.g., a mouse) are combined with human light and heavy chain constant regions. Such antibodies substantially or entirely retain the binding specificity of the non-human antibody, and are about two-thirds human sequence.

A veneered antibody is a type of humanized antibody that retains some and usually all of the CDRs and some of the non-human variable region framework residues of a non-human antibody but replaces other variable region framework residues that can contribute to B- or T cell epitopes, for example, exposed residues (Padlan, *Mol. Immunol.* 28:489, 1991) with residues from the corresponding positions of a human antibody sequence. The result is an antibody in which the CDRs are entirely or substantially from a non-human antibody and the variable region frameworks of the non-human antibody are made more human-like by the substitutions. Veneered forms of the 21F8, 30M18, 24F8, 5J24, 21B9, 22B22, 28P24, 21B16, or 28O12 antibody are included in the present disclosure.

In some embodiments, a TIGIT chimeric antibody is a mouse human chimera having mouse variable domains and human IgG1/kappa constant domains. In an embodiment, a TIGIT chimeric antibody is a chimera Fab mVH+mVL constructed from the mouse 21F8VH (SEQ ID NO: 1) and 21F8VL (SEQ ID NO: 2) domains and human IgG1/kappa Fab constant domain (Ch21F8). In an embodiment, a TIGIT chimeric antibody is a chimera Fab mVH+mVL constructed from the mouse 30M18VH (SEQ ID NO: 3) and 30M18VL (SEQ ID NO: 4) domains and human IgG1/kappa Fab constant domain (Ch30M18). In an embodiment, a TIGIT chimeric antibody is a chimera Fab mVH+mVL constructed from the mouse 24F8VH (SEQ ID NO: 5) and 24F8VL (SEQ ID NO: 6) domains and human IgG1/kappa Fab constant domain (Ch24F8). In an embodiment, a TIGIT chimeric antibody is a chimera Fab mVH+mVL constructed from the mouse 5J24VH (SEQ ID NO: 7) and 5J24VL (SEQ ID NO: 8) domains and human IgG1/kappa Fab constant domain (Ch5J24). In an embodiment, a TIGIT chimeric antibody is a chimera Fab mVH+mVL constructed from the mouse 21B9VH (SEQ ID NO: 9) and 21B9VL (SEQ ID NO: 10) domains and human IgG1/kappa Fab constant domain (Ch21B9). In an embodiment, a TIGIT chimeric antibody is a chimera Fab mVH+mVL constructed from the mouse 22B22VH (SEQ ID NO: 11) and $22B22V_L$ (SEQ ID NO: 12) domains and human IgG1/kappa Fab constant domain (Ch22B22). In an embodiment, a TIGIT chimeric antibody is a chimera Fab mVH+mVL constructed from the mouse 28P24VH (SEQ ID NO: 13) and 28P24VL (SEQ ID NO: 14) domains and human IgG1/kappa Fab constant domain (Ch28P24). In an embodiment, a TIGIT chimeric antibody is a chimera Fab mVH+mVL constructed from the mouse 21B16VH (SEQ ID NO: 15) and 21B16VL (SEQ ID NO: 16) domains and human IgG1/kappa Fab constant domain (Ch21B16). In an embodiment, a TIGIT chimeric antibody is a chimera Fab mVH+mVL constructed from the mouse 28O12VH (SEQ ID NO: 17) and 28O12VL (SEQ ID NO: 12) domains and human IgG1/kappa Fab constant domain (Ch28O12).

E. Human Antibodies

Human antibodies against TIGIT are provided by a variety of techniques described below. Some human antibodies are selected by competitive binding experiments, by the phage display method of Winter, above, or otherwise, to have the same epitope specificity as a particular mouse antibody, such as one of the mouse monoclonal antibodies described in the examples. Human antibodies can also be screened for a particular epitope specificity by using only a fragment of TIGIT as the target antigen, and/or by screening antibodies against a collection of deletion mutants of TIGIT.

Methods for producing human antibodies include the trioma method of Oestberg et al., *Hybridoma* 2:361-367 (1983); Oestberg, U.S. Pat. No. 4,634,664; and Engleman et al., U.S. Pat. No. 4,634,666, use of transgenic mice including human immunoglobulin genes (see, e.g., Lonberg et al., WO93/12227 (1993); U.S. Pat. Nos. 5,877,397, 5,874,299, 5,814,318, 5,789,650, 5,770,429, 5,661,016, 5,633,425, 5,625,126, 5,569,825, 5,545,806, *Nature* 148, 1547-1553 (1994), *Nature Biotechnology* 14, 826 (1996), Kucherlapati, WO 91/10741 (1991) and phage display methods (see, e.g., Dower et al., WO 91/17271 and McCafferty et al., WO 92/01047, U.S. Pat. Nos. 5,877,218, 5,871,907, 5,858,657, 5,837,242, 5,733,743 and 5,565,332).

F. Selection of Constant Region

The heavy and light chain variable regions of chimeric, humanized (including veneered), or human antibodies can each be linked to at least a portion of a human constant region. In some embodiments, a heavy chain variable domain described in the sections above is linked to a portion of a human heavy chain constant region and a light chain variable domain described in the sections above is linked to a portion of a human light chain constant region. In some embodiments, a heavy chain variable domain described in the sections above is linked to a portion of a human heavy chain constant region and a light chain variable domain described in the sections above is linked to a full-length human light chain constant region. A heavy chain constant region includes the Fc (fragment crystalizable) region, which is the tail region of an antibody that interacts with cell surface receptors (Fc receptors) and some proteins of the complement system. In some embodiments, a heavy chain variable domain described in the sections above is linked to a full-length human heavy chain constant region and a light chain variable domain described in the sections above is linked to a full-length human light chain constant region.

The choice of constant region (or truncation thereof) depends, in part, on whether effector functions, are desired, or even need to be enhanced. "Effector functions" refer to biological activities attributable to the Fc region of an antibody and vary depending on the antibody isotype. Non-limiting examples of antibody effector functions include: C1q binding on the C1 complex and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation. Human antibodies are classified into five isotypes (IgM, IgD, IgG, IgA, and IgE) according to their heavy chain, with each providing different functions. IgG consists of four human subclasses (IgG1, IgG2, IgG3 and IgG4) each containing a different heavy chain. They are highly homologous and differ mainly in the hinge region and the extent to which they activate the host immune system. For example, human isotypes IgG1 and IgG3 can mediate complement-mediated cytotoxicity and human isotypes IgG2 and IgG4 do not or do so at very low levels. Light chain constant regions can be of subclasses lambda or kappa. For immunotherapy against cancer or a pathogen not expressing TIGIT, in addition to human IgG1 and IgG3, human IgG2 or IgG4 or an attenuated form of human IgG1 with reduced effector function can be used. For human IgG4, inclusion of a S228P (Eu numbering) engineered mutation on the heavy chain to prevent Fab-arm exchange can be used. However, for elimination of cancer cells expressing TIGIT (e.g., tumors of T cells or NK cells) for immunosuppression, human IgG1 or IgG3 can be used. For example, for direct killing of cancer cells expressing TIGIT (e.g., some hematological malignancies) or for immunosuppression, antibodies with Fc effector function (e.g., human IgG1 or IgG3) can be used. Suitable sequences for human IgG1 or IgG3 are known in the art and include, for example, SEQ ID NO:94, and human IgG3 disclosed in U.S. Pat. No. 5,624,821.

Human constant regions show allotypic variation and isoallotypic variation between different individuals, that is, the constant regions can differ in different individuals at one or more polymorphic positions. Isoallotypes differ from allotypes in that sera recognizing an isoallotype bind to a non-polymorphic region of a one or more other isotypes. Reference to a human constant region includes a constant region with any natural allotype or any permutation of residues occupying polymorphic positions in natural allotypes.

One or several amino acids at the amino or carboxy terminus of the light and/or heavy chain, such as the C-terminal lysine of the heavy chain, may be missing or derivatized in a proportion or all of the molecules. An N-terminal glutamine of the heavy or light chain can be substituted with a glutamate residue to prevent the formation of pyroglutamate. Substitutions can be made in the constant regions to reduce or increase effector function such as complement-mediated cytotoxicity (CDC) or antibody-Dependent Cell-Mediated Cytotoxicity (ADCC) (see, e.g., Winter et al., U.S. Pat. No. 5,624,821; Tso et al., U.S. Pat. No. 5,834,597; and Lazar et al., Proc. Natl. Acad. Sci. USA, 103:4005, 2006), or to prolong half-life in humans (see, e.g., Hinton et al., J. Biol. Chem. 279:6213, 2004). Exemplary substitutions include a Gln at position 250 and/or a Leu at position 428 (Eu numbering) for increasing the half-life of an antibody.

In some embodiments, the antibodies described herein include a wild type heavy chain constant region as described above. In some embodiments, the wild type heavy chain constant region is SEQ ID NO: 94. SEQ ID NO: 92 is an exemplary heavy chain amino acid sequence comprising a wild type constant region of SEQ ID NO: 94. In other embodiments, the antibodies described herein have a variant of a wild type heavy chain constant region (or a truncation thereof) selected from variant human IgG1, variant human IgG2, variant human IgG3, or variant human IgG4. In some embodiments, the variant heavy chain constant region is SEQ ID NO: 97, SEQ ID NO: 99, or SEQ ID NO: 101. SEQ ID NO: 96, 98, and 100 are exemplary heavy chain amino acid sequences comprising a variant heavy chain constant region.

Some antibodies of the disclosure are engineered by introduction of constant region mutation(s) to have reduced effector functions, such as CDC and ADCC or antibody-dependent cellular phagocytosis (ADCP) compared with the same antibody without the mutation(s). In some embodiments, each or all of these effector functions are reduced at least 50%, 75%, 90% or 95% compared with antibodies without the mutation. Other assays are described by Shields et al, 2001 *J. Biol. Chem.*, Vol. 276, p 6591-6604; Chappel et al, 1993 *J. Biol. Chem.*, Vol 268, p 25124-25131; Lazar et al, 2006 *PNAS,* 103; 4005-4010.

Substitution of any or all of positions 234, 235, 236 and/or 237 reduces affinity for Fcγ receptors, particularly FcγRI receptor (see, e.g., U.S. Pat. No. 6,624,821). In some embodiments, an alanine residue is used for substitution, such as an L234A/L235A dual mutation to reduce effector function. Other combinations of mutations with reduced effector functions include L234A/L235A/G237A, E233P/L234V/L235A/ΔG236, A327G/A330S/P331S, K322A, L234A and L235A, L234F/L235E/P331S (Eu numbering). Optionally, positions 234, 236 and/or 237 in human IgG2 are substituted with alanine and position 235 with glutamine. (see, e.g., U.S. Pat. No. 5,624,821.) Two amino acid substitutions in the complement C1q binding site at Eu index positions 330 and 331 reduce complement fixation (see Tao et al., *J. Exp. Med.* 178:661 (1993) and Canfield and Morrison, *J. Exp. Med.* 173:1483 (1991)). Substitution into human IgG1 of IgG2 residues at positions 233-236 and IgG4 residues at positions 327, 330 and 331 reduces ADCC and CDC (see, for example, Armour K L. et al., 1999 *Eur J Immunol.* 29(8):2613-24; and Shields R L. et al., 2001. *J Biol Chem.* 276(9):6591-604). N297A, N297Q, or N297G (Eu numbering) mutations reduce glycosylation and thereby effector functions.

The antibodies of the present disclosure can be engineered, in some embodiments, to enhance Fc effector function. For example, FcγR binding can be enhanced by amino acid engineering. In some embodiments, this can be done by substitution of one or more amino acids in the Fc region. Desirable mutations can be determined by, for example, either alanine scanning or rational design and library screening. IgG variants with enhanced binding to FcRs and enhanced effector function can be identified using these technologies. Alternatively, several mutations to the Fc receptor region are known in the art, for example, as described in Smith P. et al (2012) PNAS 6181-6186.

In some embodiments, the antibodies described herein include a modified IgG1 constant domain that increases the ability of the antibody to mediate ADCC compared to wild type IgG1 without the modification. The modified IgG1 domain can be characterized by amino acid substitutions at one or more of L235V, S239D, F243L, R292P, A330L, I332E, P396L (Eu numbering). In other embodiments, the modified IgG1 domain is characterized by substitutions at S239D, A330L, and I332E (Eu numbering). In some embodiments a therapeutically effective amount of the antibody as described herein is capable of inducing cell death in at least 20%, at least 25%, at least 30%, at least 35%, at least 40%, at least 45%, at least 50%, at least 55%, at least 60%, or at least 65% of TIGIT-expressing cells within 1, 2, or 3 hours, as assessed by methods described in the art.

Alternatively, glycoform perturbation can be used to enhance Fc-mediated therapeutic antibody function. The N-linked Fc glycosylations on IgG1 antibodies are important for effector function. Sialylation, galactosylation, bisecting sugars, and fucosylation can all affect binding and activity of IgG molecules. Controlling the glycosylation patterns on therapeutic antibodies can be done a number of different ways. The type of cell producing the recombinant antibody and its culture conditions can affect glycosylation and activity of therapeutic antibodies. Furthermore, bioreactor conditions and downstream processing can also affect the glycan microheterogenity. Low or afucosylated antibodies have been shown to enhance Fc-mediating properties. Numerous ways to achieve this reduction of fucose levels by glycoengineering are well known in the art. One way is to manipulate the enzymes involved in the post-translational modification of antibodies. This can involve overexpression of glucosidases, such as $\beta$-1-4-N-acetylglucosaminyltransferase III, knocking out fucoslytransferases, or using cell lines that are naturally fucose-deficient or have been mutated to express low fucosylation levels. In addition, inhibitors of N-linked glucosidases, such as castanospermine, can also be used to obtain low fucose bearing IgG molecules.

In some embodiments amino acid engineered variants can have more broadly enhanced affinity for multiple FcγR, whereas glycoform engineered antibody can generally have more specific affinity for enhanced FcγRIIIa binding. Glycoforms interact with proximal amino acids on the Fc portion and replacement of the amino acid that come in contact with Ig oligosaccharides can result in different glycoform structures.

G. Expression of Recombinant Antibodies

Chimeric, humanized (including veneered) and human antibodies are typically produced by recombinant expression. Accordingly, the present disclosure also provides polynucleotides that encode the anti-TIGIT antibodies of this Section IIIA-G, vectors comprising the polynucleotides, and host cells comprising the vectors.

Polynucleotides encoding the anti-TIGIT antibodies of the present disclosure can be inserted into a vector for amplification, expression, or further optimization. Many vectors are available. In some embodiments, the vector system includes mammalian, bacterial, yeast systems, etc, and comprises plasmids such as, but not limited to, pAL-TER, pBAD, pcDNA, pCal, pL, pET, pGEMEX, pGEX, pCI, pCMV, pEGFP, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS420, pLexA, pACT2.2 etc, and other laboratory and commercially available vectors. Suitable vectors may include, plasmid, or viral vectors (e.g., replication defective retroviruses, adenoviruses and adeno-associated viruses). The vector components generally include, but are not limited to, one or more of the following: a signal sequence, an origin of replication, one or more marker genes, an enhancer element, a promoter (e.g. SV40, CMV, EF-1α), and a transcription termination sequence. For expression, recombinant polynucleotide constructs typically include an expression control sequence operably linked to the coding sequences of antibody chains, including naturally-associated or heterologous promoter regions. In some embodiments, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the recombinant antibodies.

Vectors comprising the polynucleotide sequence encoding an anti-TIGIT antibody of the present disclosure can be introduced to a host cell for cloning or gene expression. Suitable host cells for cloning or expressing the polynucleotide sequences in the vectors herein include prokaryote and eukaryote cells. Non-limiting examples of suitable prokaryotes include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis*, *Pseudomonas* such as *P. aeruginosa*, and *Streptomyces*. In addition to prokaryotes, eukaryotic microbes such as filamentous fungi or yeast are suitable cloning or expression hosts for anti-TIGIT antibody-encoding vectors. Non-limiting examples include *Saccharomyces cerevisiae*, *Schizosaccharomyces pombe*; *Kluyveromyces* hosts such as, e.g., *K. lactis*, *fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226), *Pichia pastoris* (EP 183,070); *Candida*; *Trichoderma reesia* (EP 244,234), *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*. Suitable host cells can also be derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, *petunia*, tomato, and tobacco can also be utilized as hosts. In some embodiments, mammalian cells are used as host cells for expressing nucleotide segments encoding immunoglobulins or fragments thereof. See Winnacker, From Genes to Clones, (VCH Publishers, NY, 1987). A number of suitable host cell lines capable of secreting intact heterologous proteins have been developed in the art, and include CHO cell lines, various COS cell lines, HeLa cells, HEK293 cells, L cells, and non-antibody-producing myelomas including Sp2/0 and NS0. In some embodiments, the cells are nonhuman. Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. In some embodiments, expression control sequences are promoters derived from endogenous genes, cytomegalovirus, SV40, adenovirus, bovine papillomavirus, and the like. See Co et al., *J. Immunol.* 148:1149 (1992).

Host cells are transformed with the above-described expression or cloning vectors for anti-TIGIT antibody production and cultured in conventional nutrient media modified as appropriate for inducing promoters, selecting transformants, or amplifying the genes encoding the desired sequences. Once expressed, antibodies can be purified according to standard procedures of the art, including HPLC purification, column chromatography, gel electrophoresis and the like (see generally, Scopes, Protein Purification (Springer-Verlag, NY, 1982)).

IV. Therapeutic Applications

The anti-TIGIT antibodies of the present disclosure can be used for enhancing immune responses in the treatment of cancer and infectious diseases. Disorders treatable by antibodies of the present disclosure include, without limitation, cancers, including hematological malignancies, solid tumors, Merkel cell carcinoma, urothelial, head and neck squamous cell, B-cell lymphomas, cancer of the uterus, cervix, testes, gastrointestinal tract (e.g., esophagus, cancer of the gastroesophageal junction, oropharynx, stomach, small or large intestines, colon, or rectum), bladder, bone, bone marrow, skin, gall bladder, heart, lung, salivary gland, adrenal gland, thyroid, ganglia, central nervous system (CNS) and peripheral nervous system (PNS), and cancers of the hematopoietic system and the immune system (e.g., spleen or thymus).

The present disclosure also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, teratocarcinomas, chemically-induced cancers, metastasis, and angiogenesis. In particular embodiments, the tumor or cancer is colon cancer, ovarian cancer, breast cancer, melanoma, lung cancer, glioblastoma, or leukemia. The use of the term(s) cancer-related diseases, disorders and conditions is meant to refer broadly to conditions that are associated, directly or indirectly, with cancer, and includes, e.g., angiogenesis and precancerous conditions such as dysplasia. In certain embodiments, a cancer can be metastatic or at risk of becoming metastatic, or can occur in a diffuse tissue, including cancers of the blood or bone marrow (e.g., leukemia).

Such cancers may or may not express TIGIT or CD155. Antibodies to TIGIT are effective against cancers not expressing TIGIT because inhibition of TIGIT interaction with CD155 stimulates an immune response against such cancers. Examples of hematological malignancies include leukemias, lymphomas and myelomas, including acute myeloid leukemia, adult T-cell leukemia, T cell large granula lymphocyte leukemia, acute lymphoblastic leukemia, chronic lymphocytic leukemia, chronic myelogenous leukemia, acute monocytic leukemia, Hodgkin's and Non-Hodgkin's lymphoma and multiple myeloma. Examples of solid tumors include, without limitation, ovarian cancer, endometrial cancer, breast cancer, lung cancer (small cell or non-small cell), colon cancer, prostate cancer, cervical cancer, pancreatic cancer, gastric cancer, esophageal cancer, hepatocellular carcinoma (liver cancer), renal cell carcinoma (kidney cancer), head-and-neck tumors, mesothelioma, melanoma, sarcomas, and brain tumors (e.g., gliomas, such as glioblastomas).

The methods of the present disclosure can be practiced in an adjuvant setting. "Adjuvant setting" refers to a clinical setting in which a subject has a history of a proliferative disease, particularly cancer, and generally (but not necessarily) has been responsive to therapy, which includes, but is not limited to, surgery, radiotherapy, and/or chemotherapy. However, because of a history of the proliferative disease, these subjects are considered at risk of developing that disease. Treatment or administration in the "adjuvant setting" refers to a subsequent mode of treatment. In some embodiments, provided herein is a method for treating or effecting prophylaxis of cancer including administering to a subject having or at risk of cancer a therapeutically effective amount of any of the antibodies disclosed herein in an adjuvant setting.

The methods provided herein can also be practiced in a "neoadjuvant setting," that is, the method can be carried out before the primary/definitive therapy. In some aspects, the subject has previously been treated. In other aspects, the subject has not previously been treated. In some aspects, the treatment is a first line therapy. In some embodiments, provided herein is a method for treating or effecting prophylaxis of cancer including administering to a subject having or at risk of cancer a therapeutically effective amount of any of the antibodies disclosed herein in a neoadjuvant setting.

Other disorders treatable by antibodies of the present disclosure include infectious diseases, of viruses, bacteria, fungi, protozoans, and other pathogens (e.g., hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus, HIV, SIV, and arboviral encephalitis virus, *chlamydia, rickettsial* bacteria, mycobacteria, staphylococci, treptocci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, and Lyme disease bacteria.

A. Administration of Antibodies

The antibodies described herein are administered in an effective regime meaning a dosage, route of administration and frequency of administration that delays the onset, reduces the severity, inhibits further deterioration, and/or ameliorates at least one sign or symptom of a disorder. If a subject is already suffering from a disorder, the regime can be referred to as a therapeutically effective regime. If the subject is at elevated risk of the disorder relative to the general population but is not yet experiencing symptoms, the regime can be referred to as a prophylactically effective regime. In some instances, therapeutic or prophylactic efficacy can be observed in an individual subject relative to historical controls or past experience in the same subject. In other instances, therapeutic or prophylactic efficacy can be demonstrated in a preclinical or clinical trial in a population of treated subjects relative to a control population of untreated subjects.

In some instances, the subject is identified as PD-L1 positive, CD155 positive, TIGIT positive, MSI high, having infiltrating T cells, having activated T cells, having high levels of molecules associated with antigen processing and presentation, TMB high, or any combination thereof. In some embodiments, a patient is selected for treatment with the antibodies described herein based on high expression of TIGIT, for example, on CD8+ cells and/or CD4+ cells and/or NK cells, relative to a control population. In some instances, the subject is identified as having an oncogene driven cancer and has a mutation in at least one gene selected from the group consisting of TP53, VHL, KRAS, BRAF, MET, FUBP1, RAC1, EGFR, CDK4, CTCF, PGR, RET, RASA1, JAK1, PHF6, NF1, CIC, ARID1A, ZFHX3, ZCCHC12, GNA11, SMAD4, USP9X, CDKN2A, FAT1, PIK3R1, SCAF4, PMS2, RNF43, SMC1A, BCOR, FGFR2, COL5A1, ATM, KMT2B, CTNNB1, MYC, RAD21, PTEN, AXL, HIF1A, EPAS1, PAK4, RHOB, TBL1XR1, KEAP1, ZFP36L2, FGFR3, FOXA1, FLT3, TRAF3, RNF111, PPP2R1A, TXNIP, STAG2, RIT1, TGIF1, FOXQ1, ATR, CYSLTR2, PCBP1, PIK3R2, ASXL1, HIST1H1C, KLF5, PIK3CB, SPOP, MECOM, CACNA1A, CTNND1, DACH1, XPO1, ZNF750, FBXW7, MUC6, KDM6A, GATA3, ZBTB20, PIK3CA, RB1, SOX17, SMARCA4, KIT, CHD8, CHD4, and APOB.

In some aspects, any of the methods described herein include the administration of a therapeutically effective amount of one or more of the anti-TIGIT antibodies described herein to subjects in need thereof. As used herein, a "therapeutically effective amount" or "therapeutically effective dosage" of an anticancer therapy (such as any of the anti-TIGIT antibodies described herein) is an amount sufficient to effect beneficial or desired results. For therapeutic use, beneficial or desired results include but are not limited to clinical results such as decreasing one or more symptoms resulting from cancer, increasing the quality of life of subjects suffering from cancer, decreasing the dose of other medications required to treat the cancer, enhancing the effect of another medication such as via targeting, delaying the progression of the disease, and/or prolonging survival. An effective dosage can be administered in one or more administrations. For purposes of this disclosure, an effective dosage of an anti-cancer therapy is an amount sufficient to accomplish therapeutic or prophylactic treatment either directly or indirectly. As is understood in the clinical context, a therapeutically effective dosage of an anti-cancer therapy may or may not be achieved in conjunction with another anti-cancer therapy.

Exemplary dosages for any of the antibodies described herein are about 0.1-20 mg/kg or 0.5-5 mg/kg body weight (e.g., about 0.5 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, or 20 mg/kg) or 10-1600 mg (such as any of less than 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1100 mg, 1200 mg, 1300 mg, 1400 mg, 1500 mg, or 1600 mg or greater, inclusive of values in between these numbers), as a fixed dosage. In one embodiment, the antibody described herein in given in an amount of about 300 to 1500 mg every three weeks. In another embodiment, the antibody described herein is given in an amount of about 300 to 1800 mg every four weeks. The dosage depends on the condition of the subject and response to prior treatment, if any, whether the treatment is prophylactic or therapeutic and whether the disorder is acute or chronic, among other factors.

Administration can be parenteral, intravenous, oral, subcutaneous, intra-arterial, intracranial, intrathecal, intraperitoneal, intratumoral, topical, intranasal or intramuscular. In some embodiments, administration into the systemic circulation is by intravenous or subcutaneous administration. Intravenous administration can be, for example, by infusion over a period such as 30-90 min.

The frequency of administration depends on the half-life of the antibody in the circulation, the condition of the subject and the route of administration among other factors. The frequency can be daily, weekly, monthly, quarterly, or at irregular intervals in response to changes in the subject's condition or progression of the disorder being treated. In an embodiment, the frequency can be in two-week cycles. In another embodiment, the frequency can be in three-week cycles. In another embodiment, the frequency is four-week cycles. In another embodiment, the frequency is six-week cycles. An exemplary frequency for intravenous administration is between weekly and quarterly over a continuous cause of treatment, although more or less frequent dosing is also possible. For subcutaneous administration, an exemplary dosing frequency is daily to monthly, although more or less frequent dosing is also possible.

The number of dosages administered depends on whether the disorder is acute or chronic and the response of the disorder to the treatment. For acute disorders or acute exacerbations of chronic disorders between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the subject.

Treatment including an anti-TIGIT antibody can alleviate a disease by increasing the median progression-free survival or overall survival time of subjects with cancer by at least about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100%, compared to control subjects, or increase either of these times by 2 weeks, 1, 2 or 3 months, or by 4 or 6 months or even 9 months or a year. In addition or alternatively, treatment including the anti-TIGIT antibody can increase the complete response rate, partial response rate, or objective response rate (complete+partial) of subjects by at least about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% compared to the control subjects. Control subjects receive the same treatment as subjects receiving the anti-TIGIT antibody except for the anti-TIGIT antibody. Thus, control subjects can receive placebo alone or a combination of placebo and some chemotherapeutic agent other than the anti-TIGIT antibody if such is also received by the subjects receiving the anti-TIGIT antibody.

The anti-TIGIT antibodies disclosed herein can enhance NK cell-mediated cytotoxicity of CD155-expressing cells (such as, but not limited to, K562 cells), by any of about 10%, 11%, 12%, 13%, 14%, 15%, 16%, 17%, 18%, 19%, 20%, 21%, 22%, 23%, 24%, 25% 26% 27%, 28%, 29%, 30%, 31%, 32%, 33%, 34%, 35% or more relative to the amount of NK cell-mediated cytotoxicity of CD155-expressing cells in the absence of one of the anti-TIGIT antibodies disclosed herein.

Typically, in a clinical trial (e.g., a phase II, phase II/III or phase III trial), increases in median progression-free survival and/or response rate of the subjects treated with the anti-TIGIT antibody, relative to the control group of subjects are statistically significant, for example, at the p=0.05 or 0.01 or even 0.001 level. The complete and partial response rates are determined by objective criteria commonly used in clinical trials for cancer, e.g., as listed or accepted by the National Cancer Institute and/or Food and Drug Administration and can include for example, tumor volume, number of tumors, metastasis, survival time, and quality of life measures, among others.

Pharmaceutical compositions for parenteral administration can be sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, such as in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively, antibodies can be in lyophilized form for constitution with a suitable vehicle, e.g., sterile pyrogen-free water, before use. The concentration of antibody in liquid formulations can vary from e.g., about 10-150 mg/ml. In some formulations the concentration is about 20-80 mg/ml.

B. Combination Therapies

The present disclosure contemplates the use of anti-TIGIT antibody alone or in combination with one or more active therapeutic agents. The additional active therapeutic agents can be small chemical molecules; macromolecules such as proteins, antibodies, peptibodies, peptides, DNA, RNA or fragments of such macromolecules; or cellular or gene therapies. The combination therapy can target different, but complementary, mechanisms of action and thereby have a synergistic therapeutic or prophylactic effect on the underlying disease, disorder, or condition. In addition, or alternatively, the combination therapy can allow for a dose reduction of one or more of the agents, thereby ameliorating, reducing or eliminating adverse effects associated with one or more of the agents.

The active therapeutic agents in such combination therapy can be formulated as a single composition or as separate compositions. If administered separately, each therapeutic agent in the combination can be given at or around the same time, or at different times. Furthermore, the therapeutic agents are administered "in combination" even if they have different forms of administration (e.g., oral capsule and intravenous), they are given at different dosing intervals, one therapeutic agent is given at a constant dosing regimen while another is titrated up, titrated down or discontinued, or each therapeutic agent in the combination is independently titrated up, titrated down, increased or decreased in dosage, or discontinued and/or resumed during a patient's course of therapy. If the combination is formulated as separate compositions, in some embodiments, the separate compositions are provided together in a kit.

In certain embodiments, any of the anti-TIGIT antibodies disclosed herein are administered or applied sequentially to one or more of the additional active therapeutic agents, e.g., where one or more of the additional active therapeutic agents is administered prior to or after the administration of the anti-TIGIT antibody according to this disclosure. In other embodiments, the antibodies are administered simultaneously with one or more of the additional active therapeutic agents, e.g., where the anti-TIGIT antibody is administered at or about the same time as one or more of the additional therapeutic agents; the anti-TIGIT antibody and one or more of the additional therapeutic agents can be present in two or more separate formulations or combined into a single formulation (i.e., a co-formulation). Regardless of whether the additional agent(s) are administered sequentially or simultaneously with the anti-TIGIT antibody, they are considered to be administered in combination for purposes of the present disclosure.

The antibodies of the present disclosure can be used in combination with at least one other (active) agent in any manner appropriate under the circumstances. In one embodiment, treatment with the at least one active agent and at least one anti-TIGIT antibody of the present disclosure is maintained over a period of time. In another embodiment, treatment with the at least one active agent is reduced or discontinued (e.g., when the subject is stable), while treatment with an anti-TIGIT antibody of the present disclosure is maintained at a constant dosing regimen. In a further embodiment, treatment with the at least one active agent is reduced or discontinued (e.g., when the subject is stable), while treatment with an anti-TIGIT antibody of the present disclosure is reduced (e.g., lower dose, less frequent dosing or shorter treatment regimen). In yet another embodiment, treatment with the at least one active agent is reduced or discontinued (e.g., when the subject is stable), and treatment with the anti-TIGIT antibody of the present disclosure is increased (e.g., higher dose, more frequent dosing or longer treatment regimen). In yet another embodiment, treatment with the at least one active agent is maintained and treatment with the anti-TIGIT antibody of the present disclosure is reduced or discontinued (e.g., lower dose, less frequent dosing or shorter treatment regimen). In yet another embodiment, treatment with the at least one active agent and treatment with the anti-TIGIT antibodies of the present disclosure are reduced or discontinued (e.g., lower dose, less frequent dosing or shorter treatment regimen).

Treatment with antibodies of the present disclosure can be combined with other treatments effective against the disorder being treated. When used in treating a proliferative condition, cancer, tumor, or precancerous disease, disorder or condition, the antibodies of the present disclosure can be combined with chemotherapy, radiation (e.g., localized radiation therapy or total body radiation therapy), stem cell treatment, surgery or treatment with other biologics.

Antibodies of the present disclosure can be administered with vaccines eliciting an immune response against a cancer. Such immune response is enhanced by the antibody of the present disclosure. The vaccine can include an antigen expressed on the surface of the cancerous cell and/or tumor of a fragment thereof effective to induce an immune response, optionally linked to a carrier molecule.

In some embodiments, one or more of the additional therapeutic agents is an immunomodulatory agent. Suitable immunomodulatory agents that can be used in the present disclosure include CD40L, B7, and B7RP1; activating monoclonal antibodies (mAbs) to stimulatory receptors, such as, anti-CD40, anti-CD38, anti-ICOS, and 4-IBB ligand; dendritic cell antigen loading (in vitro or in vivo); anti-cancer vaccines such as dendritic cell cancer vaccines; cytokines/chemokines, such as, IL1, IL2, IL12, IL18, ELC/CCL19, SLC/CCL21, MCP-1, IL-4, IL-18, TNF, IL-15, MDC, IFNα/β, M-CSF, IL-3, GM-CSF, IL-13, and anti-IL-10; bacterial lipopolysaccharides (LPS); indoleamine 2,3-dioxygenase 1 (IDO1) inhibitors and immune-stimulatory oligonucleotides.

In certain embodiments, the present disclosure provides methods for suppression of tumor growth including administration of an anti-TIGIT antibody described herein in combination with a signal transduction inhibitor (STI) to achieve additive or synergistic suppression of tumor growth. As used herein, the term "signal transduction inhibitor" refers to an agent that selectively inhibits one or more steps in a signaling pathway. Signal transduction inhibitors (STIs) contemplated by the present disclosure include: (i) bcr/abl kinase inhibitors (e.g., imatinib mesylate, GLEEVEC®); (ii) epidermal growth factor (EGF) receptor inhibitors, including kinase inhibitors (e.g., gefitinib, erlotinib, afatinib and osimertinib) and antibodies; (iii) her-2/neu receptor inhibitors (e.g., HERCEPTIN®); (iv) inhibitors of Akt family kinases or the Akt pathway (e.g., rapamycin); (v) cell cycle kinase inhibitors (e.g., flavopiridol); and (vi) phosphatidyl inositol kinase inhibitors. Agents involved in immunomodulation can also be used in combination with the anti-TIGIT antibody described herein for the suppression of tumor growth in cancer patients.

In some embodiments, one or more of the additional therapeutic agents is a chemotherapeutic agent. Examples of chemotherapeutic agents include, but are not limited to, alkylating agents such as thiotepa and cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, pomalidomide potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel, nab-paclitaxel, and docetaxel; chlorambucil; gemcitabine; 6-thioguanine; mercaptopurine; methotrexate; platinum and platinum coordination complexes such as cisplatin, carboplatin and oxaliplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; anthracyclines; and pharmaceutically acceptable salts, acids or derivatives of any of the above.

Chemotherapeutic agents also include anti-hormonal agents that act to regulate or inhibit hormonal action on tumors such as anti-estrogens, including, for example, tamoxifen, raloxifene, aromatase inhibiting 4(5)-imidazoles, 4-hydroxytamoxifen, trioxifene, keoxifene, onapristone, and toremifene; and antiandrogens such as abiraterone, enzalutamide, apalutamide, darolutamide, flutamide, nilutamide, bicalutamide, leuprolide, and goserelin; and pharmaceutically acceptable salts, acids or derivatives of any of the above. In certain embodiments, combination therapy includes a chemotherapy regimen that includes one or more chemotherapeutic agents. In certain embodiments, combination therapy includes administration of a hormone or related hormonal agent.

Additional treatment modalities that can be used in combination with an anti-TIGIT antibody include radiotherapy, an antibody against a tumor antigen, a complex of an antibody and toxin, a T cell adjuvant, bone marrow transplant, or antigen presenting cells (e.g., dendritic cell therapy), including TLR agonists which are used to stimulate such antigen presenting cells.

In certain embodiments, the present disclosure contemplates the use of the anti-TIGIT antibody described herein in combination with RNA interference-based therapies to silence gene expression. RNAi begins with the cleavage of longer double-stranded RNAs into small interfering RNAs (siRNAs). One strand of the siRNA is incorporated into a ribonucleoprotein complex known as the RNA-induced silencing complex (RISC), which is then used to identify mRNA molecules that are at least partially complementary to the incorporated siRNA strand. RISC can bind to or cleave the mRNA, both of which inhibits translation.

In certain embodiments, the present disclosure contemplates the use of the anti-TIGIT antibody described herein in combination with agents that modulate the level of adenosine. Such therapeutic agents can act on the ectonucleotides that catalyze the conversion of ATP to adenosine, including ectonucleoside triphosphate diphosphohydrolase 1 (ENTPD1, also known as CD39 or Cluster of Differentiation 39), which hydrolyzes ATP to ADP and ADP to AMP, and 5'-nucleotidase, ecto (NT5E or 5NT, also known as CD73 or Cluster of Differentiation 73), which converts AMP to adenosine. In one embodiment, the present disclosure contemplates combination with CD73 inhibitors such as those described in WO 2017/120508, WO 2018/094148 and WO 2018/067424. In one embodiment, the CD73 inhibitor is AB680. In another approach, adenosine A2a and A2b receptors are targeted. Combination with antagonists of the A2a and/or A2b receptors is also contemplated. In one embodiment, the present disclosure contemplates combination with the adenosine receptor antagonists described in WO/2018/136700 or WO 2018/204661. In one embodiment, the adenosine receptor antagonist is AB928 (etrumadenant).

In certain embodiments, the present disclosure contemplates the use of the anti-TIGIT antibody described herein in combination with inhibitors of phosphatidylinositol 3-kinases (PI3Ks), particularly the PI3Kγ isoform. PI3Kγ inhibitors can stimulate an anti-cancer immune response through the modulation of myeloid cells, such as by inhibiting suppressive myeloid cells, dampening immune-suppressive tumor-infiltrating macrophages or by stimulating macrophages and dendritic cells to make cytokines that contribute to effective T cell responses leading to decreased cancer development and spread. Exemplary PI3Kγ inhibitors that can be combined with the anti-TIGIT antibody described herein include those described in WO 2020/0247496A1. In one embodiment, the PI3Kγ inhibitor is IPI-549.

In certain embodiments, the present disclosure contemplates the use of the anti-TIGIT antibody described herein in combination with inhibitors of arginase, which has been shown to be either responsible for or to participate in inflammation-triggered immune dysfunction, tumor immune escape, immunosuppression and immunopathology of infectious disease. Exemplary arginase compounds can be found, for example, in PCT/US2019/020507 and WO/2020/102646.

In certain embodiments, the present disclosure contemplates the use of the anti-TIGIT antibody according to this disclosure with inhibitors of HIF-2α, which plays an integral role in cellular response to low oxygen availability. Under hypoxic conditions, the hypoxia-inducible factor (HIF) transcription factors can activate the expression of genes that regulate metabolism, angiogenesis, cell proliferation and survival, immune evasion, and inflammatory response. HIF-2α overexpression has been associated with poor clinical outcomes in patients with various cancers; hypoxia is also prevalent in many acute and chronic inflammatory disorders, such as inflammatory bowel disease and rheumatoid arthritis.

The present disclosure also contemplates the combination of the anti-TIGIT antibody described herein with one or more RAS signaling inhibitors. Oncogenic mutations in the RAS family of genes, e.g., HRAS, KRAS, and NRAS, are associated with a variety of cancers. For example, mutations of G12C, G12D, G12V, G12A, G13D, Q61H, G13C and G12S, among others, in the KRAS family of genes have been observed in multiple tumor types. Direct and indirect inhibition strategies have been investigated for the inhibition of mutant RAS signaling. Indirect inhibitors target effectors other than RAS in the RAS signaling pathway, and include, but are not limited to, inhibitors of RAF, MEK, ERK, PI3K, PTEN, SOS (e.g., SOS1), mTORC1, SHP2 (PTPN11), and AKT. Non-limiting examples of indirect inhibitors under development include RMC-4630, RMC-5845, RMC-6291, RMC-6236, JAB-3068, JAB-3312, TNO155, RLY-1971, BI1701963. Direct inhibitors of RAS mutants have also been explored, and generally target the KRAS-GTP complex or the KRAS-GDP complex. Exemplary direct RAS inhibitors under development include, but are not limited to, sotorasib (AMG510), MRTX849, mRNA-5671 and ARS1620. In some embodiments, the one or more RAS signaling inhibitors are selected from the group consisting of RAF inhibitors, MEK inhibitors, ERK inhibitors, PI3K inhibitors, PTEN inhibitors, SOS1 inhibitors, mTORC1 inhibitors, SHP2 inhibitors, and AKT inhibitors. In other embodiments the one or more RAS signaling inhibitors directly inhibit RAS mutants.

In some embodiments, this disclosure is directed to the combination of the anti-TIGIT antibody according to this disclosure with one or more inhibitors of anexelekto (i.e., AXL). The AXL signaling pathway is associated with tumor growth and metastasis, and is believed to mediate resistance to a variety of cancer therapies. There are a variety of AXL inhibitors under development that also inhibit other kinases in the TAM family (i.e., TYRO3, MERTK), as well as other receptor tyrosine kinases including MET, FLT3, RON and AURORA, among others. Exemplary multikinase inhibitors include gilteritinib, merestinib, cabozantinib, BMS777607, and foretinib. AXL specific inhibitors have also been developed, e.g., SGI-7079, TP-0903 (i.e., dubermatinib), BGB324 (i.e., bemcentinib) and DP3975.

In certain embodiments, the present disclosure contemplates the use of the anti-TIGIT antibody described herein in combination with adoptive cell therapy, a new and promising form of personalized immunotherapy in which immune cells with anti-tumor activity are administered to cancer patients. Adoptive cell therapy is being explored using tumor-infiltrating lymphocytes (TIL) and T cells engineered to express, for example, chimeric antigen receptors (CAR) or T cell receptors (TCR). Adoptive cell therapy generally involves collecting T cells from an individual, genetically modifying them to target a specific antigen or to enhance their anti-tumor effects, amplifying them to a sufficient number, and infusion of the genetically modified T cells into a cancer patient. T cells can be collected from the patient to whom the expanded cells are later reinfused (e.g., autologous) or can be collected from donor patients (e.g., allogeneic).

T cell-mediated immunity includes multiple sequential steps, each of which is regulated by counterbalancing stimulatory and inhibitory signals in order to optimize the response. While nearly all inhibitory signals in the immune response ultimately modulate intracellular signaling pathways, many are initiated through membrane receptors, the ligands of which are either membrane-bound or soluble (cytokines). While co-stimulatory and inhibitory receptors and ligands that regulate T cell activation are frequently not overexpressed in cancers relative to normal tissues, inhibitory ligands and receptors that regulate T cell effector functions in tissues are commonly overexpressed on tumor cells or on non-transformed cells associated with the tumor microenvironment. The functions of the soluble and membrane-bound receptor (ligand immune checkpoints) can be modulated using agonist antibodies (for co-stimulatory pathways) or antagonist antibodies (for inhibitory pathways). Thus, in contrast to most antibodies currently approved for cancer therapy, antibodies that block or agonize immune checkpoints do not target tumor cells directly, but rather target lymphocyte receptors or their ligands in order to enhance endogenous antitumor activity. [See Pardoll, (April 2012) Nature Rev. Cancer 12:252-64].

Examples of immune checkpoints (ligands and receptors), some of which are selectively upregulated in various types of tumor cells, that are candidates for blockade include PD-1 (programmed cell death protein 1); PD-L1 (programmed cell death 1 ligand 1); BTLA (B and T lymphocyte attenuator); CTLA4 (cytotoxic T-lymphocyte associated antigen 4); TIM-3 (T cell immunoglobulin mucin protein 3); LAG-3 (lymphocyte activation gene 3); TIGIT (T cell immunoreceptor with Ig and ITIM domains); and Killer Inhibitory Receptors, which can be divided into two classes based on their structural features: i) killer cell immunoglobulin-like receptors (KIRs), and ii) C-type lectin receptors (members of the type II transmembrane receptor family). Other less well-defined immune checkpoints have been described in the literature, including both receptors (e.g., the 2B4 (also known as CD244) receptor) and ligands (e.g., certain B7 family inhibitory ligands such B7-H3 (also known as CD276) and B7-H4 (also known as B7-S1, B7x and VCTN1)). [See Pardoll, (April 2012) Nature Rev. Cancer 12:252-64].

The present disclosure contemplates the use of the anti-TIGIT antibody described herein in combination with inhibitors of the aforementioned immune-checkpoint receptors and ligands, as well as yet-to-be-described immune-checkpoint receptors and ligands. Certain modulators of immune checkpoints are currently approved, and many others are in development. When it was approved for the treatment of melanoma in 2011, the fully humanized CTLA4 monoclonal antibody ipilimumab (e.g., YERVOY®; Bristol Myers Squibb) became the first immune checkpoint inhibitor to receive regulatory approval in the US. Fusion proteins including CTLA4 and an antibody (CTLA4-Ig; abatcept (e.g., ORENCIA®; Bristol Myers Squibb)) have been used for the treatment of rheumatoid arthritis, and other fusion proteins have been shown to be effective in renal transplantation patients that are sensitized to Epstein Barr Virus. The next class of immune checkpoint inhibitors to receive regulatory approval were against PD-1 and its ligands PD-L1 and PD-L2. Approved anti-PD-1 antibodies include nivolumab (e.g., OPDIVO®; Bristol Myers Squibb) and pembrolizumab (e.g., KEYTRUDA®; Merck) for various cancers, including squamous cell carcinoma, classical Hodgkin lymphoma and urothelial carcinoma. Approved anti-PD-L1 antibodies include avelumab (e.g., BAVENCIO®; EMD Serono & Pfizer), atezolizumab (e.g., TECENTRIQ®; Roche/Genentech), and durvalumab (e.g., IMFINZI®; AstraZeneca) for certain cancers, including urothelial carcinoma. In some combinations provided herein, the immune checkpoint inhibitor is selected from MEDI-0680 nivolumab, pembrolizumab, avelumab, atezolizumab, budigalimab, BI-754091, camrelizumab, cosibelimab, durvalumab, dostarlimab, cemiplimab, sintilimab, tislelizumab, toripalimab, retifanlimab, sasanlimab, and zimberelimab (AB122). In some embodiments, the immune checkpoint inhibitor is MEDI-0680 (AMP-514; WO2012/145493) or pidilizumab (CT-011). Another approach to target the PD-1 receptor is the recombinant protein composed of the extracellular domain of PD-L2 (B7-DC) fused to the Fc portion of IgG1, called AMP-224. In one embodiment, the present disclosure contemplates the use of an anti-TIGIT antibody according to this disclosure with a PD-1 antibody. In one particular embodiment, the PD-1 antibody is zimberelimab. In some embodiments an anti-TIGIT antibody is provided in an amount of about 200 to 1500 mg every three weeks and the anti-PD-1 antibody is provided in an amount of about 100 to 1200 mg every three weeks. In another embodiment, an anti-TIGIT antibody described herein is given in an amount of about 300 to 1800 mg every four weeks and the anti-PD-1 antibody is provided in an amount of about 200 to 1500 mg every four weeks. In still another embodiment, the anti-PD-1 antibody is zimberelimab and is provided in an amount of about 360 mg or 480 mg every three or four weeks.

In another aspect, the present disclosure contemplates combination with a cytokine that inhibits T cell activation (e.g., IL-6, IL-10, TGF-B, VEGF, and other immunosuppressive cytokines) or a cytokine that stimulates T cell activation, for stimulating an immune response.

In yet another aspect, T cell responses can be stimulated by a combination of the disclosed anti-TIGIT antibody and one or more of (i) an antagonist of a protein that inhibits T cell activation (e.g., immune checkpoint inhibitors) such as CTLA-4, PD-1, PD-L1, PD-L2, LAG-3, TIM-3, PVRIG, Galectin 9, CEACAM-1, BTLA, CD69, Galectin-1, CD113, GPR56, VISTA, 2B4, CD48, GARP, PD1H, LAIR1, TIM-1, and TIM-4, and/or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD2. Other agents that can be combined with the anti-TIGIT antibody of the present disclosure for the treatment of cancer include antagonists of inhibitory receptors on NK cells or agonists of activating receptors on NK cells. For example, the anti-TIGIT antibody described herein can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, W)11/131407, WO13/87699, WO13/119716, WO13/132044) or FPA-008 (WO11/140249; WO13169264; WO14/036357).

In another aspect, the disclosed anti-TIGIT antibody can be combined with one or more of: agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), or reverse/prevent T cell anergy or exhaustion), and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, ipilimumab (e.g., YERVOY®; Bristol Myers Squibb) or tremelimumab. In another aspect, the immuno-oncology agent is a PD-L1 antagonist, such as an antagonistic PD-L1 antibody. Suitable PD-L1 antibodies include, for example, atezolizumab (MPDL3280A; WO2010/077634) (e.g., TECENTRIQ®; Roche/Genentech), durvalumab (MEDI4736), BMS-936559 (WO2007/005874), and MSB0010718C (WO2013/79174). In another aspect, the immuno-oncology agent is a LAG-3 antagonist, such as an antagonistic LAG-3 antibody. Suitable LAG-3 antibodies include, for example, BMS-986016 (WO10/19570, WO14/08218), or IMP-731 or IMP-321 (WO08/132601, WO09/44273). In another aspect, the immuno-oncology agent is a CD137 (4-1BB) agonist, such as an agonistic CD137 antibody. Suitable CD137 antibodies include, for example, urelumab and PF-05082566 (WO12/32433). In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683). In another aspect, the immuno-oncology agent is an OX40 agonist, such as an agonistic OX40 antibody. Suitable OX40 antibodies include, for example, MEDI-6383 or MEDI-6469. In another aspect, the immuno-oncology agent is an OX40L antagonist, such as an antagonistic OX40 antibody. Suitable OX40L antagonists include, for example, RG-7888 (WO06/029879). In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab. In another aspect, the immuno-oncology agent is a CD27 agonist, such as an agonistic CD27 antibody. Suitable CD27 antibodies include, for example, varlilumab. In another aspect, the immuno-oncology agent is MGA271 (to B7H3) (WO11/109400). In still another embodiment, combination of anti-TIGIT antibodies according to this disclosure with an agent directed at Trop-2, e.g., the antibody drug conjugate, sacituzumab govitecan-hziy, is contemplated. In yet another embodiment, combination of the anti-TIGIT antibodies described herein with an agent that inhibits the CD47-SIRPα pathway is contemplated. An example of an anti-CD47 antibody is magrolimab.

Examples of therapeutic agents useful in combination therapy for the treatment of cardiovascular and/or metabolic-related diseases, disorders and conditions include statins (e.g., CRESTOR®, LESCOL®, LIPITOR®, MEVACOR®, PRAVACOL®, and ZOCOR®), which inhibit the enzymatic synthesis of cholesterol; bile acid resins (e.g., COLESTID®, LO-CHOLEST®, PREVALITE®, QUESTRAN®, and WELCHOL®), which sequester cholesterol and prevent its absorption; ezetimibe (ZETIA®), which blocks cholesterol absorption; fibric acid (e.g., TRICOR®), which reduces triglycerides and can modestly increase HDL; niacin (e.g., NIACOR®), which modestly lowers LDL cholesterol and triglycerides; and/or a combination of the aforementioned (e.g., VYTORIN® (ezetimibe with simvastatin). Alternative cholesterol treatments that can be candidates for use in combination with the anti-TIGIT antibody described herein include various supplements and herbs (e.g., garlic, policosanol, and guggul).

Examples of therapeutic agents useful in combination therapy for immune- and inflammatory-related diseases, disorders or conditions include, but are not limited to, the following: non-steroidal anti-inflammatory drug (NSAID) such as aspirin, ibuprofen, and other propionic acid derivatives (alminoprofen, benoxaprofen, bucloxic acid, carprofen, fenbufen, fenoprofen, fluprofen, flurbiprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, fuirofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone). Other combinations include cyclooxygenase-2 (COX-2) inhibitors.

Other active agents for combination include steroids such as prednisolone, prednisone, methylprednisolone, betamethasone, dexamethasone, or hydrocortisone. Such a combination can be especially advantageous since one or more adverse effects of the steroid can be reduced or even eliminated by tapering the steroid dose required.

Additional examples of active agents that can be used in combinations for treating, for example, rheumatoid arthritis, include cytokine suppressive anti-inflammatory drug(s) (CSAIDs); antibodies to, or antagonists of, other human cytokines or growth factors, for example, TNF, LT, IL-10, IL-2, IL-6, IL-7, IL-8, IL-15, IL-16, IL-18, EMAP-II, GM-CSF, FGF, or PDGF.

Particular combinations of active agents can interfere at different points in the autoimmune and subsequent inflammatory cascade, and include TNF antagonists such as chimeric, humanized or human TNF antibodies, REMICADE®, HUMIRA®, anti-TNF antibody fragments (e.g., CDP870), and soluble p55 or p75 TNF receptors, derivatives thereof, p75TNFRIgG (ENBREL®) or p55TNFR1gG (lenercept), soluble IL-13 receptor (sIL-13), and also TNFα-converting enzyme (TACE) inhibitors; similarly, IL-1 inhibitors (e.g., Interleukin-1-converting enzyme inhibitors) can be effective. Other combinations include Interleukin 11, anti-P7s and p-selectin glycoprotein ligand (PSGL). Other examples of agents useful in combination with the A2AR/A2BR inhibitors described herein include interferon-131a (AVONEX®); interferon-131b (BETASERON®); copaxone; hyperbaric oxygen; intravenous immunoglobulin; clabribine; and antibodies to, or antagonists of, other human cytokines or growth factors (e.g., antibodies to CD40 ligand and CD80).

In some embodiments, a combination is an antibody of the present disclosure with a second antibody directed at a surface antigen preferentially expressed on the cancer cells relative to control normal tissue. Some examples of antibodies that can be administered in combination therapy with antibodies of the present disclosure for treatment of cancer include Herceptin® (trastuzumab) against the HER2 antigen, Avastin® (bevacizumab) against VEGF, or antibodies to the EGF receptor, such as (Erbitux®, cetuximab), and Vectibix® (panitumumab). Other agents that can be administered include antibodies or other inhibitors of any of PD-1, PD-L1, CTLA-4, 4-1BB, BTLA, PVRIG, VISTA, TIM-3 and LAG-3; or other downstream signaling inhibitors, e.g., mTOR and GSK3β inhibitors; and cytokines, e.g., interferon-γ, IL-2, and IL-15. Some specific examples of additional agents include: ipilimumab, pazopanib, sunitinib, dasatinib, pembrolizumab, INCR024360, dabrafenib, trametinib, atezolizumab (MPDL3280A), erlotinib (e.g., TARCEVA®), cobimetinib, nivolumab, and zimberelimab. The choice of a second antibody or other agent for combination therapy depends on the cancer being treated. Optionally, the cancer is tested for expression or preferential expression of an antigen to guide selection of an appropriate antibody. In some embodiments, the isotype of the second antibody is human IgG1 to promote effector functions, such as ADCC, CDC and phagocytosis.

Similar combination therapies can be used in treating or preventing infectious disease, such as viral, bacterial, fungal and parasitic diseases, disorders and conditions, as well as disorders associated therewith. For example, an antibody of the present disclosure can be combined with an antibody directed against the pathogen or a vaccine against the pathogen, such as, e.g., palivizumab against rous sarcoma virus. The vaccine can be a protein of the pathogen or fragment thereof effective to induce an immune response. The antibody of the present disclosure enhances the immune response of the antibody or vaccine directed against the pathogen. An antibody of the present disclosure can also be administered with T cells or natural killer cells expanded ex vivo.

Such combination therapy includes anti-viral agents targeting various viral life-cycle stages and having different mechanisms of action, including, but not limiting to, the following: inhibitors of viral uncoating (e.g., amantadine and rimantidine); reverse transcriptase inhibitors (e.g., acyclovir, zidovudine, and lamivudine); agents that target integrase; agents that block attachment of transcription factors to viral DNA; agents (e.g., antisense molecules) that impact translation (e.g., fomivirsen); agents that modulate translation/ribozyme function; protease inhibitors; viral assembly modulators (e.g., rifampicin); antiretrovirals such as, for example, nucleoside analogue reverse transcriptase inhibitors (e.g., azidothymidine (AZT), ddl, ddC, 3TC, d4T); non-nucleoside reverse transcriptase inhibitors (e.g., efavirenz, nevirapine); nucleotide analogue reverse transcriptase inhibitors; and agents that prevent release of viral particles (e.g., zanamivir and oseltamivir). Treatment and/or prevention of certain viral infections (e.g., HIV) frequently entail a group ("cocktail") of antiviral agents Other antiviral agents contemplated for use in combination with any of the anti-TIGIT antibodies disclosed herein include, but are not limited to, the following: abacavir, adefovir, amantadine, amprenavir, ampligen, arbidol, atazanavir, ATRIPLA®, boceprevirertet, cidofovir, combivir, darunavir, delavirdine, didanosine, docosanol, edoxudine, emtricitabine, enfuvirtide, entecavir, famciclovir, fosamprenavir, foscarnet, fosfonet, ganciclovir, ibacitabine, imunovir, idoxuridine, imiquimod, indinavir, inosine, various interferons (e.g., peginterferon alfa-2a), lopinavir, loviride, maraviroc, moroxydine, methisazone, nelfinavir, nexavir, penciclovir, peramivir, pleconaril, podophyllotoxin, raltegravir, ribavirin, ritonavir, pyramidine, saquinavir, stavudine, telaprevir, tenofovir, tipranavir, trifluridine, trizivir, tromantadine, TRUVADA®, valaciclovir, valganciclovir, vicriviroc, vidarabine, viramidine, and zalcitabine.

The present disclosure contemplates the use of any of the anti-TIGIT antibodies disclosed herein in combination with antiparasitic agents. Such agents include, but are not limited to, thiabendazole, pyrantel pamoate, mebendazole, praziquantel, niclosamide, bithionol, oxamniquine, metrifonate, ivermectin, albendazole, eflornithine, melarsoprol, pentamidine, benznidazole, nifurtimox, and nitroimidazole. The skilled artisan is aware of other agents that can find utility for the treatment of parasitic disorders Embodiments of the present disclosure contemplate the use of any of the anti-TIGIT antibodies disclosed herein in combination with agents useful in the treatment or prevention of bacterial disorders. Antibacterial agents can be classified in various manners, including based on mechanism of action, based on chemical structure, and based on spectrum of activity. Examples of antibacterial agents include those that target the bacterial cell wall (e.g., cephalosporins and penicillins) or the cell membrane (e.g., polymyxins), or interfere with essential bacterial enzymes (e.g., sulfonamides, rifamycins, and quinolines). Most antibacterial agents that target protein synthesis (e.g., tetracyclines and macrolides) are bacteriostatic, whereas agents such as the aminoglycoside are bactericidal. Another means of categorizing antibacterial agents is based on their target specificity; "narrow-spectrum" agents target specific types of bacteria (e.g., Gram-positive bacteria such as *Streptococcus*), while "broad-spectrum" agents have activity against a broader range of bacteria. The skilled artisan is aware of types of anti-bacterial agents that are appropriate for use in specific bacterial infections Embodiments of the present disclosure contemplate the use of any of the anti-TIGIT antibodies disclosed herein in combination with agents useful in the treatment or prevention of fungal disorders. Antifungal agents include polyenes (e.g., amphotericin, nystatin, and pimaricin); azoles (e.g., fluconazole, itraconazole, and ketoconazole); allylamines (e.g., naftifine, and terbinafine) and morpholines (e.g., amorolfine); and antimetabolies (e.g., 5-fluorocytosine)

The present disclosure encompasses pharmaceutically acceptable salts, acids or derivatives of any of the above.

V. Other Applications

The anti-TIGIT antibodies of the present disclosure can be used for detecting TIGIT in the context of clinical diagnosis or treatment or in research. For example, the antibodies can be used to detect presence of TIGIT on T cells, natural killer cells and cancer cells as an indication a subject is suffering from a cancer or infectious disease amenable to treatment. Expression of TIGIT on T cells, natural killer cells and/or cancer cells of a subject suffering from cancer or infectious disease also provides an indication that the cancer or infectious disease is amenable to treatment with the antibodies of the present disclosure. The antibodies can also be sold as research reagents for laboratory research in detecting T cells, natural killer cells and cancer cells, and their response to various stimuli. In such uses, antibodies can be labeled with one or more detectable signal, including but not limited to fluorescent molecules, spin-labeled molecules, enzymes or radioisotopes, and can be provided in the form of kit with all the necessary reagents to perform the assay for TIGIT. The anti-TIGIT antibodies of the present disclosure can also be used to purify TIGIT, e.g., by affinity chromatography.

VI. Kits

Antibodies against TIGIT can be combined with any of the second antibodies or agents described for use in co-therapies as components of a kit. The disclosure disclosed herein provides one or more kits containing one or more of the antibodies disclosed herein as well as one or more pharmaceutically acceptable excipients or carriers (such as, without limitation, phosphate buffered saline solutions, water, sterile water, polyethylene glycol, polyvinyl pyrrolidone, lecithin, *arachis* oil, sesame oil, emulsions such as oil/water emulsions or water/oil emulsions, microemulsions, nanocarriers and various types of wetting agents). Additives such as alcohols, oils, glycols, preservatives, flavoring agents, coloring agents, suspending agents, and the like can also be included in the kits of the present disclosure along with the carrier, diluent, or excipient. In one embodiment, a pharmaceutically acceptable carrier appropriate for use in the antibody compositions disclosed herein is sterile, pathogen free, and/or otherwise safe for administration to a subject without risk of associated infection and other undue adverse side effects. In a kit, the respective agents can be provided in separate vials with instructions for combination followed by administration or instructions for separate administration. The kit can also include written instructions for proper handling and storage of any of the anti-TIGIT antibodies disclosed herein.

VII. Embodiments

Embodiment 1. An anti-TIGIT antibody or antigen-binding fragment thereof that specifically binds to human TIGIT, comprising (a) a heavy chain variable region comprising a heavy chain (HC) complementarity determining region (CDR) 1 having at least 80% sequence identity to SEQ ID NO: 36, an HC-CDR2 having at least 80% sequence identity to SEQ ID NO: 37, and an HC-CDR3 having at least 80% sequence identity to SEQ ID NO: 38; and a light chain variable region comprising a light chain (LC) CDR1 having at least 80% sequence identity to SEQ ID NO: 39, an LC-CDR2 having at least 80% sequence identity to SEQ ID NO: 40, and an LC-CDR3 having at least 80% sequence identity to SEQ ID NO: 41; (b) a heavy chain variable region comprising an HC-CDR1 having at least 80% sequence identity to SEQ ID NO: 42, an HC-CDR2 having at least 80% sequence identity to SEQ ID NO: 43, and an HC-CDR3 having at least 80% sequence identity to SEQ ID NO: 44; and a light chain variable region comprising an LC-CDR1 having at least 80% sequence identity to SEQ ID NO: 45, an LC-CDR2 having at least 80% sequence identity to SEQ ID NO: 46, and an LC-CDR3 having at least 80% sequence identity to SEQ ID NO: 47; (c) a heavy chain variable region comprising an HC-CDR1 having at least 80% sequence identity to SEQ ID NO: 48, an HC-CDR2 having at least 80% sequence identity to SEQ ID NO: 49, and an HC-CDR3 having at least 80% sequence identity to SEQ ID NO: 50; and a light chain variable region comprising an LC-CDR1 having at least 80% sequence identity to SEQ ID NO: 51, an LC-CDR2 having at least 80% sequence identity to SEQ ID NO: 52, and an LC-CDR3 having at least 80% sequence identity to SEQ ID NO: 53; (d) a heavy chain variable region comprising an HC-CDR1 having at least 80% sequence identity to SEQ ID NO: 54, an HC-CDR2 having at least 80% sequence identity to SEQ ID NO: 55, and an HC-CDR3 having at least 80% sequence identity to SEQ ID NO: 56; and a light chain variable region comprising an LC-CDR1 having at least 80% sequence identity to SEQ ID NO: 57, an LC-CDR2 having at least 80% sequence identity to SEQ ID NO: 58, and an LC-CDR3 having at least 80% sequence identity to SEQ ID NO: 59; (e) a heavy chain variable region comprising an HC-CDR1 having at least 80% sequence identity to SEQ ID NO: 60, an HC-CDR2 having at least 80% sequence identity to SEQ ID NO: 61, and an HC-CDR3 having at least 80% sequence identity to SEQ ID NO: 62; and a light chain variable region comprising an LC-CDR1 having at least 80% sequence identity to SEQ ID NO: 63, an LC-CDR2 having at least 80% sequence identity to SEQ ID NO: 64, and an LC-CDR3 having at least 80% sequence identity to SEQ ID NO: 65; (f) a heavy chain variable region comprising an HC-CDR1 having at least 80% sequence identity to SEQ ID NO: 60, an HC-CDR2 having at least 80% sequence identity to SEQ ID NO: 66, and an HC-CDR3 having at least 80% sequence identity to SEQ ID NO: 67; and a light chain variable region comprising an LC-CDR1 having at least 80% sequence identity to SEQ ID NO: 63, an LC-CDR2 having at least 80% sequence identity to SEQ ID NO: 68, and an LC-CDR3 having at least 80% sequence identity to SEQ ID NO: 65; (g) a heavy chain variable region comprising an HC-CDR1 having at least 80% sequence identity to SEQ ID NO: 69, an HC-CDR2 having at least 80% sequence identity to SEQ ID NO: 55, and an HC-CDR3 having at least 80% sequence identity to SEQ ID NO: 70; and a light chain variable region comprising an LC-CDR1 having at least 80% sequence identity to SEQ ID NO: 71, an LC-CDR2 having at least 80% sequence identity to SEQ ID NO: 68, and an LC-CDR3 having at least 80% sequence identity to SEQ ID NO: 65; (h) a heavy chain variable region comprising an HC-CDR1 having at least 80% sequence identity to SEQ ID NO: 72, an HC-CDR2 having at least 80% sequence identity to SEQ ID NO: 73, and an HC-CDR3 having at least 80% sequence identity to SEQ ID NO: 67; and a light chain variable region comprising an LC-CDR1 having at least 80% sequence identity to SEQ ID NO: 63, an LC-CDR2 having at least 80% sequence identity to SEQ ID NO: 68, and an LC-CDR3 having at least 80% sequence identity to SEQ ID NO: 65; or (i) a heavy chain variable region comprising an HC-CDR1 having at least 80% sequence identity to SEQ ID NO: 74, an HC-CDR2 having at least 80% sequence identity to SEQ ID NO: 75, and an HC-CDR3 having at least 80% sequence identity to SEQ ID NO: 67; and a light chain variable region comprising an LC-CDR1 having at least 80% sequence identity to SEQ ID NO: 63, an LC-CDR2 having at least 80% sequence identity to SEQ ID NO: 68, and an LC-CDR3 having at least 80% sequence identity to SEQ ID NO: 65.

Embodiment 2. The anti-TIGIT antibody or antigen-binding fragment thereof of embodiment 1, comprising (a) a heavy chain variable region comprising an HC-CDR1 having an amino acid sequence comprising SEQ ID NO: 36, an HC-CDR2 having an amino acid sequence comprising SEQ ID NO: 37, and an HC-CDR3 having an amino acid sequence comprising SEQ ID NO: 38; and a light chain variable region comprising an LC-CDR1 having an amino acid sequence comprising identity to SEQ ID NO: 39, an LC-CDR2 having an amino acid sequence comprising SEQ ID NO: 40, and an LC-CDR3 having an amino acid sequence comprising SEQ ID NO: 41; (b) a heavy chain variable region comprising an HC-CDR1 having an amino acid sequence comprising SEQ ID NO: 42, an HC-CDR2 having an amino acid sequence comprising SEQ ID NO: 43, and an HC-CDR3 having an amino acid sequence comprising SEQ ID NO: 44; and a light chain variable region comprising an LC-CDR1 having an amino acid sequence comprising SEQ ID NO: 45, an LC-CDR2 having an amino acid sequence comprising SEQ ID NO: 46, and an LC-CDR3 having an amino acid sequence comprising SEQ ID NO: 47; (c) a heavy chain variable region comprising an HC-CDR1 having an amino acid sequence comprising SEQ ID NO: 48, an HC-CDR2 having an amino acid sequence comprising SEQ ID NO: 49, and an HC-CDR3 having an amino acid sequence comprising SEQ ID NO: 50; and a light chain variable region comprising an LC-CDR1 having an amino acid sequence comprising SEQ ID NO: 51, an LC-CDR2 having an amino acid sequence comprising SEQ ID NO: 52, and an LC-CDR3 having an amino acid sequence comprising SEQ ID NO: 53; (d) a heavy chain variable region comprising an HC-CDR1 having an amino acid sequence comprising SEQ ID NO: 54, an HC-CDR2 having an amino acid sequence comprising SEQ ID NO: 55, and an HC-CDR3 having an amino acid sequence comprising SEQ ID NO: 56; and a light chain variable region comprising an LC-CDR1 having an amino acid sequence comprising SEQ ID NO: 57, an LC-CDR2 having an amino acid sequence comprising SEQ ID NO: 58, and an LC-CDR3 having an amino acid sequence comprising SEQ ID NO: 59; (e) a heavy chain variable region comprising an HC-CDR1 having an amino acid sequence comprising SEQ ID NO: 60, an HC-CDR2 having an amino acid sequence comprising SEQ ID NO: 61, and an HC-CDR3 having an amino acid sequence comprising SEQ ID NO: 62; and a light chain variable region comprising an LC-CDR1 having an amino acid sequence comprising SEQ ID NO: 63, an LC-CDR2 having an amino acid sequence comprising SEQ ID NO: 64, and an LC-CDR3 having an amino acid sequence comprising SEQ ID NO: 65; (f) a heavy chain variable region comprising an HC-CDR1 having an amino acid sequence comprising SEQ ID NO: 60, an HC-CDR2 having an amino acid sequence comprising SEQ ID NO: 66, and an HC-CDR3 having an amino acid sequence comprising SEQ ID NO: 67; and a light chain variable region comprising an LC-CDR1 having an amino acid sequence comprising SEQ ID NO: 63, an LC-CDR2 having an amino acid sequence comprising SEQ ID NO: 68, and an LC-CDR3 having an amino acid sequence comprising SEQ ID NO: 65; (g) a heavy chain variable region comprising an HC-CDR1 having an amino acid sequence comprising SEQ ID NO: 69, an HC-CDR2 having an amino acid sequence comprising SEQ ID NO: 55, and an HC-CDR3 having an amino acid sequence comprising SEQ ID NO: 70; and a light chain variable region comprising an LC-CDR1 having an amino acid sequence comprising SEQ ID NO: 71, an LC-CDR2 having an amino acid sequence comprising SEQ ID NO: 68, and an LC-CDR3 having an amino acid sequence comprising SEQ ID NO: 65; (h) a heavy chain variable region comprising an HC-CDR1 having an amino acid sequence comprising SEQ ID NO: 72, an HC-CDR2 having an amino acid sequence comprising SEQ ID NO: 73, and an HC-CDR3 having an amino acid sequence comprising SEQ ID NO: 67; and a light chain variable region comprising an LC-CDR1 having an amino acid sequence comprising SEQ ID NO: 63, an LC-CDR2 having an amino acid sequence comprising SEQ ID NO: 68, and an LC-CDR3 having an amino acid sequence comprising SEQ ID NO: 65; or (i) a heavy chain variable region comprising an HC-CDR1 having an amino acid sequence comprising SEQ ID NO: 74, an HC-CDR2 having an amino acid sequence comprising SEQ ID NO: 75, and an HC-CDR3 having an amino acid sequence comprising SEQ ID NO: 67; and a light chain variable region comprising an LC-CDR1 having an amino acid sequence comprising SEQ ID NO: 63, an LC-CDR2 having an amino acid sequence comprising SEQ ID NO: 68, and an LC-CDR3 having an amino acid sequence comprising SEQ ID NO: 65.

Embodiment 3. The anti-TIGIT antibody or antigen-binding fragment thereof of embodiment 1 or 2, comprising (a) a heavy chain variable region having at least 80% sequence identity to SEQ ID NO: 1, and a light chain variable region having at least 80% sequence identity to SEQ ID NO: 2; (b) a heavy chain variable region having at least 80% sequence identity to SEQ ID NO: 3, and a light chain variable region having at least 80% sequence identity to SEQ ID NO: 4; (c) a heavy chain variable region having at least 80% sequence identity to SEQ ID NO: 5, and a light chain variable region having at least 80% sequence identity to SEQ ID NO: 6; (d) a heavy chain variable region having at least 80% sequence identity to SEQ ID NO: 7, and a light chain variable region having at least 80% sequence identity to SEQ ID NO: 8; (e) a heavy chain variable region having at least 80% sequence identity to SEQ ID NO: 9, and a light chain variable region having at least 80% sequence identity to SEQ ID NO: 10; (f) a heavy chain variable region having at least 80% sequence identity to SEQ ID NO: 11, and a light chain variable region having at least 80% sequence identity to SEQ ID NO: 12; (g) a heavy chain variable region having at least 80% sequence identity to SEQ ID NO: 13, and a light chain variable region having at least 80% sequence identity to SEQ ID NO: 14; (h) a heavy chain variable region having at least 80% sequence identity to SEQ ID NO: 15, and a light chain variable region having at least 80% sequence identity to SEQ ID NO: 16; (i) a heavy chain variable region having at least 80% sequence identity to SEQ ID NO: 17, and a light chain variable region having at least 80% sequence identity to SEQ ID NO: 12; (j) a heavy chain variable region having at least 80% sequence identity to SEQ ID NO: 76, and a light chain variable region having at least 80% sequence identity to SEQ ID NO: 77; (k) a heavy chain variable region having at least 80% sequence identity to SEQ ID NO: 78, and a light chain variable region having at least 80% sequence identity to SEQ ID NO: 77; (l) a heavy chain variable region having at least 80% sequence identity to SEQ ID NO: 76, and a light chain variable region having at least 80% sequence identity to SEQ ID NO: 79; or (m) a heavy chain variable region having at least 80% sequence identity to SEQ ID NO: 78, and a light chain variable region having at least 80% sequence identity to SEQ ID NO: 79.

Embodiment 4. The anti-TIGIT antibody or antigen-binding fragment thereof of any one of embodiments 1-3, wherein the anti-TIGIT antibody or antigen-binding fragment thereof is a monoclonal antibody.

Embodiment 5. The anti-TIGIT antibody or antigen-binding fragment thereof of any one of embodiments 1-4, wherein the anti-TIGIT antibody or antigen-binding fragment thereof is a chimeric, humanized, or veneered antibody.

Embodiment 6. The anti-TIGIT antibody or antigen-binding fragment thereof of embodiment 5, wherein the chimeric antibody comprises human IgG1/kappa Fab constant domain.

Embodiment 7. The anti-TIGIT antibody or antigen-binding fragment thereof of any one of embodiments 1-3, wherein the anti-TIGIT antibody or antigen-binding fragment thereof is a human antibody.

Embodiment 8. The anti-TIGIT antibody or antigen-binding fragment thereof of any one of proceeding embodiments, wherein the anti-TIGIT antibody or antigen binding fragment thereof inhibits binding of TIGIT to CD155, optionally wherein the anti-TIGIT antibody or antigen binding fragment thereof inhibits the binding with an $IC_{50}$ of about 0.1 nM to about 10 nM, about 0.1 nM to about 5 nM, about 0.2 nM to about 2 nM, about 0.2 nM to about 0.8 nM, about 0.4 nM to about 0.8 nM, or about 0.6 nM to about 0.8 nM, measured as in Example 1.

Embodiment 9. The anti-TIGIT antibody or antigen binding fragment thereof of any one of embodiments 1-5 or 7-8, wherein the antibody further comprises a variant heavy chain constant region selected from variant human IgG1, variant human IgG2, variant human IgG3, or variant human IgG4, and optionally a human light chain constant region.

Embodiment 10. The anti-TIGIT antibody or antigen binding fragment thereof of embodiment 9, wherein the variant heavy chain constant region has enhanced or decreased effector function with reference to the wild type heavy chain constant region.

Embodiment 11. The anti-TIGIT antibody or antigen binding fragment thereof of embodiment 10, wherein the variant human IgG heavy chain constant region comprises SEQ ID NO: 97, SEQ ID NO: 99, or SEQ ID NO: 101.

Embodiment 12. The anti-TIGIT antibody or antigen binding fragment thereof of any one of embodiments 1-5 or 7-8, wherein the antibody further comprises a wild-type human IgG heavy chain constant region, and optionally a human light chain constant region.

Embodiment 13. The anti-TIGIT antibody or antigen binding fragment thereof of embodiment 12, wherein the wild-type human IgG heavy chain constant region comprises SEQ ID NO: 94.

Embodiment 14. The anti-TIGIT antibody or antigen binding fragment thereof of embodiment 12 or 13 comprising a human light chain kappa constant region, optionally wherein the human light chain constant region comprises SEQ ID NO: 95.

Embodiment 15. The anti-TIGIT antibody or antigen binding fragment thereof of embodiment 1-5 or 7-8, wherein the antibody has a heavy chain and a light chain, wherein (a) the heavy chain has an amino acid sequence comprising SEQ ID NO: 92, and the light chain has an amino acid sequence comprising SEQ ID NO: 93; or (b) the heavy chain has an amino acid sequence comprising SEQ ID NO: 96, and the light chain has an amino acid sequence comprising SEQ ID NO: 93; or (c) the heavy chain has an amino acid sequence comprising SEQ ID NO: 98, and the light chain has an amino acid sequence comprising SEQ ID NO: 93; or (d) the heavy chain has an amino acid sequence comprising SEQ ID NO: 100, and the light chain has an amino acid sequence comprising SEQ ID NO: 93.

Embodiment 16. The anti-TIGIT antibody or antigen binding fragment thereof of any one of preceding embodiments, wherein the antibody or binding fragment thereof (a) has an equilibrium binding constant (KD) of about $0.01 \times 10^{-11}$ M to about $100 \times 10^{-11}$ M, about $0.1 \times 10^{-11}$ M to about $100 \times 10^{-11}$ M, about $0.1 \times 10^{-11}$ M to about $10 \times 10^{-11}$ M, about $1 \times 10^{-11}$ M to about $100 \times 10^{-11}$ M or about $1 \times 10^{-11}$ M to about $10 \times 10^{-11}$ M, measured by surface plasmon resonance; (b) blocks binding of soluble human CD155 ligand to cell surface human TIGIT with a half maximal inhibitor concentration (IC50) of about 0.2 nM to about 2 nM, about 0.2 nM to about 0.8 nM, about 0.6 nM to about 0.8 nM, or about 0.6 nM to about 0.8 nM, measured as in Example 1; (c) binds to an epitope that includes at least the following residues of TIGIT: (i) D72 of SEQ ID NO: 80 and at least one of T55, Q56, N58, E60, S80, and K82 of SEQ ID NO: 80; (ii) E60 and D72 of SEQ ID NO: 80 and optionally at least one of T55, Q56, N58, S80, and K82 of SEQ ID NO: 80; (iii) D72 and K82 of SEQ ID NO: 80 and optionally at least one of T55, Q56, N58, E60, and S80 of SEQ ID NO: 80; (iv) E60, D72 and K82 of SEQ ID NO: 80 and optionally at least one of T55, Q56, N58, and S80 of SEQ ID NO: 80; or (v) T55, Q56, N58, E60, D72, S80, and K82 of SEQ ID NO: 80; or (d) any combination of (a), (b) and (c).

Embodiment 17. The anti-TIGIT antibody or antigen binding fragment thereof of embodiment 16, wherein the antibody or antigen binding fragment thereof competes with the antibody or antigen-binding fragment thereof of any one of embodiments 1-17 for binding to TIGIT.

Embodiment 18. The anti-TIGIT antibody or antigen binding fragment thereof of embodiment 16 or 17, wherein an excess of the antibody or antigen-binding fragment thereof competes with a reference antibody for binding to TIGIT by at least about 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% as measured in a competitive binding assay, wherein the reference antibody comprises a heavy chain having an amino acid sequence comprising SEQ ID NO: 92 and a light chain having an amino acid sequence comprising SEQ ID NO: 93.

Embodiment 19. An anti-TIGIT antibody or antigen-binding fragment thereof that specifically binds to human TIGIT, comprising a heavy chain having an amino acid sequence comprising SEQ ID NO: 92 and a light chain having an amino acid sequence comprising SEQ ID NO: 93.

Embodiment 20. A method of inhibiting binding of TIGIT to CD155 comprising contacting TIGIT with the anti-TIGIT antibody or antigen-binding fragment thereof of any one of preceding embodiments.

Embodiment 21. A method of treating a subject infected with a pathogen comprising administering to the subject an effective regime or a therapeutically effective amount of an antibody of any preceding embodiments.

Embodiment 22. The method of embodiment 21, wherein the pathogen is a virus, bacteria, fungi, or protozoan.

Embodiment 23. The method of embodiment 22, wherein the pathogen is HIV, SIV, hepatitis, herpes virus, adenovirus, influenza virus, flavivirus, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus, arboviral encephalitis virus, *chlamydia, rickettsial* bacteria, mycobacteria, staphylococci, treptocci, pneumonococci, meningococci, conococci, *klebsiella, proteus, serratia, pseudomonas, legionella*, diphtheria, *salmonella*, bacilli, cholera, tetanus, botulism, anthrax, plague, leptospirosis, and Lyme disease bacteria.

Embodiment 24. The method of any one of embodiments 21-23, wherein the subject is treated with a vaccine inducing an immune response against the pathogen which is enhanced by the antibody.

Embodiment 25. The method of embodiment 24, wherein the vaccine comprises a protein of the pathogen or fragment thereof.

Embodiment 26. The method of any one of embodiments 21-25, wherein the subject is further administered a second antibody against the pathogen, wherein an effector mediated cytotoxicity of the second antibody against the pathogen is enhanced by the antibody.

Embodiment 27. The method of any one of embodiments 21-26, wherein the subject is further administered one or more of an antiviral agent, an antiparasitic agent, an antibacterial agent, or an antifungal agent.

Embodiment 28. A method of treating or effecting prophylaxis of cancer comprising administering to a subject having or at risk of cancer an effective regime or a therapeutically effective amount of any one of the anti-TIGIT antibodies or antigen-binding fragment thereof of any one of preceding embodiments.

Embodiment 29. The method of embodiment 28, wherein the cancer is a hematological malignancy, a solid tumor, Merkel cell carcinoma, urothelial cancer, head and neck squamous cell carcinoma, a B-cell lymphoma, uterine cancer, cervical cancer, testicular cancer, gastrointestinal tract cancer, bladder cancer, bone cancer, bone marrow, skin cancer, gall bladder cancer, heart cancer, lung cancer, salivary gland cancer, adrenal gland cancer, thyroid cancer, ganglia cancer, central nervous system (CNS) and peripheral nervous system (PNS) cancer, and a cancer of the hematopoietic system, a cancer of the immune system.

Embodiment 30. The method of embodiment 28 or 29, wherein the subject is administered tumor infiltrating T cells which are activated by the antibody or antigen-binding fragment thereof.

Embodiment 31. The method of any one of embodiments 28-30, wherein the subject is administered a vaccine inducing an immune response against the cancer, which is enhanced by the antibody or antigen-binding fragment thereof.

Embodiment 32. The method of embodiment 31, wherein the vaccine comprises an antigen or a fragment thereof expressed on the surface of cancer cells.

Embodiment 33. The method of any one of embodiments 28-32, wherein the subject is administered natural killer cells whose cytotoxicity against the cancer is enhanced by the antibody or antigen-binding fragment thereof.

Embodiment 34. The method of any one of embodiments 28-33, wherein the subject is further administered a second antibody against an antigen expressed on the surface of cells of cancer, whereby an effector mediated cytotoxicity of the second antibody against the cancer is enhanced by the antibody or antigen-binding fragment thereof.

Embodiment 35. The method of any one of embodiments 28-33, wherein the subject is further administered a second antibody against an antigen expressed on the surface of an immune cell.

Embodiment 36. The method of embodiment 35, wherein the immune cell is a T cell or a natural killer cell.

Embodiment 37. The method of embodiment 35 or 36, wherein the antigen is CTLA-4, PD-1 or PD-L1.

Embodiment 38. The method of any one of embodiments 28-37, wherein the subject is further administered one or more therapies selected from the group consisting of chemotherapy, radiation, cell-based therapy, and surgery.

Embodiment 39. The method of any one of embodiments 28-38, wherein the subject is further administered an inhibitor of one or more immune-checkpoint receptors or ligands.

Embodiment 40. The method of embodiment 39, wherein the one or more immune-checkpoint receptors or ligands are selected from the group consisting of CTLA-4, PD-1, PD-L1, TIM-3, LAG-3, PVRIG, BTLA, VISTA, CD96, $A_{2a}R$, $A_{2b}R$, $A_{2a}/A_{2b}R$, arginase, CD39, CD73, IDO and TDO.

Embodiment 41. The method of embodiment 39, wherein the inhibitor is selected from the group consisting of ipilimumab, tremelimumab, nivolumab, pembrolizumab, lambrolizumab, cemiplimab, tislelizumab, zimberelimab, durvalumab, and atezolizumab.

Embodiment 42. A pharmaceutical composition comprising the antibody or antigen-binding fragment thereof of any one of embodiments 1-19 and a pharmaceutically acceptable carrier.

Embodiment 43. An anti-TIGIT antibody or antigen binding fragment thereof that binds to an epitope of human TIGIT comprising at least one of the following amino acid residues of SEQ ID NO 80: T55, Q56, N58, E60, D72, S80, and K82.

Embodiment 44. The anti-TIGIT antibody or antigen-binding fragment thereof of embodiment 43, wherein the antibody or antigen-binding fragment thereof binds to an epitope that includes at least the following residues of TIGIT: (i) D72 of SEQ ID NO: 80 and at least one of T55, Q56, N58, E60, S80, and K82 of SEQ ID NO: 80; (ii) E60 and D72 of SEQ ID NO: 80 and optionally at least one of T55, Q56, N58, S80, and K82 of SEQ ID NO: 80; (iii) D72 and K82 of SEQ ID NO: 80 and optionally at least one of T55, Q56, N58, E60, and S80 of SEQ ID NO: 80; (iv) E60, D72 and K82 of SEQ ID NO: 80 and optionally at least one of T55, Q56, N58, and S80 of SEQ ID NO: 80; or (v) T55, Q56, N58, E60, D72, S80, and K82 of SEQ ID NO: 80.

Embodiment 45. The anti-TIGIT antibody or antigen-binding fragment thereof of embodiment 43 or 44, wherein the antibody or antigen-binding fragment thereof competes with the antibody or antigen-binding fragment thereof of any one of embodiments 1-19 for binding to TIGIT.

Embodiment 46. The anti-TIGIT antibody or antigen-binding fragment thereof of embodiment 43 or 44, wherein an excess of the antibody or antigen-binding fragment thereof competes with a reference antibody for binding to TIGIT by at least about 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% as measured in a competitive binding assay, wherein the reference antibody comprises a heavy chain having an amino acid sequence comprising SEQ ID NO: 92 and a light chain having an amino acid sequence comprising SEQ ID NO: 93.

Embodiment 47. An anti-TIGIT antibody or antigen binding fragment thereof of any one of embodiments 1-19, wherein the antibody or antigen binding fragment thereof binds to an epitope of human TIGIT comprising at least one of the following amino acid residues of SEQ ID NO 80: T55, Q56, N58, E60, D72, S80, and K82.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the disclosure can be used in combination with any other unless specifically indicated otherwise.

Although the present disclosure has been described in some detail by way of illustration and example for purposes of clarity and understanding, it will be apparent that certain changes and modifications can be practiced within the scope of the appended claims.

EXAMPLES

The following examples discuss the production, characterization, and humanization of antibodies against human TIGIT and also provide exemplary methods by which binding characteristics by which the antibodies described in this application can be determined.

Example 1. Generation of Anti-TIGIT Antibodies

Anti-TIGIT antibodies were obtained from immunized mice. His-tagged human TIGIT protein with SEQ ID NO: 83 (hTIGIT-His) and cyno TIGIT protein with SEQ ID NO: 85 (cTIGIT-His) extracellular domain were transiently expressed in HEK293 cells and purified by anti-His affinity chromatography. RIMMS immunization of BALB/c mice was performed with a mixture of recombinant hTIGIT-His and cTIGIT-His protein. Plasma titer were tested prior to final boost by an ELISA assay against the immunogens to confirm good titer. After final boost, terminal bleeds were collected along with spleen, inguinal, brachia, axillary and cervical lymph nodes. Collected material was put through B-cell purification prior to fusion to generate hybridomas for initial screens.

Primary screen of hybridomas was performed using an ELISA assay 10 days after fusion. 384-well ELISA plates were coated with 1 µg/mL hTIGIT-His protein, and after blocking the plate, 20 µL hybridoma supernatants were added and allowed to bind to the plate coated TIGIT. After incubation at room temperature, the plate was washed, and antibody bound to plate coated TIGIT were then detected using HRP conjugated goat anti-mouse IgG antibody.

Positive hybridoma cells were then expanded into 48-well plates, and supernatants were collected to test antibody specificity in ELISA assays. ELISA plates were coated with either hTIGIT-His protein, or cTIGIT-His protein, and CD47-His protein (Acro Biosystems, Cat #CD7-H5227) was used as a control counter assay to deselect antibodies recognizing the His-tag of the immunogen protein. Antibodies showing positive binding to both human and cyno TIGIT, while negative to the His-tagged control protein, were then tested for functional blocking of TIGIT/CD155 binding.

Human TIGIT extracellular domain was fused to a mouse Fc sequence, and this hTIGIT-mFc (SEQ ID NO: 87) protein was expressed in HEK293 cells and purified by Protein A affinity chromatography. Recombinant human CD155 including the extracellular domains fused to a human Fc sequence (hCD155-hFc) from R&D Systems (Cat #9174-CD-01M) was used to establish a CD155/TIGIT interaction blockade assay. To test the functional blockade activity of antibodies, 0.5 μg/mL hTIGIT-mFc protein was used to coat an ELISA plate, after blocking, hybridoma supernatant was added together with 0.5 μg/mL hCD155-hFc protein. After incubation, the ELISA plate was washed, and bound hCD155-hFc was detected using HRP conjugated goat anti-human IgG antibody. Clones were identified that were able to bind to both human and cyno-TIGIT and that antibody binding was able to block CD155/TIGIT interaction.

These clones were further expanded, and antibodies were purified using a Protein G column. These purified antibodies were tested for binding to human and cyno TIGIT expressed on cell surface by flow cytometry. Stable CHO-K1 cell lines expressing full length human TIGIT clone 2A7 (Swiss-Prot Q495A1; SEQ ID NO: 80) or full length cyno TIGIT clone C10 (Swiss-Prot A0A2K5UW92; SEQ ID NO: 84) were developed. For the flow assay, cells were collected and incubated in 100 μL of HBSS buffer in the presence (or absence) of various concentrations of antibodies for 1 hr at 4° C. After washing with HBSS, antibody binding on cells was detected with 2 μg/mL of Alexa488-labeled goat anti-mouse IgG antibody (ThermoFisher Scientific, Cat #A-11001) for 30 min at 4° C. Cells were then washed and resuspended in PBS and subjected to flow cytometry using an Attune NxT flow cytometer (ThermoFisher Scientific, Waltham, Mass.). The geometric mean of the fluorescence intensity was obtained for the whole single cell population. Antibodies capable of binding to both human and cyno TIGIT expressed on cell surface were further tested for their blocking activity against recombinant human CD155 binding to human TIGIT on the surface of CHO cells. CHO-hTIGIT cells ($10^5$ cells) were incubated with 2.5 μg/mL hCD155-Fc protein in the presence of various concentrations of antibody at room temperature for 1 hr. After washing with HBSS buffer, hCD155-Fc binding to hTIGIT-CHO cells was detected with PerCP-eFluor 710 conjugated anti-CD155 antibody (ThermoFisher, Cat #1550-42). Cells were then washed and subjected to flow cytometry analysis. Table 4 shows the half maximal effective concentration ($EC_{50}$) (n=2) of antibodies binding to human and cyno TIGIT, as well as the $IC_{50}$ for the inhibition of CD155 binding to TIGIT.

TABLE 4

Purified mouse anti-TIGIT antibodies binding to TIGIT expressed on cell surface

| α-TIGIT clone | hTIGIT $EC_{50}$ (nM) | cTIGIT $EC_{50}$ (nM) | hTIGIT/hCD155 $IC_{50}$ (nM) |
|---|---|---|---|
| 22B22 | 0.507 | 0.580 | 0.83 |
| 21B16 | 0.498 | 1.201 | 1.15 |
| 28O12 | 0.638 | 0.710 | 1.16 |
| 5J24 | 0.704 | 1.634 | 1.46 |

TABLE 4-continued

Purified mouse anti-TIGIT antibodies binding to TIGIT expressed on cell surface

| α-TIGIT clone | hTIGIT $EC_{50}$ (nM) | cTIGIT $EC_{50}$ (nM) | hTIGIT/hCD155 $IC_{50}$ (nM) |
|---|---|---|---|
| 21B9 | 0.506 | 0.631 | 1.66 |
| 21F8 | 0.952 | 1.789 | 1.67 |
| 28P24 | 0.466 | 1.260 | 1.70 |
| 24F8 | 1.306 | 1.846 | 1.79 |
| 30M18 | 0.825 | 1.166 | 2.19 |

Top hybridoma cell lines were selected based on their binding affinity to both human and cyno TIGIT, and their capability of blocking CD155 binding with TIGIT. Hybridoma of these clones were expanded and determination of heavy and light chain variable region (VH and VL, respectively) sequences of mouse anti-TIGIT antibodies was carried out following standard procedures. The amino acid sequences of the mature VH and VL of antibodies 21F8, 30M18, 24F8, 5J24, 21B9, 22B22, 28P24, 21B16, and 28O12 are shown in FIGS. 1A-1I, with their CDRs underlined. Assignment of CDR sequences and numbering of amino acid positions are according to Kabat definitions.

Seven of the antibodies shown in FIGS. 1A-1I were expressed recombinantly as mouse human chimera with mouse variable domains and human IgG1/kappa constant domains. Recombinant proteins were expressed from HEK293 cells and purified by Protein A affinity chromatography.

The binding capability of these chimera anti-TIGIT antibodies to cell surface overexpressed human and cyno TIGIT was confirmed utilizing the flow cytometry assay previously described. After incubation of chimera anti-TIGIT antibody with hTIGIT-CHO or cTIGIT-CHO, bound antibody was detected using Alexa488 conjugated goat anti-human IgG antibody (ThermoFisher Scientific, Cat #A-11013). Antibody functional activity in inhibiting recombinant hCD155-hFc binding to hTIGIT-CHO-K1 cells was also determined using flow assay as previously described. The $EC_{50}$ of anti-TIGIT chimera antibodies binding to human and cyno TIGIT, as well as the $IC_{50}$ for the inhibition of hCD155 binding to hTIGIT expressing cells were determined and are presented in Table 5.

TABLE 5

Recombinant anti-TIGIT mouse/human chimera antibodies binding to TIGIT overexpressed on CHO-K1 cell surface, and their blocking activity to inhibit human CD155 binding to human TIGIT

| α-TIGIT antibody | hTIGIT-CHO $EC_{50}$ (nM) | cTIGIT-CHO $EC_{50}$ (nM) | hTIGIT-CHO/hCD155 $IC_{50}$ (nM) |
|---|---|---|---|
| Ch22B22 | 0.16 | 0.24 | 1.16 |
| Ch21B16 | 0.12 | 0.42 | 0.20 |
| Ch28O12 | 0.159 | 0.358 | 0.48 |
| Ch5J24 | 0.131 | 0.212 | 0.70 |
| Ch21B9 | 0.102 | 0.18 | 0.80 |
| Ch24F8 | 0.15 | 0.199 | 0.62 |
| Ch30M18 | 0.336 | 6.138 | 2.18 |

The ability of chimera anti-TIGIT antibodies to bind to endogenously expressed TIGIT on isolated human $CD4^+$ and $CD8^+$ cells was tested using a flow cytometry assay. Human $CD4^+$ or $CD8^+$ T cells were isolated from human whole blood using RosetteSep™ Human $CD4^+$ T cell Enrichment Cocktail (Stemcell, Cat #15022) or Human $CD8^+$ T cell enrichment Cocktail (Stemcell, Cat #15022), respectively. As shown in Table 6, comparable $EC_{50}$ for recombinant anti-TIGIT antibodies binding to human $CD4^+$ or $CD8^+$ cells were observed which were similar to their binding affinity to overexpressed full length human TIGIT on CHO-K1 cells. However, differences in max binding activity (MFImax) was observed between clones.

TABLE 6

Recombinant anti-TIGIT mouse/human chimera antibodies binding to isolated human T cells

| α-TIGIT antibody | CD4+ EC$_{50}$ (nM) | CD4+ MFI$_{max}$ | CD8+ EC$_{50}$ (nM) | CD8+ MFI$_{max}$ |
|---|---|---|---|---|
| Ch24F8 | 0.130 | 210 | 0.177 | 5800 |
| Ch5J24 | 0.073 | 125 | 0.117 | 4500 |
| Ch21B9 | 0.029 | 150 | 0.062 | 4500 |
| Ch22B22 | 0.097 | 140 | 0.175 | 5000 |
| Ch21B16 | 0.119 | 180 | 0.160 | 5200 |
| Ch28O12 | 0.141 | 190 | 0.249 | 7200 |
| Ch30M18 | 0.197 | 125 | 0.293 | 3500 |

Recombinant anti-TIGIT chimera antibodies binding to cynomolgus monkey whole blood were tested to confirm the capability of antibody binding to endogenous cyno TIGIT protein on CD4+ and CD8+ cells. Cynomolgus monkey whole blood was incubated with recombinant anti-TIGIT chimera antibodies at 20 µg/mL, 5 µg/mL, 1 µg/mL and 0.2 µg/mL. After 30 min incubation at 4° C., RBC lysis was performed for 15 min at room temperature. Cells were then washed and collected by centrifugation and blocked with a cocktail containing Fc block (BD Biosciences, Cat #564219) and Live-dead fixable Aqua (Invitrogen, Cat #L34957). Cell bound anti-TIGIT antibodies were detected with anti-human IgG Fc-Biotin (Southern Biotech, Cat #9040-08) for 30 min at 4° C., followed by washing and centrifuging the cells and a second incubation for 30 min at 4° C. with PE-conjugated Streptavidin (Invitrogen, Cat #12-4317-87). Wild type human IgG1 antibody was used as isotype control and directly conjugated anti-human TIGIT-PE (eBiosciences, Cat #12-9500-42) was used as the positive control. FIG. 2 shows that Ch24F8, Ch28O12 and Ch22B22 were capable of binding to cyno TIGIT expressed on cyno CD4+ and CD8+ cells. The geometric mean of the fluorescent intensity (gMFI) was obtained, and data were presented as fold of gMFI over isotype control.

The kinetic binding of these recombinant anti-TIGIT antibodies to human TIGIT was determined by surface plasmon resonance (SPR) using a Bio-Rad ProteOn XPR36 instrument. Recombinant antibodies were immobilized using a Protein A coated GLC sensor chip, and soluble His-tagged TIGIT (Acro Biosystems, Cat #No. TIT-H52H3) was used as the analyte. The binding constants were determined at 25° C. As shown in Table 7, clone 24F8 has the highest binding affinity as measured by the equilibrium dissociation constant ($K_D$) among the seven recombinant anti-TIGIT chimera antibodies tested.

TABLE 7

Binding kinetics of recombinant anti-TIGIT antibodies to His-tagged human TIGIT

| α-TIGIT antibody | $k_a$ (M$^{-1}$s$^{-1}$) | $k_d$ (s$^{-1}$) | $K_D$ (M) |
|---|---|---|---|
| Ch24F8 | 2.15E+06 | 7.5E−05 | 3.5E−11 |
| Ch28O12 | 1.256E+06 | 1.135E−03 | 9.04E−10 |
| Ch30M18 | 7.27E+05 | 1.730E−03 | 2.38E−09 |
| Ch5J24 | 5.57E+06 | 2.14E−02 | 3.85E−09 |
| Ch21B16 | 1.47E+06 | 9.29E−03 | 6.30E−09 |
| Ch21B9 | 1.05E+07 | 7.4E−02 | 7.1E−09 |
| Ch22B22 | 1.44E+06 | 1.41E−02 | 9.78E−09 |

Example 2. Generation of Humanized Anti-TIGIT Antibodies

Mouse antibody 24F8 was selected for humanization using the CDR grafting technique (Queen et al, Proc. Natl. Acad. Sci. USA. 86:10029-10033, 1989). The mouse variable heavy (VH) and variable light (VL) sequences of 24F8 were used to identify the closest two human germlines for each chain. For VH, IGHV4-34*09 with 70% sequence identity, and IGHV4-4*02 with 66% identity were found. For VL, IGKV1-33*01 with 70% sequence identity, and IGKV3-15*01 with 67% identity were found (Table 8).

TABLE 8

Identification of human germlines and acceptors

| Variable Chain | Human Germline | Human/Mouse Identity (%) | Human Acceptor |
|---|---|---|---|
| VH1 | IGHV4-34*09 | 70 | AAV40102.1 |
| VH2 | IGHV4-4*02 | 66 | ADX65334.1 |
| VL1 | IGKV1-33*01 | 70 | ACY78416.1 |
| VL2 | IGKV3-15*01 | 67 | ADU32611.1 |

The positioning of the three heavy chain CDR (HC-CDR) sequences in the VH chain and the three light chain CDR (LC-CDR) sequences in the VL chain were defined according to Kabat.

Human acceptors for the VH and VL frameworks were searched for within the GenBank database (Benson et al., Nucleic Acids Res. 2005, 33, D34-D38), and VH & VL sequences coding for human cDNA were identified (see Table 8).

CDR grafting for each human acceptor was performed using HC-CDR1 (SEQ ID NO: 48), HC-CDR2 (SEQ ID NO: 49), and HC-CDR3 (SEQ ID NO: 50) for the VH acceptors, and LC-CDR1 (SEQ ID NO: 51), LC-CDR2 (SEQ ID NO: 52), and LC-CDR3 (SEQ ID NO: 53) for the VL acceptors. The resultant sequences were examined for the introduction of any potential post-translation modification or chemical degradation sites and were confirmed to be free from such liabilities. Putative residues for mouse back mutation were also identified using antibody homology graphic modeling.

Oligonucleotides were designed and synthesized as Fab fragments with human IgG1/kappa constant domains for the two VH and two VL grafted human acceptors and inserted into a vector system for high throughput screening of expression levels and biophysical properties, without the need for protein purification (Zhang & Hirama, Patent Application Publication US 2012/0178110). All four combinations of VH1 (SEQ ID NO: 76) or VH2 (SEQ ID NO: 78) with VL1 (SEQ ID NO: 79) or VL2 (SEQ ID NO: 77) (FIGS. 1J-1M) were screened along with a chimera Fab mVH+mVL constructed from the mouse 24F8VH (SEQ ID NO: 5) & 24F8VL (SEQ ID NO: 6) domains and human IgG1/kappa Fab constant domains. Supernatants of the Fabs, secreted as a SASA (single-domain antibody against serum albumin) fusion proteins were analyzed by surface plasmon resonance (SPR) using a Biacore 8K instrument with Fab capture using an BSA coated chip and soluble His-tagged TIGIT as the analyte. The kinetic binding data for human and cyno TIGIT are shown in Table 9 for the five Fab fragments.

TABLE 9

Kinetic binding affinity data for humanized Fab fragments

| Fab | Analyte | $k_a$ (M$^{-1}$s$^{-1}$) | $k_d$ (s$^{-1}$) | $K_D$ (M) |
| --- | --- | --- | --- | --- |
| mVH + mVL | hTIGIT-His | 1.86E+06 | 2.37E-06 | 1.27E-12 |
| VH1 + VL2 (Hu24F8.1 Fab) | | 3.08E+06 | 1.11E-04 | 3.61E-11 |
| VH2 + VL2 (Hu24F8.2 Fab) | | 2.08E+06 | 9.39E-05 | 4.50E-11 |
| VH2 + VL1 (Hu24F8.3 Fab) | | 1.99E+06 | 4.81E-04 | 2.42E-10 |
| VH1 + VL1 (Hu24F8.4 Fab) | | 3.05E+06 | 8.55E-04 | 2.80E-10 |
| mVH + mVL | cTIGIT-His | 1.54E+06 | 7.28E-04 | 4.74E-10 |
| VH1 + VL2 (Hu24F8.1 Fab) | | 1.11E+06 | 1.40E-03 | 1.26E-09 |
| VH2 + VL2 (Hu24F8.2 Fab) | | 7.42E+05 | 8.08E-04 | 1.09E-09 |
| VH2 + VL1 (Hu24F8.3 Fab) | | 9.74E+05 | 5.85E-03 | 6.00E-09 |
| VH1 + VL1 (Hu24F8.4 Fab) | | 1.35E+06 | 1.33E-02 | 9.81E-09 |

These data demonstrated that the humanized variable domain combinations of VH1+VL2 and VH2+VL2 bound most tightly to both human and cyno TIGIT as measured by the equilibrium dissociation constant ($K_D$), and also retained the majority of the binding affinity of the mouse/human chimera Fab. As a consequence of this, constructs containing mouse framework residue back mutations were not investigated. These two VH/VL combinations (FIG. 1J and FIG. 1K) were selected for construct design of full-length Hu24F8.1 and Hu24F8.2 IgG1/kappa antibodies, respectively.

Hu24F8.1-IgG1.AA and Hu24F8.2-IgG1.AA are IgG1/kappa antibodies that have a heavy chain constant region with an amino acid sequence of SEQ ID NO: 97 and a light chain constant region with an amino acid sequence of SEQ ID NO: 95. The "IgG1.AA" designation indicates the heavy chain constant region has leucine to alanine amino acid substitutions at positions 234 and 235 (Eu numbering). In contrast, an "IgG1" designation indicates a wildtype IgG1 Fc region. For instance, Hu24F8.2-IgG1 is an IgG1/kappa antibody that has a heavy chain constant region with an amino acid sequence of SEQ ID NO: 94 and a light chain constant region with an amino acid sequence of SEQ ID NO: 95. Hu24F8.1-IgG1.AA, Hu24F8.2-IgG1.AA and Hu24F8.2-IgG1 antibodies used in these examples were produced recombinantly in HEK293 or CHO cells and purified by protein A affinity chromatography.

The purified, full-length antibodies Hu24F8.1-IgG1.AA (containing VH1+VL2) and Hu24F8.2-IgG1.AA (containing VH2+VL2), together with the full-length chimera antibody of 24F8 mouse VH+VL and human IgG1/kappa constant domains (Ch24F8), were analyzed by SPR using a Biacore T200 instrument with antibody capture using an anti-human IgG coated chip and soluble hTIGIT-His or cTIGIT-His as the analyte. The kinetic binding data for human and cyno TIGIT are shown in Table 10.

TABLE 10

Kinetic binding affinity data for humanized antibodies

| Antibody | Analyte | $k_a$ (M$^{-1}$s$^{-1}$) | $k_d$ (s$^{-1}$) | $K_D$ (M) |
| --- | --- | --- | --- | --- |
| Ch24F8 | hTIGIT-His | 8.53E+05 | 1.56E-04 | 1.83E-10 |
| Hu24F8.1-IgG1.AA | | 1.01E+06 | 1.45E-04 | 1.44E-10 |
| Hu24F8.2-IgG1.AA | | 7.96E+05 | 1.40E-04 | 1.76E-10 |
| Ch24F8 | cTIGIT-His | 6.58E+05 | 1.09E-03 | 1.66E-09 |
| Hu24F8.1-IgG1.AA | | 8.06E+05 | 1.40E-03 | 1.74E-09 |
| Hu24F8.2-IgG1.AA | | 6.79E+05 | 9.97E-04 | 1.47E-09 |

The kinetic binding affinity data for both of the full-length humanized antibodies confirmed that the binding affinity of the mouse antibody had been fully retained and that there was no need to introduce any mouse framework residue back mutations.

Example 3. In Vitro Binding Studies of Anti-TIGIT Antibodies

Binding of antibodies Hu24F8.1-IgG1.AA and Hu24F8.2-IgG1.AA to TIGIT expressed on cell surface was examined by flow cytometry. Cells expressing TIGIT on cell surface were collected and incubated in 100 µL of HBSS Buffer in the presence (or absence) of various concentrations of antibody for 1 hr at 4° C. After washing with HBSS, antibody binding on cells was detected with 2 µg/mL of Alexa488-labeled goat anti-human IgG antibody (ThermoFisher Scientific, Cat #A-11013) for 30 min at 4° C. Cells were then washed and resuspended in PBS and subjected to flow cytometry using a Attune NxT flow cytometer (ThermoFisher Scientific, Waltham, Mass.). GeoMean of fluorescence intensity was obtained for the whole single cell population, and for transient transfection, non-transfected cells were used to gate for the positive binding cell population to obtain percent of positive cells. Data was calculated by GraphPad Prism using the standard 4-parameter curve fitting.

Stable CHO-K1 cell lines expressing human TIGIT (clone 2A7) and cyno TIGIT (clone C10) were used to test Hu24F8.1-IgG1.AA and Hu24F8.2-IgG1.AA for their binding to human TIGIT and cyno TIGIT, respectively, as described above. Hu24F8.1-IgG1.AA bound to human TIGIT with an $EC_{50}$ 0.447±0.22 nM (n=8) (FIG. 3A) and to cyno TIGIT with an $EC_{50}$ of 0.237±0.33 nM (n=6) (FIG. 3B). Hu24F8.2-IgG1.AA bound to human TIGIT with an $EC_{50}$ 0.29±0.15 nM (n=8) (FIG. 3A) and to cyno TIGIT with an $EC_{50}$ of 0.35±0.16 nM (n=6) (FIG. 3B). These results show that both Hu24F8.1-IgG1.AA and Hu24F8.2-IgG1.AA bind tightly to human and cyno TIGIT expressed on a cell surface.

Binding of Hu24F8.2-IgG1.AA to mouse TIGIT (Swiss-Prot Q86176; SEQ ID NO: 88) and rat TIGIT (Swiss-Prot D3ZTQ2; SEQ ID NO: 89) was examined using CHO-K1 cells transiently transfected with full length mouse or rat TIGIT expressing constructs. Mouse TIGIT expression was confirmed using control antibody GNE10A7 (U.S. Pat. No. 9,499,596 Clark et al., 2016) and rat TIGIT expression was confirmed using control antibody eBioscience™ G1GD7 (Invitrogen, Cat #12-9501-82). Hu24F8.2-IgG1.AA does not bind to either mouse TIGIT (FIG. 4A) or rat TIGIT (FIG. 4B) when tested with up to 30 nM of antibody.

Binding of Hu24F8.2-IgG1.AA to isolated human CD8$^+$ T cells was examined by flow cytometry. CD8$^+$ T cells were isolated using the RosetteSep™ Human CD8$^+$ T cell Enrichment Cocktail (Stemcell, Cat #15023) following manufacturer recommendation. Cells were then activated with anti-CD3/CD28 beads with 20U/mL rhIL-2 supplements for 7-9 days. Activated or not-activated CD8+ cells were blocked with human Fc Block (BD Biosciences, Cat #564219) before being subjected to the flow cytometry antibody binding assay. As shown in FIG. 5A and FIG. 5B, Hu24F8.2-IgG1.AA binds to CD8+ cells with an $EC_{50}$ of 0.098±0.013 nM (n=2) with not-activated cells, and 0.14±0.036 nM (n=2) with activated CD8+ cells, respectively. Although the binding $EC_{50}$ is similar for activated and not-activated CD8+ cells, there is a significant difference in the maximum binding signal, which is consistent with elevated TIGIT expression on CD8+ on the cell surface upon activation.

Example 4. In Vitro Blocking Studies of Anti-TIGIT Antibodies

The activity of Hu24F8.1-IgG1.AA and Hu24F8.2-IgG1.AA to block the interaction of TIGIT with CD155 was analyzed by flow cytometry using CHO cells stably overexpressing human TIGIT (CHO-hTIGIT) and human CD155-Fc fusion recombinant soluble protein (hCD155-Fc), as described in Example 1. As shown in FIG. 6, both Hu24F8.1-IgG1.AA and Hu24F8.2-IgG1.AA blocked the interaction between hCD155-Fc and CHO-hTIGIT on the cell surface in a dose-dependent manner. The $IC_{50}$ for Hu24F8.1-IgG1.AA to block the TIGIT-CD155 interaction was 0.68 nM, and for Hu24F8.2-IgG1.AA it was 0.67 nM.

Example 5. Jurkat Dual Reporter Cell Line Characterization of Anti-TIGIT Antibodies The functional activity of Hu24F8.1-IgG1.AA and Hu24F8.2-IgG1.AA to block the human TIGIT receptor was assayed using Promega's TIGIT/CD155 Blockade Bioassay (Promega, Cat #J2205). In this assay, the effector cell line is a Jurkat cell line that has overexpressed TIGIT as well as a luciferase reporter that is activated downstream of T cell receptor (TCR). Another stable cell line is a CHO-K1 cell line overexpressing human CD155, in addition to a T cell activator protein that binds and activates the TCR. This CD155 aAPC/CHO-K1 cell line functions as artificial antigen-presenting cells. Co-culture of these two cell lines results in TCR activation by aAPC on the CHO-K1 cells, which would activate the reporter construct, however, that pathway activation is inhibited by a TIGIT/CD155 interaction, resulting in a low luciferase signal. The presence of an anti-TIGIT antibody would inhibit the TIGIT/CD155 interaction, releasing the TIGIT inhibitory effect, resulting in an increased luciferase signal. The assay was performed according to the manufacturer's protocol, in brief, the effecter Jurkat cells were recovered overnight in 96-well plates in a cell culture incubator, test antibody was serially diluted and added to the effecter cells, followed by antigen presenting CD155 aAPC/CHO-K1 cells. After 6 hours co-culture at 37° C. 5% $CO_2$, luciferase substrate Bio-Glo reagent was added, and the luminescence signal was read on an Envision (PerkinElmer). As shown in FIG. 7, Hu24F8.1-IgG1.AA was able to enhance the reporter activity dose dependently, with an $EC_{50}$ of 3.35±0.26 nM (n=3), whereas Hu24F8.2-IgG1.AA shown an $EC_{50}$ of 2.78±0.83 nM (n=3). Human IgG1 control did not show any effect.

Example 6. Molecular Analysis of Anti-TIGIT Antibodies

TIGIT and Fab Expression, Purification, Crystallization

Soluble protein of the mature extracellular domain of human TIGIT (residues 22-130) was expressed recombinantly in HEK293 cells. The construct (SEQ ID NO: 90) contained a C-terminal hexa-histidine tag with a $(Gly)_4$-Ala-$(Gly)_4$ linker, and asparagine residues 32 and 101 were mutated to glutamine to remove sites for N-glycosylation. The clarified supernatant was purified by affinity chromatography using a Nickel Sepharose Excel (GE Healthcare Life Sciences) column followed by size exclusion chromatography (SEC) using a Superdex 200 µg (GE Healthcare Life Sciences) column. The TIGIT protein at a concentration of 8.4 mg/mL was in a final buffer formulation of 20 mM Tris pH 7.0, 100 mM NaCl and flash frozen with liquid nitrogen.

Soluble Fab fragment (Fab24F8) of human IgG1 antibody Hu24F8.2-IgG1.AA was prepared by papain (Thermo Scientific, Cat. #20341) digestion in Phosphate Buffered Saline at 37° C. for 3 hours, followed by overnight digestion at room temperature. The cleaved Fc fragment was removed using a MabSelect SuRe Protein A (GE Healthcare Life Sciences) column and the flow-through was further purified by SEC using a Superdex 200 µg (GE Healthcare Life Sciences) column. The Fab24F8 protein at a concentration of 28 mg/mL was in a final buffer formulation of 20 mM Tris pH 7.0, 100 mM NaCl and flash frozen with liquid nitrogen.

TIGIT was mixed with Fab24F8 protein in a molar ratio of 1:1 with agitation for 60 min at 4° C. to form the Fab-TIGIT complex, followed by final SEC purification using a Superdex 200 pg (GE Healthcare Life Sciences) column and concentration of the protein eluate to 44 mg/mL. The purified complex was used in crystallization trials at 20° C. employing a standard screen with approximately 1500 different conditions. The conditions initially obtained were optimized using standard strategies, systematically varying parameters that critically influence crystallization. These conditions were further refined by systematically varying pH or precipitant concentrations. Crystals of the Fab-TIGIT complex that were suitable for structure elucidation were obtained by mixing 0.1 µL protein solution (15 mg/mL in 20 mM Tris pH 7.0; 100 mM NaCl) with 0.1 µL reservoir solution (20% (w/v) PEG3350; 0.20 M LiSO4) using the sitting drop vapor diffusion technique.

Data Collection and Structure Solution

Crystals were flash-frozen and measured at a temperature of 100 K. X-ray diffraction data were collected from crystals of the Fab-TIGIT complex at the Canadian Light Source (CLS, Saskatoon, Canada) using cryogenic conditions. The crystals belong to space group P 1. Data were processed using the computer software programs autoPROC, XDS and AIMLESS (The CCP4 Suite: Programs for Protein Crystallography". Acta Cryst. D50, 760-763), see Table 11.

TABLE 11

Data Collection and Processing Statistics for Fab24F8/TIGIT Complex

| Complex | Hu24F8.2 Fab/Human TIGIT ECD |
|---|---|
| X-ray source | CMCF-ID (08ID-1, CLS) |
| Wavelength [Å] | 0.9795 |
| Detector | PILATUS 6M |
| Temperature [K] | 100 |
| Space group | P1 |
| Cell: a; b; c; [Å] | 85.11; 86.83; 87.83 |
| α; β; γ; [°] | 94.3; 117.0; 116.1 |
| Resolution [Å] | 2.24 (2.46-2.24)[1] |
| Unique reflections | 53126 (2657) |
| Multiplicity | 2.2 (2.1) |
| Completeness [%] | 84.8 (76.4) |
| $R_{sym}$ [%] | 6.2 (48.6) |
| $R_{meas}$ [%] | 8.2 (64.8) |
| Mean(I)/σ | 9.9 (1.7) |

[1]values in parenthesis refer to the highest resolution bin.

The phase information necessary to determine and analyze the structure was obtained by molecular replacement.

Previously solved structures of a Fab (Bohrmann et al., *J. Alzheimers Dis.* 28:49-69, 2012) and TIGIT (Stengel et al., *Prov. Natl. Acad. Sci. USA,* 2012) were used as search models. There are three molecules of the Fab-TIGIT complex in the crystallographic asymmetric unit. Subsequent model building and refinement was performed according to standard protocols with program COOT and the software package CCP4, respectively. For the calculation of the free R-factor, a measure to cross-validate the correctness of the final model, about 4.6% of measured reflections were excluded from the refinement procedure. TLS refinement (using CCP4 program REFMAC5) was carried out, which resulted in lower R-factors and a higher quality of the electron density map. Automatically generated local NCS restraints were applied. The water model was built with the "Find waters" algorithm of COOT by putting water molecules in peaks of the Fo-Fc map contoured at 3.0σ followed by refinement with REFMAC5 and checking all waters with the validation tool of COOT. The criteria for the list of suspicious waters were: B-factor greater 80 Å$^2$, 2Fo-Fc map less than 1.2σ, distance to closest contact less than 2.3 Å or more than 3.5 Å. Data in a resolution range of 73.5-2.24 æ were in the final cycle of refinement and the $R_{cryst}$ and $R_{free}$ R-factors were 22.3 and 26.8%, respectively. The Ramachandran Plot of the final model shows 89.8% of all residues in the most favored region, 8.8% in the additionally allowed region, and 0.7% in the generously allowed region. See Table 12 for a summary of refinement.

TABLE 12

Refinement Statistics for Fab24F8/TIGIT

| Complex | Hu24F8.2 Fab/Human TIGIT ECD |
|---|---|
| Resolution [Å] | 73.52-2.24 |
| Number of reflections (working/test) | 50688/2467 |
| $R_{cryst}$ [%] | 22.3 |
| $R_{free}$ [%][1] | 26.8 |
| Total number of atoms: | |
| Protein | 12244 |
| Water | 427 |
| Ligand | — |
| Sulfate | 30 |
| Deviation from ideal geometry:[2] | |
| Bond lengths [Å] | 0.010 |
| Bond angles [°] | 1.47 |
| Bonded B's [Å$^2$][3] | 1.7 |
| Ramachandran plot:[4] | |
| Most favoured regions [%] | 89.8 |
| Additional allowed regions [%] | 8.8 |
| Generously allowed regions [%] | 0.7 |
| Disallowed regions [%] | 0.7 |

[1]Test-set contains 4.6% of measured reflections
[2]Root mean square deviations from geometric target values
[3] Calculated with MOLEMAN
[4] Calculated with PROCHECK Structure of Fab24F8 Bound to Human TIGIT There are three independent molecules of the complex in the crystallographic asymmetric unit, the atomic coordinates of which superimpose pairwise on one another with a root-mean-square deviation of 0.53-1.13 Å for all non-hydrogen atoms. The final model comprises residues Gln1 to Ser223 of the Fab heavy chain, Glu1 to Cys214 of the Fab light chain, and Met22 to Ser129 of TIGIT. Some short loop regions were not fully defined by electron density and are not included in the final model.

The Fab heavy chain HC-CDR2 & HC-CDR3 and all three LC-CDRs of the light chain form an extensive interaction with the large β-sheet structure of TIGIT, namely β-strands C, C', C" & F and the loops C'C" and C"D comprised from the polypeptide chains $^{55}$TQVNWEQQDQLLAICNADLGWHISPSFK$^{82}$ and $^{109}$IYH$^{111}$ of SEQ ID NO: 80 (FIGS. 8 and 9). This binding interaction results in a protein-protein interface with a surface area of 790±10 Å$^2$ (n=3) between the Fab fragment and TIGIT (PISA, EMBL-EBI). The molecular nature of this interaction is both hydrophilic and hydrophobic. TIGIT residues Thr55, Gln56, Asn58, Glu60, Asp72, Ser80 and Lys82 (shown with stick representation in FIG. 9) form direct or water-mediated hydrogen bond interactions (donor/acceptor inter-atomic distance no more than 3.1 Å) with residues of the Fab heavy and light chain CDRs. In addition, TIGIT residue Glu60 forms a salt bridge with Arg30 on the Fab light chain (Table 13). TIGIT hydrophobic residues Leu65, Ile68, Leu73, Pro79 and Ile109 (represented by spheres in FIG. 9) make van der Waals contacts with residues of the Fab heavy and light chains.

TABLE 13

Epitope Residues of TIGIT That Form Hydrogen Bonds and Salt Bridges with Paratope Residues of the Heavy and Light Chains of Fab24F8

| TIGIT Epitope | | Fab24F8 Paratope (Kabat numbering) | |
|---|---|---|---|
| Thr | 55 | LC-CDR3 | Thr 94 |
| Gln | 56 | LC-CDR3 | Tyr 92 |
| | | LC-CDR3 | Trp* 96 |
| | | HC-CDR3 | Tyr* 97 |
| Asn | 58 | LC-CDR3 | Tyr* 92 |
| Glu | 60 | LC-CDR1 | Arg 30 |
| | | LC-CDR3 | Tyr 92 |
| Asp | 72 | HC-CDR2 | Tyr 50 |
| Ser | 80 | LC-CDR2 | Tyr 53 |
| Lys | 82 | HC-CDR3 | Asn 99 |

*water-mediated hydrogen bond

FIG. 10A shows a schematic of the complex structure of the N-terminal Ig-like domain (SEQ ID NO: 91) of human CD155 (in ribbon representation) bound to human TIGIT (represented as a molecular surface), as reported by Stengel et al., 2012. FIG. 10B shows the superimposition of CD155, in the same orientation as FIG. 10A, onto a schematic of the crystal structure complex of Fab24F8 bound to TIGIT (each represented by a molecular surface). It can be clearly demonstrated that Hu24F8.2, or other antibodies derived from mouse antibody 24F8, binding to the extracellular domain of TIGIT will block CD155 from binding to TIGIT.

Example 7. Anti-TIGIT Antibody Enhances T Cell Responses Both Alone or in Combination with Anti-PD-1 Antibody This example demonstrates that Hu24F8.2-IgG1 enhances healthy or cancer subject human primary T cell responses either alone or in combination with an anti-PD-1 antibody such as AB122. Healthy and cancer subject PBMCs treated with 0.1, 1, or 10 µg/mL Hu24F8.2-IgG1 significantly increased IL-2 concentrations compared with the isotype control. In PBMCs from healthy subjects, treatment with a combination of 10 µg/mL Hu24F8.2-IgG1 and 1 µg/mL anti-human PD-1 antibody (AB122, zimberelimab) had significantly higher IL-2 levels compared with AB122 alone.

PBMCs from healthy subjects were isolated from Leukoreduction System (LRS) chambers and PBMCs from cancer subjects were isolated from CPT tubes and cultured with either 0.1, 1 or 10 µg/mL Hu24F8.2, 1 µg/mL AB122, or a combination of 10 µg/mL Hu24F8.2-IgG1 and 1 µg/mL AB122, in vitro in the presence of 1 ng/mL of SEA. Four days later, IL-2 concentration in the supernatant was measured by cytometric bead array (CBA). IgG1 isotype was included as a negative control.

Methods

Healthy subject PBMCs were isolated from LRS chambers whilst cancer subject PBMCs were isolated from CPT tubes. PBMCs were resuspended at a concentration of $2\times10^6$ cells per mL and 100 µL per well was aliquoted in a 96-well round-bottom plate. 50 µL per well of 4× concentrated antibodies resuspended in CTS Optimizer media was added to appropriate wells: Hu24F8.2-IgG1 or human IgG1 isotype control was added for a final concentration of 0.1, 1 and 10 µg/mL; and AB122 or human IgG4 isotype control was added for a final concentration of 1 µg/mL. Assay plates were incubated at 37° C., 5% $CO_2$ for 1 hour. 50 µL per well of 4× concentrated Staphylococcal enterotoxin A (SEA) resuspended in CTS Optimizer media was added to the appropriate wells for a final concentration of 1 ng/mL. Assay plates with a final well volume of 200 µL were incubated at 37° C., 5% $CO_2$ for 4 days and supernatant was collected for subsequent quantification of secreted IL-2. Supernatants were diluted 1:2 in assay diluent from the Human Soluble Protein Master Buffer Kit. Assay execution, data acquisition, and quantification were performed using the Human IL-2 Flex Set with Human Soluble Protein Master Buffer Kit according to the manufacturer's instructions.

Results

PBMCs from all donors used in the study were verified to express TIGIT on the non-T regulatory cell CD4+ T cell population that responds to SEA stimulation and CD155 (the ligand for TIGIT) on the CD14+ monocyte population. PBMCs isolated from 10 healthy subjects and 7 cancer subjects were each cultured with either 0.1, 1, or 10 µg/mL Hu24F8.2-IgG1 alone, 1 µg/mL AB122 alone, or a combination of 10 µg/mL Hu24F8.2-IgG1 and 1 µg/mL AB122 in the presence of 1 ng/mL of SEA. IL-2 concentration was measured in the supernatant 4 days later. IL-2 levels from the Hu24F8.2 treatment group were compared to IL-2 levels from the respective IgG1 isotype control treatment group, whilst IL-2 levels from the AB122 and Hu24F8.2-IgG1 combination treatment group were compared to IL-2 levels from the AB122 alone treatment group (Table 14 and Table 15). An example of IL-2 levels for one healthy subject (#566) is shown for all concentrations of Hu24F8.2-IgG1 tested in FIG. 1I. For these two subjects, there was a statistically significant increase in IL-2 secretion at all concentrations of Hu24F8.2-IgG1 tested in comparison to the respective IgG1 isotype control. For healthy subject #566, there was also a statistically significant increase in IL-2 secretion with AB122 and Hu24F8.2-IgG1 combination treatment compared with AB122 treatment alone. At the cohort level, there was a statistically significant increase in IL-2 secretion with 10 µg/mL Hu24F8.2-IgG1 treatment compared to IgG1 isotype control in both healthy and cancer subject PBMCs (FIG. 12A), and a statistically significant increase in IL-2 secretion with AB122 and Hu24F8.2-IgG1 combination treatment compared with AB122 treatment alone in the healthy subject PBMCs (FIG. 12B). In summary, 0.1 µg/mL Hu24F8.2-IgG1 significantly increased IL-2 concentrations (vs isotype) in 6/10 healthy subject PBMC samples (1.1-3.4-fold) and in 2/5 cancer subject PBMC samples (1.6-1.7-fold), 1 µg/mL Hu24F8.2-IgG1 significantly increased IL-2 concentrations (vs isotype) in 7/10 healthy subject PBMC samples (1.4-4.0-fold) and in 4/7 cancer subject PBMC samples (1.6-2.0-fold), 10 µg/mL Hu24F8.2-IgG1 significantly increased IL-2 concentrations (vs isotype) in 7/10 healthy subject PBMC samples (1.2-4.0-fold) and in 4/7 cancer subject PBMC samples (1.3-2.0-fold), and 10 µg/mL Hu24F8.2-IgG1+AB122 increased IL-2 concentrations (vs AB122 alone) in 6/10 healthy subject PBMC samples (1.9-8.3-fold).

TABLE 14

Mean[a] IL-2 levels (pg/mL) in human healthy subject PBMCs

| | | Subjects | | | | | | | | | |
|---|---|---|---|---|---|---|---|---|---|---|---|
| | | 223 | 225 | 226 | 229 | 272 | 273 | 566 | 967 | 568 | 969 |
| 0.1 µg/mL | Isotype | 452.8 | 3282 | 1552 | 2629 | nt | nt | 717.9 | 643.5 | 509.6 | 2625 |
| | Hu24F8.2-IgG1 | 377.8 | 3735 | 2353 | 3837 | nt | nt | 1763 | 998.8 | 1725 | 6706 |
| Significance[b] | | NS | * | * | * | — | — | ** | NS | *** | ** |
| Fold-change | | 0.83 | 1.13 | 1.51 | 1.45 | — | — | 2.45 | 1.55 | 3.38 | 2.55 |
| 1.0 µg/mL | Isotype | 385.2 | 3276 | 1920 | 2517 | 1035 | 321.4 | 735.9 | 565.1 | 510.6 | 2442 |
| | Hu24F8.2-IgG1 | 394.3 | 3671 | 2361 | 3588 | 1944 | 1296 | 2268 | 1270 | 1919 | 8256 |
| Significance[b] | | NS | NS | NS | * | *** | **** | *** | * | **** | **** |
| Fold-change | | 1.02 | 1.12 | 1.22 | 1.42 | 1.88 | 4.03 | 3.08 | 2.24 | 3.75 | 3.38 |
| 10.0 µg/mL | Isotype | 380.1 | 3269 | 2017 | 3448 | 1385 | 673.1 | 804.4 | 854.9 | 519.9 | 2847 |
| | Hu24F8.2-IgG1 | 294.5 | 3775 | 2329 | 4175 | 1779 | 1006 | 2515 | 1649 | 1949 | 8510 |
| Significance[b] | | NS | * | NS | * | NS | * | **** | * | **** | **** |
| Fold-change | | 0.77 | 1.15 | 1.15 | 1.21 | 1.87 | 4.03 | 3.12 | 1.92 | 3.74 | 2.98 |
| Isotype | | 430.2 | 3421 | 2070 | 3025 | 1154 | 785 | 928.1 | 733.3 | 593.4 | nt |
| AB122 | | 1080 | 5628 | 3455 | 4841 | 1728 | 1453 | 2650 | 2074 | 1593 | nt |
| 1 µg/ml AB122 + 10 µg/ml Hu24F8.2-IgG1 | | 1222 | 5762 | 3672 | 7077 | 2240 | 2067 | 7665 | 3614 | 4510 | nt |
| AB122 vs. AB122 + Hu24F8.2-IgG1 | Significance[b] | NS | NS | NS | * | * | *** | **** | **** | **** | — |
| | Fold-change | 2.84 | 1.68 | 1.77 | 2.33 | 1.94 | 2.63 | 8.25 | 4.92 | 7.6 | — |

[a] n = 3 technical replicates
[b] One way ANOVA with Sidak's multiple comparisons test (Isotype vs. Hu24F8.2 or AB122 + Hu24F8.2 vs. AB122); NS, not significant; nt, not tested; *p < 0.05, p < 0.01, *p < 0.001, ***p < 0.0001.

TABLE 15

Mean[a] IL-2 levels (pg/mL) in human cancer subject PBMCs

| | | Subjects | | | | | | |
|---|---|---|---|---|---|---|---|---|
| | | 3 | 29 | 60 | 33 | 27 | 6 | 12 |
| 0.1 µg/mL | Isotype | nt | 84.68 | nt | 47.44 | 1097 | 3438 | 1349 |
| | Hu24F8.2-IgG1 | nt | 98.07 | nt | 87.85 | 1874 | 5447 | 1871 |
| Significance[b] | | — | NS | — | NS | *** | **** | NS |
| Fold-change | | — | 1.16 | — | 1.85 | 1.71 | 1.58 | 1.38 |
| 1.0 µg/mL | Isotype | 1583 | 95.57 | 792.3 | 170 | 1068 | 3396 | 1295 |
| | Hu24F8.2-IgG1 | 2074 | 91.4 | 1557 | 119.8 | 1746 | 5992 | 2221 |
| Significance[b] | | NS | NS | * | NS | ** | **** | ** |
| Fold-change | | 1.31 | 0.95 | 1.96 | 0.7 | 1.63 | 1.76 | 1.71 |
| 10.0 µg/mL | Isotype | 1600 | 95.34 | 674.7 | 129.7 | 1153 | 3885 | 1765 |
| | Hu24F8.2-IgG1 | 1897 | 53.54 | 1363 | 94.35 | 1934 | 5073 | 3089 |
| Significance[b] | | NS | NS | * | NS | ** | ** | **** |
| Fold-change | | 1.18 | 0.56 | 2.02 | 0.72 | 1.67 | 1.3 | 1.75 |

[a] n = 3 technical replicates
[b] One way ANOVA with Sidak's multiple comparisons test (Isotype vs. Hu24F8.2); NS, not significant; nt, not tested; *p < 0.05, p < 0.01, *p < 0.001, ***p < 0.0001

These data demonstrate that Hu24F8.2-IgG1 enhances healthy or cancer subject human primary T cell responses either alone or in combination with an anti-PD-1 antibody such as AB122.

Example 8. Antibody Characterization by In Vitro Complement-Dependent Cytotoxicity (CDC) Assay CDC is an immune response where the complement system is involved in antibody-dependent cell killing through binding of complement component 1q (C1q) to the fragment crystallizable (Fc) region of an antibody. It initiates a complement cascade reaction resulting in the formation of a membrane attack complex that damages the cell membrane of target cells which express target proteins recognized by the Fab region of the antibody. In this example, the CDC activity of Hu24F8.2-IgG1 was characterized using GS-J1/TIGIT cells (GenScript M00693) in the presence of normal human serum complement (NHSC, Quidel).

Cell lysis by CDC was determined by Cell Titer-Glo® Assay Kit (Promega), which determines the number of viable cells in culture based on quantitation of ATP. Briefly, GS-J1/TIGIT cells (5000 cells/well) were treated with 10 µg/mL of Hu24F8.2-IgG1 or Human IgG1 (Abcam) negative control in the presence of 5%, 10% or 20% NHSC at 37° C. with 5% $CO_2$ for 4 hours (% NHSC optimization assay), or GS-J1/TIGIT cells (5000 cells/well) were treated with serial dilutions of Hu24F8.2-IgG1 (10 µg/mL) or Human IgG1 (10 µg/mL) in the presence of 5% NHSC at 37° C. with 5% $CO_2$ for 4 hours (CDC concentration response study). As a positive control, Raji cells (ATCC CCL-86, (5000 cells/well)) were treated with serial dilution of rituximab (10 µg/mL) in the presence of 5% NHSC at 37° C. with 5% $CO_2$ for 4 hours. Following the incubation with the test or control antibodies, Cell Titer-Glo® reagent was added, samples were incubated another 10-30 minutes at room temperature, and luminescence was read on PHERAstar FSX (BMG LabTech). Cell lysis due to CDC was calculated with the following formula: % Cell lysis=100%×(1−($RLU_{sample}$−$RLU_{NHSC}$)/($RLU_{cell+NHSC}$−$RLU_{NHSC}$)).

The results of the system control (rituximab against Raji cells) met the quality control standard in both tests. However, concentration dependent CDC activity of the test sample (Hu24F8.2-IgG1) or the negative control (Human IgG1) was not observed in either the % NHSC optimization assay or the CDC concentration response study. Results are summarized in Tables 16 and 17, respectively. FACS analysis of Hu24F8.2-IgG1 binding to GS-J1/TIGIT cells was used to confirm the lack of CDC was not due to the absence of target cell binding (data not shown).

TABLE 16

Results of % NHSC optimization assay

| Sample | Conc. (µg/mL) | Target cell | % NHSC | Mean of % Target cell Lysis | $EC_{50}$ (µg/mL) |
|---|---|---|---|---|---|
| Rituximab | 10 | Raji | 5% | 93.9 | 0.414 |
| Hu24F8.2-IgG1 | 10 | GS-J1/TIGIT | 5% | 5.77 | N/A |
| | | | 10% | 17.5 | |
| | | | 20% | −15.5 | |
| Human IgG1 | 10 | GS-J1/TIGIT | 5% | 5.39 | N/A |
| | | | 10% | 8.44 | |
| | | | 20% | −12.3 | |

TABLE 17

Results of CDC concentration response study

| Sample | Top Conc. (µg/mL) | Target cell | % NHSC | $EC_{50}$ (µg/mL) |
|---|---|---|---|---|
| Rituximab | 10 | Raji | 5% | 0.275 |
| Hu24F8.2-IgG1 | 10 | GS-J1/TIGIT | 5% | N/A |
| Human IgG1 | 10 | GS-J1/TIGIT | 5% | N/A |

Example 9. Antibody Characterization by SPR

Hu24F8.2-IgG1 was analyzed by SPR using a BioRad ProteOn XPR36 instrument with antibody capture using an anti-human IgG coated chip or a Protein A coated chip at six different densities. The analyte was soluble hTIGIT-His (stock solution prepared at 33.3 µM) which was diluted to 33 nM as the highest concentration and tested in triplicate in a three-fold dilution series over Hu24F8.2-IgG1 surface. The running buffer contained 10 mM HEPES, 150 mM NaCl, 0.05% tween-20 and 0.2 mg/mL BSA. All data were collected at 25° C. Data from all six surface densities were globally fit to a 1:1 interaction model using a local Rmax. Results are shown in Table 18.

TABLE 18

| Kinetic binding constants of Hu24F8.2-IgG1 binding to human TIGIT | | | |
|---|---|---|---|
| Capture method | $k_a$ (M$^{-1}$s$^{-1}$) | $k_d$ (s$^{-1}$) | $K_D$ (M) |
| anti-human IgG | 2.425(6)E+06 | 5.97(3)E−05 | 2.46(1)E−11 |
| Protein A | 1.671(6)E+06 | 6.31(4)E−05 | 3.77(3)E−11 |

Note:
The numbers in parentheses represent the standard errors in the last reported digits from a global fit of 6 different density surfaces.

We claim:

1. An anti-TIGIT antibody or antigen-binding fragment thereof that specifically binds to human TIGIT, comprising
   (a) a heavy chain variable region comprising an HC-CDR1 having an amino acid sequence comprising SEQ ID NO: 36, an HC-CDR2 having an amino acid sequence comprising SEQ ID NO: 37, and an HC-CDR3 having an amino acid sequence comprising SEQ ID NO: 38; and a light chain variable region comprising an LC-CDR1 having an amino acid sequence comprising identity to SEQ ID NO: 39, an LC-CDR2 having an amino acid sequence comprising SEQ ID NO: 40, and an LC-CDR3 having an amino acid sequence comprising SEQ ID NO: 41;
   (b) a heavy chain variable region comprising an HC-CDR1 having an amino acid sequence comprising SEQ ID NO: 42, an HC-CDR2 having an amino acid sequence comprising SEQ ID NO: 43, and an HC-CDR3 having an amino acid sequence comprising SEQ ID NO: 44; and a light chain variable region comprising an LC-CDR1 having an amino acid sequence comprising SEQ ID NO: 45, an LC-CDR2 having an amino acid sequence comprising SEQ ID NO: 46, and an LC-CDR3 having an amino acid sequence comprising SEQ ID NO: 47;
   (c) a heavy chain variable region comprising an HC-CDR1 having an amino acid sequence comprising SEQ ID NO: 48, an HC-CDR2 having an amino acid sequence comprising SEQ ID NO: 49, and an HC-CDR3 having an amino acid sequence comprising SEQ ID NO: 50; and a light chain variable region comprising an LC-CDR1 having an amino acid sequence comprising SEQ ID NO: 51, an LC-CDR2 having an amino acid sequence comprising SEQ ID NO: 52, and an LC-CDR3 having an amino acid sequence comprising SEQ ID NO: 53;
   (d) a heavy chain variable region comprising an HC-CDR1 having an amino acid sequence comprising SEQ ID NO: 54, an HC-CDR2 having an amino acid sequence comprising SEQ ID NO: 55, and an HC-CDR3 having an amino acid sequence comprising SEQ ID NO: 56; and a light chain variable region comprising an LC-CDR1 having an amino acid sequence comprising SEQ ID NO: 57, an LC-CDR2 having an amino acid sequence comprising SEQ ID NO: 58, and an LC-CDR3 having an amino acid sequence comprising SEQ ID NO: 59;
   (e) a heavy chain variable region comprising an HC-CDR1 having an amino acid sequence comprising SEQ ID NO: 60, an HC-CDR2 having an amino acid sequence comprising SEQ ID NO: 61, and an HC-CDR3 having an amino acid sequence comprising SEQ ID NO: 62; and a light chain variable region comprising an LC-CDR1 having an amino acid sequence comprising SEQ ID NO: 63, an LC-CDR2 having an amino acid sequence comprising SEQ ID NO: 64, and an LC-CDR3 having an amino acid sequence comprising SEQ ID NO: 65;
   (f) a heavy chain variable region comprising an HC-CDR1 having an amino acid sequence comprising SEQ ID NO: 60, an HC-CDR2 having an amino acid sequence comprising SEQ ID NO: 66, and an HC-CDR3 having an amino acid sequence comprising SEQ ID NO: 67; and a light chain variable region comprising an LC-CDR1 having an amino acid sequence comprising SEQ ID NO: 63, an LC-CDR2 having an amino acid sequence comprising SEQ ID NO: 68, and an LC-CDR3 having an amino acid sequence comprising SEQ ID NO: 65;
   (g) a heavy chain variable region comprising an HC-CDR1 having an amino acid sequence comprising SEQ ID NO: 69, an HC-CDR2 having an amino acid sequence comprising SEQ ID NO: 55, and an HC-CDR3 having an amino acid sequence comprising SEQ ID NO: 70; and a light chain variable region comprising an LC-CDR1 having an amino acid sequence comprising SEQ ID NO: 71, an LC-CDR2 having an amino acid sequence comprising SEQ ID NO: 68, and an LC-CDR3 having an amino acid sequence comprising SEQ ID NO: 65;
   (h) a heavy chain variable region comprising an HC-CDR1 having an amino acid sequence comprising SEQ ID NO: 72, an HC-CDR2 having an amino acid sequence comprising SEQ ID NO: 73, and an HC-CDR3 having an amino acid sequence comprising SEQ ID NO: 67; and a light chain variable region comprising an LC-CDR1 having an amino acid sequence comprising SEQ ID NO: 63, an LC-CDR2 having an amino acid sequence comprising SEQ ID NO: 68, and an LC-CDR3 having an amino acid sequence comprising SEQ ID NO: 65; or
   (i) a heavy chain variable region comprising an HC-CDR1 having an amino acid sequence comprising SEQ ID NO: 74, an HC-CDR2 having an amino acid sequence comprising SEQ ID NO: 75, and an HC-CDR3 having an amino acid sequence comprising SEQ ID NO: 67; and a light chain variable region comprising an LC-CDR1 having an amino acid sequence comprising SEQ ID NO: 63, an LC-CDR2 having an amino acid sequence comprising SEQ ID NO: 68, and an LC-CDR3 having an amino acid sequence comprising SEQ ID NO: 65.

2. The anti-TIGIT antibody or antigen-binding fragment thereof of claim 1, comprising
   (a) a heavy chain variable region having at least 80% sequence identity to SEQ ID NO: 1, and a light chain variable region having at least 80% sequence identity to SEQ ID NO: 2;
   (b) a heavy chain variable region having at least 80% sequence identity to SEQ ID NO: 3, and a light chain variable region having at least 80% sequence identity to SEQ ID NO: 4;
   (c) a heavy chain variable region having at least 80% sequence identity to SEQ ID NO: 5, and a light chain variable region having at least 80% sequence identity to SEQ ID NO: 6;

(d) a heavy chain variable region having at least 80% sequence identity to SEQ ID NO: 7, and a light chain variable region having at least 80% sequence identity to SEQ ID NO: 8;
(e) a heavy chain variable region having at least 80% sequence identity to SEQ ID NO: 9, and a light chain variable region having at least 80% sequence identity to SEQ ID NO: 10;
(f) a heavy chain variable region having at least 80% sequence identity to SEQ ID NO: 11, and a light chain variable region having at least 80% sequence identity to SEQ ID NO: 12;
(g) a heavy chain variable region having at least 80% sequence identity to SEQ ID NO: 13, and a light chain variable region having at least 80% sequence identity to SEQ ID NO: 14;
(h) a heavy chain variable region having at least 80% sequence identity to SEQ ID NO: 15, and a light chain variable region having at least 80% sequence identity to SEQ ID NO: 16;
(i) a heavy chain variable region having at least 80% sequence identity to SEQ ID NO: 17, and a light chain variable region having at least 80% sequence identity to SEQ ID NO: 12;
(j) a heavy chain variable region having at least 80% sequence identity to SEQ ID NO: 76, and a light chain variable region having at least 80% sequence identity to SEQ ID NO: 77;
(k) a heavy chain variable region having at least 80% sequence identity to SEQ ID NO: 78, and a light chain variable region having at least 80% sequence identity to SEQ ID NO: 77;
(l) a heavy chain variable region having at least 80% sequence identity to SEQ ID NO: 76, and a light chain variable region having at least 80% sequence identity to SEQ ID NO: 79; or
(m) a heavy chain variable region having at least 80% sequence identity to SEQ ID NO: 78, and a light chain variable region having at least 80% sequence identity to SEQ ID NO: 79.

3. The anti-TIGIT antibody or antigen-binding fragment thereof of claim 1, wherein the anti-TIGIT antibody or antigen-binding fragment thereof is a monoclonal antibody.

4. The anti-TIGIT antibody or antigen-binding fragment thereof of claim 1, wherein the anti-TIGIT antibody or antigen-binding fragment thereof is a chimeric, humanized, or veneered antibody.

5. The anti-TIGIT antibody or antigen-binding fragment thereof of claim 4, wherein the chimeric antibody comprises human IgG1/kappa Fab constant domain.

6. The anti-TIGIT antibody or antigen binding fragment thereof of claim 1, wherein the antibody further comprises a variant heavy chain constant region selected from variant human IgG1, variant human IgG2, variant human IgG3, or variant human IgG4, and optionally a human light chain constant region.

7. The anti-TIGIT antibody or antigen binding fragment thereof of claim 6, wherein the variant heavy chain constant region has enhanced or decreased effector function with reference to the wild type heavy chain constant region.

8. The anti-TIGIT antibody or antigen binding fragment thereof of claim 1, wherein the antibody further comprises a wild-type human IgG heavy chain constant region, and optionally a human light chain constant region.

9. The anti-TIGIT antibody or antigen binding fragment thereof of claim 1, wherein the antibody has a heavy chain and a light chain, wherein
(a) the heavy chain has an amino acid sequence comprising SEQ ID NO: 92, and the light chain has an amino acid sequence comprising SEQ ID NO: 93; or
(b) the heavy chain has an amino acid sequence comprising SEQ ID NO: 96, and the light chain has an amino acid sequence comprising SEQ ID NO: 93; or
(c) the heavy chain has an amino acid sequence comprising SEQ ID NO: 98, and the light chain has an amino acid sequence comprising SEQ ID NO: 93; or
(d) the heavy chain has an amino acid sequence comprising SEQ ID NO: 100, and the light chain has an amino acid sequence comprising SEQ ID NO: 93.

10. The anti-TIGIT antibody or antigen binding fragment thereof of claim 1, wherein the antibody or binding fragment thereof
(a) has an equilibrium binding constant (KD) of about $0.01\times10^{11}$ M to about $100\times10^{11}$ M, about $0.1\times10^{11}$ M to about $100\times10^{11}$ M, about $0.1\times10^{11}$ M to about $10\times10^{11}$ M, about $1\times10^{11}$ M to about $100\times10^{11}$ M or about $1\times10^{11}$ M to about $10\times10^{11}$ M, measured by surface plasmon resonance; and/or
(b) binds to an epitope that includes at least the following residues of TIGIT:
(i) D72 of SEQ ID NO: 80 and at least one of T55, Q56, N58, E60, S80, and K82 of SEQ ID NO: 80,
(ii) E60 and D72 of SEQ ID NO: 80 and optionally at least one of T55, Q56, N58, S80, and K82 of SEQ ID NO: 80,
(iii) D72 and K82 of SEQ ID NO: 80 and optionally at least one of T55, Q56, N58, E60, and S80 of SEQ ID NO: 80,
(iv) E60, D72 and K82 of SEQ ID NO: 80 and optionally at least one of T55, Q56, N58, and S80 of SEQ ID NO: 80, or
(v) T55, Q56, N58, E60, D72, S80, and K82 of SEQ ID NO: 80.

11. The anti-TIGIT antibody or antigen binding fragment thereof of claim 10, wherein an excess of the antibody or antigen-binding fragment thereof competes with a reference antibody for binding to TIGIT by at least about 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% as measured in a competitive binding assay, wherein the reference antibody comprises a heavy chain having an amino acid sequence comprising SEQ ID NO: 92 and a light chain having an amino acid sequence comprising SEQ ID NO: 93.

12. An anti-TIGIT antibody or antigen-binding fragment thereof that specifically binds to human TIGIT, comprising a heavy chain having an amino acid sequence comprising SEQ ID NO: 92 and a light chain having an amino acid sequence comprising SEQ ID NO: 93.

13. A method of inhibiting binding of TIGIT to CD155 comprising contacting TIGIT with the anti-TIGIT antibody or antigen-binding fragment thereof of claim 1.

14. A method of treating or effecting prophylaxis of cancer comprising administering to a subject having or at risk of cancer an effective regime or a therapeutically effective amount of the anti-TIGIT antibody or antigen-binding fragment thereof of claim 1.

15. A pharmaceutical composition comprising the antibody or antigen-binding fragment thereof of claim 1 and a pharmaceutically acceptable carrier.

16. An anti-TIGIT antibody or antigen binding fragment thereof of claim 1, wherein the antibody or antigen binding fragment thereof binds to an epitope of human TIGIT comprising at least one of the following amino acid residues of SEQ ID NO 80: T55, Q56, N58, E60, D72, S80, and K82.

* * * * *